(12) United States Patent
Ambrosino et al.

(10) Patent No.: US 9,109,037 B2
(45) Date of Patent: Aug. 18, 2015

(54) ANTI-SOD1 ANTIBODIES AND USES THEREOF

(75) Inventors: Donna Ambrosino, Jamaica Plain, MA (US); Gregory Babcock, Marlborough, MA (US); Teresa Broering, Brookline, MA (US); Zuoshang Xu, Wellesley, MA (US)

(73) Assignee: University of Massachusetts, Boston, MA (US)

( * ) Notice: Subject to any disclaimer, the term of this patent is extended or adjusted under 35 U.S.C. 154(b) by 16 days.

(21) Appl. No.: 13/882,017

(22) PCT Filed: Oct. 25, 2011

(86) PCT No.: PCT/US2011/057699
§ 371 (c)(1),
(2), (4) Date: Oct. 15, 2013

(87) PCT Pub. No.: WO2012/058220
PCT Pub. Date: May 3, 2012

(65) Prior Publication Data
US 2014/0044722 A1    Feb. 13, 2014

Related U.S. Application Data

(60) Provisional application No. 61/406,831, filed on Oct. 26, 2010.

(51) Int. Cl.
*A61K 39/395* (2006.01)
*C07K 16/40* (2006.01)
*A61K 45/06* (2006.01)
*A61K 39/00* (2006.01)

(52) U.S. Cl.
CPC ............. *C07K 16/40* (2013.01); *A61K 39/3955* (2013.01); *A61K 45/06* (2013.01); *A61K 2039/505* (2013.01); *C07K 2317/21* (2013.01); *C07K 2317/34* (2013.01); *C07K 2317/92* (2013.01)

(58) Field of Classification Search
None
See application file for complete search history.

(56) References Cited

U.S. PATENT DOCUMENTS

| 7,439,324 | B2 | 10/2008 | Cashman |
| 7,763,710 | B2 | 7/2010 | Cashman |
| 7,794,692 | B2 | 9/2010 | Chakrabartty et al. |
| 1,002,035 | A1 | 1/2011 | Chakrabartty et al. |
| 7,887,803 | B2 | 2/2011 | Cashman |
| 7,977,314 | B2 | 7/2011 | Cashman |
| 1,021,209 | A1 | 9/2011 | Cashman et al. |
| 8,075,891 | B2 | 12/2011 | Cashman |
| 2002/0086014 | A1* | 7/2002 | Korman et al. ............ 424/144.1 |
| 2006/0246517 | A1 | 11/2006 | Cashman |
| 2007/0003977 | A1 | 1/2007 | Cashman et al. |
| 2007/0292410 | A1 | 12/2007 | Cashman et al. |
| 2008/0020651 | A1 | 1/2008 | Segawa et al. |
| 2008/0132685 | A1 | 6/2008 | Chakrabartty et al. |
| 2008/0206251 | A1 | 8/2008 | Cashman et al. |
| 2009/0068194 | A1 | 3/2009 | Julien et al. |
| 2009/0098151 | A1 | 4/2009 | Cashman |
| 2011/0124018 | A1 | 5/2011 | Cashman et al. |
| 2011/0135673 | A1 | 6/2011 | Cashman |

OTHER PUBLICATIONS

International Search Report for International Patent Application PCT/US2011/057699, mailed May 4, 2012 (4 pages).
International Preliminary Report on Patentability issued in International Application No. PCT/US2011/057699, issued Apr. 30, 2013 (8 pages).
Written Opinion of the International Searching Authority issued in International Application No. PCT/US2011/057699, mailed May 4, 2012 (7 pages).
Extended European Search Report for European Patent Application No. 11836951.1, dated Apr. 1, 2014.
Broering et al., "Identification of human monoclonal antibodies specific for human SOD1 recognizing distinct epitopes and forms of SOD1," PLOS One 8:e61210 (2013) (13 pages).
Gros-Louis et al., "Intracerebroventricular infusion of monoclonal antibody or its derived Fab fragment against misfolded forms of SOD1 mutant delays mortality in a mouse model of ALS," J. Neurochem. 113:1188-1199 (2010).
Kerman et al., "Amyotrophic lateral sclerosis is a non-amyloid disease in which extensive misfolding of SOD1 is unique to the familial form," Acta Neuropathol 119:335-344 (2010).
Rakhit et al., "An immunological epitope selective for pathological monomer-misfolded SOD1 in ALS," Nat Med 13:754-759 (2007).

* cited by examiner

*Primary Examiner* — Jeffrey Stucker
*Assistant Examiner* — Stephen Gucker
(74) *Attorney, Agent, or Firm* — Clark & Elbing LLP

(57) ABSTRACT

The present invention features anti-SOD1 antibodies and methods of using the antibodies for the treatment of amyotrophic lateral sclerosis (ALS) or the amelioration of symptoms associated with ALS.

25 Claims, 84 Drawing Sheets

FIG. 1

Anti-human SOD1 595-16 VH

V segment:    VHDP-44
    D segment:    D3-10
    J segment:    JH4b

SEQ ID NO:1

```
              E   V   Q   L   V   Q   S   G   G   G   L   G   H   P   G   G   S
    1        GAG GTT CAG CTG GTG CAG TCT GGG GGA GGC TTG GGA CAT CCT GGG GGG TCC
SEQ ID NO:2
                                                         CDR1 SEQ ID:3 (aa)  4 (nt)
                                                         ~~~~~~~~~~~~~~~
              L   R   L   S   C   A   G   S   G   F   T   F   S   S   Y   S   M
   52        CTG AGA CTC TCC TGT GCA GGC TCT GGA TTC ACT TTC AGT AGT TAT TCT ATG

CDR1                                                           CDR2
             ~~~~~                                                         ~~~~~~~~
              H   W   L   R   Q   A   P   G   K   G   L   K   W   V   S   A   I
  103        CAC TGG CTT CGC CAG GCT CCA GGA AAA GGT CTG AAG TGG GTA TCA GCT ATT

CDR2 SEQ ID:5 (aa)  6 (nt)
             ~~~~~~~~~~~~~~~~~~~~~~~~~~~~~~~~~~~~~~~~~~~~~~~~~~~~~~~~~~~~~~~~~
              G   T   A   G   G   T   Y   Y   A   D   S   V   K   G   R   F   T
  154        GGT ACT GCT GGT GGC ACA TAC TAT GCA GAC TCC GTG AAG GGC CGA TTC ACC

I   S   R   D   N   A   K   N   S   F   Y   L   Q   M   N   S   L
  205        ATC TCC AGA GAC AAT GCC AAG AAC TCC TTC TAT CTT CAA ATG AAC AGC CTG

CDR3
                                                                       ~~~~~~~~~~~~~~~~~~~~
              R   A   E   D   M   A   V   Y   Y   C   A   R   E   Y   F   F   G
  256        AGA GCC GAG GAC ATG GCT GTG TAT TAC TGT GCA AGA GAG TAT TTC TTT GGT

CDR3 SEQ ID:7 (aa)  8 (nt)
             ~~~~~~~~~~~~~~~~~~~~~~~~~~
              S   G   N   Y   G   Y   W   G   Q   G   T   L   V   T   A   S   S
  307        TCG GGA AAT TAT GGA TAC TGG GGC CAG GGA ACC CTG GTC ACC GCC TCC TCA
```

FIG. 2

Anti-human SOD1 595-16 VK

V segment: L6
J segment: JK1

SEQ ID NO:9

```
        E   I   V   L   T   Q   S   P   A   T   L   S   L   S   P   G   E
  1    GAA ATT GTG TTG ACA CAG TCT CCA GCC ACC CTG TCT TTG TCT CCA GGG GAA
```
SEQ ID NO:10

CDR1 SEQ ID:11 (aa) 12 (nt)
                                                         ~~~~~~~~~~~~~~~~~~~~~~~~~~~~~~~~~~
```
        R   A   T   L   S   C   R   A   S   Q   S   V   S   S   Y   L   A
 52    AGA GCC ACC CTC TCC TGC AGG GCC AGT CAG AGT GTT AGC AGC TAC TTA GCC
```

CDR2
                                                                           ~~~~~~~~~
```
        W   Y   Q   Q   K   P   G   Q   A   P   R   L   L   I   Y   D   A
103    TGG TAC CAA CAG AAA CCT GGC CAG GCT CCC AGG CTC CTC ATC TAT GAT GCA
```

CDR2 SEQ ID:13 (aa) 14 (nt)
~~~~~~~~~~~~~~~~~~~~~~
```
        S   N   R   A   T   G   I   P   A   R   F   S   G   S   G   S   G
154    TCC AAC AGG GCC ACT GGC ATC CCA GCC AGG TTC AGT GGC AGT GGG TCT GGG
```

```
        T   D   F   T   L   T   I   S   S   L   E   P   E   D   F   A   V
205    ACA GAC TTC ACT CTC ACC ATC AGC AGC CTA GAG CCT GAA GAT TTT GCA GTT
```

CDR3 SEQ ID:15 (aa) 16 (nt)
                         ~~~~~~~~~~~~~~~~~~~~~~~~~~~~~~~~
```
        Y   Y   C   Q   Q   R   S   N   W   P   P   T   F   G   Q   G   T
256    TAT TAC TGT CAG CAG CGT AGC AAC TGG CCT CCG ACG TTC GGC CAA GGG ACC
```

```
        K   V   E   I   K
307    AAG GTG GAG ATC AAA
```

FIG. 3

Anti-human SOD1 595-16-M1 VH

V segment: VHDP-44
D segment: D3-10
J segment: JH4b

SEQ ID NO:17

```
         E   V   Q   L   V   Q   S   G   G   G   L   V   K   P   G   G   S
  2     GAG GTT CAG CTG GTG CAG TCT GGG GGA GGC TTG GTA AAA CCT GGG GGG TCC
SEQ ID NO:18
                                                  CDR1 SEQ ID:3 (aa) 4 (nt)
                                                  ~~~~~~~~~~~~~~
         L   R   L   S   C   A   G   S   G   F   T   F   S   S   Y   S   M
 52     CTG AGA CTC TCC TGT GCA GGC TCT GGA TTC ACT TTC AGT AGT TAT TCT ATG

CDR1                                              CDR2
         ~~~~                                              ~~~~~~~~
         H   W   L   R   Q   A   P   G   K   G   L   E   W   V   S   A   I
103     CAC TGG CTT CGC CAG GCT CCA GGA AAA GGT CTG GAG TGG GTA TCA GCT ATT

CDR2 SEQ ID:5 (aa) 6 (nt)
         ~~~~~~~~~~~~~~~~~~~~~~~~~~~~~~~~~~~~~~~~~~~~~~~~~~
         G   T   A   G   G   T   Y   Y   A   D   S   V   K   G   R   F   T
154     GGT ACT GCT GGT GGC ACA TAC TAT GCA GAC TCC GTG AAG GGC CGA TTC ACC

I   S   R   D   N   A   K   N   S   L   Y   L   Q   M   N   S   L
205     ATC TCC AGA GAC AAT GCC AAG AAC TCC TTG TAT CTT CAA ATG AAC AGC CTG

CDR3
                                                              ~~~~~~~~~~~~~~~~~~~~
         R   A   E   D   T   A   V   Y   Y   C   A   R   E   Y   F   F   G
256     AGA GCC GAG GAC ACG GCT GTG TAT TAC TGT GCA AGA GAG TAT TTC TTT GGT

CDR3 SEQ ID:7 (aa) 8 (nt)
         ~~~~~~~~~~~~~~~~~~~~~~~~~
         S   G   N   Y   G   Y   W   G   Q   G   T   L   V   T   V   S   S
307     TCG GGG AAT TAT GGA TAC TGG GGC CAG GGA ACC CTG GTC ACC GTC TCC TCA
```

FIG. 4

Anti-human SOD1 591-37 VH

V segment:    VHDP-44
    D segment:    D3-03
    J segment:    JH3b

SEQ ID NO:19

```
            E   V   Q   L   V   Q   S   G   G   G   L   V   H   P   G   G   S
  1     GAG GTT CAG CTG GTG CAG TCT GGG GGA GGC TTG GTA CAT CCT GGG GGG TCC
SEQ ID NO:20
                                                        CDR1 SEQ ID:21 (aa) 22 (nt)
                                                        ~~~~~~~~~~~~~~~~~~~~
            L   R   L   S   C   A   G   S   G   F   T   F   S   R   Y   A   L
 52     CTG AGA CTC TCC TGT GCA GGC TCT GGA TTC ACC TTC AGT CGC TAT GCT TTA

CDR1                                                                CDR2
        ~~~~~                                                               ~~~~~~~~~~
            H   W   V   R   Q   A   P   G   K   G   L   E   W   V   S   A   I
103     CAC TGG GTT CGC CAG GCT CCA GGA AAA GGT CTG GAG TGG GTA TCA GCT ATT

CDR2 SEQ ID:23 (aa) 24 (nt)
        ~~~~~~~~~~~~~~~~~~~~~~~~~~~~~~~~~~~~~~~~~~~~~~~~~~~~~~~~
            G   I   G   G   G   T   F   Y   A   D   S   V   K   G   R   F   T
154     GGT ATT GGT GGT GGC ACA TTC TAT GCA GAC TCC GTG AAG GGC CGA TTC ACC

I   S   R   D   N   A   K   N   S   L   Y   L   Q   M   N   S   L
205     ATC TCC AGA GAC AAT GCC AAG AAC TCC TTG TAT CTT CAA ATG AAC AGC CTG

CDR3
                                                                        ~~~~~~~~~~~~~~~~~~~~
            R   A   E   D   M   A   V   Y   Y   C   A   R   D   T   Y   Y   D
256     AGA GCC GAG GAC ATG GCT GTG TAT TAC TGT GCA AGA GAT ACG TAT TAC GAT

CDR3 SEQ ID:25 (aa) 26 (nt)
        ~~~~~~~~~~~~~~~~~~~~~~~~~~~~~
            F   F   D   A   F   D   I   W   G   Q   G   T   M   V   T   V   S
307     TTT TTT GAT GCT TTT GAT ATC TGG GGC CAA GGG ACA ATG GTC ACC GTC TCT

S
358     TCA
```

FIG. 5

Anti-human SOD1 591-37 VK

V segment: L15
J segment: JK4

SEQ ID NO:27

```
          D   I   Q   M   T   Q   S   P   S   S   L   S   A   S   V   G   D
1         GAC ATC CAG ATG ACC CAG TCT CCA TCC TCA CTG TCT GCA TCT GTA GGA GAC
SEQ ID NO:28
```

CDR1 SEQ ID:29 (aa) 30 (nt)
                                              ~~~~~~~~~~~~~~~~~~~~~~~~~~~~~~~~~~~~~~
```
          R   V   T   I   T   C   R   A   S   Q   G   I   S   S   W   L   A
52        AGA GTC ACC ATC ACT TGT CGG GCG AGT CAG GGT ATT AGC AGC TGG TTA GCC
```

CDR2
                                                                      ~~~~~~~~~~
```
          W   Y   Q   Q   K   P   E   K   A   P   K   S   L   I   Y   A   A
103       TGG TAT CAG CAG AAA CCA GAG AAA GCC CCT AAG TCC CTG ATC TAT GCT GCA
```

CDR2 SEQ ID:31 (aa) 32 (nt)
   ~~~~~~~~~~~~~~~~~~~~~~
```
          S   S   L   Q   S   G   V   P   S   R   F   S   G   S   G   S   G
154       TCC AGT TTG CAA AGT GGG GTC CCA TCA AGG TTC AGC GGC AGT GGA TCT GGG
```

```
          T   D   F   T   L   T   I   S   S   L   Q   P   E   D   F   A   T
205       ACA GAT TTC ACT CTC ACC ATC AGC AGC CTG CAG CCT GAA GAT TTT GCA ACT
```

CDR3 SEQ ID:33 (aa) 34 (nt)
                        ~~~~~~~~~~~~~~~~~~~~~~~~~~~~~~~~
```
          Y   Y   C   Q   Q   Y   D   S   Y   P   L   T   F   G   G   G   T
256       TAT TAC TGC CAA CAG TAT GAT AGT TAC CCT CTC ACT TTC GGC GGA GGG ACC
```

```
          K   V   E   I   K
307       AAG GTG GAG ATC AAA
```

FIG. 6

Anti-human SOD1 591-37-M1 VH

V segment:    VHDP-44
    D segment:    D3-03
    J segment:    JH3b

SEQ ID NO:35

```
            E   V   Q   L   V   Q   S   G   G   G   L   V   K   P   G   G   S
1           GAG GTT CAG CTG GTG CAG TCT GGG GGA GGC TTG GTA AAA CCT GGG GGG TCC
```
SEQ ID NO:36

CDR1 SEQ ID:21 (aa) 22 (nt)

```
            L   R   L   S   C   A   G   S   G   F   T   F   S   R   Y   A   L
52          CTG AGA CTC TCC TGT GCA GGC TCT GGA TTC ACC TTC AGT CGC TAT GCT TTA
```

CDR1                                                                                                                CDR2

```
            H   W   V   R   Q   A   P   G   K   G   L   E   W   V   S   A   I
103         CAC TGG GTT CGC CAG GCT CCA GGA AAA GGT CTG GAG TGG GTA TCA GCT ATT
```

CDR2 SEQ ID:23 (aa) 24 (nt)

```
            G   I   G   G   G   T   F   Y   A   D   S   V   K   G   R   F   T
154         GGT ATT GGT GGT GGC ACA TTC TAT GCA GAC TCC GTG AAG GGC CGA TTC ACC
```

```
            I   S   R   D   N   A   K   N   S   L   Y   L   Q   M   N   S   L
205         ATC TCC AGA GAC AAT GCC AAG AAC TCC TTG TAT CTT CAA ATG AAC AGC CTG
```

CDR3

```
            R   A   E   D   T   A   V   Y   Y   C   A   R   D   T   Y   Y   D
256         AGA GCC GAG GAC ACG GCT GTG TAT TAC TGT GCA AGA GAT ACG TAT TAC GAT
```

CDR3 SEQ ID:25 (aa) 26 (nt)

```
            F   F   D   A   F   D   I   W   G   Q   G   T   M   V   T   V   S
307         TTT TTT GAT GCT TTT GAT ATC TGG GGC CAA GGG ACA ATG GTC ACC GTC TCT
```

```
            S
358         TCA
```

FIG. 7

Anti-human SOD1 358-11 VH

| V segment: | VH3-33 |
|---|---|
| D segment: | D7-27 |
| J segment: | JH3b |

SEQ ID NO:37

```
          Q   V   Q   L   V   E   S   G   G   G   V   V   Q   P   G   R   S
   1      CAG GTG CAG CTG GTG GAG TCT GGG GGA GGC GTG GTC CAG CCT GGG AGG TCC
SEQ ID NO:38
                                                      CDR1 SEQ ID:39 (aa) 40 (nt)
                                                      ~~~~~~~~~~~~~~~~~~
          L   R   L   S   C   A   A   S   G   F   T   F   S   N   Y   G   I
  52      CTG AGA CTC TCC TGT GCA GCG TCT GGA TTC ACC TTC AGT AAC TAT GGC ATA

CDR1                                                          CDR2
          ~~~~~~                                                  ~~~~~~~~~~~~
          H   W   V   R   Q   A   P   G   K   G   L   E   W   V   A   I   I
 103      CAC TGG GTC CGC CAG GCT CCA GGC AAG GGG CTG GAG TGG GTG GCT ATT ATA

CDR2 SEQ ID:41 (aa) 42 (nt)
          ~~~~~~~~~~~~~~~~~~~~~~~~~~~~~~~~~~~~~~~~~~~~~~~~~
          W   H   D   G   S   N   S   Y   Y   V   D   S   V   K   G   R   F
 154      TGG CAT GAT GGA AGT AAT TCA TAT TAT GTA GAC TCC GTG AAG GGC CGA TTC

T   M   S   R   D   N   S   K   N   T   V   Y   L   Q   M   N   S
 205      ACC ATG TCC AGA GAC AAT TCC AAG AAC ACG GTG TAT CTG CAA ATG AAC AGC

CDR3
                                                                    ~~~~~~~~~~~~
          L   R   A   E   D   T   A   V   Y   F   C   A   R   I   I   G   G
 256      CTG AGA GCC GAG GAC ACG GCT GTG TAT TTC TGT GCG AGA ATA ATT GGG GGC

CDR3 SEQ ID:43 (aa) 44 (nt)
          ~~~~~~~~~~~~~~~~~~~~~~~
          A   F   D   I   W   G   Q   G   T   M   V   T   V   S   S
 307      GCT TTT GAT ATC TGG GGC CAA GGG ACA ATG GTC ACC GTC TCT TCA
```

FIG. 8

Anti-human SOD1 358-11 VK

V segment: L15
J segment: JK5

SEQ ID NO:45
```
          D   I   Q   M   T   Q   S   P   S   S   L   S   A   S   V   G   D
    1    GAC ATC CAG ATG ACC CAG TCT CCA TCC TCA CTG TCT GCA TCT GTA GGA GAC
SEQ ID NO:46
                                                 CDR1 SEQ ID:47 (aa) 48 (nt)
                                                 ~~~~~~~~~~~~~~~~~~~~~~~~~~~~~~~
          R   V   T   I   T   C   R   A   S   Q   G   I   S   S   W   L   A
   52    AGA GTC ACC ATC ACT TGT CGG GCG AGT CAG GGT ATT AGC AGC TGG TTA GCC
                                                                       CDR2
                                                                       ~~~~~~~~
          W   Y   Q   Q   K   P   E   K   A   P   K   S   L   I   Y   A   A
  103    TGG TAT CAG CAG AAA CCA GAG AAA GCC CCT AAG TCC CTG ATC TAT GCT GCA

CDR2 SEQ ID:49 (aa) 50 (nt)
     ~~~~~~~~~~~~~~~~~~~~~
          S   S   L   Q   S   G   V   P   S   R   F   S   G   S   G   S   G
  154    TCC AGT TTG CAA AGT GGG GTC CCA TCA AGG TTC AGC GGC AGT GGA TCT GGG

T   D   F   T   L   T   I   S   S   L   Q   P   E   D   F   A   T
  205    ACA GAT TTC ACT CTC ACC ATC AGC AGC CTG CAG CCT GAA GAT TTT GCA ACT
                              CDR3 SEQ ID:51 (aa) 52 (nt)
                              ~~~~~~~~~~~~~~~~~~~~~~~~~~~~~~~~~~
          Y   Y   C   Q   Q   Y   N   S   Y   P   I   T   F   G   Q   G   T
  256    TAT TAC TGC CAA CAG TAT AAT AGT TAC CCG ATC ACC TTC GGC CAA GGG ACA

R   L   E   I   K
  307    CGA CTG GAG ATC AAA
```

FIG. 9

Anti-human SOD1 358-11-M1 VH

V segment: VH3-33
D segment: D7-27
J segment: JH3b

SEQ ID NO:53

```
            Q   V   Q   L   V   E   S   G   G   G   V   V   Q   P   G   R   S
1           CAG GTG CAG CTG GTG GAG TCT GGG GGA GGC GTG GTC CAG CCT GGG AGG TCC
SEQ ID NO:54
                                                    CDR1 SEQ ID:39 (aa) 40 (nt)
                                                    ~~~~~~~~~~~~~~~~~
            L   R   L   S   C   A   A   S   G   F   T   F   S   N   Y   G   I
52          CTG AGA CTC TCC TGT GCA GCG TCT GGA TTC ACC TTC AGT AAC TAT GGC ATA

CDR1                                                            CDR2
            ~~~~~~                                                          ~~~~~~~~~~~~
            H   W   V   R   Q   A   P   G   K   G   L   E   W   V   A   I   I
103         CAC TGG GTC CGC CAG GCT CCA GGC AAG GGG CTG GAG TGG GTG GCT ATT ATA

CDR2 SEQ ID:41 (aa) 42 (nt)
            ~~~~~~~~~~~~~~~~~~~~~~~~~~~~~~~~~~~~~~~~~~~~~~~~~~~~~~~~~~~~~~~~~
            W   H   D   G   S   N   S   Y   Y   V   D   S   V   K   G   R   F
154         TGG CAT GAT GGA AGT AAT TCA TAT TAT GTA GAC TCC GTG AAG GGC CGA TTC

T   I   S   R   D   N   S   K   N   T   L   Y   L   Q   M   N   S
205         ACC ATC TCC AGA GAC AAT TCC AAG AAC ACG CTG TAT CTG CAA ATG AAC AGC

CDR3
                                                                        ~~~~~~~~~~~~~~~~
            L   R   A   E   D   T   A   V   Y   F   C   A   R   I   I   G   G
256         CTG AGA GCC GAG GAC ACG GCT GTG TAT TTC TGT GCG AGA ATA ATT GGG GGC

CDR3 SEQ ID:43 (aa) 44 (nt)
            ~~~~~~~~~~~~~~~~~
            A   F   D   I   W   G   Q   G   T   M   V   T   V   S   S
307         GCT TTT GAT ATC TGG GGC CAA GGG ACA ATG GTC ACC GTC TCT TCA
```

FIG. 10

Anti-human SOD1 358-22 VH

| V segment: | VH3-33 |
|---|---|
| D segment: | D1-20 |
| J segment: | JH3b |

SEQ ID NO:55

```
          Q   V   Q   L   V   E   S   G   G   G   V   V   Q   P   G   R   S
   1     CAG GTG CAA CTG GTG GAG TCT GGG GGA GGC GTG GTC CAG CCT GGG AGG TCC
SEQ ID NO:56
                                                      CDR1 SEQ ID:57 (aa) 58 (nt)
                                                      ~~~~~~~~~~~~~~~~~
          L   R   L   S   C   A   A   S   G   F   T   F   R   S   Y   G   M
  52     CTG AGA CTC TCC TGT GCA GCG TCT GGA TTC ACC TTC AGG AGT TAT GGC ATG

CDR1                                                          CDR2
         ~~~~~                                                       ~~~~~~~~~
          H   W   V   R   Q   A   P   G   K   G   L   E   W   V   T   L   I
 103     CAC TGG GTC CGC CAG GCT CCA GGC AAG GGG CTG GAG TGG GTG ACA CTT ATA

CDR2 SEQ ID:59 (aa) 60 (nt)
         ~~~~~~~~~~~~~~~~~~~~~~~~~~~~~~~~~~~~~~~~~~~~~~~~~~~~~~~~~
          W   Y   D   G   S   N   K   Y   Y   A   D   S   V   K   G   R   F
 154     TGG TAT GAT GGA AGT AAT AAA TAC TAT GCA GAC TCC GTG AAG GGC CGA TTC

T   I   S   R   D   N   S   K   N   T   L   Y   L   Q   M   N   S
 205     ACC ATC TCC AGA GAC AAT TCC AAG AAC ACG CTG TAT CTG CAA ATG AAC AGC

CDR3
                                                                ~~~~~~~~~~
          L   R   V   E   D   T   A   V   Y   Y   C   A   R   E   G   F   N
 256     CTG AGA GTC GAG GAC ACG GCT GTG TAT TAC TGT GCG AGA GAA GGG TTT AAC

CDR3 SEQ ID:61 (aa) 62 (nt)
         ~~~~~~~~~~~~~~~~~~~~~~~~~~
          W   D   A   F   D   I   W   G   Q   G   T   M   V   T   V   S   S
 307     TGG GAT GCT TTT GAT ATC TGG GGC CAA GGG ACA ATG GTC ACC GTC TCT TCA
```

FIG. 11

Anti-human SOD1 358-22 VK

V segment:   A27
J segment:   JK2

SEQ ID NO: 63

```
          E   I   V   L   T   Q   S   P   G   T   L   S   L   S   P   G   E
  1      GAA ATT GTG TTG ACG CAG TCT CCA GGC ACC CTG TCT TTG TCT CCA GGG GAA
SEQ ID NO:64
                                          CDR1 SEQ ID:65 (aa) 66 (nt)
                                          ~~~~~~~~~~~~~~~~~~~~~~~~~~~~~~~~
          R   A   T   L   S   C   R   A   S   Q   S   V   R   I   S   Y   L
 52      AGA GCC ACC CTC TCC TGC AGG GCC AGT CAG AGT GTT CGC ATC AGC TAC TTA

CDR1                                                           CDR2
         ~~~~~                                                          ~~~~~~
          A   W   Y   Q   Q   K   P   G   Q   A   P   R   L   L   I   Y   G
103      GCC TGG TAC CAG CAG AAA CCT GGC CAG GCT CCC AGG CTC CTC ATC TAT GGT

CDR2 SEQ ID:67 (aa) 68 (nt)
         ~~~~~~~~~~~~~~
          T   F   S   R   A   T   G   I   P   D   R   F   S   G   S   G   S
154      ACA TTC AGC AGG GCC ACT GGC ATC CCA GAC AGG TTC AGT GGC AGT GGG TCT

G   T   D   F   T   L   T   I   S   R   L   E   P   E   D   F   A
205      GGG ACA GAC TTC ACT CTC ACC ATC AGC AGA CTG GAG CCT GAA GAT TTT GCA

CDR3 SEQ ID:69 (aa) 70 (nt)
                                  ~~~~~~~~~~~~~~~~~~~~~~~~~~~~~~~
          V   Y   Y   C   Q   Q   Y   G   S   S   M   Y   T   F   G   Q   G
256      GTG TAT TAC TGT CAG CAG TAT GGT AGC TCA ATG TAC ACT TTT GGC CAG GGG

T   K   L   E   I   K
307      ACC AAG CTG GAG ATC AAA
```

FIG. 12

Anti-human SOD1 358-22-M1 VH

V segment: VH3-33
D segment: D1-20
J segment: JH3b

SEQ ID NO:71

```
          Q   V   Q   L   V   E   S   G   G   V   V   Q   P   G   R   S
    2     CAG GTG CAA CTG GTG GAG TCT GGG GGA GGC GTG GTC CAG CCT GGG AGG TCC
SEQ ID NO:72
                                                    CDR1 SEQ ID:57 (aa) 58 (nt)
                                                         ~~~~~~~~~~~~~~~~
          L   R   L   S   C   A   A   S   G   F   T   F   R   S   Y   G   M
   52     CTG AGA CTC TCC TGT GCA GCG TCT GGA TTC ACC TTC AGG AGT TAT GGC ATG

CDR1                                                        CDR2
          ~~~~~                                                       ~~~~~~~~~~
          H   W   V   R   Q   A   P   G   K   G   L   E   W   V   T   L   I
  103     CAC TGG GTC CGC CAG GCT CCA GGC AAG GGG CTG GAG TGG GTG ACA CTT ATA

CDR2 SEQ ID:59 (aa) 60 (nt)
          ~~~~~~~~~~~~~~~~~~~~~~~~~~~~~~~~~~~~~~~~~~~~~~~~~~~~~
          W   Y   D   G   S   N   K   Y   Y   A   D   S   V   K   G   R   F
  154     TGG TAT GAT GGA AGT AAT AAA TAC TAT GCA GAC TCC GTG AAG GGC CGA TTC

T   I   S   R   D   N   S   K   N   T   L   Y   L   Q   M   N   S
  205     ACC ATC TCC AGA GAC AAT TCC AAG AAC ACG CTG TAT CTG CAA ATG AAC AGC

CDR3
                                                              ~~~~~~~~~~~~~~~~~~
          L   R   A   E   D   T   A   V   Y   Y   C   A   R   E   G   F   N
  256     CTG AGA GCC GAG GAC ACG GCT GTG TAT TAC TGT GCG AGA GAA GGG TTT AAC

CDR3 SEQ ID:61 (aa) 62 (nt)
          ~~~~~~~~~~~~~~~~~~~~~~~~~~
          W   D   A   F   D   I   W   G   Q   G   T   M   V   T   V   S   S
  307     TGG GAT GCT TTT GAT ATC TGG GGC CAA GGG ACA ATG GTC ACC GTC TCT TCA
```

FIG. 13

Anti-human SOD1 597-120 VH

V segment: VH3-07
D segment: D6-19
J segment: JH4b

SEQ ID NO:73

```
         E   V   H   L   V   E   S   G   G   G   L   V   Q   S   G   G   S
  1     GAG GTG CAC CTG GTG GAG TCT GGG GGA GGC TTG GTC CAG TCT GGG GGG TCC
SEQ ID NO:74
                                              CDR1 SEQ ID:75 (aa) 76 (nt)
                                                   ~~~~~~~~~~~~
         L   R   L   S   C   A   A   S   G   F   S   I   S   G   Y   W   M
 52     CTG AGA CTC TCC TGT GCA GCC TCT GGA TTC AGC ATT AGT GGC TAT TGG ATG

CDR1                                                         CDR2
        ~~~~~                                                    ~~~~~~~~~~
         S   W   V   R   Q   A   P   G   K   G   L   E   W   V   A   N   I
103     AGC TGG GTC CGC CAG GCT CCA GGG AAA GGG CTG GAG TGG GTG GCC AAC ATA

CDR2 SEQ ID:77 (aa) 78 (nt)
        ~~~~~~~~~~~~~~~~~~~~~~~~~~~~~~~~~~~~~~~~~~~~~~
         K   Q   D   G   G   E   K   Y   Y   G   D   S   V   K   G   R   F
154     AAG CAA GAT GGA GGT GAG AAG TAC TAT GGG GAC TCT GTG AAG GGC CGA TTC

T   I   S   R   D   N   A   E   N   S   L   Y   L   Q   M   S   S
205     ACC ATC TCC AGA GAC AAC GCC GAA AAC TCA CTG TAT CTG CAA ATG AGC AGC

CDR3 SEQ ID:79 (aa) 80 (nt)
                                              ~~~~~~~~~~~~~~~~~
         L   R   A   E   D   T   A   V   Y   Y   C   V   M   A   G   G   L
256     CTG AGA GCC GAG GAC ACG GCT GTG TAT TAC TGT GTA ATG GCG GGT GGC CTT

CDR3
        ~~~~~~~
         D   Y   W   G   Q   G   A   L   V   T   V   S   S
307     GAC TAC TGG GGC CAG GGA GCC CTG GTC ACC GTC TCC TCA
```

FIG. 14

Anti-human SOD1 597-120 VK

V segment:    L6
    J segment:    JK2

SEQ ID NO:81

```
          E   I   V   L   T   Q   S   P   A   T   L   S   L   S   P   G   E
1        GAA ATT GTG TTG ACA CAG TCT CCA GCC ACC CTG TCT TTG TCT CCA GGG GAA
SEQ ID NO:82
                                              CDR1 SEQ ID:83 (aa) 84 (nt)
                                              ~~~~~~~~~~~~~~~~~~~~~~~~~~~~~~
          R   A   T   L   S   C   R   A   S   Q   S   V   S   S   Y   L   A
52       AGA GCC ACC CTC TCC TGC AGG GCC AGT CAG AGT GTT AGC AGC TAC TTA GCC

CDR2
                                                                      ~~~~~~~~~
          W   Y   Q   Q   K   P   G   Q   A   P   R   L   L   I   Y   D   A
103      TGG TAC CAA CAG AAA CCT GGC CAG GCT CCC AGG CTC CTC ATC TAT GAT GCA

CDR2 SEQ ID:85 (aa) 86 (nt)
         ~~~~~~~~~~~~~~~~~~~~
          S   N   R   A   T   G   I   P   A   R   F   S   G   S   G   S   G
154      TCC AAC AGG GCC ACT GGC ATC CCA GCC AGG TTC AGT GGC AGT GGG TCT GGG

T   D   F   T   L   T   I   S   S   L   E   P   E   D   F   A   V
205      ACA GAC TTC ACT CTC ACC ATC AGC AGC CTA GAG CCT GAA GAT TTT GCA GTT

CDR3 SEQ ID:87 (aa) 88 (nt)
                    ~~~~~~~~~~~~~~~~~~~~~~~~~~~~~~
          Y   Y   C   Q   Q   R   S   N   W   Y   T   F   G   Q   G   T   K
256      TAT TAC TGT CAG CAG CGT AGC AAC TGG TAC ACT TTT GGC CAG GGG ACC AAG

L   E   I   K
307      CTG GAG ATC AAA
```

FIG. 15

Anti-human SOD1 597-120-M1 VH

V segment: VH3-07
D segment: D6-19
J segment: JH4b

SEQ ID NO:89

```
        E   V   Q   L   V   E   S   G   G   G   L   V   Q   P   G   G   S
  1    GAG GTG CAG CTG GTG GAG TCT GGG GGA GGC TTG GTC CAG CCT GGG GGG TCC
```
SEQ ID NO:90

CDR1 SEQ ID:75 (aa) 76 (nt)

```
        L   R   L   S   C   A   A   S   G   F   S   I   S   G   Y   W   M
 52    CTG AGA CTC TCC TGT GCA GCC TCT GGA TTC AGC ATT AGT GGC TAT TGG ATG
```

CDR1                                                                    CDR2

```
        S   W   V   R   Q   A   P   G   K   G   L   E   W   V   A   N   I
103    AGC TGG GTC CGC CAG GCT CCA GGG AAA GGG CTG GAG TGG GTG GCC AAC ATA
```

CDR2 SEQ ID:77 (aa) 78 (nt)

```
        K   Q   D   G   G   E   K   Y   Y   G   D   S   V   K   G   R   F
154    AAG CAA GAT GGA GGT GAG AAG TAC TAT GGG GAC TCT GTG AAG GGC CGA TTC
```

```
        T   I   S   R   D   N   A   K   N   S   L   Y   L   Q   M   N   S
205    ACC ATC TCC AGA GAC AAC GCC AAG AAC TCA CTG TAT CTG CAA ATG AAC AGC
```

CDR3 SEQ ID:79 (aa) 80 (nt)

```
        L   R   A   E   D   T   A   V   Y   Y   C   V   M   A   G   G   L
256    CTG AGA GCC GAG GAC ACG GCT GTG TAT TAC TGT GTA ATG GCG GGT GGC CTT
```

CDR3

```
        D   Y   W   G   Q   G   T   L   V   T   V   S   S
307    GAC TAC TGG GGC CAG GGA ACC CTG GTC ACC GTC TCC TCA
```

FIG. 16

Anti-human SOD1 311-3 VH

V segment:    VH4-34
    D segment:   unidentified
    J segment:    JH4b

SEQ ID NO:91

```
          Q   V   Q   L   Q   Q   W   G   A   G   L   L   K   P   S   E   T
    1    CAG GTG CAG CTA CAG CAG TGG GGC GCA GGA CTG TTG AAG CCT TCG GAG ACC
SEQ ID NO:92
                                                      CDR1 SEQ ID:93 (aa) 94 (nt)
                                                       ~~~~~~~~~~~~~~~~
          L   S   L   T   C   A   V   Y   G   G   S   F   S   G   Y   Y   W
   52    CTG TCC CTC ACC TGC GCT GTC TAT GGT GGG TCC TTC AGT GGT TAC TAC TGG

CDR1                                                     CDR2
         ~~~~~                                                    ~~~~~~~~
          N   W   I   R   Q   P   P   G   M   G   L   E   W   I   G   E   I
  103    AAC TGG ATC CGC CAG CCC CCA GGA ATG GGG CTG GAA TGG ATT GGA GAA ATC

CDR2 SEQ ID:95 (aa) 96 (nt)
         ~~~~~~~~~~~~~~~~~~~~~~~~~~~~~~~~~~~~~~~~~~~~~~
          H   Q   S   G   G   P   H   Y   N   P   S   L   K   S   R   V   S
  154    CAT CAA AGT GGA GGC CCC CAC TAC AAC CCG TCC CTC AAG AGT CGA GTC AGC

I   S   V   D   T   S   K   N   Q   V   N   L   K   L   S   S   V
  205    ATT TCA GTA GAC ACG TCC AAA AAC CAG GTC AAC CTG AAG CTG AGC TCT GTG

CDR3 SEQ ID:97 (aa) 98 (nt)
                                                     ~~~~~~~~~~~~~~~~
          T   A   A   D   T   A   I   Y   Y   C   T   E   L   D   D   Y   W
  256    ACC GCC GCG GAT ACG GCT ATT TAT TAC TGT ACG GAG TTG GAT GAC TAT TGG

G   Q   G   T   L   V   T   V   S   S
  307    GGC CAG GGA ACC CTG GTC ACC GTC TCC TCA
```

FIG. 17

Anti-human SOD1 311-3 VK

V segment:     L6
J segment:     JK1

SEQ ID NO:99

```
          E    I    V    L    T    Q    S    P    A    T    L    S    L    S    P    G    E
1         GAA  ATT  GTG  TTG  ACA  CAG  TCT  CCA  GCC  ACC  CTG  TCT  TTG  TCT  CCA  GGG  GAA
```
SEQ ID NO:100

```
                                                     CDR1 SEQ ID:101 (aa) 102 (nt)
                                                     ~~~~~~~~~~~~~~~~~~~~~~~~~~~~~~~~~~~~~~
          R    A    T    L    S    C    R    A    S    Q    S    V    S    S    Y    L    A
52        AGA  GCC  ACC  CTC  TCC  TGC  AGG  GCC  AGT  CAG  AGT  GTT  AGC  AGC  TAC  TTA  GCC

CDR2
                                                                                     ~~~~~~~
          W    Y    Q    Q    K    P    G    Q    A    P    R    L    L    I    Y    N    A
103       TGG  TAC  CAA  CAG  AAA  CCT  GGC  CAG  GCT  CCC  AGG  CTC  CTC  ATC  TAT  AAT  GCA

CDR2 SEQ ID:103 (aa) 104 (nt)
      ~~~~~~~~~~~~~~~~~~~~~~~
          S    N    R    A    T    G    I    P    A    R    F    S    G    S    G    S    G
154       TCC  AAC  AGG  GCC  ACT  GGC  ATC  CCA  GCC  AGG  TTC  AGT  GGC  AGT  GGG  TCT  GGG

T    D    F    T    L    T    I    G    S    L    E    P    E    D    F    A    V
205       ACA  GAC  TTC  ACT  CTC  ACC  ATC  GGC  AGC  CTA  GAG  CCT  GAA  GAT  TTT  GCA  GTT

CDR3 SEQ ID:105 (aa) 106 (nt)
                                 ~~~~~~~~~~~~~~~~~~~~~~~~~~~~~~~~~~
          Y    Y    C    Q    Q    R    S    N    W    P    R    T    F    G    Q    G    T
256       TAT  TAC  TGT  CAG  CAG  CGT  AGC  AAC  TGG  CCT  CGG  ACG  TTC  GGC  CAA  GGG  ACC

K    V    E    I    K
307       AAG  GTG  GAG  ATC  AAA
```

FIG. 18

Anti-human SOD1 311-3-M1 VH

V segment:    VH4-34
    D segment:    unidentified
    J segment:    JH4b

SEQ ID NO:107

```
         Q   V   Q   L   Q   Q   W   G   A   G   L   L   K   P   S   E   T
  1     CAG GTG CAG CTA CAG CAG TGG GGC GCA GGA CTG TTG AAG CCT TCG GAG ACC
SEQ ID NO:108
                                                    CDR1 SEQ ID:93 (aa) 94 (nt)
                                                    ~~~~~~~~~~~~~~~~
         L   S   L   T   C   A   V   Y   G   G   S   F   S   G   Y   Y   W
 52     CTG TCC CTC ACC TGC GCT GTC TAT GGT GGG TCC TTC AGT GGT TAC TAC TGG
        CDR1                                                            CDR2
        ~~~~~                                                         ~~~~~~~~
         N   W   I   R   Q   P   P   G   K   G   L   E   W   I   G   E   I
103     AAC TGG ATT CGC CAG CCC CCA GGA AAG GGG CTG GAA TGG ATT GGA GAA ATC
                    CDR2 SEQ ID:95 (aa) 96 (nt)
        ~~~~~~~~~~~~~~~~~~~~~~~~~~~~~~~~~~~~~~~~~~~~~~~~~~~~~~~~
         H   Q   S   G   G   P   H   Y   N   P   S   L   K   S   R   V   T
154     CAT CAA AGT GGA GGC CCC CAC TAC AAC CCG TCC CTC AAG AGT CGA GTC ACC

I   S   V   D   T   S   K   N   Q   F   S   L   K   L   S   S   V
205     ATT TCA GTA GAC ACG TCC AAA AAC CAG TTC TCC CTG AAG CTG AGC TCT GTG
                                               CDR3 SEQ ID:97 (aa) 98 (nt)
                                               ~~~~~~~~~~~~~~~
         T   A   A   D   T   A   V   Y   Y   C   T   E   L   D   D   Y   W
256     ACC GCC GCG GAT ACG GCT GTG TAT TAC TGT ACG GAG TTG GAT GAC TAT TGG

G   Q   G   T   L   V   T   V   S   S
307     GGC CAG GGA ACC CTG GTC ACC GTC TCC TCA
```

FIG. 19

Anti-human SOD1 311-3-M1 VK

V segment: L6
J segment: JK1

SEQ ID NO:109

```
        E   I   V   L   T   Q   S   P   A   T   L   S   L   S   P   G   E
  1    GAA ATT GTG TTG ACA CAG TCT CCA GCC ACC CTG TCT TTG TCT CCA GGG GAA
```
SEQ ID NO:110

CDR1 SEQ ID:101 (aa) 102 (nt)

```
        R   A   T   L   S   C   R   A   S   Q   S   V   S   S   Y   L   A
 52    AGA GCC ACC CTC TCC TGC AGG GCC AGT CAG AGT GTT AGC AGC TAC TTA GCC
```

CDR2

```
        W   Y   Q   Q   K   P   G   Q   A   P   R   L   L   I   Y   D   A
103    TGG TAC CAA CAG AAA CCT GGC CAG GCT CCC AGG CTC CTC ATC TAT GAT GCA
```

CDR2 SEQ ID:111 (aa) 112 (nt)

```
        S   N   R   A   T   G   I   P   A   R   F   S   G   S   G   S   G
154    TCC AAC AGG GCC ACT GGC ATC CCA GCC AGG TTC AGT GGC AGT GGG TCT GGG
```

```
        T   D   F   T   L   T   I   S   S   L   E   P   E   D   F   A   V
205    ACA GAC TTC ACT CTC ACC ATC AGC AGC CTA GAG CCT GAA GAT TTT GCA GTT
```

CDR3 SEQ ID:105 (aa) 106 (nt)

```
        Y   Y   C   Q   Q   R   S   N   W   P   R   T   F   G   Q   G   T
256    TAT TAC TGT CAG CAG CGT AGC AAC TGG CCT CGG ACG TTC GGC CAA GGG ACC
```

```
        K   V   E   I   K
307    AAG GTG GAG ATC AAA
```

FIG. 20

Anti-human SOD1 312-19 VH

| V segment: | VH1-69 |
|---|---|
| D segment: | D3-10 |
| J segment: | JH4b |

SEQ ID NO:113

```
          Q    V    Q    L    V    Q    S    G    A    E    V    K    K    P    G    S    S
    1     CAG  GTC  CAG  CTG  GTG  CAG  TCT  GGG  GCT  GAG  GTG  AAG  AAG  CCT  GGG  TCC  TCG
SEQ ID NO:114
                                                                  CDR1 SEQ ID:115 (aa) 116 (nt)
                                                                       ~~~~~~~~~~~~~~~~~~~~~~
          V    K    V    S    C    K    A    S    G    G    T    F    N    N    F    V    I
    52    GTG  AAG  GTC  TCC  TGC  AAG  GCT  TCT  GGA  GGC  ACC  TTC  AAC  AAC  TTC  GTT  ATC

CDR1                                                                       CDR2
          ~~~~                                                                       ~~~~~~~~
          G    W    V    R    Q    A    P    G    Q    G    L    E    W    M    G    R    I
    103   GGC  TGG  GTG  CGA  CAG  GCC  CCT  GGA  CAA  GGA  CTT  GAG  TGG  ATG  GGA  AGG  ATC

CDR2 SEQ ID:117 (aa) 118 (nt)
              ~~~~~~~~~~~~~~~~~~~~~~~~~~~~~~~~~~~~~~~~~~~~~~~~~~~~~~~~~~~~~~~~
          I    P    I    L    D    I    A    N    Y    A    Q    K    F    Q    G    R    V
    154   ATC  CCT  ATC  CTT  GAT  ATA  GCA  AAC  TAC  GCA  CAG  AAG  TTC  CAG  GGC  AGA  GTC

T    I    T    A    D    K    S    T    S    T    V    Y    M    E    L    N    S
    205   ACG  ATT  ACC  GCG  GAC  AAA  TCC  ACG  AGC  ACA  GTT  TAC  ATG  GAG  CTG  AAC  AGC

CDR3
                                                                                      ~~~~~~~~~~~~~~~~~
          L    R    S    E    D    T    A    V    Y    Y    C    A    R    T    G    N    Y
    256   CTG  AGA  TCT  GAG  GAC  ACG  GCC  GTA  TAC  TAC  TGT  GCG  AGA  ACG  GGG  AAT  TAT

CDR3 SEQ ID:119 (aa) 120 (nt)
          ~~~~~~~~~~~~~~~~~~~~~~~~~~~~~
          Y    K    P    Y    D    Y    W    G    Q    G    T    L    V    T    V    S    S
    307   TAT  AAG  CCC  TAT  GAC  TAC  TGG  GGC  CAG  GGA  ACC  CTG  GTC  ACC  GTC  TCC  TCA
```

FIG. 21

Anti-human SOD1 312-19 VK

V segment: A26
J segment: JK5

SEQ ID NO:121

```
      E   I   V   L   T   Q   S   P   D   F   Q   S   V   T   P   K   E
  1   GAA ATT GTG CTG ACT CAG TCT CCA GAC TTT CAG TCT GTG ACT CCA AAG GAG
```
SEQ ID NO:122

```
                                          CDR1 SEQ ID:123 (aa) 124 (nt)
                                          ~~~~~~~~~~~~~~~~~~~~~~~~~~~~~~~~
      K   V   T   I   T   C   R   A   S   Q   S   I   G   S   S   L   H
 52   AAA GTC ACC ATC ACC TGC CGG GCC AGT CAG AGC ATT GGT AGT AGC TTA CAC
```

```
                                                                  CDR2
                                                                  ~~~~~~~~
      W   Y   Q   Q   K   P   D   Q   S   P   K   L   L   I   K   Y   A
103   TGG TAC CAG CAG AAA CCA GAT CAG TCT CCA AAG CTC CTC ATC AAG TAT GCT
```

```
      CDR2 SEQ ID:125 (aa) 126 (nt)
      ~~~~~~~~~~~~~~~~~~~~
      S   Q   S   F   S   G   V   P   S   R   F   S   G   S   G   S   G
154   TCC CAG TCC TTC TCA GGG GTC CCC TCG AGG TTC AGT GGC AGT GGA TCT GGG
```

```
      T   D   F   T   L   T   I   N   S   L   E   A   E   D   A   A   A
205   ACA GAT TTC ACC CTC ACC ATC AAT AGC CTG GAA GCT GAA GAT GCT GCA GCG
```

```
             CDR3 SEQ ID:127 (aa) 128 (nt)
             ~~~~~~~~~~~~~~~~~~~~~~~~~~~~~~~~~~~~
      Y   Y   C   H   Q   S   S   S   L   P   I   T   F   G   Q   G   T
256   TAT TAC TGT CAT CAG AGT AGT AGT TTA CCG ATC ACC TTC GGC CAA GGG ACA
```

```
      R   L   E   I   K
307   CGA CTG GAG ATC AAA
```

FIG. 22

Anti-human SOD1 312-19-M1 VH

V segment: VH1-69
D segment: D3-10
J segment: JH4b

SEQ ID NO:129

```
        Q   V   Q   L   V   Q   S   G   A   E   V   K   K   P   G   S   S
  1     CAG GTC CAG CTG GTG CAG TCT GGG GCT GAG GTG AAG AAG CCT GGG TCC TCG
```
SEQ ID NO:130

CDR1 SEQ ID:115 (aa) 116 (nt)

```
        V   K   V   S   C   K   A   S   G   G   T   F   N   N   F   V   I
 52     GTG AAG GTC TCC TGC AAG GCT TCT GGA GGC ACC TTC AAC AAC TTC GTT ATC
```

CDR1                                                                CDR2

```
        G   W   V   R   Q   A   P   G   Q   G   L   E   W   M   G   R   I
103     GGC TGG GTG CGA CAG GCC CCT GGA CAA GGA CTT GAG TGG ATG GGA AGG ATC
```

CDR2 SEQ ID:117 (aa) 118 (nt)

```
        I   P   I   L   D   I   A   N   Y   A   Q   K   F   Q   G   R   V
154     ATC CCT ATC CTT GAT ATA GCA AAC TAC GCA CAG AAG TTC CAG GGC AGA GTC
```

```
        T   I   T   A   D   K   S   T   S   T   A   Y   M   E   L   S   S
205     ACG ATT ACC GCG GAC AAA TCC ACG AGC ACA GCC TAC ATG GAG CTG AGC AGC
```

CDR3

```
        L   R   S   E   D   T   A   V   Y   Y   C   A   R   T   G   N   Y
256     CTG AGA TCT GAG GAC ACG GCC GTA TAC TAC TGT GCG AGA ACG GGG AAT TAT
```

CDR3 SEQ ID:119 (aa) 120 (nt)

```
        Y   K   P   Y   D   Y   W   G   Q   G   T   L   V   T   V   S   S
307     TAT AAG CCC TAT GAC TAC TGG GGC CAG GGA ACC CTG GTC ACC GTC TCC TCA
```

FIG. 23

Anti-human SOD1 591-33 VH

V segment:    VH3-07
    D segment:    D2-08
    J segment:    JH4b

SEQ ID NO:131

```
          E   V   Q   L   V   E   S   G   G   G   L   V   Q   P   G   G   S
  1       GAG GTG CAG TTG GTG GAG TCT GGG GGA GGC TTG GTC CAG CCT GGG GGG TCC
SEQ ID NO:132
                                                     CDR1 SEQ ID:133 (aa) 134 (nt)
                                                     ~~~~~~~~~~~~~~~
          L   R   L   S   C   A   A   S   G   F   T   F   S   R   Y   W   M
  52      CTG AGA CTC TCC TGT GCA GCC TCT GGA TTC ACC TTT AGT CGC TAT TGG ATG

CDR1                                                          CDR2
          ~~~~~                                                         ~~~~~~~~
          S   W   V   R   Q   A   P   G   K   G   L   E   W   M   A   N   I
 103      AGC TGG GTC CGC CAG GCT CCA GGG AAA GGG CTG GAG TGG ATG GCC AAC ATA

CDR2 SEQ ID:135 (aa) 136 (nt)
          ~~~~~~~~~~~~~~~~~~~~~~~~~~~~~~~~~~~~~~~~~~~~~~~~~~~~~~~~~~~
          K   Q   D   G   S   E   T   H   Y   V   D   S   V   K   G   R   F
 154      AAG CAA GAT GGA AGT GAG ACA CAC TAT GTG GAC TCT GTG AAG GGC CGA TTC

T   I   S   R   D   N   A   K   N   S   L   Y   L   Q   M   N   S
 205      ACC ATC TCC AGA GAC AAC GCC AAG AAC TCA CTG TAT CTG CAA ATG AAC AGC

CDR3 SEQ ID:137 (aa) 138 (nt)
                                                     ~~~~~~~~~~~~~
          L   R   A   E   D   T   A   V   Y   Y   C   A   I   G   D   Y   W
 256      CTG AGA GCC GAG GAC ACG GCT GTG TAT TAC TGT GCG ATT GGT GAC TAC TGG

G   Q   G   T   L   V   T   V   S   S
 307      GGC CAG GGA ACC CTG GTC ACC GTC TCC TCA
```

FIG. 24

Anti-human SOD1 591-33 VK

V segment: L15
J segment: JK4

SEQ ID NO:139

```
           D   I   Q   M   T   Q   S   P   S   S   L   S   A   S   V   G   D
  1        GAC ATC CAG ATG ACC CAG TCT CCA TCC TCA CTG TCT GCA TCT GTA GGA GAC
SEQ ID NO:140
                                           CDR1 SEQ ID:141 (aa) 142 (nt)
                                           ~~~~~~~~~~~~~~~~~~~~~~~~~~~~~~~~~~~
           R   V   T   I   T   C   R   A   S   Q   D   I   S   S   W   L   A
 52        AGA GTC ACC ATC ACT TGT CGG GCG AGT CAG GAT ATT AGC AGC TGG TTA GCC

CDR2
                                                                       ~~~~~~~~
           W   Y   Q   Q   K   P   E   K   A   P   K   S   L   I   Y   A   A
103        TGG TAT CAG CAG AAA CCA GAG AAA GCC CCT AAG TCC CTG ATC TAT GCT GCA

CDR2 SEQ ID:143 (aa) 144 (nt)
    ~~~~~~~~~~~~~~~~~~~~
           S   S   L   Q   S   G   V   P   S   R   F   S   G   S   G   S   G
154        TCC AGT TTG CAA AGT GGG GTC CCA TCA AGG TTC AGC GGC AGT GGA TCT GGG

T   D   F   T   L   T   I   S   S   L   Q   P   E   D   F   A   T
205        ACA GAT TTC ACT CTC ACC ATC AGC AGC CTG CAG CCT GAA GAT TTT GCA ACT

CDR3 SEQ ID:145 (aa) 146 (nt)
                          ~~~~~~~~~~~~~~~~~~~~~~~~~~~~~
           Y   Y   C   Q   Q   Y   K   S   Y   P   L   T   F   G   G   G   T
256        TAT TAC TGC CAA CAG TAT AAA AGT TAC CCG CTC ACT TTC GGC GGA GGG ACC

K   V   E   I   K
307        AAG GTG GAG ATC AAA
```

FIG. 25

Anti-human SOD1 <u>591-33-M1</u> VH

V segment:    VH3-07
    D segment:    D2-08
    J segment:    JH4b

SEQ ID NO:147

```
          E   V   Q   L   V   E   S   G   G   G   L   V   Q   P   G   G   S
  1      GAG GTG CAG TTG GTG GAG TCT GGG GGA GGC TTG GTC CAG CCT GGG GGG TCC
SEQ ID NO:148
                                                CDR1 SEQ ID:133 (aa) 134 (nt)
                                                ~~~~~~~~~~~~~~~~
          L   R   L   S   C   A   A   S   G   F   T   F   S   R   Y   W   M
 52      CTG AGA CTC TCC TGT GCA GCC TCT GGA TTC ACC TTT AGT CGC TAT TGG ATG

CDR1                                                          CDR2
         ~~~~~                                                         ~~~~~~~~
          S   W   V   R   Q   A   P   G   K   G   L   E   W   V   A   N   I
103      AGC TGG GTC CGC CAG GCT CCA GGG AAA GGG CTG GAG TGG GTG GCC AAC ATA

CDR2 SEQ ID:135 (aa) 136 (nt)
         ~~~~~~~~~~~~~~~~~~~~~~~~~~~~~~~~~~~~~~~~~~~~~~~~~~~~~~~~~~
          K   Q   D   G   S   E   T   H   Y   V   D   S   V   K   G   R   F
154      AAG CAA GAT GGA AGT GAG ACA CAC TAT GTG GAC TCT GTG AAG GGC CGA TTC

T   I   S   R   D   N   A   K   N   S   L   Y   L   Q   M   N   S
205      ACC ATC TCC AGA GAC AAC GCC AAG AAC TCA CTG TAT CTG CAA ATG AAC AGC

CDR3 SEQ ID:137 (aa) 138 (nt)
                                                ~~~~~~~~~~~~~
          L   R   A   E   D   T   A   V   Y   Y   C   A   I   G   D   Y   W
256      CTG AGA GCC GAG GAC ACG GCT GTG TAT TAC TGT GCG ATT GGT GAC TAC TGG

G   Q   G   T   L   V   T   V   S   S
307      GGC CAG GGA ACC CTG GTC ACC GTC TCC TCA
```

FIG. 26

Anti-human SOD1 114-41 VH

V segment: VH1-18
D segment: D5-24
J segment: JH4b

SEQ ID NO:149

```
        Q   V   Q   L   V   Q   S   G   A   E   V   K   T   P   G   A   S
  1    CAG GTT CAG CTG GTG CAG TCT GGA GCT GAA GTG AAG ACG CCT GGG GCC TCA
SEQ ID NO:150
                                               CDR1 SEQ ID:151 (aa) 152 (nt)
                                                       ~~~~~~~~~~~~~~~~~~~~
        V   K   V   S   C   K   A   S   G   Y   T   F   T   S   F   G   I
 52    GTG AAG GTC TCC TGC AAG GCT TCT GGT TAC ACC TTT ACC AGC TTT GGT ATC
       CDR1                                                              CDR2
       ~~~~                                                              ~~~~~~~~~
        S   W   V   R   Q   A   P   G   Q   G   L   E   W   M   G   W   I
103    AGC TGG GTG CGA CAG GCC CCT GGA CAA GGG CTT GAG TGG ATG GGA TGG ATC
                    CDR2 SEQ ID:153 (aa) 154 (nt)
       ~~~~~~~~~~~~~~~~~~~~~~~~~~~~~~~~~~~~~~~~~~~~~~~~~~~~~~~
        S   V   Y   N   D   Y   T   N   Y   A   Q   K   F   Q   G   R   V
154    AGC GTT TAC AAT GAT TAC ACA AAC TAT GCA CAG AAG TTC CAG GGC AGA GTC

T   M   T   T   D   T   S   T   S   T   A   Y   M   E   L   R   S
205    ACC ATG ACC ACA GAC ACA TCC ACG AGC ACA GCC TAC ATG GAA CTG AGG AGC
                                                                      CDR3
                                                                      ~~~~~~~~~~~~~~~~~
        L   R   S   D   D   T   A   M   Y   Y   C   A   R   K   R   G   G
256    CTG AGA TCT GAC GAC ACG GCC ATG TAT TAC TGT GCG AGA AAG AGG GGT GGG
       CDR3 SEQ ID:155 (aa) 156 (nt)
       ~~~~~~~~~~~~~~~~
        D   M   D   Y   W   G   Q   G   T   L   V   T   V   S   S
307    GAT ATG GAC TAT TGG GGC CAG GGA ACC CTG GTC ACC GTC TCC TCA
```

FIG. 27

Anti-human SOD1 114-41 VK

V segment: L5
J segment: JK1

SEQ ID NO:157

```
          D   I   Q   M   T   Q   S   P   S   S   V   S   A   S   V   G   D
  1       GAC ATC CAG ATG ACC CAG TCT CCA TCT TCC GTG TCT GCA TCT GTA GGA GAC
SEQ ID NO:158
                                              CDR1 SEQ ID:159 (aa) 160 (nt)
                                              ~~~~~~~~~~~~~~~~~~~~~~~~~~~~~~
          R   V   T   I   T   C   R   A   S   Q   D   I   S   S   W   L   A
 52       AGA GTC ACC ATC ACT TGT CGG GCG AGT CAG GAT ATT AGC AGC TGG TTA GCC
                                                                          CDR2
                                                                          ~~~~
          W   Y   Q   H   K   P   G   K   A   P   K   L   L   I   Y   L   A
103       TGG TAT CAG CAT AAA CCA GGG AAA GCC CCT AAG CTC CTG ATC TAT CTT GCA

CDR2 SEQ ID:161 (aa) 162 (nt)
     ~~~~~~~~~~~~~~~~~~~~~
          S   S   L   Q   S   G   V   P   S   R   F   S   G   S   G   S   G
154       TCC AGT TTG CAA AGT GGG GTC CCA TCA AGG TTC AGC GGC AGT GGA TCT GGG

T   D   F   T   L   T   I   S   S   L   Q   P   E   D   F   A   T
205       ACA GAT TTC ACT CTC ACC ATC AGC AGC CTG CAG CCT GAA GAT TTT GCA ACT
                              CDR3 SEQ ID:163 (aa) 164 (nt)
                              ~~~~~~~~~~~~~~~~~~~~~~~~~~~~
          Y   Y   C   Q   Q   A   N   S   F   P   W   T   F   G   Q   G   T
256       TAC TAT TGT CAA CAG GCT AAT AGT TTT CCG TGG ACG TTC GGC CAA GGG ACC

K   V   E   I   K
307       AAG GTG GAG ATC AAA
```

FIG. 28

Anti-human SOD1 114-41-M1 VH

V segment: VH1-18
D segment: D5-24
J segment: JH4b

SEQ ID NO:165

```
         Q   V   Q   L   V   Q   S   G   A   E   V   K   K   P   G   A   S
    1    CAG GTT CAG CTG GTG CAG TCT GGA GCT GAA GTG AAG AAG CCT GGG GCC TCA
SEQ ID NO:166
                                                   CDR1 SEQ ID:151 (aa) 152 (nt)
         V   K   V   S   C   K   A   S   G   Y   T   F   T   S   F   G   I
   52    GTG AAG GTC TCC TGC AAG GCT TCT GGT TAC ACC TTT ACC AGC TTT GGT ATC
         CDR1                                                          CDR2
         S   W   V   R   Q   A   P   G   Q   G   L   E   W   M   G   W   I
  103    AGC TGG GTG CGA CAG GCC CCT GGA CAA GGG CTT GAG TGG ATG GGA TGG ATC
                      CDR2 SEQ ID:153 (aa) 154 (nt)
         S   V   Y   N   D   Y   T   N   Y   A   Q   K   F   Q   G   R   V
  154    AGC GTT TAC AAT GAT TAC ACA AAC TAT GCA CAG AAG TTC CAG GGC AGA GTC

T   M   T   T   D   T   S   I   S   T   A   Y   M   E   L   R   S
  205    ACC ATG ACC ACA GAC ACA TCC ACG AGC ACA GCC TAC ATG GAA CTG AGG AGC
                                                                      CDR3
         L   R   S   D   D   T   A   V   Y   Y   C   A   R   K   G   G
  256    CTG AGA TCT GAC GAC ACG GCC GTG TAT TAC TGT GCG AGA AAG AGG GGT GGG
         CDR3 SEQ ID:155 (aa) 156 (nt)
         D   M   D   Y   W   G   Q   G   T   L   V   T   V   S   S
  307    GAT ATG GAC TAT TGG GGC CAG GGA ACC CTG GTC ACC GTC TCC TCA
```

FIG. 29

Anti-human SOD1 306-155 VH

V segment:    VH5-51
    D segment:    D6-13
    J segment:    JH4b

SEQ ID NO:167

```
            E   V   Q   L   V   Q   S   G   A   E   V   K   K   P   G   E   S
  1        GAG GTG CAG CTG GTG CAG TCT GGA GCA GAG GTG AAA AAG CCC GGG GAG TCT
SEQ ID NO:168
                                                       CDR1 SEQ ID:169 (aa) 170 (nt)
                                                       ~~~~~~~~~~~~~~~~
            L   K   I   S   C   K   G   S   G   Y   S   F   T   S   Y   W   I
 52        CTG AAG ATC TCC TGT AAG GGT TCT GGA TAC AGT TTT ACC AGC TAC TGG ATC
           CDR1                                                          CDR2
           ~~~                                                           ~~~~~~~~
            G   W   V   R   Q   M   P   G   K   G   L   E   W   M   G   I   I
103        GGC TGG GTG CGC CAG ATG CCC GGG AAA GGC CTG GAG TGG ATG GGG ATC ATC
                      CDR2 SEQ ID:171 (aa) 172 (nt)
           ~~~~~~~~~~~~~~~~~~~~~~~~~~~~~~~~~~~~~~~~~~~~~~~~~~
            Y   P   G   D   S   D   T   R   Y   S   P   S   F   Q   G   Q   V
154        TAT CCT GGT GAC TCT GAT ACC AGA TAC AGC CCG TCC TTC CAA GGC CAG GTC

T   I   S   A   D   K   S   I   S   T   A   Y   L   Q   W   S   S
205        ACC ATC TCA GCC GAC AAG TCC ATC AGC ACC GCC TAC CTG CAG TGG AGC AGC
                                                                         CDR3
                                                                         ~~~~~~~~~~~~~~~~
            L   K   A   S   D   T   A   M   Y   Y   C   A   R   Q   G   S   G
256        CTG AAG GCC TCG GAC ACC GCC ATG TAT TAC TGT GCG AGA CAG GGC AGC GGC
           CDR3 SEQ ID:173 (aa) 174 (nt)
           ~~~~~~~~~~~~~~~~~~~~~~~~~~~~~~
            W   Y   G   N   Y   F   D   Y   W   G   Q   G   T   L   V   T   V
307        TGG TAC GGG AAC TAC TTT GAC TAC TGG GGC CAG GGA ACC CTG GTC ACC GTC

S   S
358        TCC TCA
```

FIG. 30

Anti-human SOD1 306-155 VK

V segment: A27
J segment: JK2

SEQ ID NO:175

```
         E   I   V   L   T   Q   S   P   G   T   L   S   L   S   P   G   E
  1     GAA ATT GTG TTG ACG CAG TCT CCA GGC ACC CTG TCT TTG TCT CCA GGG GAA
```
SEQ ID NO:176

CDR1 SEQ ID:177 (aa) 178 (nt)
```
         R   A   T   L   S   C   R   A   S   Q   S   F   S   R   G   Y   L
 52     AGA GCC ACC CTC TCC TGC AGG GCC AGT CAG AGT TTT AGC AGA GGC TAC TTA
```

CDR1                                                                 CDR2
```
         A   W   Y   Q   Q   K   P   G   Q   A   P   R   L   L   I   Y   G
103     GCC TGG TAC CAG CAG AAA CCT GGC CAG GCT CCC AGG CTC CTC ATC TAT GGT
```

CDR2 SEQ ID:179 (aa) 180 (nt)
```
         A   S   S   R   V   T   G   I   P   D   R   F   S   G   S   G   S
154     GCA TCC AGC AGG GTC ACT GGC ATC CCA GAC AGG TTC AGT GGC AGT GGG TCT
```

```
         G   T   D   F   T   L   T   I   S   R   L   E   P   E   D   F   A
205     GGG ACA GAC TTC ACT CTC ACC ATC AGC AGA CTG GAG CCT GAA GAT TTT GCG
```

CDR3 SEQ ID:181 (aa) 182 (nt)
```
         V   Y   Y   C   Q   Q   Y   D   S   S   P   Y   T   F   G   Q   G
256     GTG TAT TAC TGT CAG CAG TAT GAT AGC TCA CCG TAC ACT TTT GGC CAG GGG
```

```
         T   K   L   E   I   K
307     ACC AAG CTG GAG ATC AAA
```

FIG. 31

Anti-human SOD1 14-173 VH

V segment: VH3-07
D segment: D2-15
J segment: JH5b

SEQ ID NO:183

```
          E   V   Q   L   V   E   S   G   G   G   L   V   Q   P   G   G   S
  1      GAG GTG CAG CTG GTG GAG TCT GGG GGA GGC TTG GTC CAG CCT GGG GGG TCC
SEQ ID NO:184
                                                     CDR1 SEQ ID:185 (aa) 186 (nt)
                                                     ~~~~~~~~~~~~
          L   R   L   S   C   A   A   S   G   F   T   F   S   S   F   W   M
  52     CTG AGA CTC TCC TGT GCA GCC TCT GGA TTC ACC TTT AGT AGC TTT TGG ATG

CDR1                                                          CDR2
         ~~~~                                                          ~~~~~~~~
          S   W   V   R   Q   A   P   G   K   G   L   E   W   V   A   N   I
  103    AGT TGG GTC CGC CAG GCT CCA GGG AAA GGG CTG GAG TGG GTG GCC AAC ATA

CDR2 SEQ ID:187 (aa) 188 (nt)
                         ~~~~~~~~~~~~~~~~~~~~~~~~~~~~~~~~~~~~~~~~~~~~~~~~~
          K   H   D   G   S   E   Q   D   Y   V   D   S   V   K   G   R   F
  154    AAG CAC GAT GGA AGT GAG CAA GAC TAT GTG GAC TCT GTG AAG GGC CGA TTC

T   I   S   R   D   N   A   K   N   S   L   Y   L   Q   M   N   S
  205    ACC ATC TCC AGA GAC AAC GCC AAG AAC TCA CTG TAT CTG CAA ATG AAC AGC

CDR3 SEQ ID:189 (aa) 190 (nt)
                                                  ~~~~~~~~~~~~~~~~~~
          L   R   A   E   D   T   A   V   Y   Y   C   A   R   G   G   I   W
  256    CTG AGA GCC GAG GAC ACG GCT GTG TAT TAC TGT GCA AGG GGG GGT ATC TGG

CDR3
              ~~~~~~~~~~
          F   G   P   W   G   Q   G   T   L   V   T   V   S   S
  307    TTC GGC CCC TGG GGC CAG GGA ACC CTG GTC ACC GTC TCC TCA
```

FIG. 32

Anti-human SOD1 14-173 VK

V segment: L24
J segment: JK2

SEQ ID NO:191

```
         V   I   W   M   T   Q   S   P   S   L   L   S   A   S   T   G   D
   1    GTC ATC TGG ATG ACC CAG TCT CCA TCC TTA CTC TCT GCA TCT ACA GGA GAC
SEQ ID NO:192
                                       CDR1 SEQ ID:193 (aa) 194 (nt)
                                      ~~~~~~~~~~~~~~~~~~~~~~~~~~~~~~~~~~~~
         R   V   T   I   S   C   R   M   S   Q   G   I   S   S   Y   L   A
  52    AGA GTC ACC ATC AGT TGT CGG ATG AGT CAG GGC ATT AGC AGT TAT TTA GCC

CDR2
                                                                   ~~~~~~~~
         W   Y   Q   Q   K   P   G   K   A   P   E   V   L   I   Y   A   V
 103    TGG TAT CAG CAA AAA CCA GGG AAA GCC CCT GAG GTC CTG ATC TAT GCT GTA

CDR2 SEQ ID:195 (aa) 196 (nt)
      ~~~~~~~~~~~~~~~~~~~~~~~
         S   T   L   Q   S   G   V   P   S   R   F   S   G   S   G   S   G
 154    TCC ACT TTG CAA AGT GGG GTC CCA TCA AGG TTC AGT GGC AGT GGA TCT GGG

T   D   F   T   L   T   I   S   C   L   Q   S   E   D   F   A   T
 205    ACA GAT TTC ACT CTC ACC ATC AGC TGC CTG CAG TCT GAA GAT TTT GCA ACT
                            CDR3 SEQ ID:197 (aa) 198 (nt)
                         ~~~~~~~~~~~~~~~~~~~~~~~~~~~~~~~~~~~~~
         Y   Y   C   Q   Q   Y   Y   S   F   P   Y   T   F   G   Q   G   T
 256    TAT TAC TGT CAA CAG TAT TAT AGT TTC CCG TAC ACT TTT GGC CAG GGG ACC

K   L   E   I   K
 307    AAG CTG GAG ATC AAA
```

FIG. 33

Anti-human SOD1 14-173-M1 VK

V segment:  L24
J segment:  JK2

SEQ ID NO:199

```
         V   I   W   M   T   Q   S   P   S   L   L   S   A   S   T   G   D
1        GTC ATC TGG ATG ACC CAG TCT CCA TCC TTA CTC TCT GCA TCT ACA GGA GAC
```
SEQ ID NO:200

CDR1 SEQ ID:193 (aa) 194 (nt)
                                        ~~~~~~~~~~~~~~~~~~~~~~~~~~~~~~~~~~~~~
```
         R   V   T   I   S   C   R   M   S   Q   G   I   S   S   Y   L   A
52       AGA GTC ACC ATC AGT TGT CGG ATG AGT CAG GGC ATT AGC AGT TAT TTA GCC
```

CDR2
                                                                    ~~~~~~~~~~
```
         W   Y   Q   Q   K   P   G   K   A   P   E   L   L   I   Y   A   V
103      TGG TAT CAG CAA AAA CCA GGG AAA GCC CCT GAG CTC CTG ATC TAT GCT GTA
```

CDR2 SEQ ID:195 (aa) 196 (nt)
     ~~~~~~~~~~~~~~~~~~~~~~~
```
         S   T   L   Q   S   G   V   P   S   R   F   S   G   S   G   S   G
154      TCC ACT TTG CAA AGT GGG GTC CCA TCA AGG TTC AGT GGC AGT GGA TCT GGG
```

```
         T   D   F   T   L   T   I   S   S   L   Q   S   E   D   F   A   T
205      ACA GAT TTC ACT CTC ACC ATC AGC TCT CTG CAG TCT GAA GAT TTT GCA ACT
```
                            CDR3 SEQ ID:197 (aa) 198 (nt)
                            ~~~~~~~~~~~~~~~~~~~~~~~~~~~~~~~~~~~
```
         Y   Y   C   Q   Q   Y   Y   S   F   P   Y   T   F   G   Q   G   T
256      TAT TAC TGT CAA CAG TAT TAT AGT TTC CCG TAC ACT TTT GGC CAG GGG ACC
```

```
         K   L   E   I   K
307      AAG CTG GAG ATC AAA
```

FIG. 34

Anti-human SOD1 303-8 VH

V segment:     VH1-69
    D segment:     D1-14
    J segment:     JH4b

SEQ ID NO:201

```
            Q   V   Q   L   V   Q   S   G   A   E   V   K   K   P   G   S   S
  1         CAG GTC CAG CTG GTG CAG TCT GGG GCT GAG GTG AAG AAG CCT GGG TCC TCG
SEQ ID NO:202
                                                CDR1 SEQ ID:203 (aa) 204 (nt)
                                                ~~~~~~~~~~~~~~
            V   K   V   S   C   K   A   S   G   G   S   F   S   I   Y   V   I
 52         GTG AAG GTC TCC TGC AAG GCT TCT GGA GGC TCC TTC AGC ATC TAT GTT ATC

CDR1                                                        CDR2
            ~~~~~                                                       ~~~~~
            S   W   V   R   Q   A   P   G   Q   G   L   E   W   M   G   R   I
103         AGC TGG GTG CGA CAG GCC CCT GGA CAA GGG CTT GAG TGG ATG GGA AGG ATC

CDR2 SEQ ID:205 (aa) 206 (nt)
            ~~~~~~~~~~~~~~~~~~~~~~~~~~~~~~~~~~~~~~~~~~~~~~~~~~~~~~
            I   P   I   L   G   T   T   N   Y   A   Q   K   F   Q   G   R   V
154         ATC CCT ATC CTT GGT ACA ACA AAC TAC GCA CAG AAG TTC CAG GGC AGA GTC

T   I   T   A   D   K   S   T   S   T   A   Y   M   E   L   S   S
205         ACG ATT ACC GCG GAC AAA TCC ACG AGC ACA GCC TAC ATG GAG CTG AGC AGC

CDR3
                                                                        ~~~~~
            L   R   S   E   D   T   A   V   Y   Y   C   A   R   P   D   S   P
256         CTG AGA TCT GAG GAC ACG GCC GTG TAT TAC TGT GCG AGA CCG GAC TCC CCG

CDR3 SEQ ID:207 (aa) 208 (nt)
            ~~~~~~~~~~~~~~~~~~~~~~~~~~~~~
            N   H   S   N   T   F   D   Y   W   G   Q   G   T   L   V   T   V
307         AAC CAT AGT AAT ACA TTT GAC TAC TGG GGC CAG GGA ACC CTG GTC ACC GTC

S   S
358         TCC TCA
```

FIG. 35

Anti-human SOD1 303-8 VK

V segment: L15
J segment: JK2

SEQ ID NO:209

```
        D   I   Q   M   T   Q   S   P   S   S   L   S   A   S   V   G   D
  1     GAC ATC CAG ATG ACC CAG TCT CCA TCC TCA CTG TCT GCA TCT GTA GGA GAC
SEQ ID NO:210
                                        CDR1 SEQ ID:211 (aa) 212 (nt)
                                        ~~~~~~~~~~~~~~~~~~~~~~~~~~~~~~~~~~
        R   V   T   I   T   C   R   A   S   Q   G   I   S   S   W   L   A
 52     AGA GTC ACC ATC ACT TGT CGG GCG AGT CAG GGT ATT AGC AGC TGG TTA GCC

CDR2
                                                                    ~~~~~~~~
        W   Y   Q   Q   K   P   E   K   A   P   K   S   L   I   Y   G   A
103     TGG TAT CAG CAG AAA CCA GAG AAA GCC CCT AAG TCC CTG ATC TAT GGT GCA

CDR2 SEQ ID:213 (aa) 214 (nt)
     ~~~~~~~~~~~~~~~~~~~~~~~~~~
        S   S   L   Q   S   G   V   P   S   R   F   S   G   S   G   S   G
154     TCC AGT TTG CAA AGT GGG GTC CCA TCA AGG TTC AGC GGC AGT GGA TCT GGG

T   D   F   T   L   T   I   S   S   L   Q   P   E   D   F   A   T
205     ACA GAT TTC ACT CTC ACC ATC AGC AGC CTG CAG CCT GAA GAT TTT GCA ACT

CDR3 SEQ ID:215 (aa) 216 (nt)
                          ~~~~~~~~~~~~~~~~~~~~~~~~~~~~~~~~~~
        Y   Y   C   Q   Q   Y   N   S   Y   P   Y   T   F   G   Q   G   T
256     TAT TAC TGC CAA CAG TAT AAT AGT TAC CCG TAC ACT TTT GGC CAG GGG ACC

K   L   E   I   K
307     AAG CTG GAG ATC AAA
```

FIG. 36

Anti-human SOD1 312-56 VH

V segment:    VH1-69
    D segment:    undetermined
    J segment:    JH6b

SEQ ID NO:217

```
         Q   V   Q   V   V   Q   S   G   A   E   V   K   K   P   G   S   S
  1     CAG GTC CAG GTG GTG CAG TCT GGG GCT GAG GTG AAG AAG CCT GGG TCC TCG
```
SEQ ID NO:218

CDR1 SEQ ID:219 (aa) 220 (nt)

```
         V   K   V   S   C   K   A   S   G   G   T   F   S   S   Y   A   I
 52     GTG AAG GTC TCC TGC AAG GCT TCT GGA GGC ACC TTC AGC AGC TAT GCT ATC

CDR1                                                            CDR2
         S   W   V   R   Q   A   P   G   Q   G   L   E   W   M   G   R   I
103     AGC TGG GTG CGA CAG GCC CCT GGA CAA GGG CTT GAG TGG ATG GGA AGG ATC

CDR2 SEQ ID:221 (aa) 222 (nt)
         I   P   I   L   G   T   A   K   Y   A   Q   K   F   Q   G   R   V
154     ATC CCT ATC CTT GGT ACA GCA AAG TAC GCA CAG AAG TTC CAG GGC AGA GTC

T   I   I   A   D   K   S   T   S   T   A   Y   M   E   L   S   S
205     ACG ATT ATC GCG GAC AAA TCC ACG AGC ACA GCC TAC ATG GAG CTG AGC AGC

CDR3
         L   R   S   E   D   T   A   V   Y   Y   C   A   R   D   Q   D   Y
256     CTG AGA TCT GAG GAC ACG GCC GTG TAT TAC TGT GCG AGA GAT CAG GAC TAC

CDR3 SEQ ID:223 (aa) 224 (nt)
         Y   G   M   D   V   W   G   Q   G   T   T   V   T   V   S   S
307     TAC GGT ATG GAC GTC TGG GGC CAA GGG ACC ACG GTC ACC GTC TCC TCA
```

FIG. 37

Anti-human SOD1 312-56 VK

V segment: L5
J segment: JK1

SEQ ID NO:225

```
          D   I   Q   M   T   Q   S   P   S   S   V   S   A   S   V   G   D
  1       GAC ATC CAG ATG ACC CAG TCT CCA TCT TCC GTG TCT GCA TCT GTA GGA GAC
SEQ ID NO:226
                                          CDR1 SEQ ID:227 (aa)  228 (nt)
                                          ~~~~~~~~~~~~~~~~~~~~~~~~~~~~~~~~~~~
          R   V   T   I   T   C   R   A   S   Q   G   I   S   S   W   L   A
  52      AGA GTC ACC ATC ACT TGT CGG GCG AGT CAG GGT ATT AGC AGC TGG TTA GCC

CDR2
                                                                      ~~~~~~~~
          W   Y   Q   H   K   P   G   K   A   P   K   L   L   I   Y   A   A
 103      TGG TAT CAG CAT AAA CCA GGG AAA GCC CCT AAG CTC CTG ATC TAT GCT GCA

CDR2 SEQ ID:229 (aa)  230 (nt)
          ~~~~~~~~~~~~~~~~~~~~~~~~~~~~~~
          S   S   L   Q   S   G   V   P   S   R   F   S   G   S   G   S   G
 154      TCC AGT TTG CAA AGT GGG GTC CCA TCA AGG TTC AGC GGC AGT GGA TCT GGG

T   D   F   T   L   T   I   S   S   L   Q   P   E   D   F   A   T
 205      ACA GAT TTC ACT CTC ACC ATC AGC AGC CTG CAG CCT GAA GAT TTT GCA ACT
                              CDR3 SEQ ID:231 (aa)  232 (nt)
                              ~~~~~~~~~~~~~~~~~~~~~~~~~~~~~~~~~~~~~~~~
          Y   Y   C   Q   Q   T   N   N   F   P   W   T   F   G   Q   G   T
 256      TAC TAT TGT CAA CAG ACT AAT AAT TTC CCG TGG ACG TTC GGC CAA GGG ACC

K   V   E   I   K
 307      AAG GTG GAG ATC AAA
```

| | G | G1 | G1a | G1b | G1c | G2 | G3 | G4 | G4a | G4b | G4c |
|---|---|---|---|---|---|---|---|---|---|---|---|
| | 38–77 | 38–52 | 38–47 | 40–49 | 42–51 | 46–60 | 54–68 | 63–77 | 63–71 | 66–74 | 69–77 |
| 595-16 | + | – | + | + | – | – | – | – | – | – | – |
| 311-3 | + | – | – | + | + | – | – | – | – | – | – |
| 591-37 | + | – | – | – | – | – | – | + | + | – | – |

FIG. 45

```
                                                                595-16 epitope
                                                                 SEQ ID NO: 307
                                                                                        311-3 epitope
                                                                                        SEQ ID NO: 313

1  ATKAVCVLKGDGPVQGIINFEQKESNGPVKVWGSIKGLTEG|LHGFHVHEF|GDNTAGCTSA 358-11 epitope            591-33 epitope
                                                                      SEQ ID NO: 311            SEQ ID NO: 315

61  GH|FNPLSRKH|GGPKDEER|HVGDLGNVT|ADKDGVADVSIEDSVISI|SGDHCIIGRTLVVH|

591-37 epitope
      SEQ ID NO: 309

591-33 epitope

121  E|KADDLGKGGNEESTKTGNAGSRLACGVIGIAQ
```

FIG. 46A

| Epitope, 1st | epitope, 2nd | #1<br>597-120 | #1a<br>312-19 | #1b<br>114-41 | #2<br>306-155 | #3<br>358-22 | #4<br>14-173 |
|---|---|---|---|---|---|---|---|
| #1 | 597-120 | compete | compete | compete | both bind | both bind | compete |
| #1a | 312-19 | compete | compete | compete | both bind | both bind | both bind |
| #1b | 114-41 | compete | compete | compete | both bind | both bind | both bind |
| #2 | 306-155 | both bind | both bind | both bind | compete | both bind | compete |
| #3 | 358-22 | both bind | both bind | both bind | both bind | compete | compete |
| #4 | 14-173 | compete | both bind | compete | compete | compete | compete |
| #1b | 358-13 | compete | compete | compete | both bind | both bind | compete |
| #2 | 16-62 | both bind | both bind | both bind | compete | both bind | compete |
| low affinity | 595-1 | low affinity | low affinity | low affinity | low affinity | low affinity | low affinity |
| weak binding | 108-2 | weak binding | weak binding | weak binding | weak binding | weak binding | weak binding |
| #2 | 108-45 | both bind | both bind | both bind | compete | both bind | both bind |
| weak binding | 108-83 | weak binding | weak binding | weak binding | weak binding | weak binding | weak binding |
| #1a | 114-50 | compete | compete | compete | both bind | both bind | both bind |
| weak binding | 14-111 | weak binding | weak binding | weak binding | weak binding | weak binding | weak binding |
| weak binding | 14-138 | weak binding | weak binding | weak binding | weak binding | weak binding | weak binding |
| #1a | 167-3 | compete | compete | compete | both bind | both bind | both bind |
| #1a | 17-55 | compete | compete | compete | both bind | both bind | both bind |
| #1a | 303-1 | compete | compete | compete | both bind | both bind | both bind |
| #5 | 303-8 | both bind | compete | both bind | both bind | compete | compete |
| #1c | 311-1 | both bind | compete | both bind | both bind | both bind | both bind |
| #1a | 311-18 | compete | compete | compete | both bind | both bind | both bind |
| weak binding | 312-38 | weak binding | weak binding | weak binding | weak binding | weak binding | weak binding |
| #1a | 312-10 | compete | compete | compete | both bind | both bind | both bind |
| low affinity | 312-4 | low affinity | low affinity | low affinity | low affinity | low affinity | low affinity |
| weak binding | 312-48 | weak binding | weak binding | weak binding | weak binding | weak binding | weak binding |
| #5 | 312-56 | both bind | compete | both bind | both bind | compete | compete |
| #1a | 312-84 | compete | compete | compete | both bind | both bind | both bind |
| #1a | 359-10 | compete | compete | compete | both bind | both bind | both bind |
| #1 | 595-19 | compete | compete | compete | both bind | both bind | compete |
| weak binding | 597-110 | weak binding | weak binding | weak binding | weak binding | weak binding | weak binding |
| #1a | 842-9 | compete | compete | compete | both bind | both bind | both bind |
| weak binding | 843-156 | weak binding | weak binding | weak binding | weak binding | weak binding | weak binding |

FIG. 46B

| Epitope, 2nd | Epitope, 1st | conf #1 597-120 | conf #1a 312-19 | conf #1b 114-41 | conf #2 306-155 | conf #3 358-22 | conf #4 14-173 |
|---|---|---|---|---|---|---|---|
| #1 | 597-120 | compete | compete | compete | both bind | both bind | compete |
| #1a | 312-19 | compete | compete | compete | both bind | both bind | both bind |
| #1b | 114-41 | compete | compete | compete | both bind | both bind | compete |
| #2 | 306-155 | both bind | both bind | both bind | compete | both bind | compete |
| #3 | 358-22 | both bind | both bind | both bind | both bind | compete | compete |
| #4 | 14-173 | compete | both bind | both bind | compete | compete | compete |
| #1b | 358-13 | compete | compete | compete | both bind | both bind | both bind |
| #2 | 16-62 | both bind | both bind | both bind | compete | both bind | compete |
| low affinity | 595-1 | low affinity | low affinity | low affinity | low affinity | low affinity | low affinity |
| weak binding | 108-2 | weak binding | weak binding | weak binding | weak binding | weak binding | weak binding |
| #2 | 108-45 | both bind | both bind | both bind | compete | both bind | both bind |
| weak binding | 108-83 | weak binding | weak binding | weak binding | weak binding | weak binding | weak binding |
| #1a | 114-50 | compete | compete | compete | both bind | both bind | both bind |
| weak binding | 14-111 | weak binding | weak binding | weak binding | weak binding | weak binding | weak binding |
| weak binding | 14-138 | weak binding | weak binding | weak binding | weak binding | weak binding | weak binding |
| #1a | 167-3 | compete | compete | compete | both bind | both bind | both bind |
| #1a | 17-55 | compete | compete | compete | both bind | both bind | both bind |
| #1a | 303-1 | compete | compete | compete | both bind | both bind | both bind |
| #5 | 303-8 | both bind | compete | both bind | both bind | compete | compete |
| #1c | 311-1 | both bind | compete | both bind | both bind | both bind | both bind |
| #1a | 311-18 | compete | compete | compete | both bind | both bind | both bind |
| weak binding | 312-38 | weak binding | weak binding | weak binding | weak binding | weak binding | weak binding |
| #1a | 312-10 | compete | compete | compete | both bind | both bind | both bind |
| low affinity | 312-4 | low affinity | low affinity | low affinity | low affinity | low affinity | low affinity |
| weak binding | 312-48 | weak binding | weak binding | weak binding | weak binding | weak binding | weak binding |
| #5 | 312-56 | both bind | compete | both bind | both bind | compete | compete |
| #1a | 312-84 | compete | compete | compete | both bind | both bind | both bind |
| #1a | 359-10 | compete | compete | compete | both bind | both bind | both bind |
| #1 | 595-19 | compete | compete | compete | both bind | both bind | compete |
| weak binding | 597-110 | both bind | compete | compete | both bind | both bind | both bind |
| #1a | 842-9 | compete | compete | compete | both bind | both bind | both bind |
| weak binding | 843-156 | weak binding | weak binding | weak binding | weak binding | weak binding | weak binding |

Overlapping = compete for binding
Touching = compete one direction but not other direction
Not overlapping or touching = do not compete

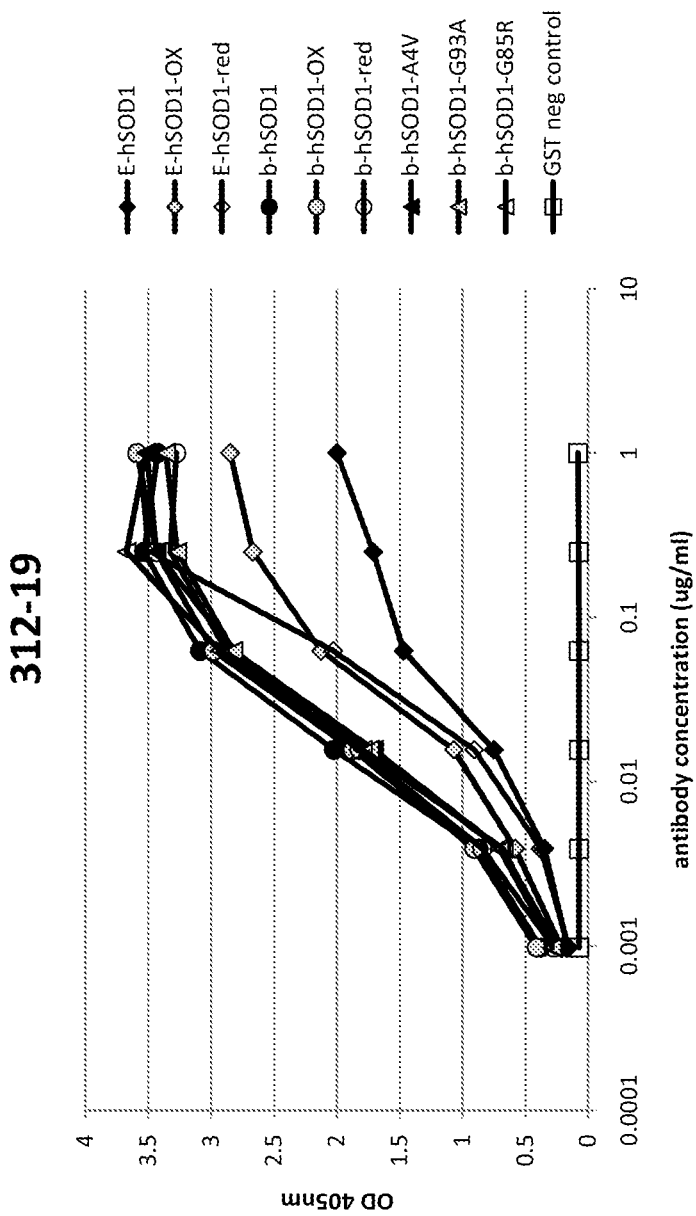

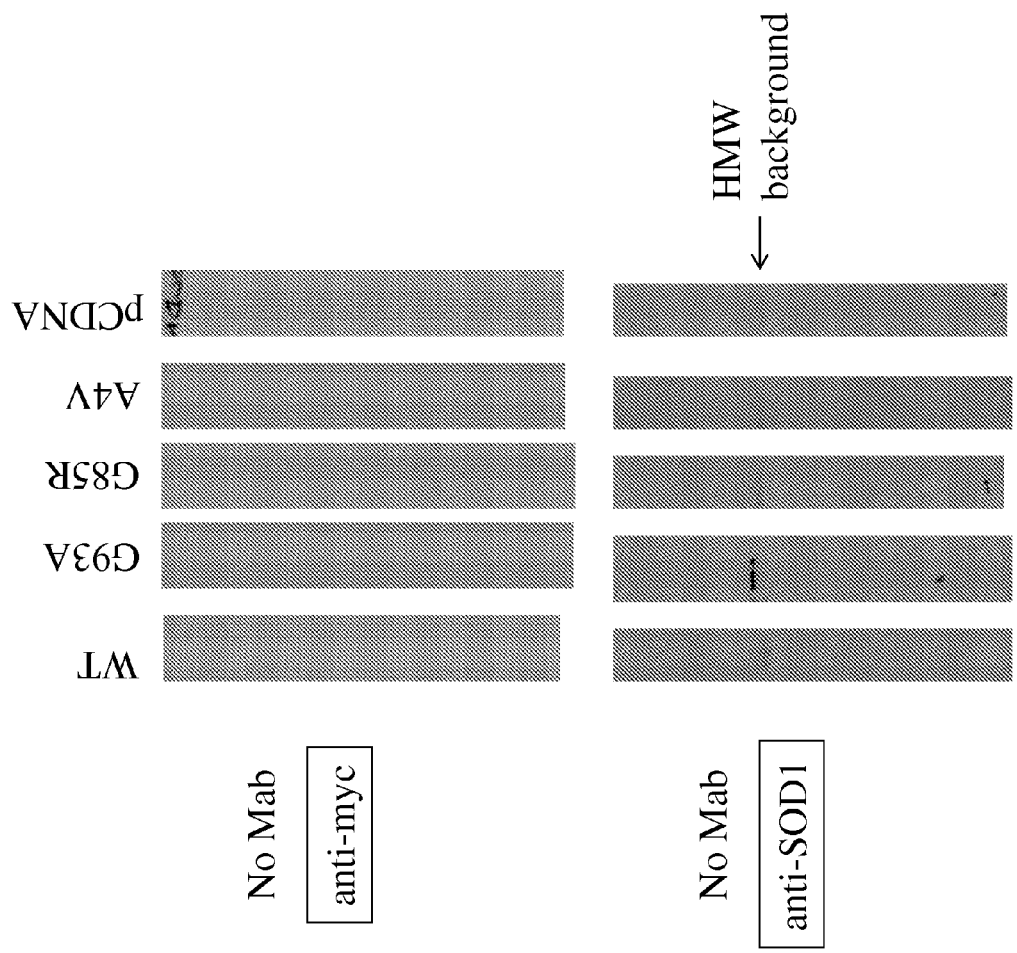

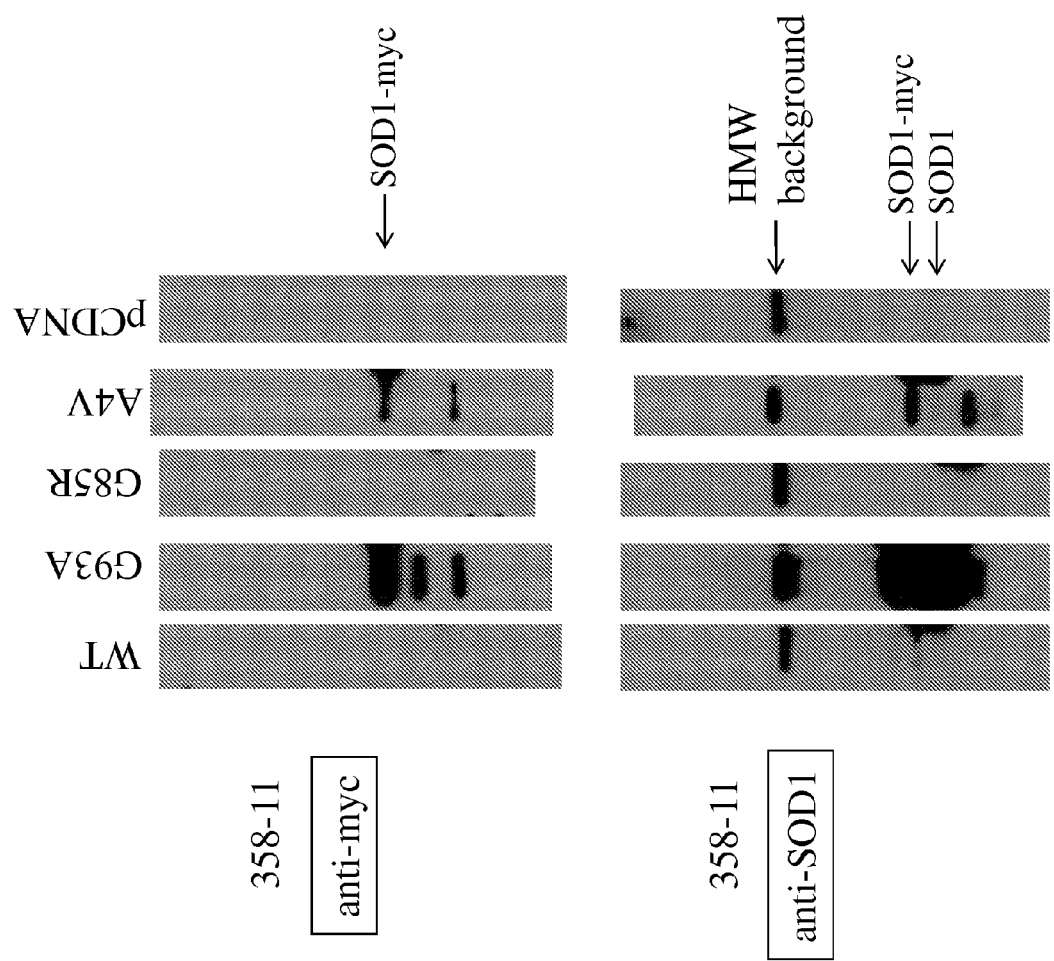

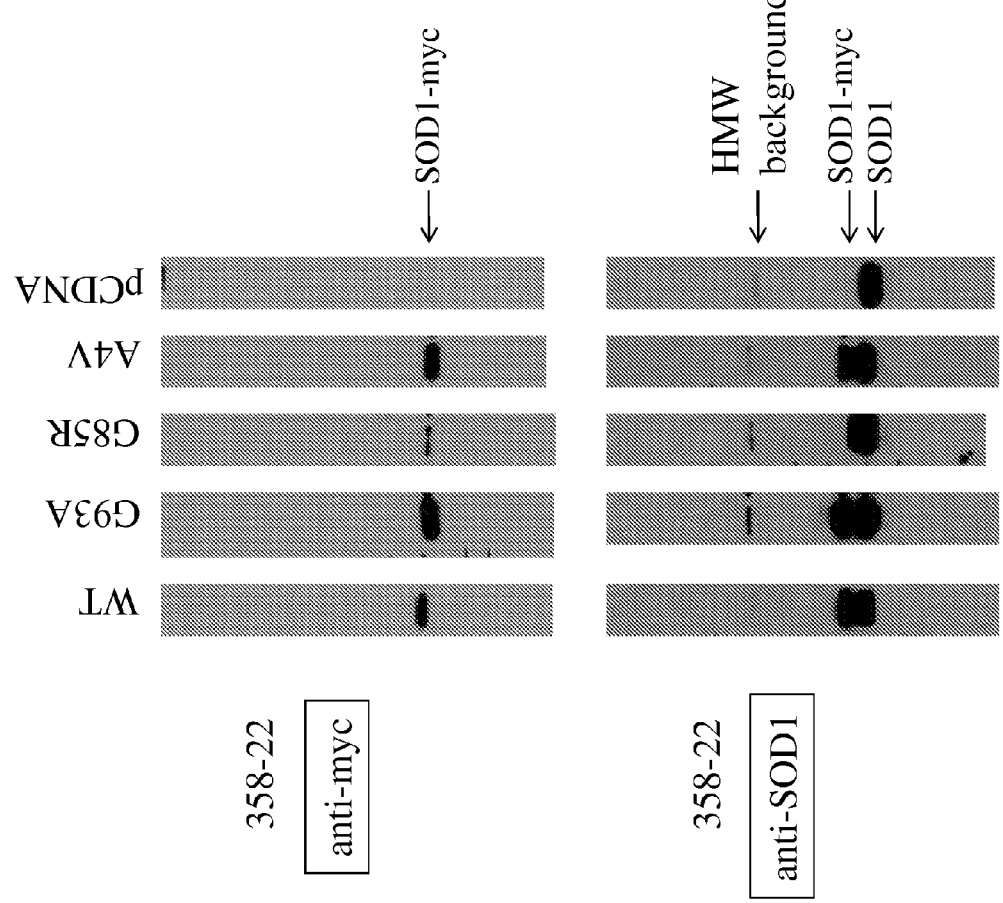

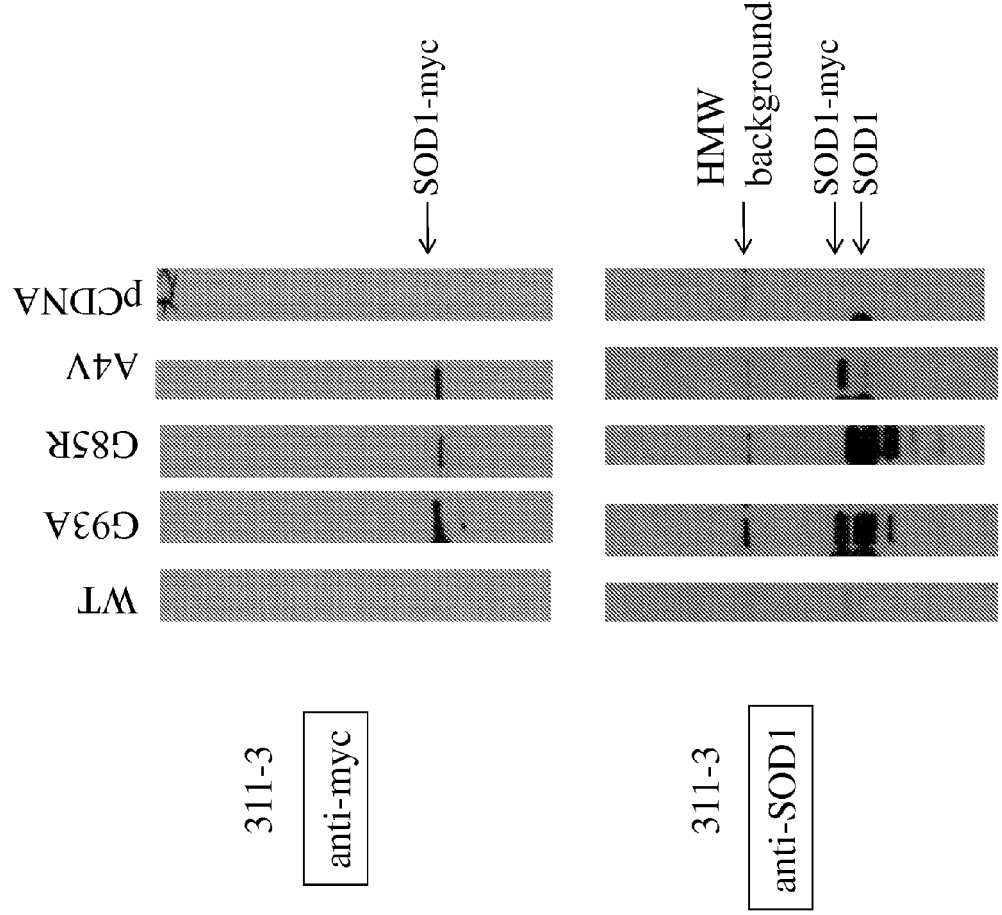

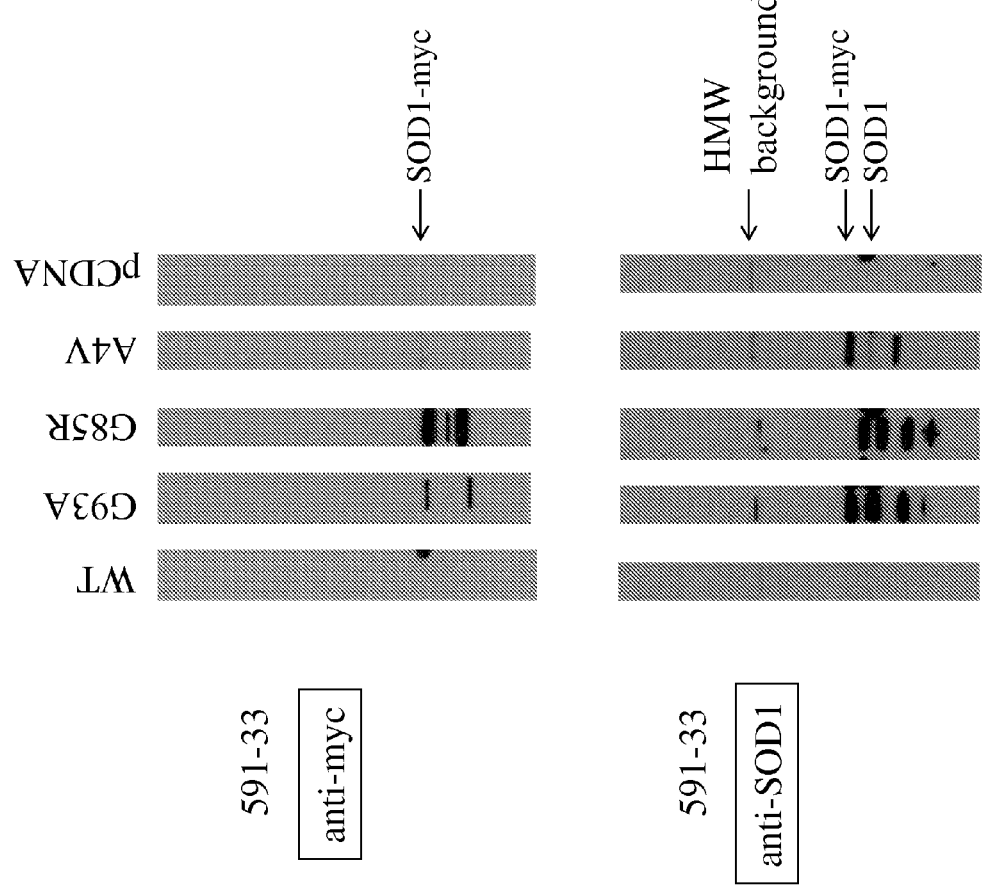

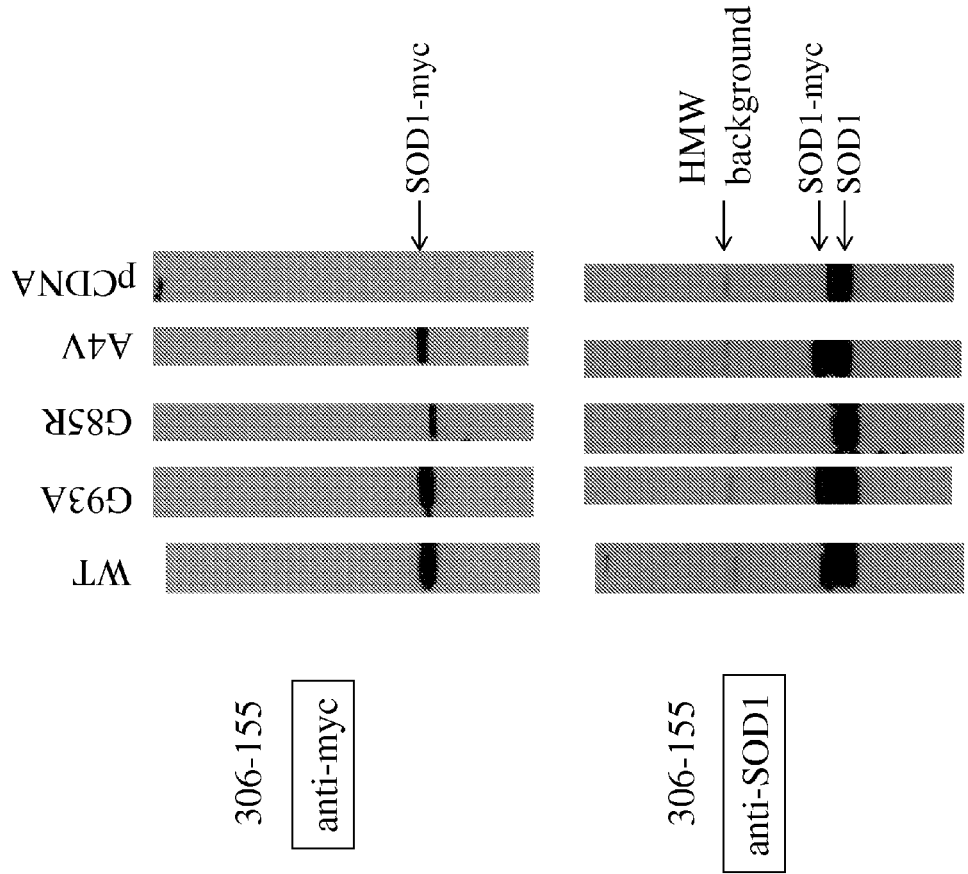

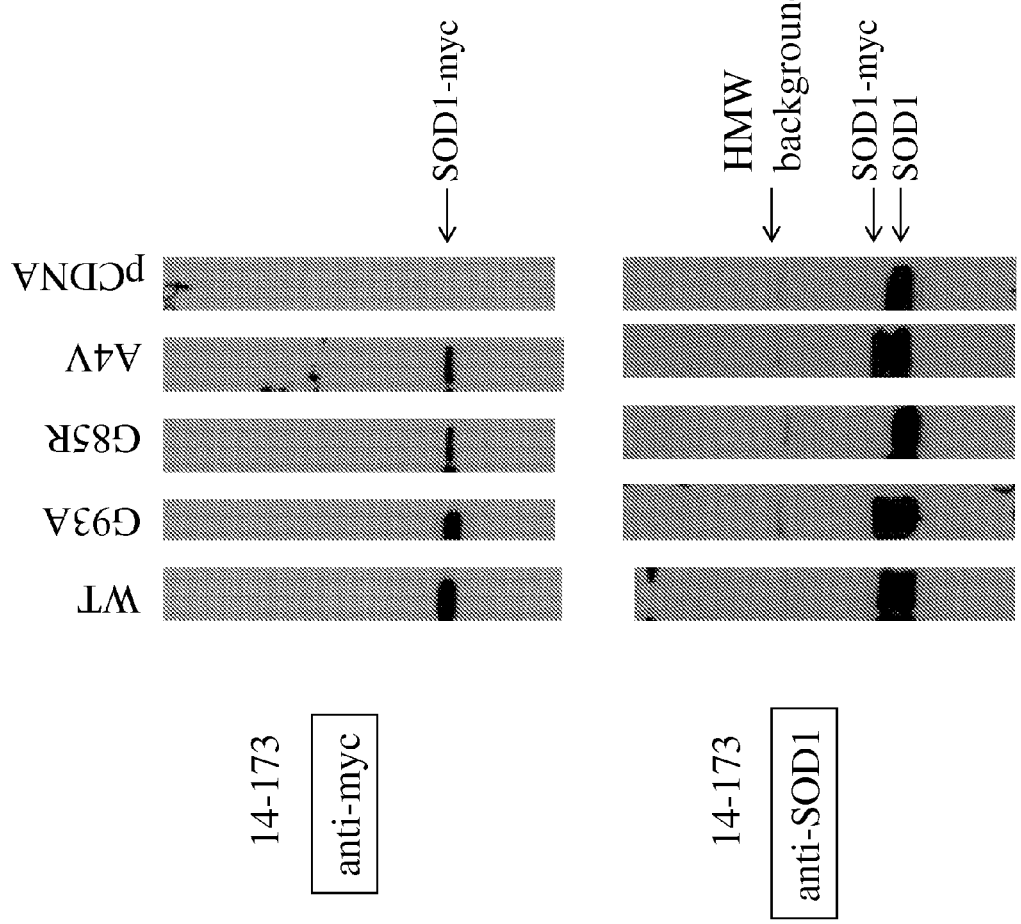

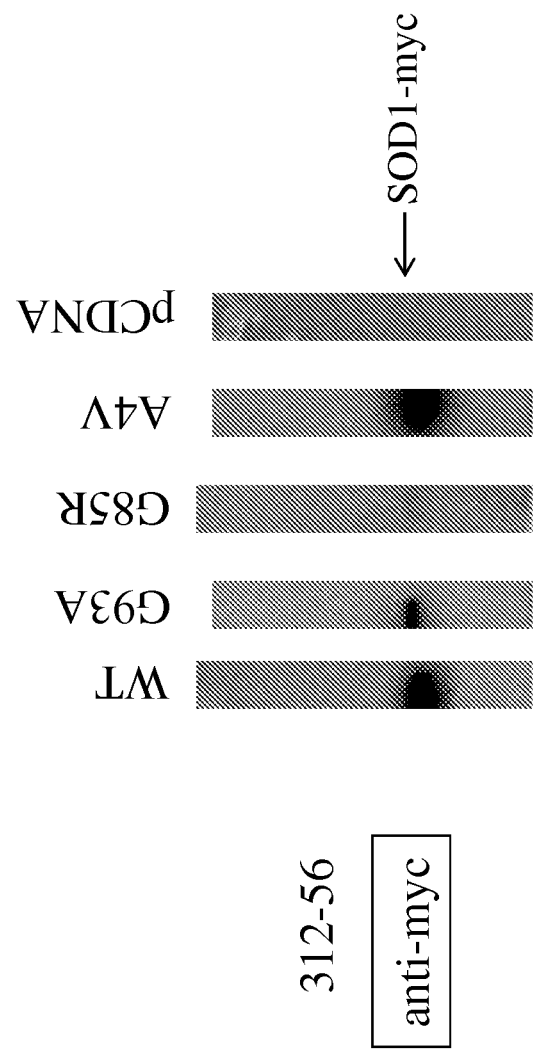

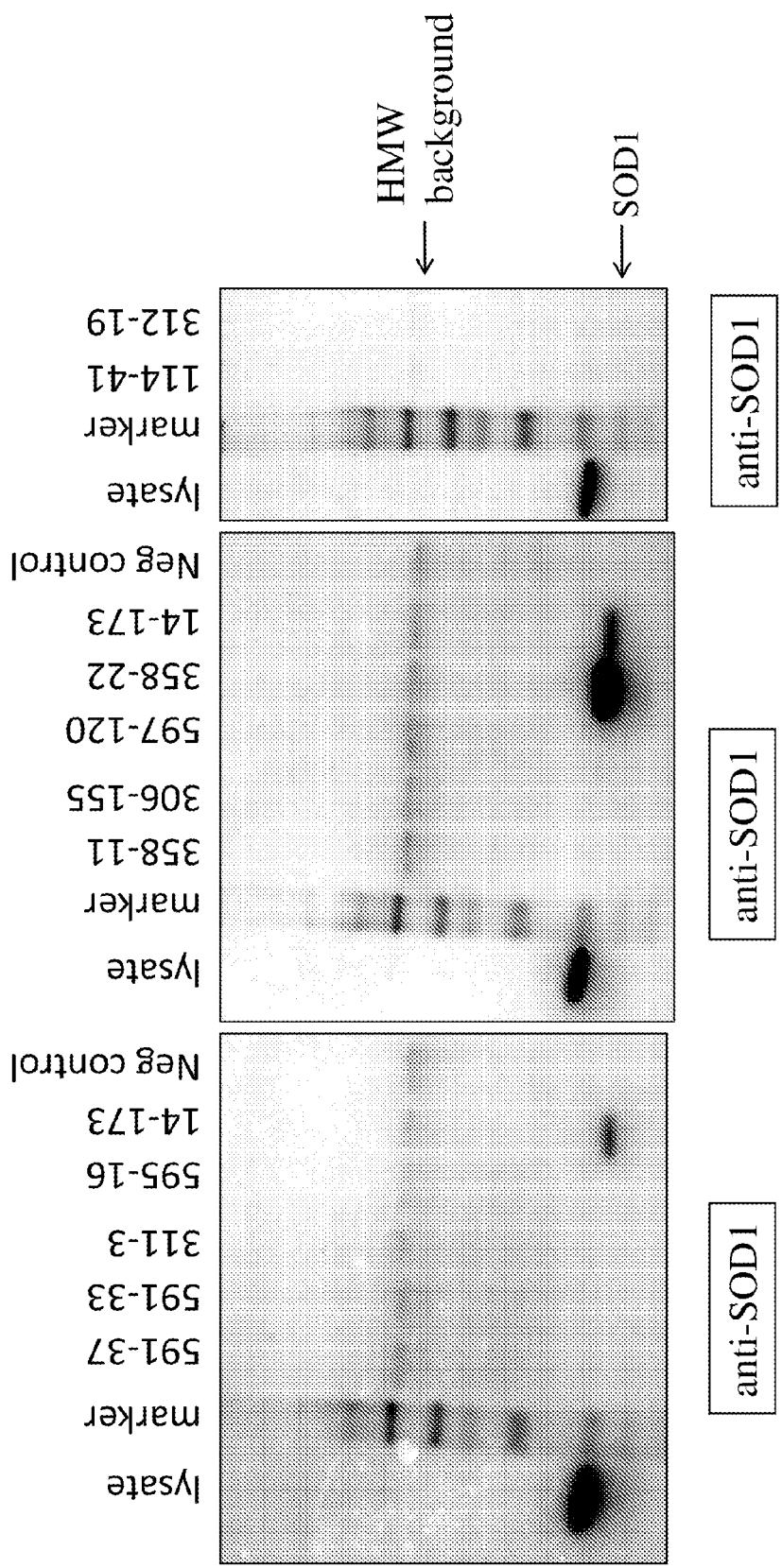

FIG. 53

| | 595-16 | 311-3 | 591-33 | 591-37 | 358-11 | 597-120 | 306-155 | 114-41 | 312-19 | 14-173 | 358-22 | 303-8 | 312-56 |
|---|---|---|---|---|---|---|---|---|---|---|---|---|---|
| 595-16 | | compete | both bind | both bind | both bind | compete | compete | compete | compete | compete | compete | NA | NA |
| 311-3 | compete | | both bind | both bind | both bind | compete | compete | compete | compete | compete | compete | NA | NA |
| 591-33 | both bind | both bind | | compete | both bind | compete | compete | compete | compete | compete | compete | compete | NA |
| 591-37 | both bind | both bind | compete | | both bind | compete | compete | compete | compete | compete | compete | compete | NA |
| 358-11 | both bind | both bind | both bind | both bind | | compete | compete | compete | compete | compete | compete | NA | NA |
| 597-120 | compete | compete | compete | compete | compete | | both bind | compete | both bind | compete | both bind | both bind | both bind |
| 306-155 | compete | compete | compete | compete | compete | both bind | | both bind | compete | both bind | both bind | both bind | both bind |
| 114-41 | compete | compete | compete | compete | compete | compete | both bind | | both bind | both bind | both bind | both bind | both bind |
| 312-19 | compete | compete | compete | compete | compete | both bind | compete | both bind | | both bind | compete | compete | compete |
| 14-173 | compete | compete | compete | compete | compete | both bind | both bind | both bind | both bind | | compete | compete | compete |
| 358-22 | compete | compete | compete | compete | compete | both bind | both bind | both bind | compete | compete | | compete | compete |
| 303-8 | NA | NA | compete | compete | NA | both bind | both bind | both bind | compete | compete | compete | | compete |
| 312-56 | NA | NA | NA | NA | NA | both bind | both bind | both bind | compete | compete | compete | compete | | om
ANTI-SOD1 ANTIBODIES AND USES THEREOF

CROSS-REFERENCE TO RELATED APPLICATIONS

This application is the U.S. National Stage filing under 35 U.S.C. §371 of International Application No. PCT/US2011/057699, filed Oct. 25, 2011, which claims the benefit of the filing date of U.S. Patent Application No. 61/406,831, filed on Oct. 26, 2010.

BACKGROUND OF THE INVENTION

Amyotrophic lateral sclerosis (ALS) is a progressive neurodegenerative disorder causing muscle weakness, followed by loss of motor function, leading to death. ALS patients typically live just three to five years following the first manifestation of symptoms. In a clinical setting, ALS is distinguished from other motor neuron diseases on the basis of initial symptom presentation, but may in fact belong to a group of motor neuron diseases sharing some substantive aspects of their pathophysiology or even etiology.

The pathology of ALS is manifested by motor neuron degeneration and death. Cortical motor cells disappear leading to retrograde axonal loss and gliosis in the corticospinal tract with ultimate atrophy of the spinal cord. During disease progression the ventral roots thin, and there is a loss of large myelinated fibers in motor nerves. Findings sometimes include a loss of frontal or temporal cortical neurons, and this can manifest symptomatically as ALS with frontotemporal dementia (ALS-FTD) although the typical course of the disease leaves cognitive functions intact. Intracellular inclusions in degenerating neurons and glia are common pathological findings of ALS; these include microfilament inclusions in spinal motor neurons, which may be associated with immunoreactive SOD1 particularly, but not exclusively, in familial ALS (FALS).

In Europe and North America, the incidence of ALS is about 2 cases per year per 100,000, while prevalence is around 5 cases per 100,000 with approximately 7,000 cases diagnosed annually in the US. Incidence increases with age, especially after 40, to a peak in the mid 70's. While age is a principle risk factor, family history is also important, with about 1 in 10 cases of ALS being familial. A number of environmental and behavioral risk factors, including smoking, have been proposed but none substantiated. Genetic analyses of sporadic ALS cases (SALS) have demonstrated significant associations between SALS and a range of loci. Mutations in loci more typically associated with FALS (superoxide dismutase 1 and others) have also been detected in SALS cases.

The majority of FALS cases follow an autosomal dominant inheritance pattern. About 20% of FALS patients are classified as Type 1 FALS, where the neurodegenerative phenotype is associated with inherited mutations to the superoxide dismutase type 1 (SOD1) gene localized in chromosome 21q22. Over 140 mutations of the SOD1 gene have been reported, almost all associated with ALS, but with significant variation in penetrance, age of onset, as well as nature and progression of symptoms. Some inherited SOD1 mutants with particularly weak penetrance and presumably, de novo somatic SOD1 mutants, may present as idiopathic (sporadic) ALS. It is also possible that a range of other genetic, physiological or environmental factors, isolated or in combination, may deleteriously impact the production and assembly of normal SOD1 enzyme, even in a genotypic background of wild type SOD1, and that this may in turn be linked to at least some further cases of idiopathic ALS.

Though the etiology of ALS is unclear, numerous mechanisms have been proposed, including SOD1-mediated toxicity. SOD1 is a copper and zinc containing metalloenzyme serving to deactivate superoxide radicals. It is ubiquitously expressed and is one of the most common intracellular enzymes, suggesting the function of the enzyme is important to the mediation of oxidative damage to cells. However, the loss of SOD1 function is not sufficient to account for the narrow and specific pathogenesis of the disease and it is generally thought, consistent with the dominant inheritance pattern, that it is some positive property of the mutant SOD1 that is implicated rather than a lack of function in the mutants.

One of the proposed mechanisms of mutant SOD1 toxicity is misfolding of the protein. Most SOD1 mutants fail to stably incorporate one or more metal ions and consequently fail to assemble as wild-type SOD1. The misfolded protein typically exposes reactive residues that are internal to the enzyme in wild-type SOD1, and perhaps as a consequence, SOD1 appears to form aggregates in ALS. These aggregates could be toxic themselves, or a secondary effect of the misfolding that is not the primary toxic mechanism.

There is evidence that mutant SOD1 expression is related to disease progression. Mutant SOD1 expression in non-neuronal cells may also be involved in the pathogenesis of ALS, while other evidence indicates that some properties of spinal cord tissue predispose cells to a pathological pathway that might damage other tissues subsequently, were a patient to survive the neurodegenerative disease. However, it is not clear what serves to initiate disease, and most type 1 FALS patients carry and presumably express mutant SOD1 for decades prior to the onset of the symptoms.

Several mouse and rat models expressing mutant forms of SOD1 exist. The experimentally induced mutations G93A, G37R, and G85R in the transgenic mouse models have phenotypes similar to human ALS. While there are also naturally occurring mouse models, the transgenic SOD1 mouse is considered the most accurate representation of the disease process.

The treatment options for ALS are limited. Riluzole is the only drug to have any established impact on survival in ALS. Riluzole can slow ALS progression to a modest degree, but its precise mechanism of action in ALS is unclear and ultimately it offers neither a cure nor sustained remediation of the condition. Multiple drugs have been tested for effectiveness in treating ALS but all others have failed to show efficacy in human clinical trials.

There is a need for effective therapeutics to treat and ameliorate the symptoms of ALS and diagnostics to assist in the identification of patients suffering from ALS.

SUMMARY OF THE INVENTION

ALS is a form of motor neuron disease caused by the degeneration of motor neurons, ultimately leading to impairment of mobility, speech, and respiratory functions. We have discovered anti-SOD1 antibodies that bind to mutant or misfolded SOD1 protein. The anti-SOD1 antibodies may also bind to wild-type SOD1. We have further discovered that the anti-SOD1 antibodies of the invention provide protection in an in vivo animal model and are useful for the treatment of ALS or amelioration of symptoms associated with ALS. We have also discovered various epitopes (linear or conformational) in SOD1 that are recognized by the anti-SOD1 antibodies of the invention. We have also discovered that anti-SOD1 antibodies that bind to the epitopes described herein (e.g., antibodies that compete with the anti-SOD1 antibodies described herein for binding to SOD1) and bind with an affinity of less than 50 nM (e.g., 25 nM, 20 nM, 10 nM, 5 nM, 1 nM, 500 pM, 250 pM, 100 pM, 50 pM, 10 pM or lower) also provide protection in an in vivo animal model and are useful for the treatment of ALS or amelioration of symptoms associated with ALS.

Accordingly, in a first aspect, the invention features an isolated anti-SOD1 monoclonal antibody, or antigen binding fragment thereof, wherein the antibody binds to an epitope of SOD1 protein, wherein the epitope comprises one or more amino acid sequences selected from the group consisting of amino acids 40-47 (SEQ ID NO: 307), amino acids 42-49 (SEQ ID NO: 313), amino acids 63-71 (SEQ ID NO: 309), amino acids 80-88 (SEQ ID NO: 311), and amino acids 107-121 (SEQ ID NO: 315) of human SOD1. In one embodiment the monoclonal antibody binds to an epitope that consists of amino acids 40-47 (SEQ ID NO: 307), amino acids 42-49 (SEQ ID NO: 313), amino acids 63-71 (SEQ ID NO: 309), amino acids 80-88 (SEQ ID NO: 311), or amino acids 107-121 (SEQ ID NO: 315) of human SOD1. In another embodiment, the anti-SOD1 antibody binds to one, two, three, four, or all five of the above-listed epitopes.

In various embodiments, the anti-SOD1 antibody of the invention can bind to a misfolded SOD1 protein, a mutant SOD1 protein, or a wild-type SOD1 protein. Such binding abilities are not mutually exclusive and a single antibody may bind to one or more forms of SOD1. The anti-SOD1 antibody of the invention may bind specifically to human SOD1 or may bind to human or mouse SOD1.

In another aspect, the invention features an isolated anti-SOD1 antibody, or antigen binding fragment thereof, wherein the monoclonal antibody binds to an epitope of SOD1 protein and wherein the antibody includes a heavy chain variable domain, a light chain variable domain, or both. The heavy chain variable domain of the anti-SOD1 antibody can include a CDRH1, a CDRH2, or a CDRH3, or combinations thereof, selected from the sequences provided below.

(a) CDRH1 can include an amino acid sequence selected from SEQ ID NOs: 3, 21, 39, 57, 75, 93, 115, 133, 151, 169, 185, 203, and 219;

(b) CDRH2 can include an amino acid sequence selected from SEQ ID NOs: 5, 23, 41, 59, 77, 95, 117, 135, 153, 171, 187, 205, and 221; and (c) CDRH3 can include an amino acid sequence selected from SEQ ID NOs: 7, 25, 43, 61, 79, 97, 119, 137, 155, 173, 189, 207, and 223.

The anti-SOD1 antibody of the invention desirably includes a CDRH1, CDRH2, and a CDRH3 of any one of the antibodies provided in Table 1 or 2.

In various embodiments of the invention, the light chain variable domain includes a CDRL1, a CDRL2, or a CDRL3, or combinations thereof, selected from the sequences provided below.

(a) CDRL1 can include an amino acid sequence selected from SEQ ID NOs: 11, 29, 47, 65, 83, 101, 123, 141, 159, 177, 193, 211, and 227

(b) CDRL2 can include an amino acid sequence selected from SEQ ID NOs: 13, 31, 49, 67, 85, 103, 111, 125, 143, 161, 179, 195, 213, and 229; and (c) CDRL3 can include an amino acid sequence selected from SEQ ID NOs: 15, 33, 51, 69, 87, 105, 127, 145, 163, 181, 197, 215, and 231.

The anti-SOD1 antibody of the invention desirably includes a CDRL1, CDRL2, and a CDRL3 of any one of the antibodies provided in Table 1 or Table 2, below.

In one embodiment, the anti-SOD1 antibody of the invention includes a CDRH1, CDRH2, CDRH3, CDRL1, CDRL2, and CDRL3 of any one of the antibodies provided in Tables 1 and 2.

The anti-SOD1 antibody of the invention can include a heavy chain variable domain amino acid sequence selected from the amino acid sequence set forth in SEQ ID NOs: 1, 17, 19, 35, 37, 53, 55, 71, 73, 89, 91, 107, 113, 129, 131, 147, 149, 165, 167, 183, 201, and 217. The anti-SOD1 antibody of the invention can include a light chain variable domain amino acid sequence selected from the amino acid sequence set forth in SEQ ID NOs: 9, 27, 45, 63, 81, 99, 109, 121, 139, 157, 175, 191, 199, 209, and 225. Desirably, the anti-SOD1 antibody of the invention includes a heavy chain variable domain amino acid sequence and a light chain variable domain amino acid sequence selected from a single antibody provided in Tables 1 and 2.

Examples of anti-SOD1 antibodies of the invention include antibody 595-16, 595-16-M1, 591-37, 597-31-M1, 358-11, 358-11-M1, 358-22, 358-22-M1, 597-120, 597-120-M1, 311-3, 311-3-M1, 312-19, 312-19-M1, 591-33, 591-33-M1, 114-41, 114-41-M1, 306-155, 14-173, 14-173-M1, 303-8, and 312-56. Examples of heavy chain and light chain variable domain sequences of anti-SOD1 antibodies of the invention that include a leader sequence, also encompassed by the invention, are provided in SEQ ID NOs: 233-306.

In another aspect, the invention features an anti-SOD1 antibody that competes with the binding of antibody 595-16, 595-16-M1, 591-37, 597-31-M1, 358-11, 358-11-M1, 358-22, 358-22-M1, 597-120, 597-120-M1, 311-3, 311-3-M1, 312-19, 312-19-M1, 591-33, 591-33-M1, 114-41, 114-41-M1, 306-155, 14-173, 14-173-M1, 303-8, or 312-56 to the SOD1 protein. In one aspect the antibody competes with any of the above-referenced antibodies and binds to an epitope of SOD1 with an affinity of less than 50 nM (e.g., 25 nM, 20 nM, 10 nM, 5 nM, 1 nM, 500 pM, 250 pM, 100 pM, 50 pM, 10 pM or lower).

In various embodiments of the invention, the heavy and light chains of the anti-SOD1 antibody can be full-length (e.g., an antibody can include at least one, and preferably two, complete heavy chains, and at least one, and preferably two, complete light chains) or can include an antigen-binding fragment. In yet other embodiments, the anti-SOD1 antibody has a heavy chain constant region chosen from, e.g., the heavy chain constant regions of $IgG_1$, $IgG_2$, $IgG_3$, $IgG_4$, IgM, $IgA_1$, $IgA_2$, IgD, and IgE. Desirably, the heavy chain constant region is IgG ($IgG_1$, $IgG_2$, $IgG_3$, or $IgG_4$). In another embodiment, the antibody has a light chain constant region chosen from, e.g., the light chain constant regions of kappa or lambda, preferably kappa (e.g., human kappa). In one embodiment, the antibody constant region is altered, e.g., mutated, to modify the properties of the antibody (e.g., to increase or decrease one or more of: Fc receptor binding, antibody glycosylation, the number of cysteine residues, effector cell function, or complement function).

In various embodiments of the above aspects of the invention, the anti-SOD1 antibody can bind to a conformational or a linear epitope of mutant, misfolded, or wild-type SOD1 protein. Such binding abilities are not mutually exclusive and a single antibody may bind to one or more forms of SOD1. In additional embodiments, the anti-SOD1 antibody can bind specifically to human SOD1 or can bind to both human SOD1 and mouse SOD1.

In various embodiments of any of the above aspects of the invention, the anti-SOD1 antibody binds to SOD1 with a Kd value of 50 nM or lower (e.g., 25 nM, 20 nM, 10 nM, 5 nM, 1 nM, 500 pM, 250 pM, 100 pM, 50 pM, 10 pM or lower).

In various embodiments of any of the above aspects of the invention, the anti-SOD1 antibody, or antigen binding fragment thereof, is a monoclonal antibody. In additional embodiments, the monoclonal antibody is a chimeric, humanized, or fully human antibody, or fragment thereof. In additional aspects of the invention, the monoclonal antibody, or antigen binding fragment thereof, is a single chain antibody; a diabody; an Fab, Fab', F(ab')$_2$, Fv, scFv, dsFv, or ds-scFv, fragment; an antibody dimer; a bispecific antibody; a minibody; or multimers thereof.

The anti-SOD1 antibody, or antigen binding fragment thereof, of the invention may optionally be conjugated to an exogenous molecule. Non-limiting examples of exogenous molecules are described herein and include cytotoxins, detectable labels, and inhibitory nucleic acid molecules. In one embodiment, any of the anti-SOD1 antibodies of the invention may be conjugated to an inhibitory RNA (e.g., siRNA) molecule.

The invention also features a composition that includes any one or more of the anti-SOD1 antibodies, or antigen binding fragments thereof, of the invention. Desirably the composition further includes a pharmaceutically acceptable carrier or excipient.

The invention further features a nucleic acid molecule that encodes any of the anti-SOD1 antibodies, or antigen binding fragments thereof, of the invention. Exemplary nucleic acid molecules that encode anti-SOD1 antibodies of the invention are provided in Tables 1 and 2 and are included in the scope of the invention. The invention also includes a vector that includes a nucleic acid molecule encoding an anti-SOD1 antibody of the invention. The invention also includes a host cell transformed with a vector of the invention.

In another aspect, the invention features a method of producing an anti-SOD1 antibody, where the method includes culturing a host cell that includes a nucleic acid encoding an anti-SOD1 antibody, or antigen binding fragment thereof, under conditions for expression of the nucleic acid molecule, and recovering the antibody from the host cell culture medium.

In yet another aspect, the invention features a hybridoma cell line that produces or expresses any of the anti-SOD1 antibodies, or antigen binding fragments thereof, of the invention.

In another aspect, the invention features a method of treating ALS (sporadic or familial) in a subject (e.g., mammalian subject such as a human or mouse) that includes administering to the subject an anti-SOD1 antibody, or antigen binding fragment thereof, of any of the aspects of the invention described herein. In one embodiment, the method includes administering antibody 595-16, 595-16-M1, 591-37, 597-31-M1, 358-11, 358-11-M1, 358-22, 358-22-M1, 597-120, 597-120-M1, 311-3, 311-3-M1, 312-19, 312-19-M1, 591-33, 591-33-M1, 114-41, 114-41-M1, 306-155, 14-173, 14-173-M1, 303-8, or 312-56. In another embodiment, the method includes administering an antibody that competes with antibody 595-16, 595-16-M1, 591-37, 597-31-M1, 358-11, 358-11-M1, 358-22, 358-22-M1, 597-120, 597-120-M1, 311-3, 311-3-M1, 312-19, 312-19-M1, 591-33, 591-33-M1, 114-41, 114-41-M1, 306-155, 14-173, 14-173-M1, 303-8, or 312-56 for binding to SOD1 and desirably binds to SOD1 with an affinity less than 50 nM (e.g., 25 nM, 20 nM, 10 nM, 5 nM, 1 nM, 500 pM, 250 pM, 100 pM, 50 pM, 10 pM or lower).

In various embodiments of the above aspect, the anti-SOD1 antibody, or antigen binding fragment thereof, is provided in an amount and for a time effective to reduce or ameliorate or minimize worsening of at least one symptom of ALS. Non-limiting examples of symptoms of ALS include muscle weakness, muscle atrophy, difficulty swallowing, muscle cramping or stiffness, weight loss, or slurred speech.

The therapeutic methods of the invention may include administering more than one (e.g., two, three, four, or more) anti-SOD1 antibody, or antigen-binding fragment thereof, of the invention. The therapeutic methods of the invention may also include administering an additional therapeutic agent. Non-limiting examples of additional therapeutic agents include riluzole, agents for the treatment of one or more symptoms of ALS, therapeutic antibodies, or a therapeutic antibody conjugated to an exogenous molecule.

The anti-SOD1 antibody may be in a pharmaceutical composition that further includes a pharmaceutically acceptable carrier or excipient. The anti-SOD1 antibody may be in a kit or a pharmaceutical pack and the kit or pharmaceutical pack may further include more than one (e.g., two, three, four, or more) anti-SOD1 antibodies, or antigen binding fragments thereof, of the invention or one or more additional therapeutic agents. Non-limiting examples of additional therapeutic agents include riluzole, agents for the treatment of one or more symptoms of ALS, therapeutic antibodies, or an antibody conjugated to an exogenous molecule.

The invention also includes the use of the anti-SOD1 antibodies of the invention in methods and kits for the diagnosis of ALS or an increased risk of developing ALS. For the diagnostic methods and compositions, the anti-SOD1 antibody of the invention will preferably detect mutant or misfolded SOD1 and will not detect wild-type, natively folded SOD1. The anti-SOD1 antibody will bind to mutant or misfolded forms of SOD1 in a sample from a subject where a mutant or misfolded form of SOD1 is present or suspected to be present. If mutant or misfolded SOD1 is detected using an antibody of the invention, the subject may be diagnosed with ALS or an increased risk of developing ALS. The diagnostic methods and compositions can be used as an initial screen, a single test, or in conjunction with additional clinical and neurological testing used by a clinician in the diagnosis of ALS.

Other features and advantages of the invention will be apparent from the following description of the preferred embodiments thereof, and from the claims.

BRIEF DESCRIPTION OF THE DRAWINGS

FIG. 1 is a representation of the amino acid and nucleic acid sequences of the VH chain expressed by clone 595-16. The V-segment, D-segment and J-segment genes are listed above the amino acid and nucleic acid sequences. The CDRs identified by the Kabat method are overlined.

FIG. 2 is a representation of the amino acid and nucleic acid sequences of the VK chain expressed by clone 595-16. The V-segment and J-segment genes are listed above the amino acid and nucleic acid sequences. The CDRs identified by the Kabat method are overlined.

FIG. 3 is a representation of the amino acid and nucleic acid sequences of the VH chain expressed by clone 595-16 that have been modified (595-16-M1). The V-segment, D-segment and J-segment genes are listed above the amino acid and nucleic acid sequences. The CDRs identified by the Kabat method are overlined. Amino acids and nucleotides that were modified are underlined.

FIG. 4 is a representation of the amino acid and nucleic acid sequences of the VH chain expressed by clone 591-37. The V-segment, D-segment and J-segment genes are listed above the amino acid and nucleic acid sequences. The CDRs identified by the Kabat method are overlined.

FIG. 5 is a representation of the amino acid and nucleic acid sequences of the VK chain expressed by clone 591-37. The V-segment and J-segment genes are listed above the amino acid and nucleic acid sequences. The CDRs identified by the Kabat method are overlined.

FIG. 6 is a representation of the amino acid and nucleic acid sequences of the VH chain expressed by clone 591-37 that have been modified (591-37-M1). The V-segment, D-segment and J-segment genes are listed above the amino acid and nucleic acid sequences. The CDRs identified by the Kabat method are overlined. Amino acids and nucleotides that were modified are underlined.

FIG. 7 is a representation of the amino acid and nucleic acid sequences of the VH chain expressed by clone 358-11. The V-segment, D-segment and J-segment genes are listed above the amino acid and nucleic acid sequences. The CDRs identified by the Kabat method are overlined.

FIG. 8 is a representation of the amino acid and nucleic acid sequences of the VK chain expressed by clone 358-11. The V-segment and J-segment genes are listed above the amino acid and nucleic acid sequences. The CDRs identified by the Kabat method are overlined.

FIG. 9 is a representation of the amino acid and nucleic acid sequences of the VH chain expressed by clone 358-11 that have been modified (358-11-M1). The V-segment, D-segment and J-segment genes are listed above the amino acid and nucleic acid sequences. The CDRs identified by the Kabat method are overlined. Amino acids and nucleotides that were modified are underlined.

FIG. 10 is a representation of the amino acid and nucleic acid sequences of the VH chain expressed by clone 358-22. The V-segment, D-segment and J-segment genes are listed above the amino acid and nucleic acid sequences. The CDRs identified by the Kabat method are overlined.

FIG. 11 is a representation of the amino acid and nucleic acid sequences of the VK chain expressed by clone 358-22. The V-segment and J-segment genes are listed above the amino acid and nucleic acid sequences. The CDRs identified by the Kabat method are overlined.

FIG. 12 is a representation of the amino acid and nucleic acid sequences of the VH chain expressed by clone 358-22 that have been modified (358-22-M1). The V-segment, D-segment and J-segment genes are listed above the amino acid and nucleic acid sequences. The CDRs identified by the Kabat method are overlined. Amino acids and nucleotides that were modified are underlined.

FIG. 13 is a representation of the amino acid and nucleic acid sequences of the VH chain expressed by clone 597-120. The V-segment, D-segment and J-segment genes are listed above the amino acid and nucleic acid sequences. The CDRs identified by the Kabat method are overlined.

FIG. 14 is a representation of the amino acid and nucleic acid sequences of the VK chain expressed by clone 597-120. The V-segment and J-segment genes are listed above the amino acid and nucleic acid sequences. The CDRs identified by the Kabat method are overlined.

FIG. 15 is a representation of the amino acid and nucleic acid sequences of the VH chain expressed by clone 597-120 that have been modified (597-120-M1). The V-segment, D-segment and J-segment genes are listed above the amino acid and nucleic acid sequences. The CDRs identified by the Kabat method are overlined. Amino acids and nucleotides that were modified are underlined.

FIG. 16 is a representation of the amino acid and nucleic acid sequences of the VH chain expressed by clone 311-3. The V-segment, D-segment and J-segment genes are listed above the amino acid and nucleic acid sequences. The CDRs identified by the Kabat method are overlined.

FIG. 17 is a representation of the amino acid and nucleic acid sequences of the VK chain expressed by clone 311-3. The V-segment and J-segment genes are listed above the amino acid and nucleic acid sequences. The CDRs identified by the Kabat method are overlined.

FIG. 18 is a representation of the amino acid and nucleic acid sequences of the VH chain expressed by clone 311-3 that have been modified (311-3-M1). The V-segment, D-segment and J-segment genes are listed above the amino acid and nucleic acid sequences. The CDRs identified by the Kabat method are overlined. Amino acids and nucleotides that were modified are underlined.

FIG. 19 is a representation of the amino acid and nucleic acid sequences of the VK chain expressed by clone 311-3 that have been modified (311-3-M1). The V-segment and J-segment genes are listed above the amino acid and nucleic acid sequences. The CDRs identified by the Kabat method are overlined. Amino acids and nucleotides that were modified are underlined.

FIG. 20 is a representation of the amino acid and nucleic acid sequences of the VH chain expressed by clone 312-19. The V-segment, D-segment and J-segment genes are listed above the amino acid and nucleic acid sequences. The CDRs identified by the Kabat method are overlined.

FIG. 21 is a representation of the amino acid and nucleic acid sequences of the VK chain expressed by clone 312-19. The V-segment and J-segment genes are listed above the amino acid and nucleic acid sequences. The CDRs identified by the Kabat method are overlined.

FIG. 22 is a representation of the amino acid and nucleic acid sequences of the VH chain expressed by clone 312-19 that have been modified (312-19-M1). The V-segment, D-segment and J-segment genes are listed above the amino acid and nucleic acid sequences. The CDRs identified by the Kabat method are overlined. Amino acids and nucleotides that were modified are underlined.

FIG. 23 is a representation of the amino acid and nucleic acid sequences of the VH chain expressed by clone 591-33. The V-segment, D-segment and J-segment genes are listed above the amino acid and nucleic acid sequences. The CDRs identified by the Kabat method are overlined.

FIG. 24 is a representation of the amino acid and nucleic acid sequences of the VK chain expressed by clone 591-33. The V-segment and J-segment genes are listed above the amino acid and nucleic acid sequences. The CDRs identified by the Kabat method are overlined.

FIG. 25 is a representation of the amino acid and nucleic acid sequences of the VH chain expressed by clone 591-33 that have been modified (591-33-M1). The V-segment, D-segment and J-segment genes are listed above the amino acid and nucleic acid sequences. The CDRs identified by the Kabat method are overlined. Amino acids and nucleotides that were modified are underlined.

FIG. 26 is a representation of the amino acid and nucleic acid sequences of the VH chain expressed by clone 114-41. The V-segment, D-segment and J-segment genes are listed above the amino acid and nucleic acid sequences. The CDRs identified by the Kabat method are overlined.

FIG. 27 is a representation of the amino acid and nucleic acid sequences of the VK chain expressed by clone 114-41. The V-segment and J-segment genes are listed above the amino acid and nucleic acid sequences. The CDRs identified by the Kabat method are overlined.

FIG. 28 is a representation of the amino acid and nucleic acid sequences of the VH chain expressed by clone 114-41 that have been modified (114-41-M1). The V-segment, D-segment and J-segment genes are listed above the amino acid and nucleic acid sequences. The CDRs identified by the Kabat method are overlined. Amino acids and nucleotides that were modified are underlined.

FIG. 29 is a representation of the amino acid and nucleic acid sequences of the VH chain expressed by clone 306-155. The V-segment, D-segment and J-segment genes are listed above the amino acid and nucleic acid sequences. The CDRs identified by the Kabat method are overlined.

FIG. 30 is a representation of the amino acid and nucleic acid sequences of the VK chain expressed by clone 306-155. The V-segment and J-segment genes are listed above the amino acid and nucleic acid sequences. The CDRs identified by the Kabat method are overlined.

FIG. 31 is a representation of the amino acid and nucleic acid sequences of the VH chain expressed by clone 14-173. The V-segment, D-segment and J-segment genes are listed above the amino acid and nucleic acid sequences. The CDRs identified by the Kabat method are overlined.

FIG. 32 is a representation of the amino acid and nucleic acid sequences of the VK chain expressed by clone 14-173. The V-segment and J-segment genes are listed above the amino acid and nucleic acid sequences. The CDRs identified by the Kabat method are overlined.

FIG. 33 is a representation of the amino acid and nucleic acid sequences of the VK chain expressed by clone 14-173 that have been modified (14-173-M1). The V-segment and J-segment genes are listed above the amino acid and nucleic acid sequences. The CDRs identified by the Kabat method are overlined. Amino acids and nucleotides that were modified are underlined.

FIG. 34 is a representation of the amino acid and nucleic acid sequences of the VH chain expressed by clone 303-8. The V-segment, D-segment and J-segment genes are listed above the amino acid and nucleic acid sequences. The CDRs identified by the Kabat method are overlined.

FIG. 35 is a representation of the amino acid and nucleic acid sequences of the VK chain expressed by clone 303-8. The V-segment and J-segment genes are listed above the amino acid and nucleic acid sequences. The CDRs identified by the Kabat method are overlined.

FIG. 36 is a representation of the amino acid and nucleic acid sequences of the VH chain expressed by clone 312-56. The V-segment, D-segment and J-segment genes are listed above the amino acid and nucleic acid sequences. The CDRs identified by the Kabat method are overlined.

FIG. 37 is a representation of the amino acid and nucleic acid sequences of the VK chain expressed by clone 312-56. The V-segment and J-segment genes are listed above the amino acid and nucleic acid sequences. The CDRs identified by the Kabat method are overlined.

FIG. 38 is an alignment of the native nucleotide sequence of human SOD1 with the codon-optimized nucleotide sequence of human SOD1.

Figure 39:
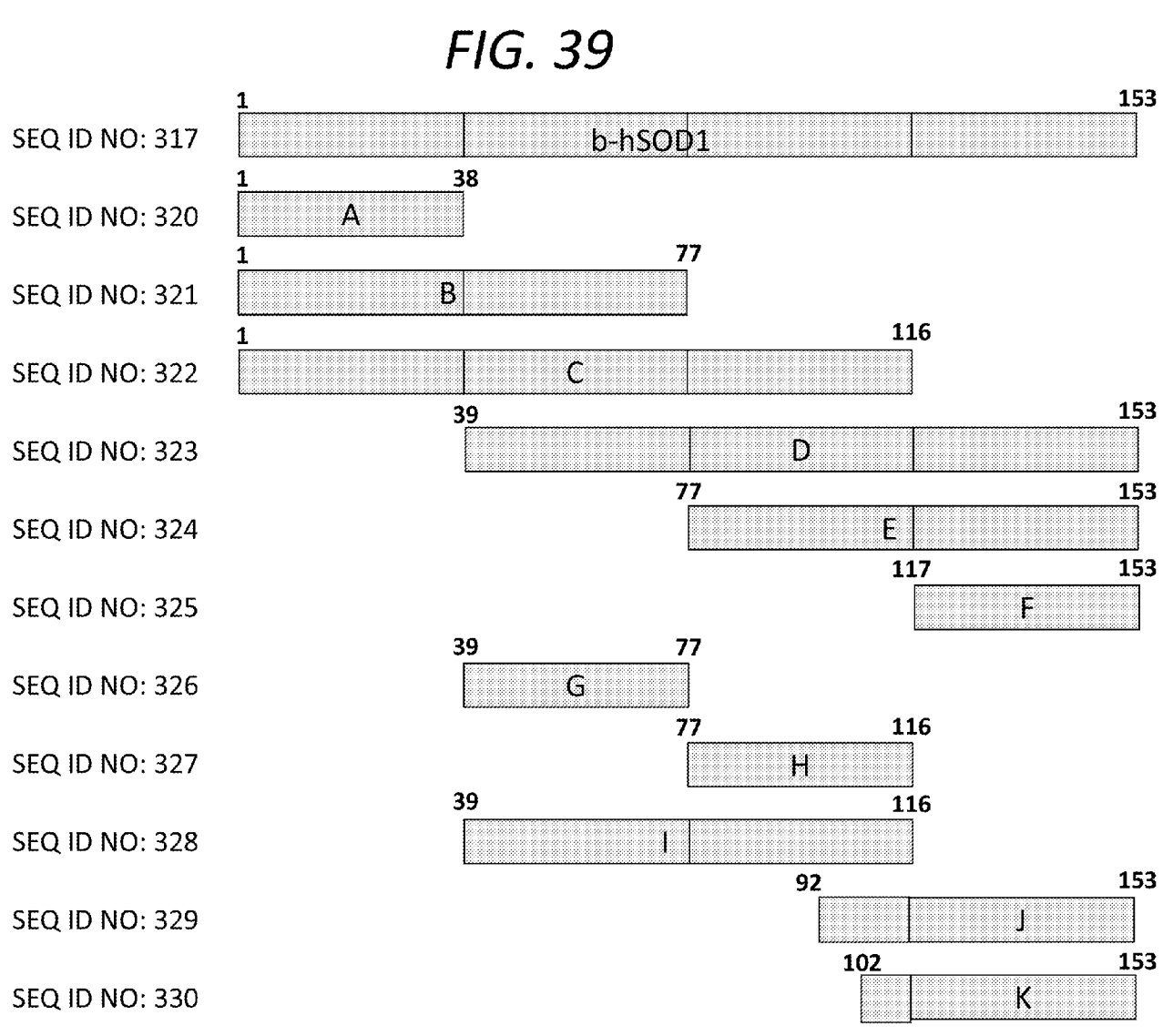

FIG. 39 is a schematic representation of the bacterially-expressed truncations of the human SOD1 protein Amino acid numbers are shown above the bars and fragment names represented as letters are shown within the bars.

Figure 40:
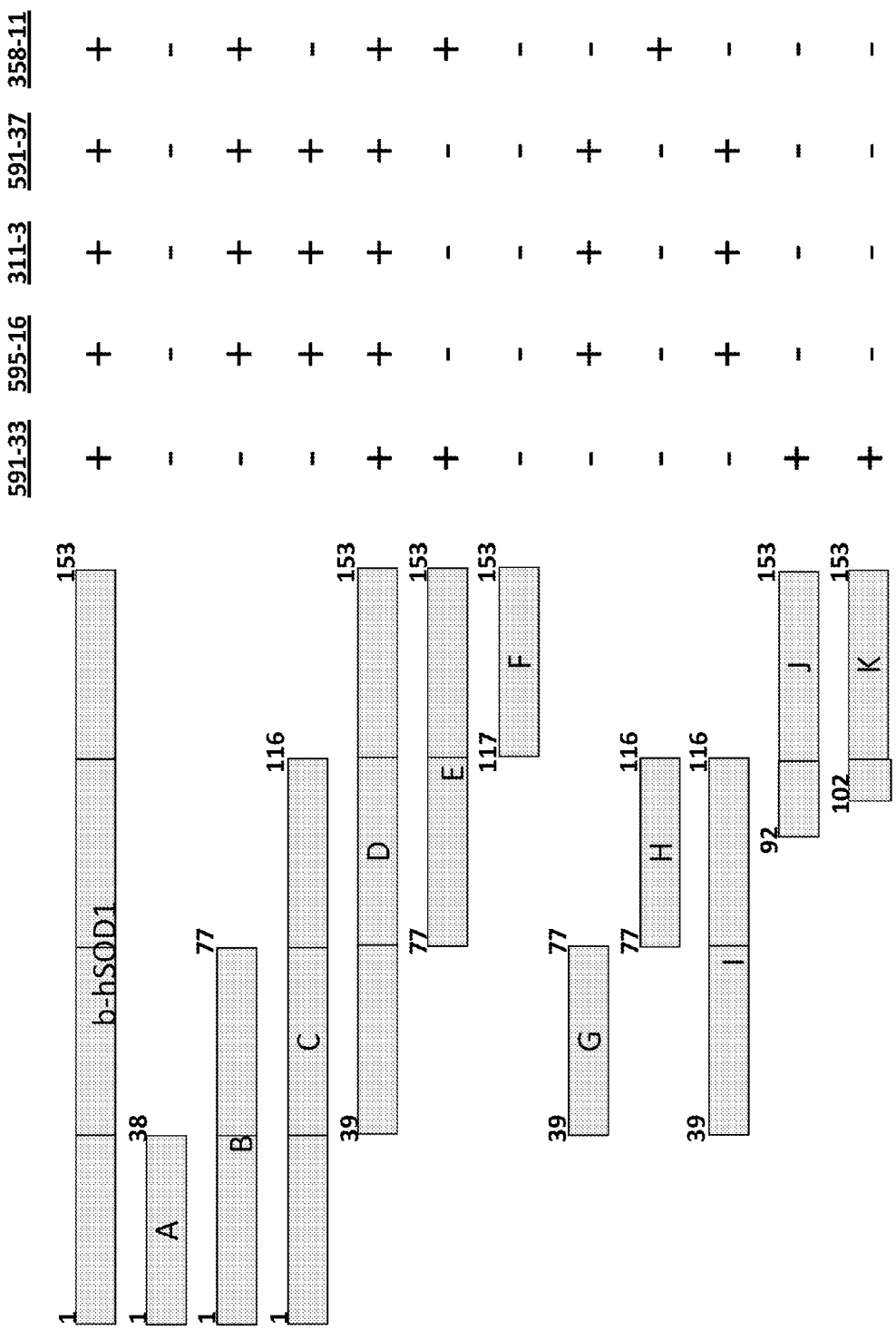

FIG. 40 shows a schematic of the truncated human SOD1 proteins from FIG. 39 on the left-hand side. Antibodies tested in ELISA against the truncated proteins are shown in the upper right hand portion of the figure. Recognition of the truncated fragments in ELISA is shown as a + or a −.

Figure 41:
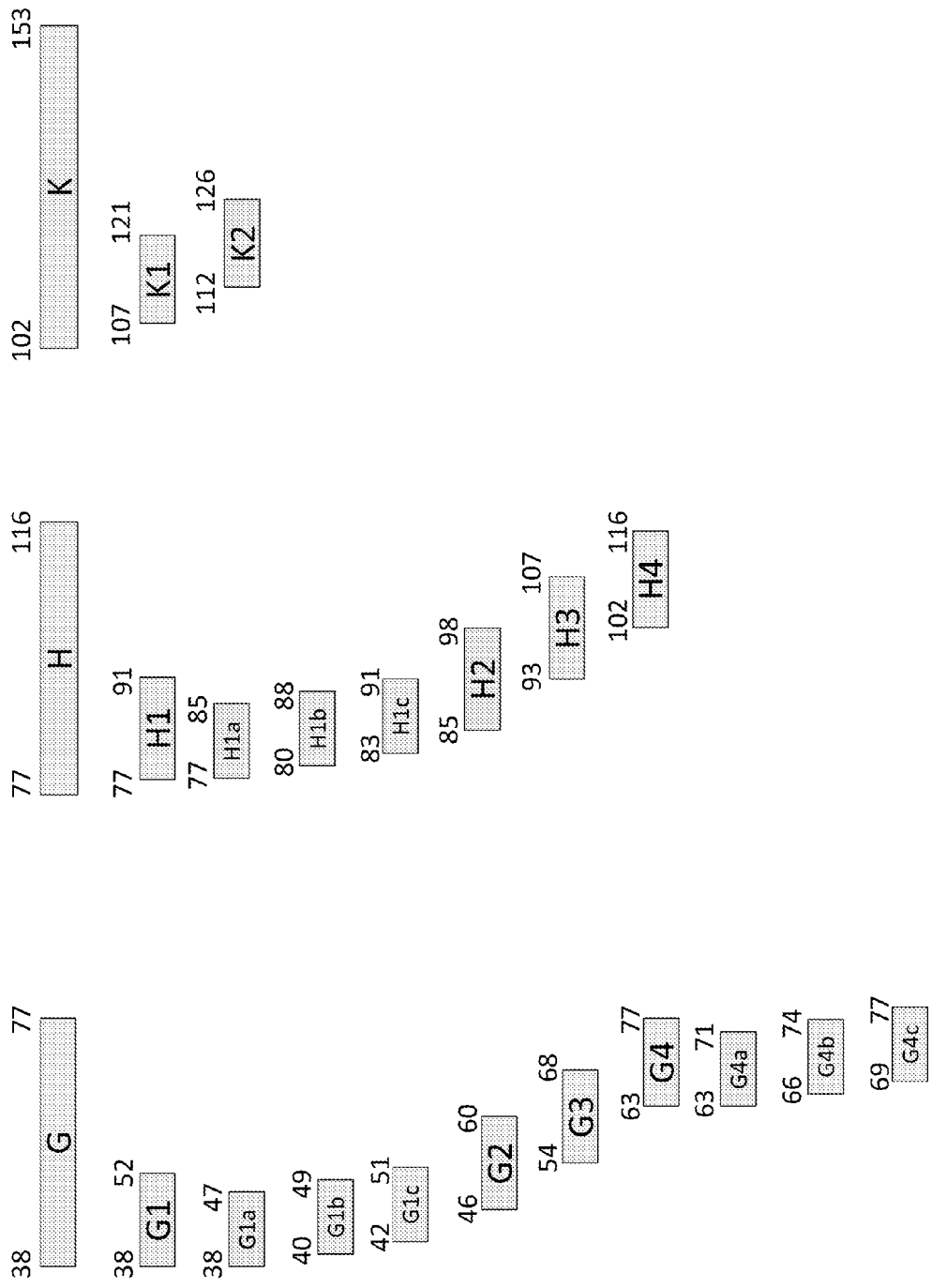

FIG. 41 is a schematic representation of peptides representing amino acid sequences of the hSOD1 protein Amino acid numbers are located above the bars and the peptide name is listed within the bars.

FIG. 42 shows the schematic of the peptides encompassing amino acids 38-77 of hSOD1 protein from FIG. 41 on the left-hand side. Antibodies tested in ELISA against the peptides are shown in the upper right hand portion of the figure. Recognition of the peptides in ELISA is shown as a + or a −.

Figure 43:
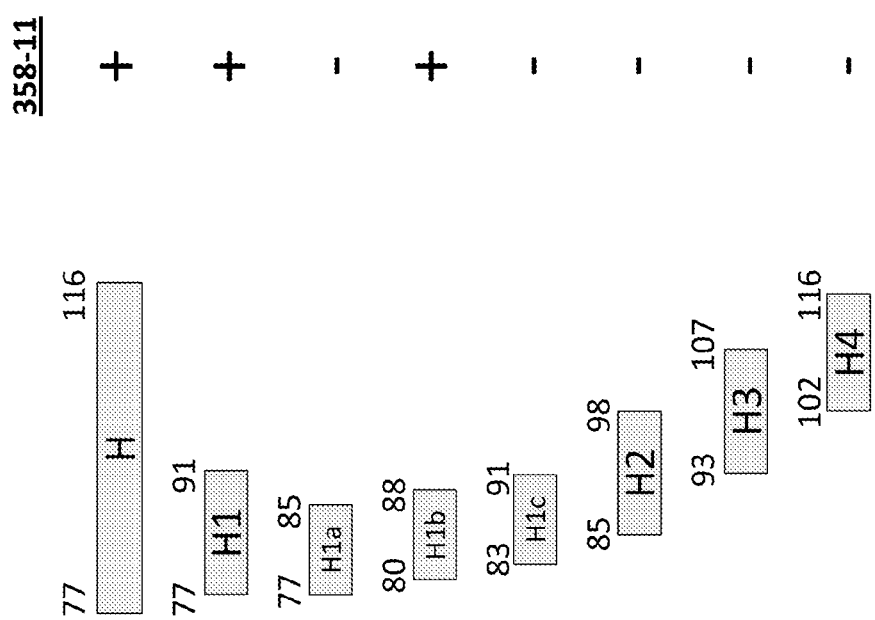

FIG. 43 shows the schematic of the peptides encompassing amino acids 77-116 of hSOD1 protein from FIG. 41 on the left-hand side. Antibodies tested in ELISA against the peptides are shown in the upper right hand portion of the figure. Recognition of the peptides in ELISA is shown as a + or a −.

Figure 44:
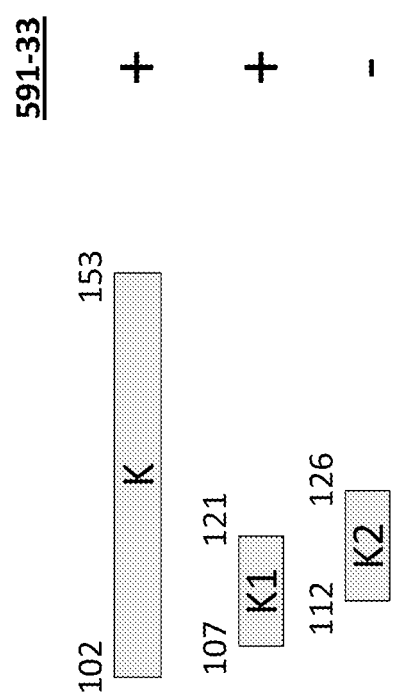

FIG. 44 shows the schematic of the peptides encompassing amino acids 102-153 of hSOD1 protein from FIG. 41 on the left-hand side. Antibodies tested in ELISA against the peptides are shown in the upper right hand portion of the figure. Recognition of the peptides in ELISA is shown as a + or a −.

FIG. 45 shows the amino acid sequence of the hSOD1 protein (SEQ ID NO: 317). Epitopes recognized by antibodies 595-16, 311-3, 591-37, 358-11 and 591-33 are shown by a box with the appropriate antibody listed above the box.

FIGS. 46A-46B show the results from competition studies for antibody binding to b-hSOD1. A) Six selected antibodies with unique sequence are listed across the top of the chart and were tested for the capacity to bind to SOD1 after individually saturating the b-hSOD1 with various conformation-dependent antibodies specific for SOD1 that are listed along the left of the chart. If the antibody listed across the top of the chart was able to bind after b-hSOD1 was saturated with the antibody along the left side of the chart, the square is marked—both bind. If the second antibody was unable to bind, the square is marked—compete. Antibodies that demonstrated weak binding or low affinity for b-hSOD1 are indicated in the chart. B) The experiment was performed as in A, but the antibodies across the top of the chart were bound to saturation to b-hSOD1 followed by assessment of binding of the various antibodies along the left of the chart. Based on the pattern of competition, antibodies were grouped and labeled as having similar antigen binding regions and therefore epitope.

Figure 47:
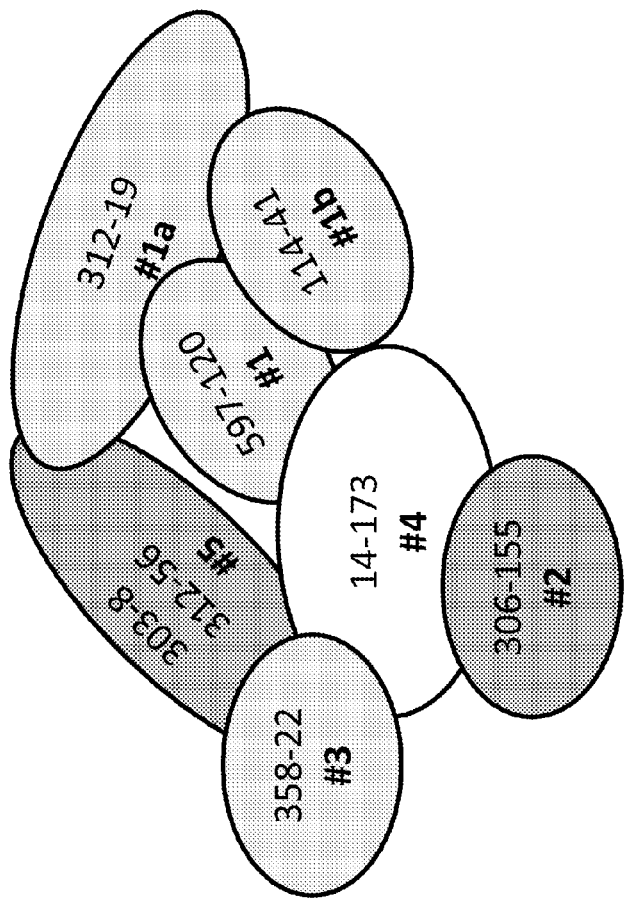
Figure 48A:
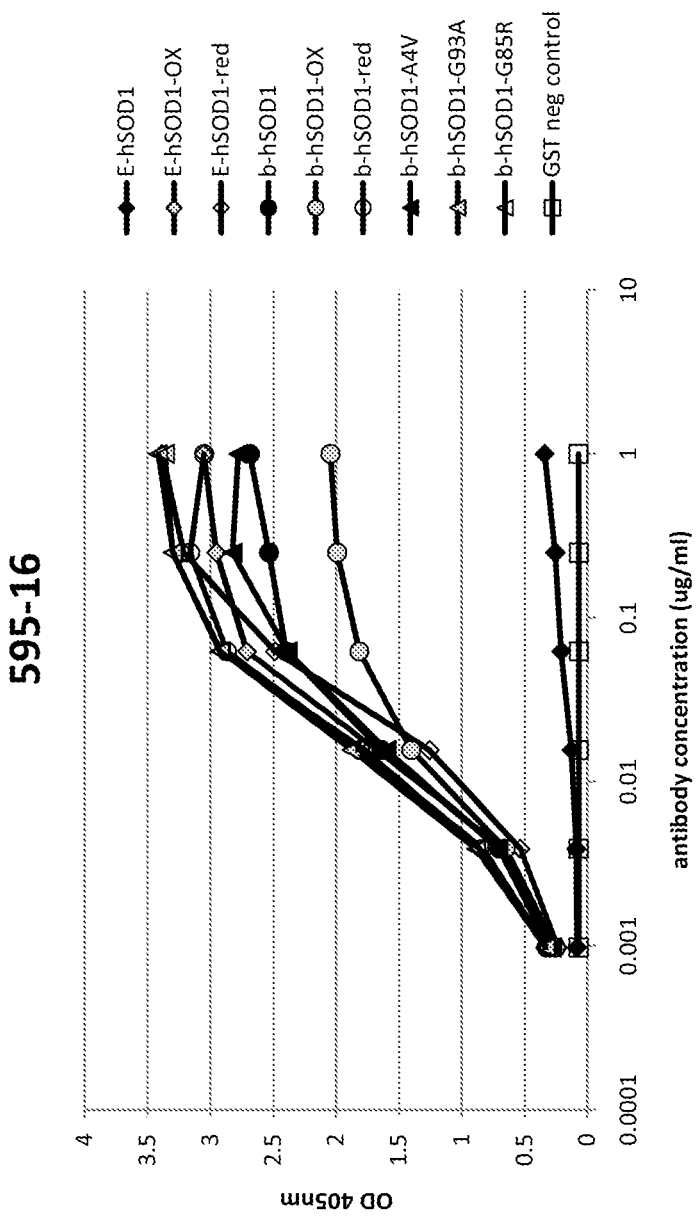
Figure 48C:
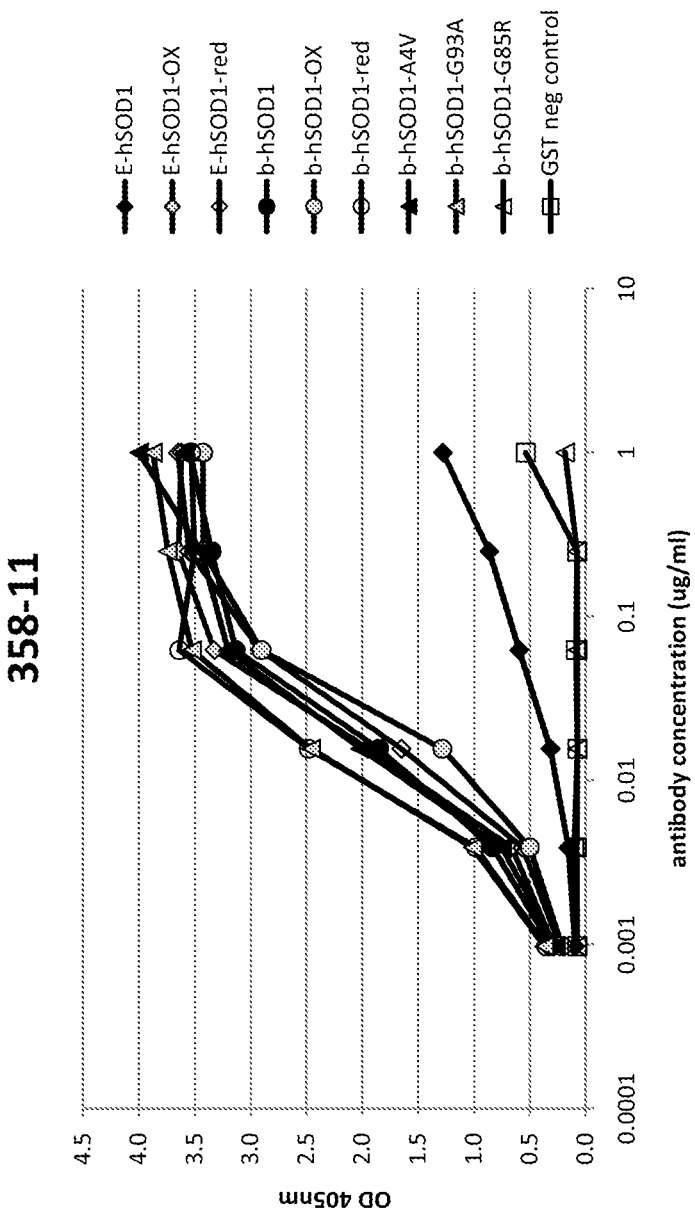
Figure 48D:
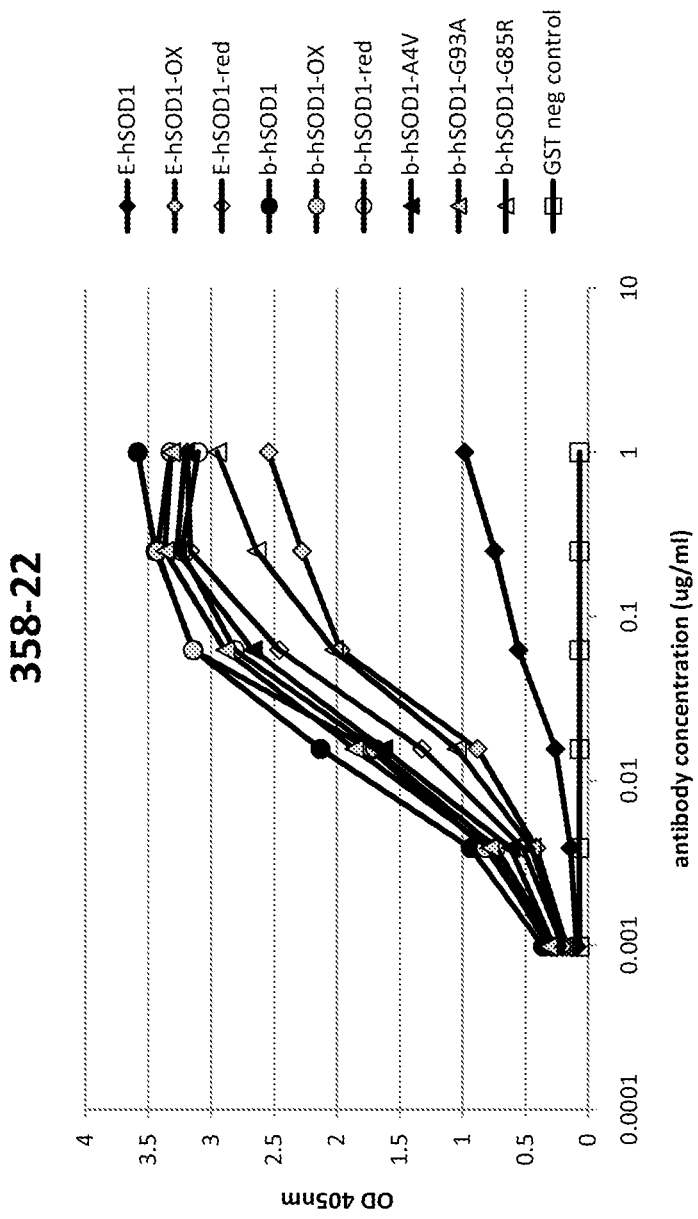
Figure 48E:
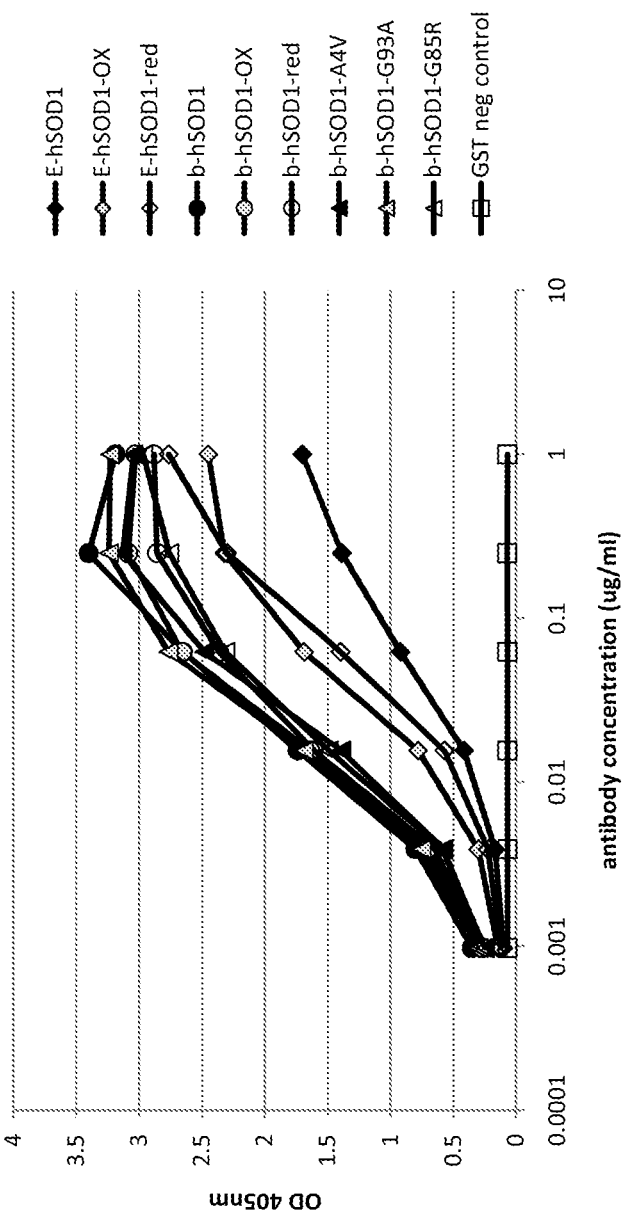
Figure 48F:
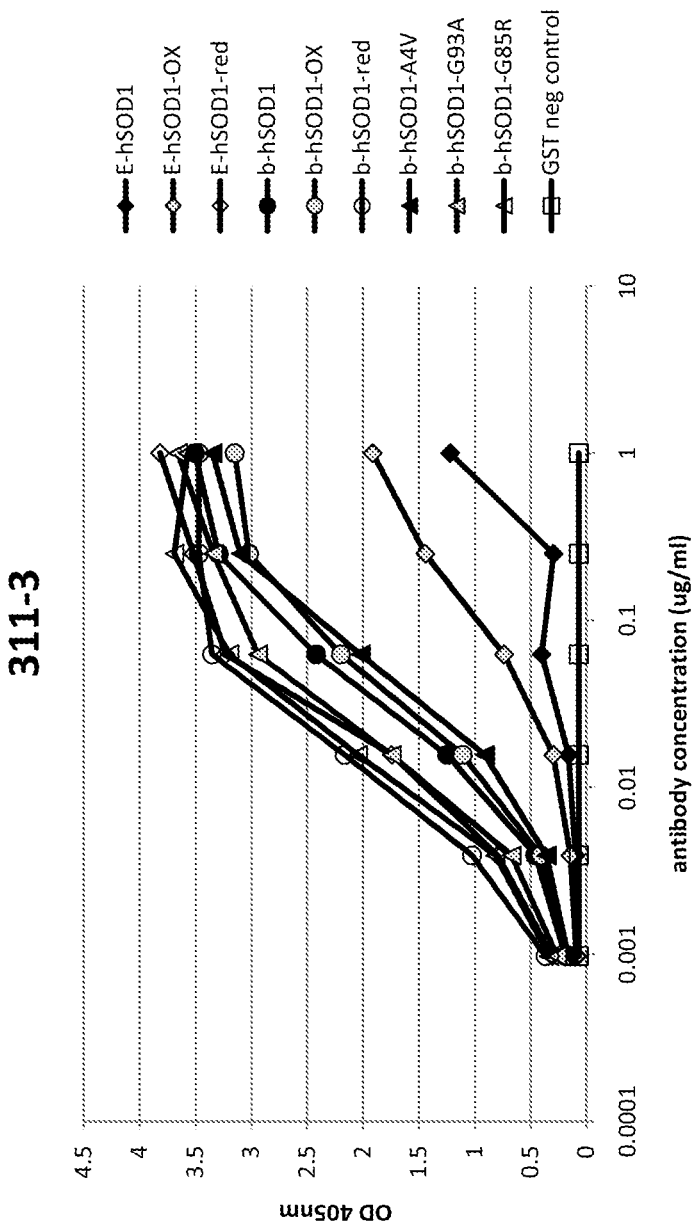
Figure 48H:
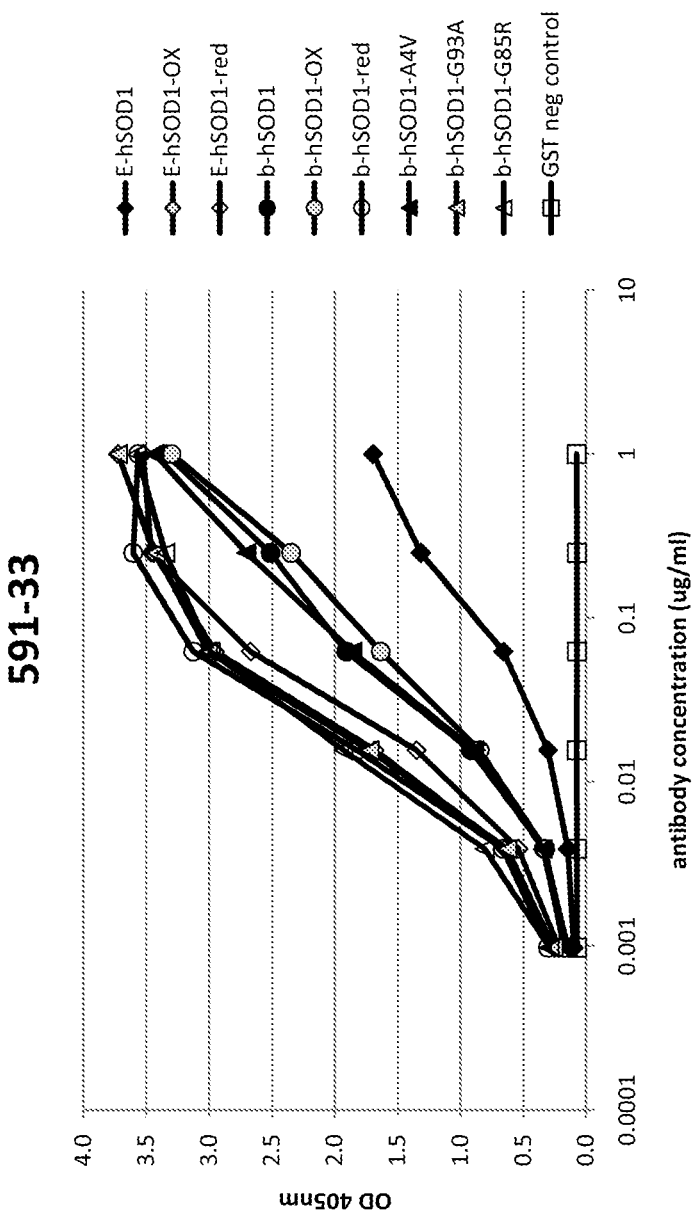
Figure 48I:
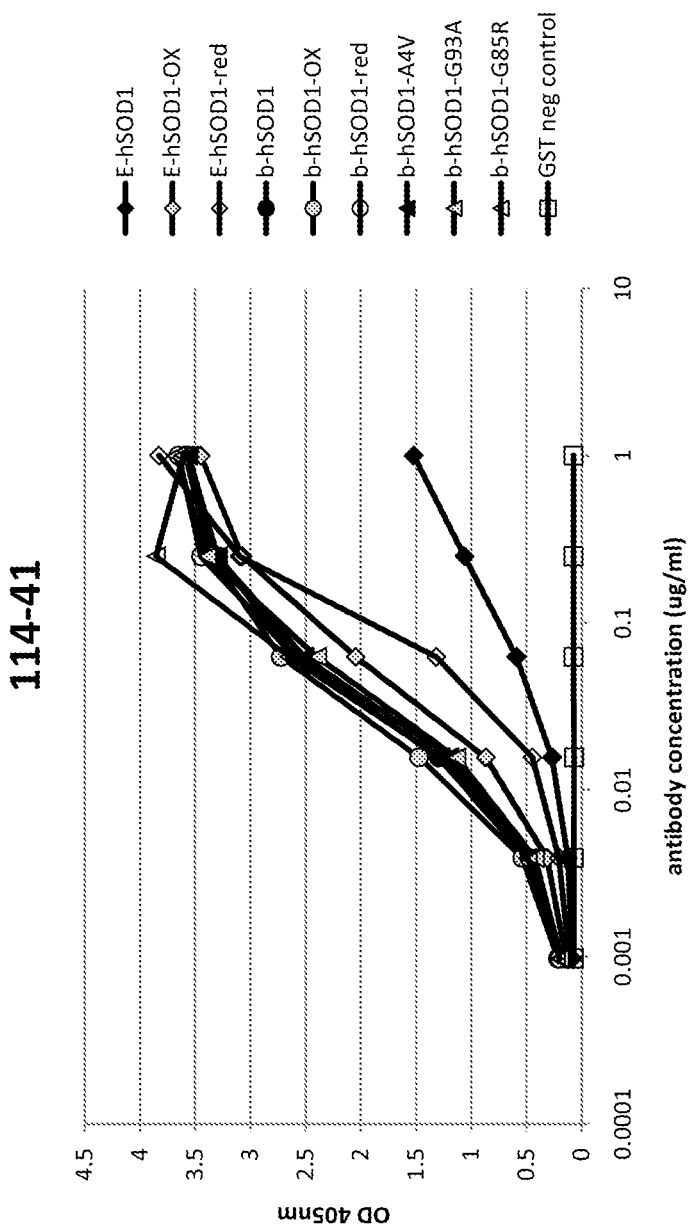
Figure 48J:
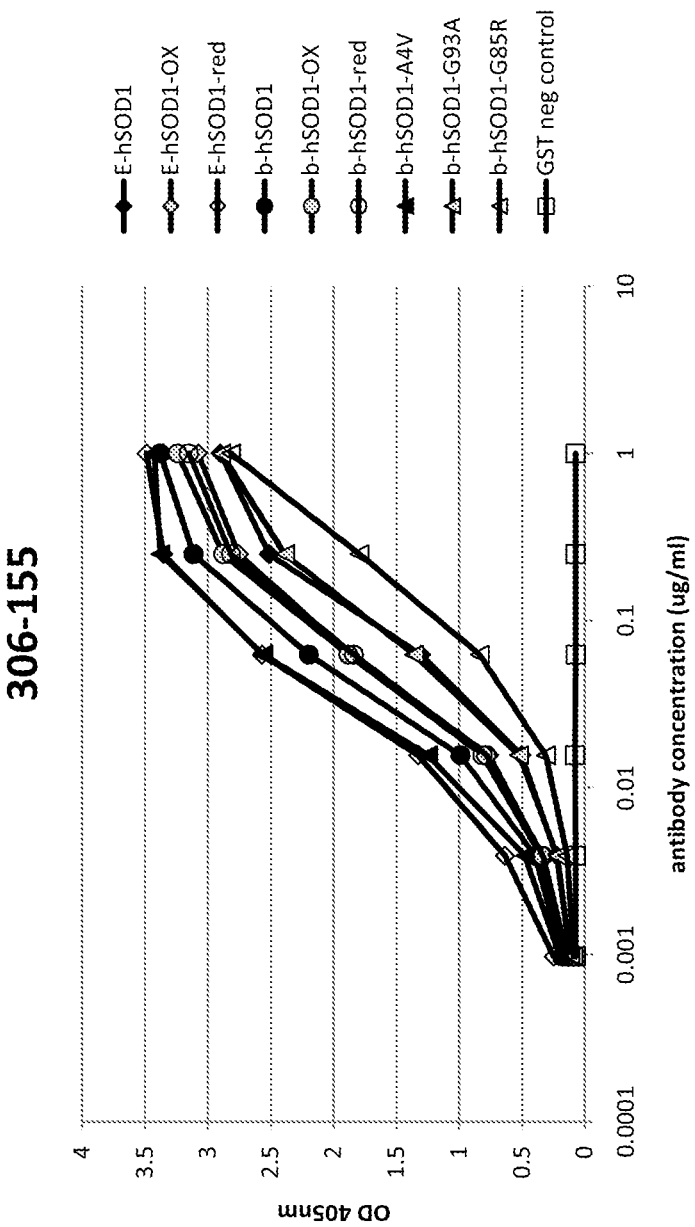
Figure 48K:
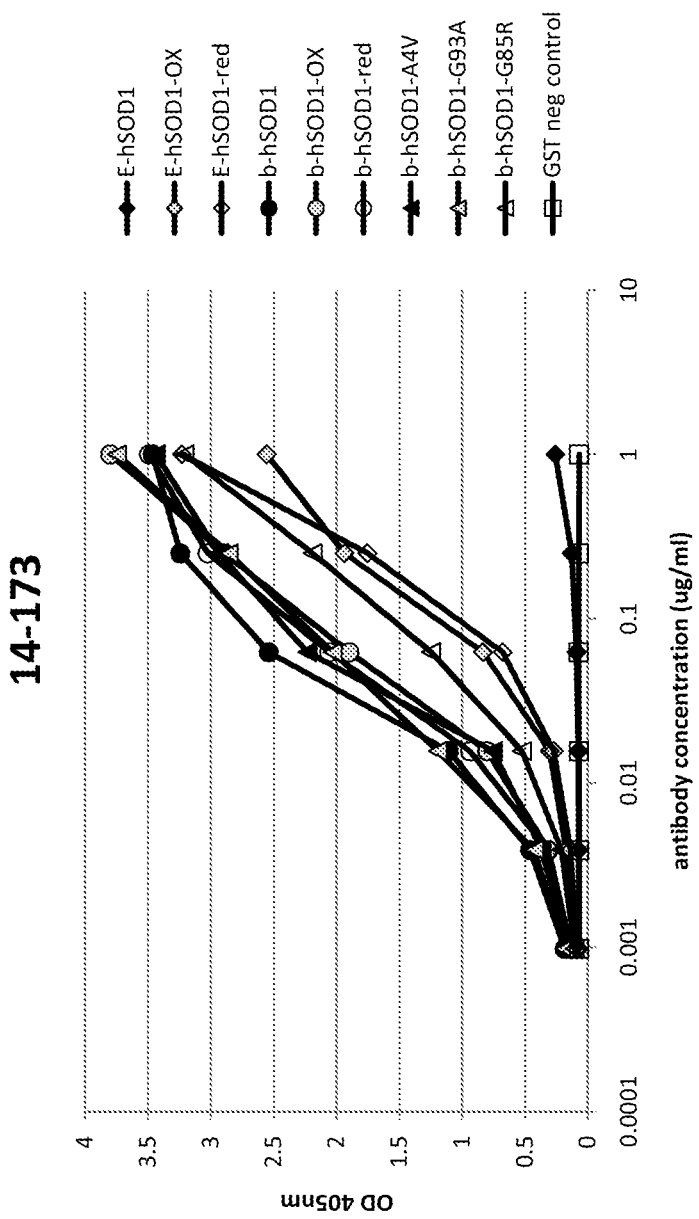
Figure 48L:
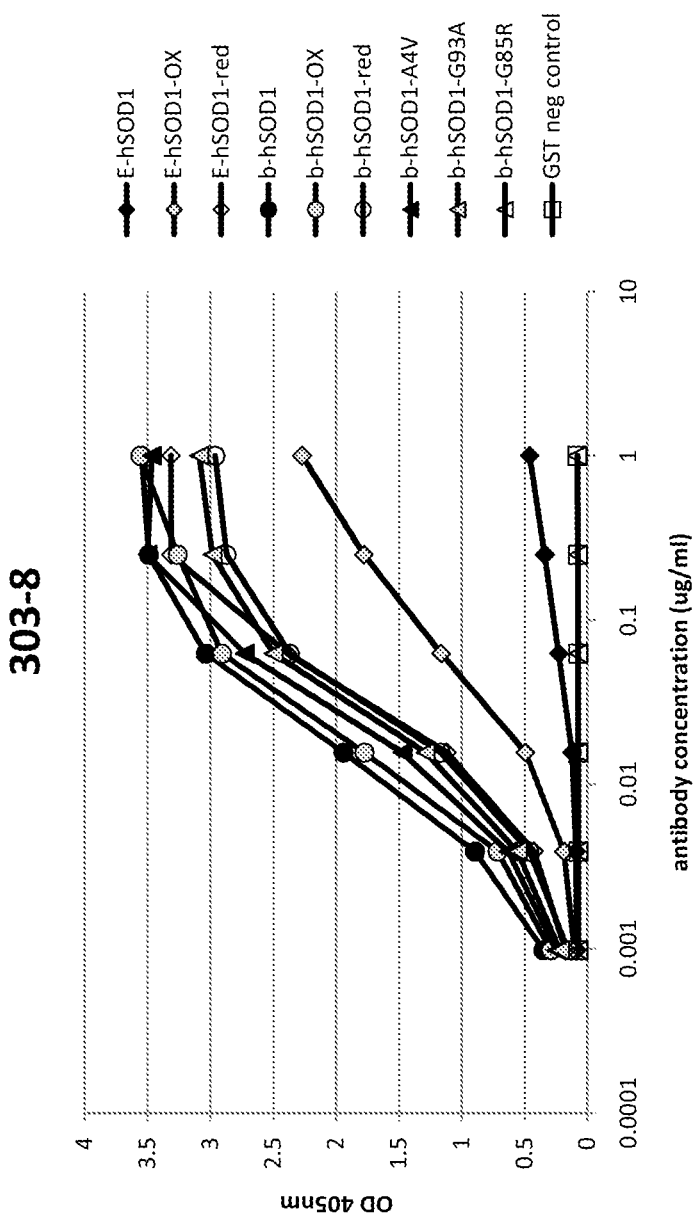
Figure 48M:
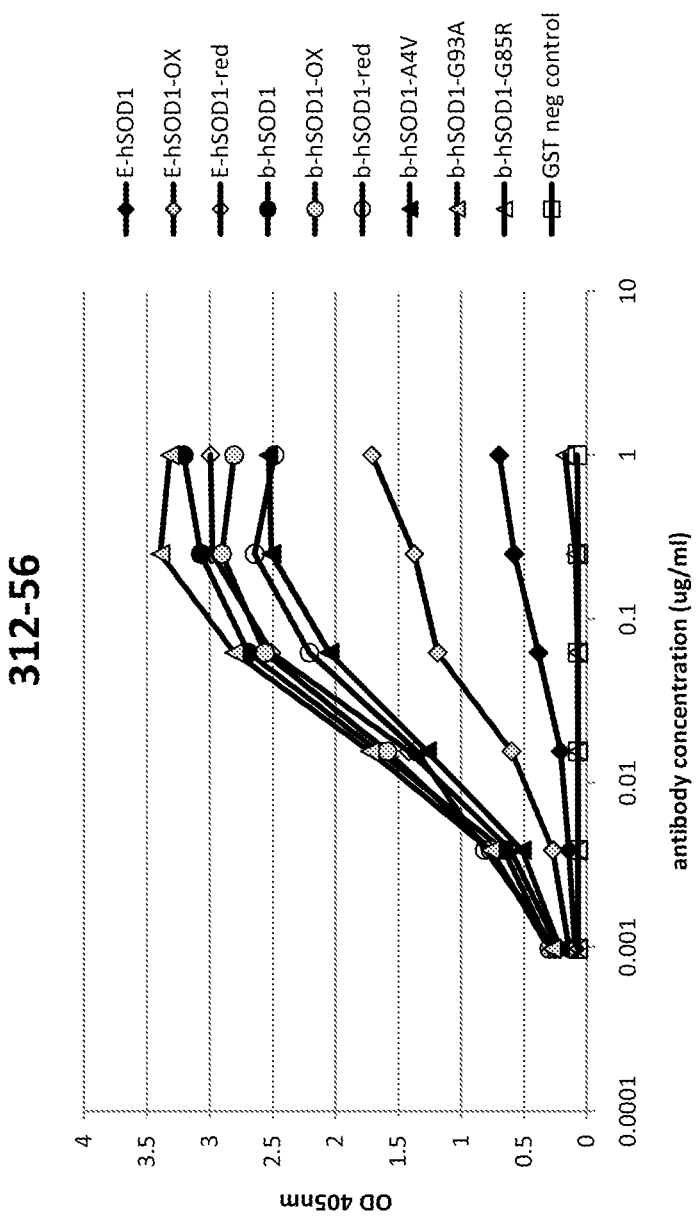

FIG. 47 is a graphical representation of the different SOD1 conformation-dependent epitopes of eight selected antibodies. Ovals that overlap represent antibodies that compete and are unable to bind b-hSOD1 simultaneously. Ovals that touch, but do not overlap, represent antibodies that compete when one of the antibodies is bound first, but do not compete for binding when the order of antibody binding is reversed. Ovals that do not overlap represent antibodies that can bind b-hSOD1 simultaneously and thus do not compete.

Figure 48B:
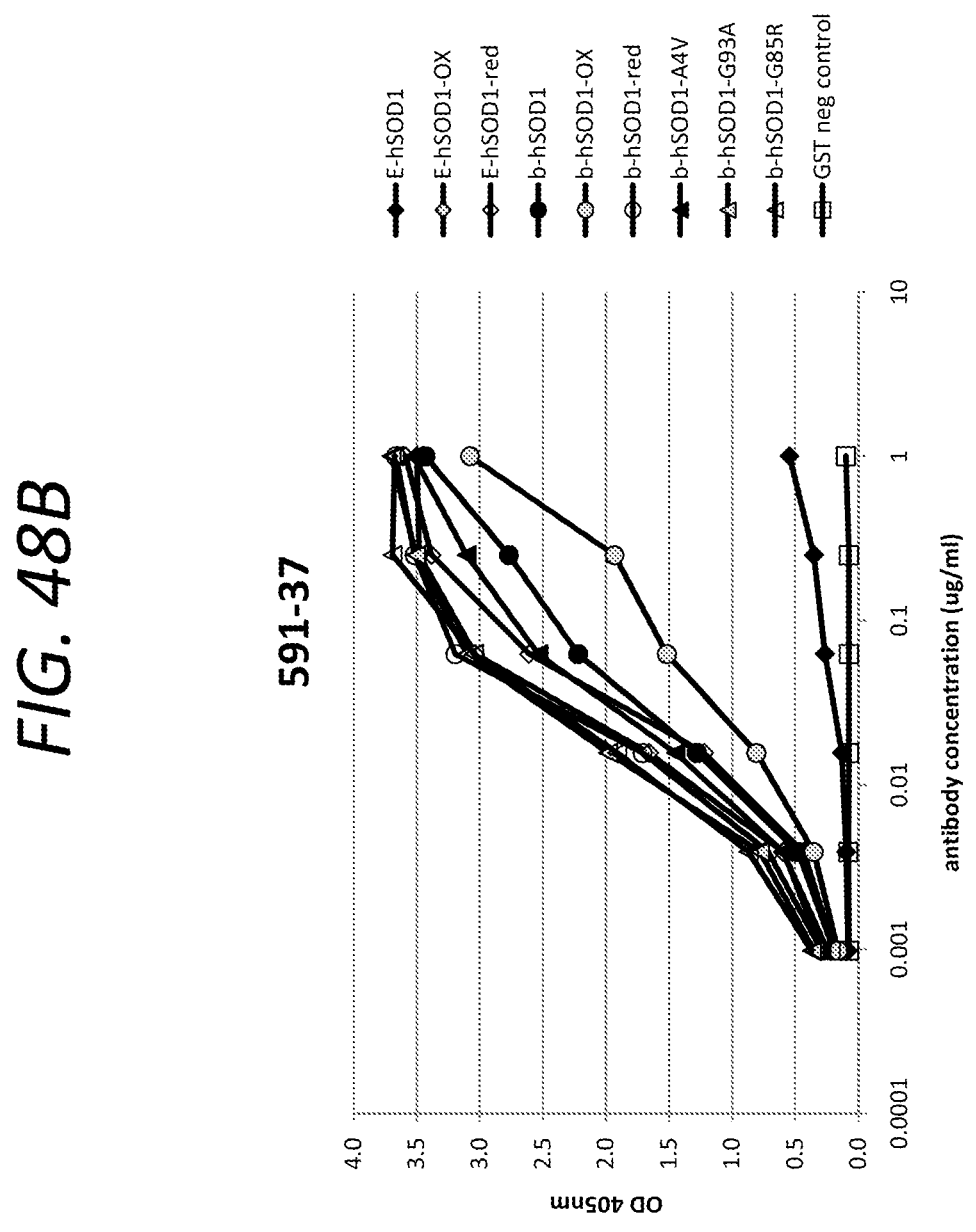

FIGS. 48A-M show graphs of results from SOD1-specific antibodies binding to various SOD1 proteins as determined by ELISA. hSOD1 purified from human erythrocytes (E-hSOD1) was modified with oxidation (E-hSOD1-OX) or reduction (E-hSOD1-red). hSOD1 purified from bacteria as a glutathione sulfotransferase fusion protein (b-hSOD1) was modified with oxidation (b-hSOD1-OX) or reduction (b-hSOD1-red). Point mutants were introduced into the gene expressing b-hSOD1 and individually expressed and purified—alanine at amino acid position 4 to a valine (A4V), glycine at amino acid position 93 to an alanine (G93A), and glycine at amino acid position 85 to an arginine (G85R). Thirteen SOD1 specific antibodies (A through M) were assayed for the capacity to bind the various SOD1 proteins. The antibody used in the ELISA is listed above the graph and the proteins tested in ELISA are listed in the legend to the right of the graph.

Figure 49A:
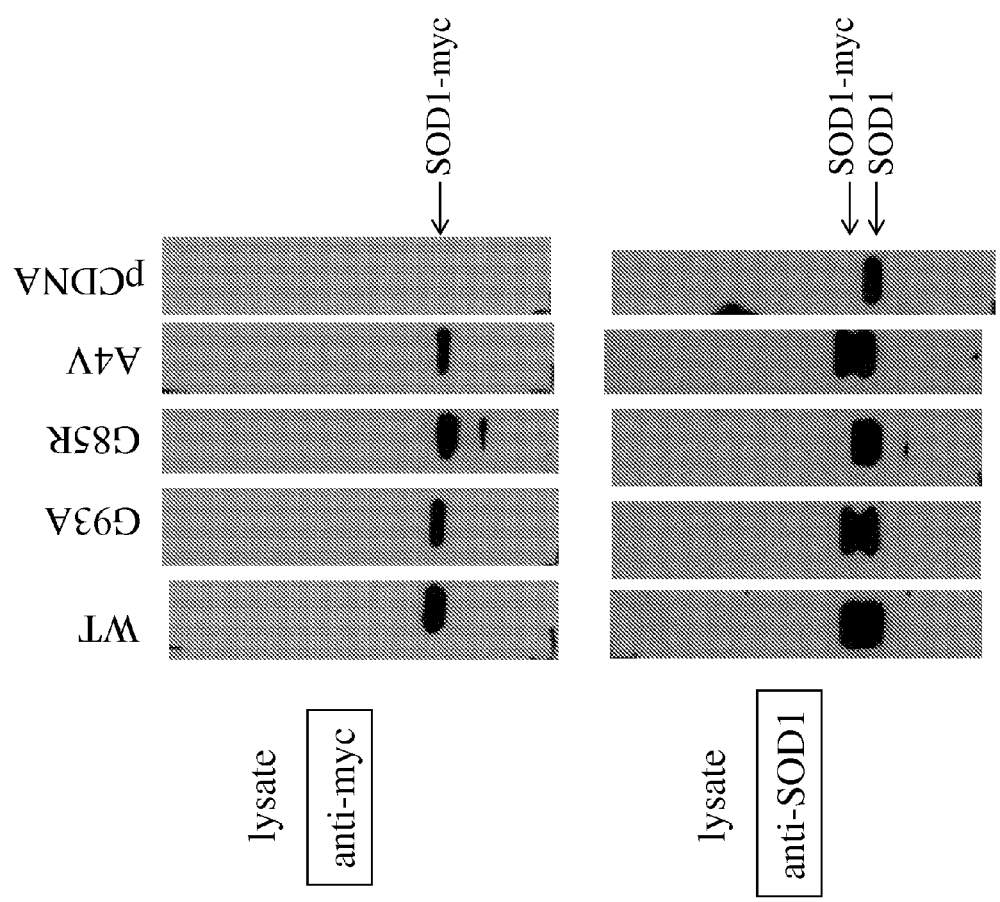

FIGS. 49A-P show immunoblots detecting the immunoprecipitation of various hSOD1 proteins expressed in human cells using thirteen antibodies specific for SOD1. The human-derived cell line, HEK-293T, was transiently transfected with constructs engineered to express hSOD1 with a myc epitope tag. Point mutants were introduced into the gene expressing hSOD1 with a myc tag and also expressed—alanine at amino acid position 4 to a valine (A4V), glycine at amino acid position 93 to an alanine (G93A), and glycine at amino acid position 85 to an arginine (G85R). The HEK-293T cell line also has endogenously expressed hSOD1 that lacks the myc tag. Cells were also transfected with negative control DNA that did not express SOD1-pcDNA. A) The expression of the SOD1 proteins was determined by lysing the cells and analyzing the lysates by SDS-PAGE and immunoblotting with antibody specific for the myc tag or polyclonal antibody specific for hSOD1. The position of migration of hSOD1-myc and hSOD1 are indicated to the right of the immunoblots. B) Lysates were used in immunoprecipitations with protein A sepharose beads alone (no Mab) and analyzed by SDS-PAGE and immunoblots with antibody specific for the myc tag or polyclonal antibody specific for hSOD1. The position of migration of a non-specific high molecular weight (HMW) band is indicated to the right of the immunoblots. C) Lysates were used in immunoprecipitations with protein A sepharose beads and an isotype matched negative control antibody (Neg cont Mab) and analyzed by SDS-PAGE and immunoblots. D-P) Lysates were used in immunoprecipitations with protein A sepharose beads and separately tested with thirteen antibodies specific for SOD1 and analyzed by SDS-PAGE and immunoblots. The precipitating antibody is listed to the left of the immunoblots and the protein found in the lysate is listed above the immunoblots.

FIG. 50 shows immunoblots detecting the immunoprecipitation of mouse SOD1 protein expressed in mouse cells using eleven antibodies specific for hSOD1. Expression of SOD1 in mouse neuroblastoma cells (MNA) was assessed by SDS-PAGE followed by immunoblot with rabbit anti-SOD1 (lysate). The position of migration of SOD1 as well as position of a non-specific high molecular weight (HMW) band is indicated to the right of the immunoblots. MNA lysates were precipitated with 11 human anti-hSOD1 antibodies as well as a control, isotype matched irrelevant antibody (Neg control) which are listed above the immunoblots.

Figure 51:
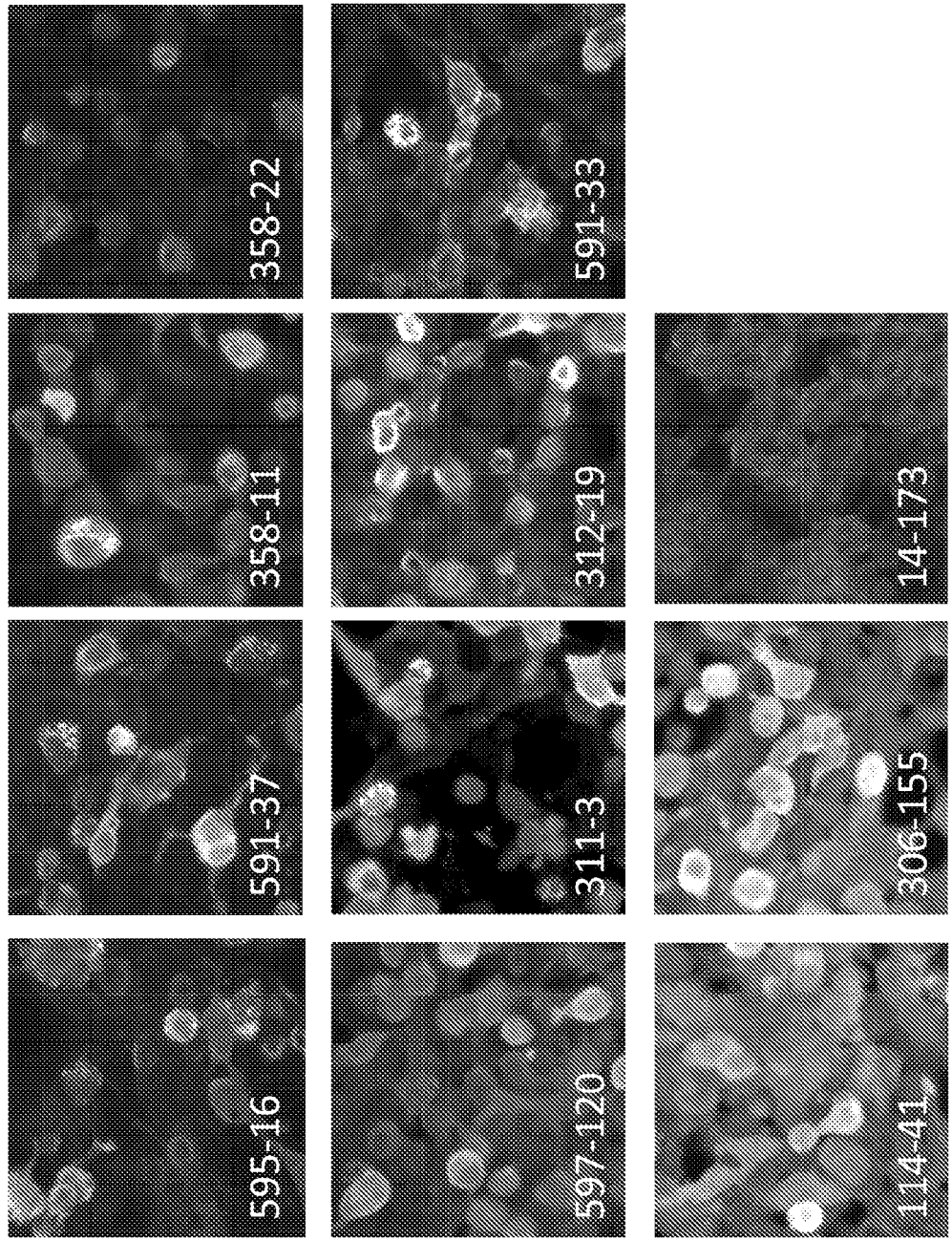

FIG. 51 shows fluorescent images of human cells expressing various hSOD1 proteins and stained with eleven SOD1 specific antibodies. HEK-293T cells were transiently transfected with a construct to express hSOD1 with a myc tag and an engineered point mutant changing the glycine at amino acid position 93 to an alanine (G93A). The HEK-293T cell line also has endogenously expressed hSOD1 that would lack the myc tag. The antibody used for staining is listed in the lower left corner of each image.

Figure 52:
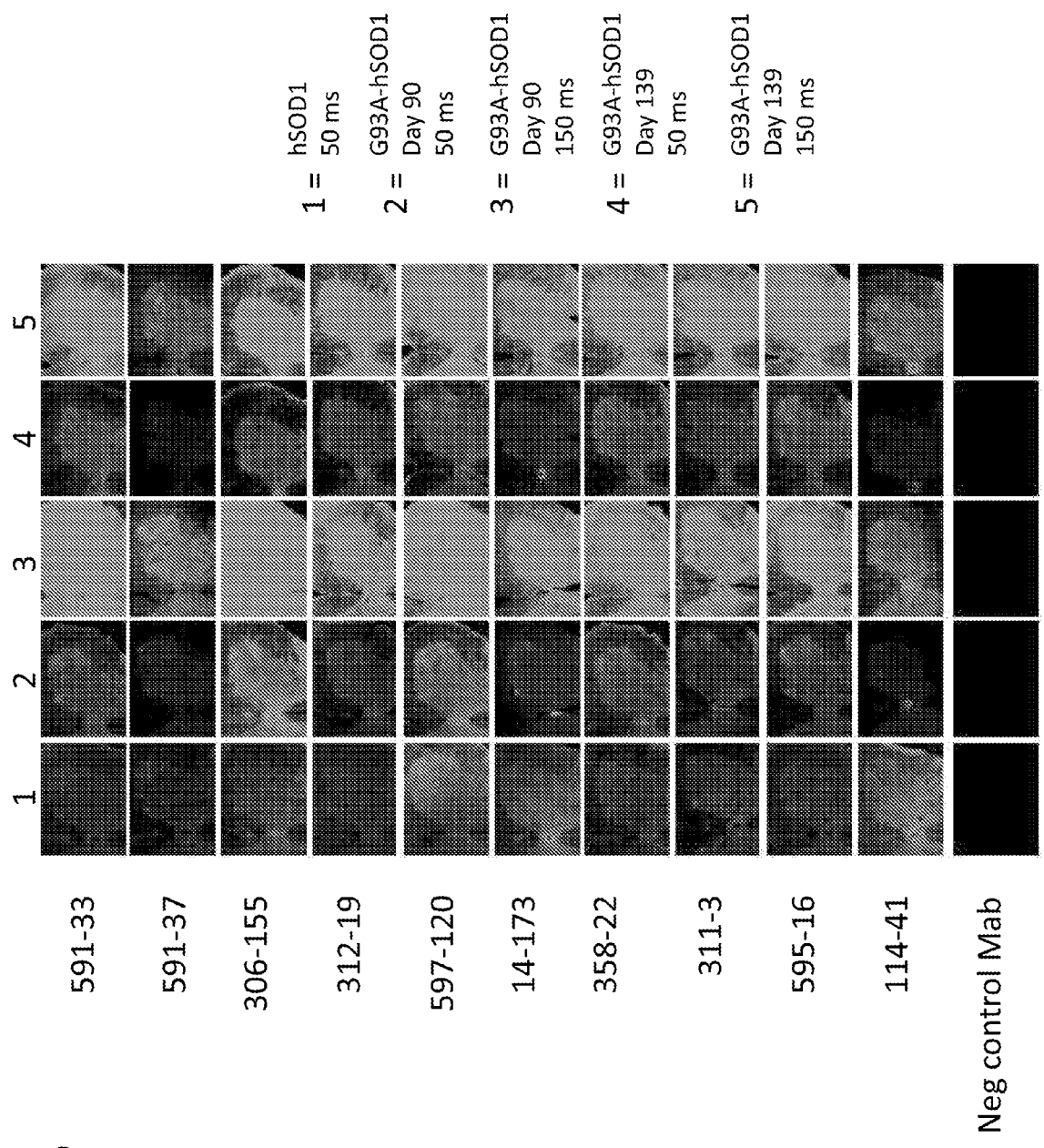

FIG. 52 shows images of immunohistochemistry staining of spinal cord tissue from mice transgenic for various hSOD1 proteins with ten SOD1 specific antibodies. Tissue was analyzed from mice transgenic for hSOD1 (1) or transgenic for hSOD1 with a point mutation changing the glycine at amino acid position 93 to an alanine (G93A) prior to the onset of ALS symptoms at 90 days after birth (2 and 3) or at the end stage of the ALS disease at 139 days after birth (4 and 5). Tissue sections were separately incubated with eleven SOD1 specific antibodies and imaged with a fluorescent microscope. Images were collected with a 50 msec exposure time (1, 2 and 4) or a 150 msec exposure time (3 and 5). An isotype matched negative control antibody (Neg control mab) was also tested.

FIG. 53 shows the results from competition studies for binding b-hSOD1 for linear and conformation-dependent SOD1-specific antibodies. Thirteen antibodies were bound to saturation to b-hSOD1 and are listed along the left of the chart. The capacity of a second antibody listed along the top of the chart to bind to the saturated b-hSOD1 was assessed and the results for each pair of antibodies marked in the chart. If the second antibody listed across the top of the chart was able to bind after b-hSOD1 was saturated with the antibody along the left side of the chart, the square is marked—both bind. If the second antibody was unable to bind, the square is marked—compete.

Figure 54A:
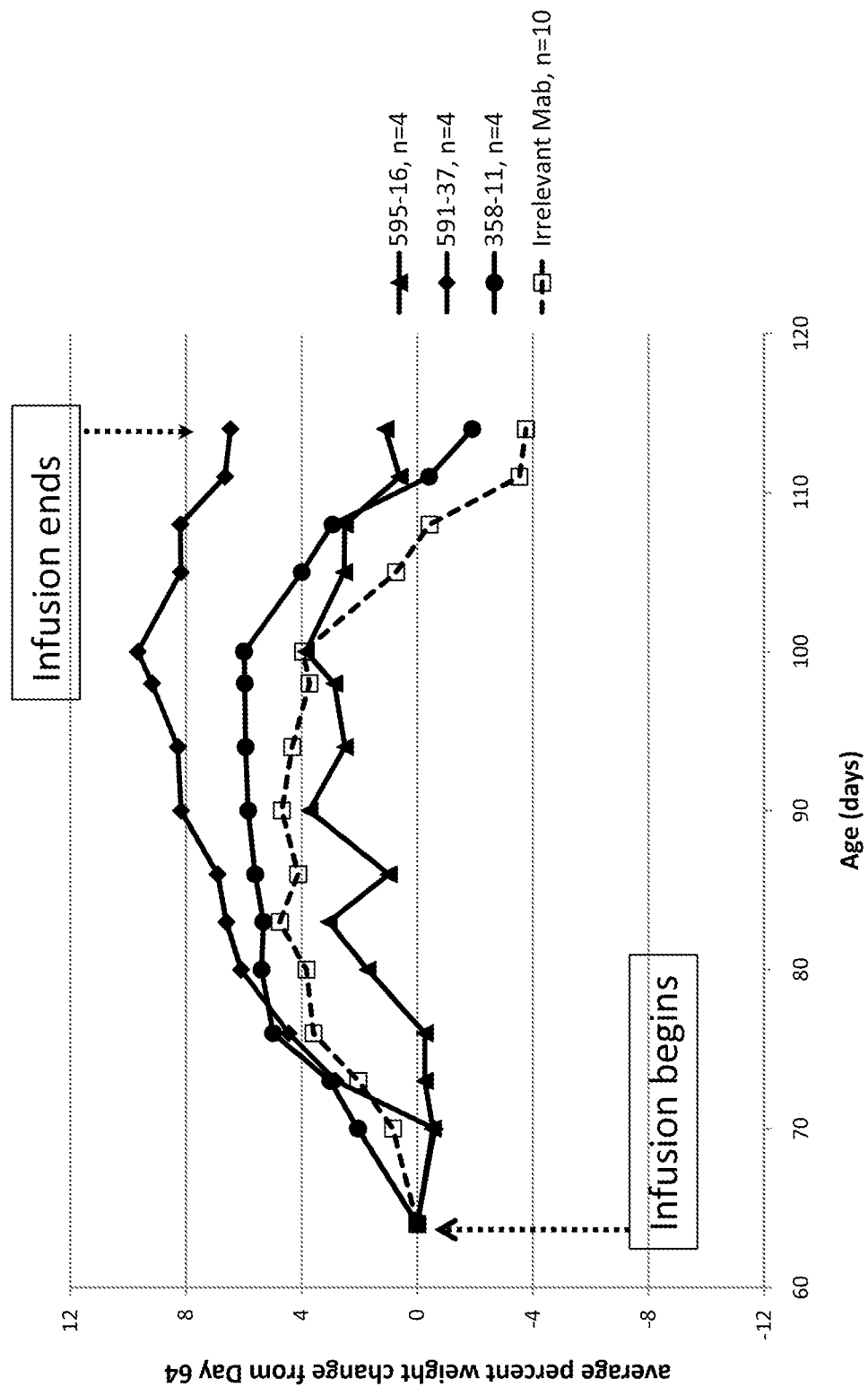
Figure 54B:
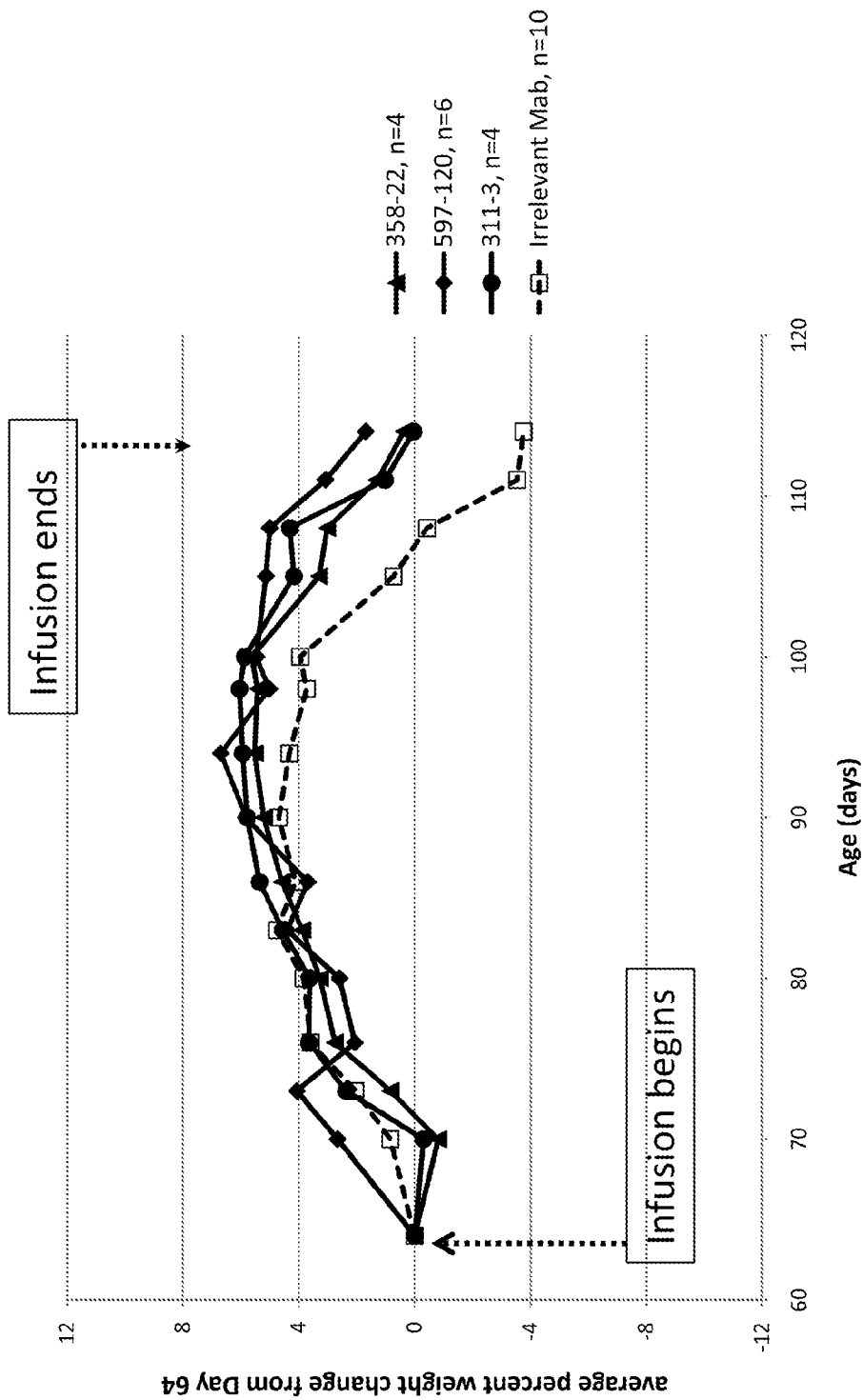
Figure 54C:
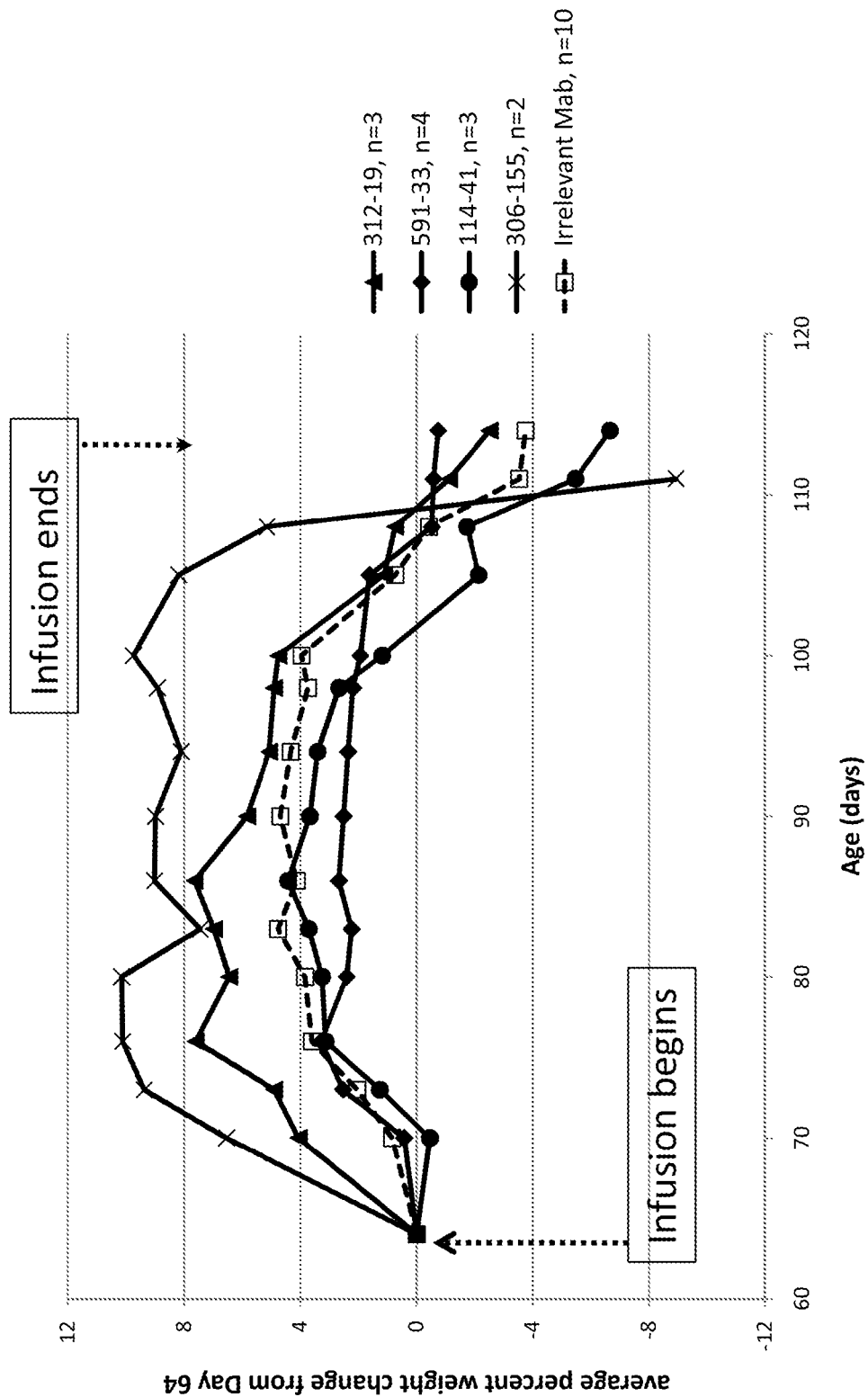

FIGS. 54A-C are graphs showing the average weight change of B6SJL-Tg(SOD1G93A)1Gur/J mice treated with monoclonal antibodies of the present invention and a control antibody. All weights were normalized as a percentage of the mouse weight at the time treatment was initiated. The time at which antibody treatment was initiated and discontinued is shown in the graph. The irrelevant control antibody is replicated on each of the three graphs.

DETAILED DESCRIPTION OF THE INVENTION

ALS is a form of motor neuron disease caused by the degeneration of motor neurons, ultimately leading to impairment of mobility, speech, and respiratory functions.

Familial, or hereditary, ALS occurs in 5-10% of all ALS cases. The remaining cases are considered "sporadic" and the causes are as yet unknown. Evidence of a misfunctioning SOD1 protein has suggested a role for the protein in both familial ALS and sporadic ALS and mutations in the SOD1 protein have been found in up to 20% of familial ALS cases. One hypothesis is that aggregation of SOD1 protein, either by mutation, misfolding, protein aggregation, or otherwise, leads to a disruption of cellular function that ultimately causes ALS.

We have discovered anti-SOD1 antibodies that bind to mutant or misfolded SOD1 protein. The anti-SOD1 antibodies may also bind to wild type SOD1. We have further discovered that the anti-SOD1 antibodies of the invention provide protection in an in vivo animal model and are useful for the treatment of ALS or amelioration of symptoms associated with ALS. We have also discovered various epitopes (linear or conformational) in SOD1 that are recognized by the anti-SOD1 antibodies of the invention. We have also discovered that anti-SOD1 antibodies that bind to the epitopes described herein (e.g., antibodies that compete with the anti-SOD1 antibodies described herein for binding to SOD1) and bind with an affinity of less than 50 nM, (e.g., 25 nM, 20 nM, 10 nM, 5 nM, 1 nM, 500 pM, 250 pM, 100 pM, 50 pM, 10 pM or lower), also provide protection in an in vivo animal model and are useful for the treatment of ALS or amelioration of symptoms associated with ALS.

In order that the present invention may be more readily understood, certain terms are first defined. Additional definitions are set forth throughout the detailed description.

I. Definitions

"Amyotrophic lateral sclerosis" or "ALS" as used herein refers to a disease of the nerve cells in the brain and spinal cord that control voluntary muscle movement. ALS is also known as Lou Gehrig's disease. As used herein, ALS includes both familial and sporadic forms of ALS. Symptoms of ALS include, but are not limited to, difficulty breathing or swallowing; head drop due to weak spinal and neck muscles; muscle cramps; muscle weakness that worsens over time;

muscle contractions; muscle spasms; paralysis; speech problems; voice changes; drooling; ankle, feet, and leg swelling; and weight loss. Diagnosis of ALS is complicated but generally involves a complete neurological exam and clinical testing.

The term "SOD," "SOD-1," or "SOD1" as used herein refers to superoxide dismutase-1 and includes all analog and mutant forms from all species, particularly human SOD1 (hSOD1). The amino acid sequence (SEQ ID NO: 317) and the nucleic acid sequence (SEQ ID NO: 318) of human SOD1 is provided in FIGS. 45 and 38, respectively. In humans, three forms of superoxide dismutase have been identified. SOD1 is located in the cytoplasm and is generally found as a dimer. SOD2 is found in the mitochondria and SOD3 is extracellular and both are generally found as tetramers. SOD1 and SOD3 contain copper and zinc, while SOD2 has manganese in its reactive centre.

"Wild-type SOD1" refers to a SOD1 protein having a native or naturally occurring amino acid sequence. The amino acid sequence of human SOD1 is provided in SEQ ID NO: 317 and the nucleic acid sequence is provided in SEQ ID NO: 318. "Wild-type" can also refer to the normal native structure of a specific protein (e.g. the atomic level coordinates of the crystal structure of native dimeric SOD1 protein is available in the Protein Data Bank under the reference 2C9V. Wild-type folded SOD1 is optionally referred to as "natively folded" SOD1, "normally folded" SOD1, or "properly folded" SOD1.

"Misfolded" as used herein refers to the secondary and tertiary structure of a protein, and indicates that the protein has adopted a conformation that is not normal for that protein in its properly functioning state. Although misfolding can be caused by mutations in a protein, such as amino acid deletion, substitution, or addition, wild-type sequence protein can also be misfolded in disease, and expose disease-specific epitopes for instance, as a result of microenvironmental conditions and/or amino acid modification such as nitration, oxidation, carbonylation or other modification. Misfolded SOD1 includes abnormally folded SOD1 conformations that may or may not be due to mutations in the SOD1 protein sequence.

"Mutant SOD1" refers to forms of SOD1, which may or may not be endogenous forms of SOD1, that occur as a result of genetic mutation, amino acid substitution, alteration, or deletion. Generally, mutant SOD1 includes any alteration in the amino acid sequence that has been shown to be associated with disease, including but not limited to familial or sporadic ALS. Non-limiting examples of mutations in SOD1 associated with ALS include A4V, H46R, G85R, and G93A.

The term "antibody" as used herein includes intact antibodies (monoclonal or polyclonal), fragments of antibodies, antibody dimers; bispecific antibodies; minibodies; single chain antibodies; single domain antibodies; and diabodies. Also included are intact antibodies and fragments that have been mutated or altered either in their constant and/or variable region (e.g., mutations to produce chimeric, partially humanized, or fully humanized antibodies, as well as to produce antibodies with a desired trait, e.g., enhanced SOD1 binding and/or reduced FcR binding). Generally, an "intact antibody" refers to a protein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. The heavy chain constant region includes three domains, $C_H1$, $C_H2$ and $C_H3$. Each light chain is comprised of a light chain variable region (abbreviated herein as $V_L$) and a light chain constant region. The light chain constant region includes one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (CIq) of the classical complement system. Fragments of antibodies, also included in the present invention, generally include an "antigen binding portion" of an antibody (e.g., an Fab, Fab', F(ab')$_2$, Fd, Fv, scFv, dsFv, or ds-scFv). The term "antigen-binding portion" of an antibody (or simply "antibody portion"), as used herein, refers to one or more fragments of an antibody that retain the ability to specifically bind to an antigen (e.g., SOD1). Examples of binding fragments include but are not limited to (i) an Fab fragment, a monovalent fragment that includes one constant and one variable domain of the heavy and light chains (e.g., a $V_L$, $V_H$, $C_L$ and $C_H1$ domains) and may be generated by enzymatic cleavage (e.g., papain cleavage) of an intact antibody; (ii) an Fab' fragment, a monovalent fragment similar to the Fab fragment but that is generated by cleavage C-terminal to the first disulfide bridge (e.g., by pepsin cleavage followed by treatment with a mild reducing agent to release the disulfide bridge) and that has additional amino acids at the C-terminus as compared to the Fab fragment; (iii) an F(ab')$_2$ fragment, a bivalent fragment that includes two Fab fragments linked by a disulfide bridge at the hinge region; (iv) an Fd fragment consisting of the $V_H$ and $C_H1$ domains; (v) an Fv fragment which includes the $V_L$ and $V_H$ domains of a single arm of an antibody; (vi) a single-chain variable fragment (scFv), which is a fusion protein of the $V_L$ and $V_H$ domains connected by a short peptide linker (generally 10 to 24 amino acids) that is usually rich in glycine for flexibility, as well as serine or threonine for solubility, and can either connect the N-terminus of the $V_H$ with the C-terminus of the $V_L$, or the N-terminus of the $V_L$ with the C-terminus of the $V_H$; (vii) a disulfide-stabilized Fv fragment (dsFv) in which the $V_H$-$V_L$ heterodimer is stabilized by an interchain disulfide bond engineered between structurally conserved framework positions distant from complementarity-determining regions; (viii) a ds-scFv, in which the scFv fragment is stabilized by an interchain disulfide bond; (ix) a single domain Ab, which includes the variable domain of either the heavy or the light chain (e.g., a $V_H$ domain); (x) an isolated complementarity determining region; and (xi) a combination of two or more (e.g., 2, 3, 4, 5, or 6) isolated CDRs which may optionally be joined by a synthetic linker. Antibodies and antibody fragments are obtained using conventional techniques known to those with skill in the art, and are screened for utility using assays known in the art and described herein. Antigen-binding portions can be produced by recombinant DNA techniques, or by enzymatic or chemical cleavage of intact immunoglobulins.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which typically include different antibodies directed against different determinants (epitopes), each monoclonal antibody is directed against a single determinant (epitope) on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495, 1975, or may be made by recombinant DNA methods (see, e.g., U.S. Pat. No. 4,816,567). The "monoclonal antibodies" may also be isolated from phage antibody libraries using the techniques known in the art (e.g., Clackson et al., *Nature* 352:624-628, 1991 and Marks et al., *J. Mol. Biol.* 222:581-597, 1991, for example).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. U.S.A.* 81:6851-6855, 1984).

"Humanized" forms of non-human (e.g., murine) antibodies are chimeric antibodies which contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522-525, 1986; Riechmann et al., *Nature* 332:323-329, 1988; and Presta, *Curr. Opin. Struct. Biol.* 2:593-596, 1992.

The term "human antibody" or "fully human antibody" includes antibodies having variable and constant regions (if present) of human germline immunoglobulin sequences. Human antibodies of the invention can include amino acid residues not encoded by human germline immunoglobulin sequences (e.g., mutations introduced by random or site-specific mutagenesis in vitro or by somatic mutation in vivo) (see, Lonberg, N. et al. (1994) *Nature* 368(6474): 856-859); Lonberg, N. (1994) Handbook of Experimental Pharmacology 113:49-101; Lonberg, N. and Huszar, D. (1995) *Intern. Rev. Immunol. Vol.* 13: 65-93, and Harding, F. and Lonberg, N. (1995) *Ann. N.Y. Acad. Sci* 764:536-546). However, the term "human antibody" does not include antibodies in which CDR sequences derived from the germline of another mammalian species, such as a mouse, have been grafted onto human framework sequences (i.e., humanized antibodies).

The term "hypervariable region," "HVR," or "HV," when used herein, refers to the regions of an antibody variable domain which are hypervariable in sequence and/or form structurally defined loops. Generally, antibodies comprise six hypervariable regions; three in the $V_H$ (H1, H2, H3), and three in the $V_L$ (L1, L2, L3). A number of hypervariable region delineations are in use and are encompassed herein including but not limited to the Kabat Complementarity Determining Regions (CDRs) (Kabat et al., Sequences of Proteins of Immunological Interest, 5th Ed. Public Health Service, National Institutes of Health, Bethesda, Md. (1991)) and Chothia's reference to the location of the structural loops (Chothia & Lesk J. Mol. Biol. 196:901-17 (1987)). The AbM hypervariable regions represent a compromise between the Kabat CDRs and Chothia structural loops, and are used by Oxford Molecular's AbM antibody modeling software. Hypervariable regions may also be identified using a combination of such methods, for example, one method for the identification of CDRH1 and CDRH2 and another method for the identification of CDRH3. Hypervariable regions or CDRs may include extended hypervariable regions as follows: 24-36 (L1), 46-56 (L2) and 89-97 (L3) in the $V_L$ and 26-35 (H1), 49-65 or 50 to 65 (H2) and 93-102 (H3) in the $V_H$. The variable domain residues are numbered according to Kabat for each of these definitions. Computer generated programs based on the above methods, including but not limited to VBASE and IMGT can also be used to identify hypervariable regions.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

The term "recombinant human antibody" as used herein includes human antibodies that are prepared, expressed, created or isolated by recombinant means, such as (a) antibodies isolated from an animal (e.g., a mouse) that is transgenic for human immunoglobulin genes or a hybridoma prepared therefrom, (b) antibodies isolated from a host cell transformed to express the antibody, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "antibody mutant" or "antibody variant" refers to an amino acid sequence variant of a reference antibody (e.g., a species-dependent antibody) wherein one or more of the amino acid residues of the reference antibody have been modified. Such mutants necessarily have less than 100% sequence identity or similarity with the reference antibody. In a preferred embodiment, the antibody mutant will have an amino acid sequence having at least 75% amino acid sequence identity or similarity with the amino acid sequence of either the heavy or light chain variable domain of the reference antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e., same residue) or similar (i.e., amino acid residue from the same group based on common side-chain properties, see below) with the reference antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

A "diabody" as used herein refers to an antibody that includes a $V_H$ domain connected to a $V_L$ domain on the same polypeptide chain ($V_H$-$V_L$) connected by a peptide linker that is too short to allow pairing between the two domains on the same chain. This forces pairing with the complementary domains of another chain and promotes the assembly of a dimeric molecule with two functional antigen binding sites. Diabodies can be monospecific, bispecific, or multispecific.

A "bispecific" or "bifunctional antibody" is a hybrid antibody having two different heavy/light chain pairs and two different binding sites. Bispecific antibodies can be produced by a variety of methods known in the art including fusion of hybridomas or linking of Fab fragments. See, e.g., Songsivilai & Lachmann, Clin. Exp. Immunol. 79:315-321 (1990); Kostelny et al, J. Immunol. 148, 1547-1553 (1992). As used herein, antibodies or antigen binding fragments thereof can be bispecific.

By "epitope" is meant a sequence of amino acids which, either as a result of linear structure or three dimensional conformation, forms the binding site for an antibody. Epitopes can be formed both from contiguous amino acids or noncontiguous amino acids juxtaposed by tertiary folding of a protein. Epitopes formed from contiguous amino acids are typically retained on exposure to denaturing solvents, whereas conformational epitopes formed by tertiary folding are typically lost on treatment with denaturing solvents. An epitope typically includes at least 3, 4, 5, 6, 7, 8, 9, 10, 11, 12, 13, 14 or 15 amino acids in a unique linear or spatial conformation. Methods of determining spatial conformation of epitopes include techniques in the art and those described herein, for example, x-ray crystallography and 2-dimensional nuclear magnetic resonance. See, e.g., Epitope Mapping Protocols in Methods in Molecular Biology, Vol. 66, G. E. Morris, Ed. (1996).

A "conformational epitope" refers to a sequence of discontinuous amino acid residues to form a three-dimensional structure in order for binding between the epitope and the antibody to occur.

A "non-conformational epitope" or "linear epitope" refers to a linear epitope which is typically comprised of a continuous amino acid sequence which is sufficient for binding with an antibody capable of binding to such an epitope. A linear epitope can be distinguished from a conformational epitope in that under denaturing conditions, (e.g., in an immunoblot assay as described herein), the epitope can still be bound by an antibody that recognizes such an epitope. Linear epitopes can be used for vaccine development, the raising of antibodies thereto, and/or for the use in active immunotherapy alone or in combination with passive immunotherapy. Conformational epitopes can also be used for such purposes but will generally be placed within the context of a protein scaffold so as to retain epitope conformation.

Epitopes that are "disease specific" in the context of the present specification, are epitopes that are presented or accessible selectively by one or more misfolded forms of SOD1 that are characteristic of a particular disease (e.g., ALS). A "disease specific" or "ALS specific" epitope refers to an epitope that is selectively presented or accessible on monomeric SOD1 or misfolded SOD1 in monomeric, dimeric or aggregated forms, but not on the molecular surface of the native, correctly folded, homodimeric form of SOD1. Non-limiting examples of epitopes of the invention include amino acids 40-47 (SEQ ID: 307), 42-49 (SEQ ID: 313), 63-71 (SEQ ID: 309), 80-88 (SEQ ID: 311), and 107-121 (SEQ ID NO:315) of hSOD1 (SEQ ID NO: 317). Such epitopes may be linear or conformational epitopes. These exemplary epitopes are provided in the amino acid sequence of hSOD1 provided in FIG. 45.

As used herein, the terms "specific binding," "selective binding," "selectively binds," and "specifically binds," refer to the ability of an antibody to bind to a SOD1 protein or nucleic acid of the invention, without substantially recognizing and binding other molecules present in a sample (e.g., a biological sample which includes a SOD1 polypeptide or nucleic acid of the invention). In one non-limiting example, an antibody that specifically binds a mutant or misfolded SOD1 polypeptide of the invention does not bind wild-type SOD1 protein. In another non-limiting example, an antibody that specifically binds SOD1 protein does not bind SOD2 or SOD3.

An antibody is said to "competitively inhibit" binding of a reference antibody to a given epitope if it preferentially binds to that epitope to the extent that it blocks, to some degree, binding of the reference antibody to the epitope. Competitive binding is determined in an assay in which the immunoglobulin under test inhibits specific binding of a reference antibody to a common antigen, such as SOD1. Numerous types of competitive binding assays are known, for example: solid phase direct or indirect radioimmunoassay (RIA), solid phase direct or indirect enzyme immunoassay (EIA), sandwich competition assay (see Stahli et al, *Methods in Enzymology* 9:242 (1983)); solid phase direct biotin-avidin EIA (see Kirkland et al, *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using $I^{125}$ label (see Morel et al, MoI. Immunol. 25(1):7 (1988)); solid phase direct biotin-avidin EIA (Cheung et al., Virology 176:546 (1990)); and direct labeled RIA. (Moldenhauer et al, Scand J. Immunol 32:77 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Usually, when a competing antibody is present in excess, it will inhibit specific binding of a reference antibody to a common antigen by at least 50-55%, 55-60%, 60-65%, 65-70%, 70-75%, or more.

As used herein, the term "affinity" refers to a measure of the strength of the binding of an individual epitope with the complementarity determining region of an immunoglobulin molecule. See, e.g., Harlow et al., Antibodies: A Laboratory Manual, (Cold Spring Harbor Laboratory Press, 2nd ed. 1988) at pages 27-28. The term "$K_D$," as used herein, is intended to refer to the dissociation equilibrium constant of a particular antibody-antigen interaction. Typically, the antibodies of the invention bind to SOD1 with a dissociation equilibrium constant ($K_D$) of less than approximately $10^{-7}$M, such as less than approximately $10^{-8}$M, $10^{-9}$M or $10^{-10}$M or even lower when determined using standard methods known in the art. Affinity is measured using any art known methods or platforms such as the surface plasmon resonance (SPR) technology in a BIACORE instrument or an OCTET instrument.

As used herein, the term "avidity" refers to the overall stability of the complex between a population of immunoglobulins and an antigen, that is, the functional combining strength of an immunoglobulin mixture with the antigen. See, e.g., Harlow et al., supra, at pages 29-34. Avidity is related to both the affinity of individual immunoglobulin molecules in the population with specific epitopes, and also the valencies of the immunoglobulins and the antigen. For example, the interaction between a bivalent monoclonal antibody and an antigen with a highly repeating epitope structure, such as a polymer, would be one of high avidity. Antibodies can also be described or specified in terms of their cross-reactivity.

As used herein, the term "cross-reactivity" refers to the ability of an antibody, specific for one antigen, to react with a second antigen; a measure of relatedness between two different antigenic substances. Thus, an antibody is cross-reactive if it binds to an epitope other than the one that induced its formation. The cross-reactive epitope generally contains many of the same complementary structural features as the inducing epitope, and in some cases, may actually fit better than the original. For example, certain antibodies have some degree of cross-reactivity, in that they bind related, but non-identical epitopes, e.g., epitopes with at least 95%, at least 90%, at least 85%, at least 80%, at least 75%, at least 70%, at least 65%, at least 60%, at least 55%, and at least 50% identity (as calculated using methods known in the art and described herein) to a reference epitope. An antibody can be said to have little or no cross-reactivity if it does not bind epitopes with less than 95%, less than 90%, less than 85%, less than 80%, less than 75%, less than 70%, less than 65%, less than 60%, less than 55%, and less than 50% identity (as calculated using methods known in the art and described herein) to a reference epitope.

The term "$K_{off}$" as used herein, is intended to refer to the off-rate constant for the dissociation of an antibody from the antibody/antigen complex.

As used herein, "isotype" refers to the antibody class (e.g., IgG, IgM, IgA, IgD, or IgE) that is encoded by heavy chain constant region genes. In one embodiment, a human monoclonal antibody of the invention is of the IgG isotype. In another embodiment, a human monoclonal antibody of the invention is of the $IgG_1$ or $IgG_2$ isotype.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived. Antibody glycoslylation can occur in the variable region or the constant region and the glycosylation pattern can be altered to increase or decrease antibody function (e.g., ADCC activity) as desired.

By "substantially identical" is meant a nucleic acid or amino acid sequence that, when optimally aligned, for example using the methods described below, shares at least 70%, 71%, 72%, 73%, 74%, 75%, 80%, 81%, 82%, 83%, 84%, 85%, 90%, 95%, 96%, 97%, 98%, 99%, or even 100% sequence identity with a second nucleic acid or amino acid sequence, e.g., an anti-SOD1 antibody sequence disclosed herein. "Substantial identity" may be used to refer to various types and lengths of sequence, such as a full-length sequence, epitopes or immunogenic peptides, functional domains, coding and/or regulatory sequences, exons, introns, promoters, and genomic sequences. Percent identity between two polypeptides or nucleic acid sequences is determined in various ways that are within the skill in the art, for instance, using publicly available computer software such as Smith Waterman Alignment (Smith, T. F. and M. S. Waterman, *J. Mol. Biol.* 147:195-7, 1981); "BestFit" (Smith and Waterman, Advances in Applied Mathematics, 482-489, 1981) as incorporated into GeneMatcher Plus™; BLAST program (Basic Local Alignment Search Tool), BLAST-2, BLAST-P, BLAST-N, BLAST-X, WU-BLAST-2, ALIGN, ALIGN-2, CLUSTAL, or Megalign (DNASTAR) software. In addition, those skilled in the art can determine appropriate parameters for measuring alignment, including any algorithms needed to achieve maximal alignment over the length of the sequences being compared. In general, for proteins, the length of comparison sequences will be at least 6 amino acids, preferably at least 7, 8, 9, 10, 20, 30, 40, 50, 60, 70, 80, 90, 100, 110, 120, 130, 140, 150, 160, 170, 180, 190, 200, 210, 220, 230, 240, or 250 amino acids or more. For nucleic acids, the length of comparison sequences will generally be at least 20, 25, 30, 50, 100, 125, 150, 200, 250, 300, 350, 400, 450, 500, 550, 600, 650, 700, 750 nucleotides or more. It is understood that for the purposes of determining sequence identity when comparing a DNA sequence to an RNA sequence, a thymine nucleotide is equivalent to a uracil nucleotide. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

A "consensus sequence" is a sequence formed from the most frequently occurring amino acids (or nucleotides) in a family of related sequences. In a family of proteins, each position in the consensus sequence is occupied by the amino acid occurring most frequently at that position in the family. If two amino acids occur equally frequently, either can be included in the consensus sequence. A "consensus framework" of an immunoglobulin refers to a framework region in the consensus immunoglobulin sequence.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

By "purified" or "isolated" is meant separated from other components that naturally accompany it. Typically, a compound (e.g., antibody or antigen binding fragment thereof) is isolated when it is at least 50%, by weight, free from proteins, flanking nucleic acids, antibodies, and naturally-occurring organic molecules with which it is naturally associated. Preferably, the antibody, or antigen binding fragment thereof, is at least 75%, more preferably, at least 80%, 85%, or 90%, and most preferably, at least 95% or 99%, by weight, purified or isolated. The antibody, or antigen binding fragment thereof, is preferably at least 2, 3, 4, 5, or 10 times as pure or isolated as the starting material, as measured using polyacrylamide gel electrophoresis, column chromatography, optical density, HPLC analysis, or Western blot analysis (Ausubel et al., supra).

By "reduce or inhibit" is meant the ability to cause an overall decrease preferably of at least 5%, 6%, 7%, 8%, 9%, 10%, 15%, 20%, 25%, 30%, 35%, 40%, 45%, 50% or more, and more preferably an overall decrease of at least 60%, 70%, 75%, 80%, 85%, 90%, 95% or more. For example, in some embodiments of the invention, reduce or inhibit can refer to the levels (polypeptide or mRNA levels) or a biological activity of a SOD1 protein or symptoms of the disorder (e.g., ALS) being treated.

By "subject" is meant a mammal, including, but not limited to, a human or non-human mammal, such as a cow, a horse, a sheep, a pig, a goat, a dog, or a cat.

By "pharmaceutically acceptable carrier" is meant a carrier that is physiologically acceptable to the treated mammal while retaining the therapeutic properties of the compound with which it is administered. One exemplary pharmaceutically acceptable carrier substance is physiological saline. Other physiologically acceptable carriers and their formulations are known to one skilled in the art and described, for example, in Remington's Pharmaceutical Sciences, (20$^{th}$ edition), ed. A. Gennaro, 2000, Lippincott, Williams & Wilkins, Philadelphia, Pa. One or more of the antibodies, or antigen binding fragments thereof, of the invention may be administered in a pharmaceutically acceptable carrier to a subject (e.g., a human).

A "pharmaceutically acceptable salt" refers to a salt that retains the desired biological activity of the parent compound and does not impart any undesired toxicological effects (see e.g., Berge, S. M., et al. (1977) J. Pharm. Sci. 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine, and the like.

By "therapeutic amount" is meant an amount that when administered, either by direct administration or by an ex vivo approach, to a patient suffering from a SOD1 mediated disorder (e.g., ALS) is sufficient to cause a qualitative or quantitative reduction (e.g., at least a 5%, 10%, 15%, 20%, 25%, 30%, 35%, 40%, 45%, 50%, 60%, 70%, 80%, 90%, or even 100% reduction) in one or more (e.g., 2, 3, 4, 5, or 6) of the symptoms of the disorder. A therapeutic amount in some embodiments includes a prophylactic amount which refers to an amount that, when administered, results in a decrease (e.g., at least a 5%, 10%, 15%, 20%, 25%, 30%, 35%, 40%, 45%, 50%, 60%, 70%, 80%, 90%, or even 100% reduction) in the likelihood of developing a SOD1 mediated disorder (e.g., ALS).

By "treating" or "ameliorating" is meant treating or ameliorating a condition or symptom(s) of the condition. To "treat disease" or use for "therapeutic treatment" refers to administering the treatment to a subject already suffering from a disease to improve the subject's condition. Preferably, the subject is diagnosed with or identified as having a predisposition for developing a SOD1 mediated disorder (e.g., ALS). As compared with an equivalent untreated control, such amelioration or degree of treatment is at least 5%, 10%, 20%, 30%, 40%, 50%, 60%, 70%, 80%, 90%, 95%, 99%, or 100%, as measured by any standard technique. Symptoms of ALS that can be ameliorated or treated by the antibodies of the invention include but are not limited to difficulty breathing or swallowing; head drop due to weak spinal and neck muscles; muscle cramps; muscle weakness that worsens over time; muscle contractions; muscle spasms; paralysis; speech problems; voice changes; drooling; ankle, feet, and leg swelling; and weight loss. Improvements in symptoms of ALS can be measured using standard methods known in the art including neurological testing and clinical testing.

The term "nucleic acid molecule," as used herein, is intended to include DNA molecules and RNA molecules. A nucleic acid molecule may be single-stranded or double-stranded, but preferably is double-stranded DNA.

The term "isolated nucleic acid molecule," as used herein in reference to nucleic acids encoding antibodies or antibody portions (e.g., $V_H$, $V_L$, one or more CDRs) that bind to SOD1, is intended to refer to a nucleic acid molecule in which the nucleotide sequences encoding the antibody or antibody portion are free of other nucleotide sequences encoding antibodies that bind antigens other than SOD1, which other sequences may naturally flank the nucleic acid in human genomic DNA.

By "vector" is meant a DNA molecule, usually derived from a plasmid or bacteriophage, into which fragments of DNA may be inserted or cloned. A recombinant vector will contain one or more unique restriction sites, and may be capable of autonomous replication in a defined host or vehicle organism such that the cloned sequence is reproducible. A vector contains a promoter operably-linked to a gene or coding region such that, upon transfection into a recipient cell, an RNA or an encoded protein is expressed.

II. Anti-SOD1 Antibodies

The present invention encompasses purified monoclonal antibodies that bind to SOD1, including mutant, misfolded, or wild-type SOD1. The monoclonal antibodies of the invention may be mouse, chimeric, humanized, or fully human. The monoclonal antibodies of the invention include the anti-SOD1 antibodies described herein, as well as any antibody that binds to any of the epitopes described herein or competes with any of the antibodies described herein for binding to SOD1. A detailed description of the antibodies of the invention as well as methods for the production and identification of the antibodies of the invention are described in detail below.

Antibodies, also known as immunoglobulins, are typically tetrameric glycosylated proteins composed of two light (L) chains of approximately 25 kDa each and two heavy (H) chains of approximately 50 kDa each. Two types of light chain, termed lambda and kappa, may be found in antibodies. Depending on the amino acid sequence of the constant domain of heavy chains, immunoglobulins can be assigned to five major classes: A, D, E, G, and M, and several of these may be further divided into subclasses (isotypes), e.g., $IgG_1$, $IgG_2$, $IgG_3$, $IgG_4$, $IgA_1$, and $IgA_2$. Each light chain includes an N-terminal variable (V) domain ($V_L$) and a constant (C) domain ($C_L$). Each heavy chain includes an N-terminal V domain ($V_H$), three or four C domains ($C_H$1-3), and a hinge region. The $C_H$ domain most proximal to $V_H$ is designated as $C_H$1. The $V_H$ and $V_L$ domains consist of four regions of relatively conserved sequences called framework regions (FR1, FR2, FR3, and FR4), which form a scaffold for three regions of hypervariable sequences (complementarity determining regions, CDRs). The CDRs contain most of the residues responsible for specific interactions of the antibody with the antigen. CDRs are referred to as CDR1, CDR2, and CDR3. Accordingly, CDR constituents on the heavy chain are referred to as CDRH1, CDRH2, and CDRH3, while CDR constituents on the light chain are referred to as CDRL1, CDRL2, and CDRL3. The CDRs typically refer to the Kabat CDRs, as described in Sequences of Proteins of Immunological Interest, US Department of Health and Human Services (1991), eds. Kabat et al. Another standard for characterizing the antigen binding site is to refer to the hypervariable loops as described by Chothia. See, e.g., Chothia, D. et al. (1992) J. Mol. Biol. 227:799-817; and Tomlinson et al. (1995) EMBO J. 14:4628-4638. Still another standard is the AbM definition used by Oxford Molecular's AbM antibody modeling software. See, generally, e.g., Protein Sequence and Structure Analysis of Antibody Variable Domains. In: Antibody Engineering Lab Manual (Ed.: Duebel, S, and Kontermann, R., Springer-Verlag, Heidelberg). Embodiments described with respect to Kabat CDRs can alternatively be implemented using similar described relationships with respect to Chothia hypervariable loops or to the AbM-defined loops, or combinations of any of these methods.

The anti-SOD1 antibodies of the present invention and the nucleic acid molecules of the present invention that encode the antibodies include the CDR amino acid and nucleic acid sequences shown in Table 1 below and in FIGS. 1-37.

TABLE 1

| Antibody | CDRH1 | CDRH2 | CDRH3 | CDRL1 | CDRL2 | CDRL3 |
|---|---|---|---|---|---|---|
| 595-16 | | | | | | |
| Amino acid: | (SEQ ID NO: 3) | (SEQ ID NO: 5) | (SEQ ID NO: 7) | (SEQ ID NO: 11) | (SEQ ID NO: 13) | (SEQ ID NO: 15) |
| Nuc. Acid: | (SEQ ID NO: 4) | (SEQ ID NO: 6) | (SEQ ID NO: 8) | (SEQ ID NO: 12) | (SEQ ID NO: 14) | (SEQ ID NO: 16) |
| 591-37 | | | | | | |
| Amino acid: | (SEQ ID NO: 21) | (SEQ ID NO: 23) | (SEQ ID NO: 25) | (SEQ ID NO: 29) | (SEQ ID NO: 31) | (SEQ ID NO: 33) |
| Nuc. Acid: | (SEQ ID NO: 22) | (SEQ ID NO: 24) | (SEQ ID NO: 26) | (SEQ ID NO: 30) | (SEQ ID NO: 32) | (SEQ ID NO: 34) |
| 358-11 | | | | | | |
| Amino acid: | (SEQ ID NO: 39) | (SEQ ID NO: 41) | (SEQ ID NO: 43) | (SEQ ID NO: 47) | (SEQ ID NO: 49) | (SEQ ID NO: 51) |
| Nuc. Acid: | (SEQ ID NO: 40) | (SEQ ID NO: 42) | (SEQ ID NO: 44) | (SEQ ID NO: 48) | (SEQ ID NO: 50) | (SEQ ID NO: 52) |
| 358-22 | | | | | | |
| Amino acid: | (SEQ ID NO: 57) | (SEQ ID NO: 59) | (SEQ ID NO: 61) | (SEQ ID NO: 65) | (SEQ ID NO: 67) | (SEQ ID NO: 69) |
| Nuc. Acid: | (SEQ ID NO: 58) | (SEQ ID NO: 60) | (SEQ ID NO: 62) | (SEQ ID NO: 66) | (SEQ ID NO: 68) | (SEQ ID NO: 70) |
| 597-120 | | | | | | |
| Amino acid: | (SEQ ID NO: 75) | (SEQ ID NO: 77) | (SEQ ID NO: 79) | (SEQ ID NO: 83) | (SEQ ID NO: 85) | (SEQ ID NO: 87) |
| Nuc. Acid: | (SEQ ID NO: 76) | (SEQ ID NO: 78) | (SEQ ID NO: 80) | (SEQ ID NO: 84) | (SEQ ID NO: 86) | (SEQ ID NO: 88) |
| 311-3 | | | | | | |
| Amino acid: | (SEQ ID NO: 93) | (SEQ ID NO: 95) | (SEQ ID NO: 97) | (SEQ ID NO: 101) | (SEQ ID NO: 103) | (SEQ ID NO: 105) |
| Nuc. Acid: | (SEQ ID NO: 94) | (SEQ ID NO: 96) | (SEQ ID NO: 98) | (SEQ ID NO: 102) | (SEQ ID NO: 104) | (SEQ ID NO: 106) |
| 311-3-M1 | | | | | | |
| Amino acid: | (SEQ ID NO: 93) | (SEQ ID NO: 95) | (SEQ ID NO: 97) | (SEQ ID NO: 101) | (SEQ ID NO: 111) | (SEQ ID NO: 105) |
| Nuc. Acid: | (SEQ ID NO: 94) | (SEQ ID NO: 96) | (SEQ ID NO: 98) | (SEQ ID NO: 102) | (SEQ ID NO: 112) | (SEQ ID NO: 106) |
| 312-19 | | | | | | |
| Amino acid: | (SEQ ID NO: 115) | (SEQ ID NO: 117) | (SEQ ID NO: 119) | (SEQ ID NO: 123) | (SEQ ID NO: 125) | (SEQ ID NO: 127) |
| Nuc. Acid: | (SEQ ID NO: 116) | (SEQ ID NO: 118) | (SEQ ID NO: 120) | (SEQ ID NO: 124) | (SEQ ID NO: 126) | (SEQ ID NO: 128) |
| 591-33 | | | | | | |
| Amino acid: | (SEQ ID NO: 133) | (SEQ ID NO: 135) | (SEQ ID NO: 137) | (SEQ ID NO: 141) | (SEQ ID NO: 143) | (SEQ ID NO: 145) |
| Nuc. Acid: | (SEQ ID NO: 134) | (SEQ ID NO: 136) | (SEQ ID NO: 138) | (SEQ ID NO: 142) | (SEQ ID NO: 144) | (SEQ ID NO: 146) |
| 114-41 | | | | | | |
| Amino acid: | (SEQ ID NO: 151) | (SEQ ID NO: 153) | (SEQ ID NO: 155) | (SEQ ID NO: 159) | (SEQ ID NO: 161) | (SEQ ID NO: 163) |
| Nuc Acid: | (SEQ ID NO: 152) | (SEQ ID NO: 154) | (SEQ ID NO: 156) | (SEQ ID NO: 160) | (SEQ ID NO: 162) | (SEQ ID NO: 164) |
| 306-155 | | | | | | |
| Amino acid: | (SEQ ID NO: 169) | (SEQ ID NO: 171) | (SEQ ID NO: 173) | (SEQ ID NO: 177) | (SEQ ID NO: 179) | (SEQ ID NO: 181) |
| Nuc. Acid: | (SEQ ID NO: 170) | (SEQ ID NO: 172) | (SEQ ID NO: 174) | (SEQ ID NO: 178) | (SEQ ID NO: 180) | (SEQ ID NO: 182) |
| 14-173 | | | | | | |
| Amino acid: | (SEQ ID NO: 185) | (SEQ ID NO: 187) | (SEQ ID NO: 189) | (SEQ ID NO: 193) | (SEQ ID NO: 195) | (SEQ ID NO: 197) |
| Nuc. Acid: | (SEQ ID NO: 186) | (SEQ ID NO: 188) | (SEQ ID NO: 190) | (SEQ ID NO: 194) | (SEQ ID NO: 196) | (SEQ ID NO: 198) |
| 303-8 | | | | | | |
| Amino acid: | (SEQ ID NO: 203) | (SEQ ID NO: 205) | (SEQ ID NO: 207) | (SEQ ID NO: 211) | (SEQ ID NO: 213) | (SEQ ID NO: 215) |
| Nuc. Acid: | (SEQ ID NO: 204) | (SEQ ID NO: 206) | (SEQ ID NO: 208) | (SEQ ID NO: 212) | (SEQ ID NO: 214) | (SEQ ID NO: 216) |
| 312-56 | | | | | | |
| Amino acid: | (SEQ ID NO: 219) | (SEQ ID NO: 221) | (SEQ ID NO: 223) | (SEQ ID NO: 227) | (SEQ ID NO: 229) | (SEQ ID NO: 231) |
| Nuc. Acid: | (SEQ ID NO: 220) | (SEQ ID NO: 222) | (SEQ ID NO: 224) | (SEQ ID NO: 228) | (SEQ ID NO: 230) | (SEQ ID NO: 232) |

The anti-SOD1 antibodies of the invention include any antibody that includes a CDRH1, CDRH2, CDRH3, CDRL1, CDRL2, or CDRL3, or combinations thereof, as provided for any one of the antibodies shown in Table 1 or FIGS. 1-37. Desirably, the anti-SOD1 antibodies include the CDRH1, CDRH2, CDRH3, CDRL1, CDRL2, and CDRL3 of any one of the antibodies shown in Table 1. The invention also includes any nucleic acid sequence that encodes a CDRH1, CDRH2, CDRH3, CDRL1, CDRL2, or CDRL3 as provided for any one of the antibodies shown in Table 1 or FIGS. 1-37. Desirably, the nucleic acids include the CDRH1, CDRH2, CDRH3, CDRL1, CDRL2, and CDRL3 nucleic acid sequences of any one of the antibodies shown in Table 1. It is known in the art that antibody heavy and light chain CDR3 domains play a particularly important role in the binding specificity/affinity of an antibody for an antigen. Accordingly, the anti-SOD antibodies of the invention, or the nucleic acid molecules thereof, desirably include at least the heavy and/or light chain CDR3s of antibodies as shown in Table 1 or FIGS. 1-37.

The complete amino acid and nucleic acid sequences for the heavy chain variable region and light chain variable region of the antibodies listed in Table 1 are provided in Table 2 and in FIGS. 1-37. Table 2 includes additional anti-SOD1 antibodies of the invention with modifications to the variable regions and these are referred to as "M1." Modifications include mutations in the variable region sequences that modify immunogenicity, glycosylation, or susceptibility to alterations at that amino acid positions. Such targeted mutations are exemplary of possible mutations to the antibodies of the invention and should not be construed as limiting. Several of the "M1" antibodies are not listed in Table 1 because the alterations are in the framework regions and not the CDRs.

TABLE 2

| Antibody | Heavy Chain Variable Region | Light Chain Variable Region |
| --- | --- | --- |
| 595-16 | | |
| Amino acid: | SEQ ID NO: 1 | SEQ ID NO: 9 |
| Nucleic Acid: | SEQ ID NO: 2 | SEQ ID NO: 10 |
| 595-16-M1 | | |
| Amino acid: | SEQ ID NO: 17 | SEQ ID NO: 9 |
| Nucleic Acid: | SEQ ID NO: 18 | SEQ ID NO: 10 |
| 591-37 | | |
| Amino acid: | SEQ ID NO: 19 | SEQ ID NO: 27 |
| Nucleic Acid: | SEQ ID NO: 20 | SEQ ID NO: 28 |
| 591-37-M1 | | |
| Amino acid: | SEQ ID NO: 35 | SEQ ID NO: 27 |
| Nucleic Acid: | SEQ ID NO: 36 | SEQ ID NO: 28 |
| 358-11 | | |
| Amino acid: | SEQ ID NO: 37 | SEQ ID NO: 45 |
| Nucleic Acid: | SEQ ID NO: 38 | SEQ ID NO: 46 |
| 358-11-M1 | | |
| Amino acid: | SEQ ID NO: 53 | SEQ ID NO: 45 |
| Nucleic Acid: | SEQ ID NO: 54 | SEQ ID NO: 46 |
| 358-22 | | |
| Amino acid: | SEQ ID NO: 55 | SEQ ID NO: 63 |
| Nucleic Acid: | SEQ ID NO: 56 | SEQ ID NO: 64 |
| 358-22-M1 | | |
| Amino acid: | SEQ ID NO: 71 | SEQ ID NO: 63 |
| Nucleic Acid: | SEQ ID NO: 72 | SEQ ID NO: 64 |
| 597-120 | | |
| Amino acid: | SEQ ID NO: 73 | SEQ ID NO: 81 |
| Nucleic Acid: | SEQ ID NO: 74 | SEQ ID NO: 82 |

TABLE 2-continued

| Antibody | Heavy Chain Variable Region | Light Chain Variable Region |
| --- | --- | --- |
| 597-120-M1 | | |
| Amino acid: | SEQ ID NO: 89 | SEQ ID NO: 81 |
| Nucleic Acid: | SEQ ID NO: 90 | SEQ ID NO: 82 |
| 311-3 | | |
| Amino acid: | SEQ ID NO: 91 | SEQ ID NO: 99 |
| Nucleic Acid: | SEQ ID NO: 92 | SEQ ID NO: 100 |
| 311-3-M1 | | |
| Amino acid: | SEQ ID NO: 107 | SEQ ID NO: 109 |
| Nucleic Acid: | SEQ ID NO: 108 | SEQ ID NO: 110 |
| 312-19 | | |
| Amino acid: | SEQ ID NO: 113 | SEQ ID NO: 121 |
| Nucleic Acid: | SEQ ID NO: 114 | SEQ ID NO: 122 |
| 312-19-M1 | | |
| Amino acid: | SEQ ID NO: 129 | SEQ ID NO: 121 |
| Nucleic Acid: | SEQ ID NO: 130 | SEQ ID NO: 122 |
| 591-33 | | |
| Amino acid: | SEQ ID NO: 131 | SEQ ID NO: 139 |
| Nucleic Acid: | SEQ ID NO: 132 | SEQ ID NO: 140 |
| 591-33-M1 | | |
| Amino acid: | SEQ ID NO: 147 | SEQ ID NO: 139 |
| Nucleic Acid: | SEQ ID NO: 148 | SEQ ID NO: 140 |
| 114-41 | | |
| Amino acid: | SEQ ID NO: 149 | SEQ ID NO: 157 |
| Nucleic Acid: | SEQ ID NO: 150 | SEQ ID NO: 158 |
| 114-41-M1 | | |
| Amino acid: | SEQ ID NO: 165 | SEQ ID NO: 157 |
| Nucleic Acid: | SEQ ID NO: 166 | SEQ ID NO: 158 |
| 306-155 | | |
| Amino acid: | SEQ ID NO: 167 | SEQ ID NO: 175 |
| Nucleic Acid: | SEQ ID NO: 168 | SEQ ID NO: 176 |
| 14-173 | | |
| Amino acid: | SEQ ID NO: 183 | SEQ ID NO: 191 |
| Nucleic Acid: | SEQ ID NO: 184 | SEQ ID NO: 192 |
| 14-173-M1 | | |
| Amino acid: | SEQ ID NO: 183 | SEQ ID NO: 199 |
| Nucleic Acid: | SEQ ID NO: 184 | SEQ ID NO: 200 |
| 303-8 | | |
| Amino acid: | SEQ ID NO: 201 | SEQ ID NO: 209 |
| Nucleic Acid: | SEQ ID NO: 202 | SEQ ID NO: 210 |
| 312-56 | | |
| Amino acid: | SEQ ID NO: 217 | SEQ ID NO: 225 |
| Nucleic Acid: | SEQ ID NO: 218 | SEQ ID NO: 226 |

The anti-SOD1 antibodies of the invention include any antibody that includes a heavy chain variable domain or a light chain variable domain or both as shown in Table 2 or FIGS. 1-37. The invention also includes any nucleic acid molecule encoding an antibody that includes a heavy chain variable domain or a light chain variable domain nucleic acid sequence, or both, as shown in Table 2 or FIGS. 1-37.

Anti-SOD1 antibodies of this invention may optionally comprise antibody constant regions or parts thereof. For example, a $V_L$ domain may be attached at its C-terminal end to a light chain constant domain like Cκ or Cλ. Similarly, a $V_H$ domain or portion thereof may be attached to all or part of a heavy chain like IgA, IgD, IgE, IgG, and IgM, and any isotype subclass. Constant regions are known in the art (see, for example, Kabat et al., Sequences of Proteins of Immunological Interest, No. 91-3242, National Institutes of Health Publications, Bethesda, Md. (1991)). Therefore, antibodies within the scope of this invention may include $V_H$ and $V_L$ domains, or an antigen-binding portion thereof, combined with constant regions known in the art.

In certain embodiments, the $V_H$ and/or $V_L$ domains may be reverted to germline sequence, i.e., the FR of these domains are mutated using conventional molecular biology techniques to match those produced by the germline cells. In other embodiments, the FR sequences remain diverged from the consensus germline sequences. Non-limiting examples of such mutations to the antibodies of the invention include 59546-M1 ($V_H$), 358-11-M1 ($V_H$), 358-22-M1 ($V_H$), 597-120-M1 ($V_H$), 311-3-M1 ($V_H$+$V_L$), 312-19-M1 ($V_H$), 591-33-M1 ($V_H$), 114-41-M1 ($V_H$), and 14-173-M1 ($V_L$).

Additional examples of mutations described herein include mutation of the $V_H$ gene DP44, which contains the unnatural amino acids L13 and M260, and can be mutated to the natural amino acids K13 and T87 (595-16-M1 and 591-37-M1). Undesirable amino acids such as those that are glycosylated can also be mutated to amino acids that lack glycosylation such as the N56 converted to D56 in 311-3-M1 $V_L$. In addition, an unpaired cysteine can be mutated to serine such as C77 to S77 in 14-173-M1 $V_L$.

The anti-SOD1 antibodies may or may not include the framework region of the antibodies shown in FIGS. 1-37. Desirably, the anti-SOD1 antibodies are fully human antibodies and include the variable region sequences shown in FIGS. 1-37.

In another embodiment, the invention provides a fully human anti-SOD1 antibody including: (1) human heavy chain framework regions and human heavy chain CDRs, where at least one of the human heavy chain CDRs includes an amino acid sequence selected from the human heavy chain CDR amino acid sequences described herein; and (2) human light chain framework regions and human light chain CDRs, where at least one of the human heavy chain CDRs includes an amino acid sequence selected from the human light chain CDR amino acid sequences described herein, where the antibody retains the ability to bind to SOD1. The ability of the antibody to bind SOD1 can be determined using standard binding assays, such as those sets described herein.

Also included within the anti-SOD1 antibodies of the invention are the anti-SOD1 antibodies having a leader sequence included for secretion of the antibody protein, and nucleic acid molecules encoding the same. The amino acid and nucleic acid sequences for the antibodies with the leader sequences are provided in SEQ ID NOs: 233-306. In addition, the native leader associated with the antibody can be substituted with heterologous leaders that enhance antibody expression such as the osteonectin leader (SEQ ID NOs: 350-351).

The anti-SOD1 antibodies of the invention bind to SOD1, including wild type, mutant, misfolded, or aggregated SOD1. Desirably, the antibody binds to mutant or misfolded SOD1 and may optionally also bind to wild-type SOD1. The misfolded SOD1 bound by the antibody may include wild type or mutant sequence. Epitopes in the SOD1 protein that are recognized by the antibodies of the invention include but are not limited to amino acids include amino acids 40-47 (amino acids EGLHGFFHV; SEQ ID NO: 307), 42-49 (amino acids LHGFHVHE; SEQ ID NO: 313), 63-71 (amino acids HFNPLSRKH; SEQ ID NO: 309), 80-88 (amino acids HVGDLGNVT; SEQ ID NO: 311), and 107-121 (amino acids SGDHCIIGRTLVVHE; SEQ ID NO: 315) of human SOD1. Such epitopes may be linear or conformational epitopes. Also included in the invention are anti-SOD1 antibodies that bind to any of the epitopes described herein or that compete with any of the antibodies described herein for binding to the SOD1 protein. In one embodiment, an antibody or antibody-binding fragment thereof, specifically binds an epitope containing a sequence that is at least 70% identical (e.g., at least 71%, 72%, 73%, 74%, 75%, 80%, 81%, 82%, 83%, 84%, 85%, 90%, 95%, 96%, 97%, 98%, 99%, or 100% identical) to amino acids 40-47, 42-49, 63-71, 80-88, or 107-121, or combinations thereof, of the sequence of SEQ ID NO: 317. Antibodies that recognize the same epitope can be identified using routine techniques such as an immunoassay, for example, by showing the ability of one antibody to block the binding of another antibody to a target antigen, i.e., a competitive binding assay. Specifically excluded from the antibodies of the invention are the antibodies described in U.S. Patent Publication Nos. 20070292410 or 20090068194 (e.g., the monoclonal antibodies produced by hybridoma cell lines deposited with the International Depositary Authority of Canada under accession numbers ADI-290806-01, ADI-290806-02 and ADI-290806-03).

Anti-SOD1 antibodies of the invention can bind to SOD1 with high affinity, e.g., with a Kd less than $10^{-7}$ M, $10^{-8}$ M, $10^{-9}$ M, $10^{-10}$ M, $10^{-11}$ M or lower. For example, the anti-SOD1 antibodies or fragments thereof can bind to SOD1 with an affinity between 5 pM and 500 nM, e.g., between 50 pM and 100 nM, e.g., between 500 pM and 50 nM. The invention also includes antibodies that compete with any of the antibodies described herein for binding to SOD1 and that have an affinity of 50 nM or lower (e.g., 20 nM or lower, 10 nM or lower, 500 pM or lower, 50 pM or lower, or 5 pM or lower). In yet another embodiment, the anti-SOD1 antibodies have dissociation kinetics in the range of 0.5-20 nM. The affinity and binding kinetics of the anti-SOD1 antibody can be tested using any method known in the art including but not limited to biosensor technology (e.g., OCTET or BIACORE).

The anti-SOD1 antibodies of the invention can be selected not only for binding to SOD1 but also for the ability to reduce or inhibit one or more SOD1-associated activities. Non-limiting examples of anti-SOD1 antibody activity include: a reduction (e.g., by at least 10%, 20%, 30%, 40%, 50%, 60%, 70%, 80%, 90%, 95%, or more) in SOD1 activity or protein levels, clearance of SOD1 proteins including, but not limited to, mutated or misfolded SOD1, increased (e.g., by at least 10%, 20%, 30%, 40%, 50%, 60%, 70%, 80%, 90%, 95%, or more) survival of neurons, increased (e.g., by at least 10%, 20%, 30%, 40%, 50%, 60%, 70%, 80%, 90%, 95%, or more) number of neurons present in a subject or an animal model, increased (e.g., by at least 10%, 20%, 30%, 40%, 50%, 60%, 70%, 80%, 90%, 95%, or more) preservation of intact neurons, and increased (e.g., by at least 10%, 20%, 30%, 40%, 50%, 60%, 70%, 80%, 90%, 95%, or more) survival or time to onset of disease in a subject or an animal model (e.g., G93A mutant mouse model or G85R mutant mouse model).

III. Production of Anti-SOD-1 Antibodies

Numerous methods known to those skilled in the art are available for obtaining antibodies, or antigen-binding fragments thereof, of the invention. For example, antibodies can be produced using recombinant DNA methods. Monoclonal antibodies may also be produced by generation of hybridomas (see e.g., Kohler and Milstein (1975) Nature, 256: 495-499) in accordance with known methods. Hybridomas formed in this manner are then screened using standard methods, such as enzyme-linked immunosorbent assay (ELISA) and surface plasmon resonance (e.g., OCTET or BIACORE) analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptides thereof (e.g., any of the epitopes described herein as a linear epitope or within a scaffold as a conformational epitope).

One exemplary method of making antibodies includes screening protein expression libraries that express antibodies or fragments thereof (e.g., scFv), e.g., phage or ribosome display libraries. Phage display is described, for example, in Ladner et al., U.S. Pat. No. 5,223,409; Smith (1985) Science 228:1315-1317; Clackson et al. (1991) Nature, 352: 624-628; Marks et al. (1991) J. Mol. Biol., 222: 581-597WO92/18619; WO 91/17271; WO 92/20791; WO 92/15679; WO 93/01288; WO 92/01047; WO 92/09690; and WO 90/02809.

In addition to the use of display libraries, the specified antigen (e.g., any of the linear or conformation epitopes described herein) can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) Nature Genetics 7:13-21, US 2003-0070185, WO 96/34096, published Oct. 31, 1996, and PCT Application No. PCT/US96/05928, filed Apr. 29, 1996.

In another embodiment, a monoclonal antibody is obtained from the non-human animal, and then modified, e.g., humanized, deimmunized, chimeric, using recombinant DNA techniques known in the art. A variety of approaches for making chimeric antibodies have been described. See e.g., Morrison et al., Proc. Natl. Acad. Sci. U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B.

Humanized antibodies may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

Humanized antibodies, or fragments thereof, can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4:214; and by U.S. Pat. No. 5,585,089; U.S. Pat. No. 5,693,761; U.S. Pat. No. 5,693,762; U.S. Pat. No. 5,859,205; and U.S. Pat. No. 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

One system useful for generating hybridomas which produce human monoclonal antibodies of the invention is the murine system. Hybridoma production in the mouse is well known in the art, including immunization protocols and techniques for isolating and fusing immunized splenocytes. In one embodiment, human monoclonal antibodies directed against SOD1 are generated using transgenic mice carrying parts of the human immune system rather than the mouse system. In one embodiment, the invention employs transgenic mice, referred to herein as "HuMAb mice" which contain a human immunoglobulin gene miniloci that encodes unrearranged human heavy ($\mu$ and $\gamma$) and K light chain immunoglobulin sequences, together with targeted mutations that inactivate the endogenous $\mu$ and K chain loci (Lonberg, N. et al. (1994) Nature 368(6474): 856-859). Accordingly, the mice exhibit reduced expression of mouse IgM or K, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. NY. Acad. Sci 764:536-546).

To generate fully human monoclonal antibodies to SOD1, transgenic mice containing human immunoglobulin genes can be immunized with a purified or enriched preparation of the SOD1 antigen (or epitope fragments thereof as described herein) and/or cells expressing SOD1, as described, for example, by Lonberg et al. (1994) Nature 368(6474): 856-859; Fishwild et al. (1996) Nature Biotechnology 14: 845-851 and WO 98/24884. As described herein, HuMAb mice are immunized with recombinant SOD1 proteins. Alternatively, mice can be immunized with DNA encoding SOD1. Preferably, the mice will be 6-16 weeks of age upon the first infusion. For example, a purified or enriched preparation (10-100 μg) of the recombinant SOD1 antigen can be used to immunize the HuMAb mice intraperitoneally.

To generate hybridomas producing human monoclonal antibodies to SOD1, splenocytes and lymph node cells from immunized mice can be isolated and fused to an appropriate immortalized cell line, such as a mouse myeloma cell line. The resulting hybridomas can then be screened for the production of antigen-specific antibodies. Methods for screening antibodies are known in the art and include ELISA, FLISA (fluorescence-linked immunosorbent assay), and surface plasmon resonance.

Human antibodies of the invention also can be produced in a host cell using, for example, a combination of recombinant DNA techniques and gene transfection methods as is well known in the art (Morrison, S. (1985) Science 229:1202).

For example, in one embodiment, the gene(s) of interest, e.g., human antibody genes, can be ligated into an expression vector such as a eukaryotic expression plasmid, examples of which are well known in the art. The purified plasmid with the cloned antibody genes can be introduced in eukaryotic host cells such as CHO-cells or NSO-cells or alternatively other eukaryotic cells like a plant derived cells, fungi or yeast cells. Exemplary methods used to introduce these genes are described in the art and include electroporation, lipofectin, lipofectamine, or other. After introducing these antibody genes in the host cells, cells expressing the antibody can be identified and selected. These cells can then be amplified for their expression level and scaled up to produce antibodies. Recombinant antibodies can be isolated and purified from these culture supernatants and/or cells.

A leader sequence that includes a secretion sequence is generally included. Non-limiting examples include the amino acid and nucleic acid sequences for each of the antibodies with a leader sequence as provided in SEQ ID NOs: 233-306. Alternatively, a leader that improves antibody expression when compared to the native leader could be included, such as the osteonectin leader (SEQ ID NOs: 350-351). It should be noted that, after secretion of the antibody, the leader sequence is cleaved and the final antibody product does not include the leader sequence.

The cloned antibody genes can be alternatively expressed in other expression systems such as *E. coli* or in complete organisms or can be synthetically expressed. In one example of synthetic expression, vectors are used that include CDR sequences from the specific naturally occurring antibody grafted onto framework sequences from a different antibody with different properties (see, e.g., Riechmann, L. et al, 1998, Nature 332:323-327; Jones, P. et al, 1986, Nature 321:522-525; and Queen, C. et al., 1989, Proc. Natl. Acad. Sci. U.S.A. 86: 10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual residues evenly across the variable region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody. Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

Plasmids for use in construction of expression vectors can be constructed so that PCR amplified V heavy and V kappa light chain cDNA sequences can be used to reconstruct complete heavy and light chain minigenes. These plasmids can be used to express completely human $IgG_1K$ or $IgG_4K$ antibodies. Fully human and chimeric antibodies of the present invention also include $IgG_2$, $IgG_3$, IgE, IgA, IgM, and IgD antibodies. Similar plasmids can be constructed for expression of other heavy chain isotypes, or for expression of antibodies comprising lambda light chains. Thus, in another aspect of the invention, one or more structural features of an anti-SOD1 antibody of the invention are used to create structurally related human anti-SOD1 antibodies that retain at least one functional property of the antibodies of the invention, such as, for example, binding to SOD1 or clearance of SOD1 (i.e., reducing levels of wild-type, aggregated, misfolded, or mutant SOD1, or combinations thereof). In one embodiment, one or more CDR regions of antibodies of the invention can be combined recombinantly with known human framework regions and CDRs to create additional, recombinantly-engineered, human anti-SOD1 antibodies of the invention. The heavy and light chain variable framework regions can be derived from the same or different human antibody sequences. The human antibody sequences can be the sequences of naturally occurring human antibodies or can be consensus sequences of several human antibodies. See Kettleborough et al, Protein Engineering 4:773 (1991); Kolbinger et al, Protein Engineering 6:971 (1993) and Carter et al, WO 92/22653.

For additional antibody production techniques, see Antibodies: A Laboratory Manual, eds. Harlow et al., Cold Spring Harbor Laboratory, 1988. The present invention is not necessarily limited to any particular source, method of production, or other special characteristics of an antibody.

IV. Antibody Modifications

The anti-SOD1 antibodies of the invention may include additional modifications including but not limited to modifications to the amino acid sequence of the antibody (e.g., the variable regions) and post-translational modifications. Modifications to the anti-SOD1 antibodies may provide additional advantages such as increased affinity; decreased off-rate; increased solubility, stability, and in vivo or in vitro circulating time of the antibody; decreased immunogenicity; or reduced susceptibility to post-translational modifications. Post-translational modifications include, for example, acetylation, acylation, ADP-ribosylation, amidation, deamidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, isomerization, demethylation, formation of covalent cross-links, formation of cysteine, formation of pyroglutamate, formylation, gamma-carboxylation, glycosylation, GPI anchor formation, hydroxylation, hydrolysis, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination (see, for example, Creighton, "Proteins: Structures and Molecular Properties," 2nd Ed., W. H. Freeman and Co., N.Y., 1992; "Postranslational Covalent Modification of Proteins," Johnson, ed., Academic Press, New York, 1983; Seifter et al., *Meth. Enzymol.*, 182:626-646, 1990; Rattan et al., *Ann. N.Y. Acad. Sci.*, 663:48-62, 1992). Additionally, the anti-SOD1 antibodies of the invention may include, for example, e.g., N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression.

The invention also includes chemically-modified derivatives of the anti-SOD1 antibodies of the invention, which may provide additional advantages such as increased solubility, stability, and circulating time of the polypeptide, or decreased immunogenicity (see, e.g., U.S. Pat. No. 4,179,337; incorporated by reference). The chemical moieties for derivitization may be selected from water soluble polymers such as, for example, polyethylene glycol, ethylene glycol/propylene glycol copolymers, carboxymethylcellulose, dextran, polyvinyl alcohol, and the like. The anti-SOD1 antibodies of the invention may be modified at random positions within the molecule, or at predetermined positions within the molecule and may include one, two, or three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). As noted above, the polyethylene glycol may have a branched structure. Branched polyethylene glycols are described, for example, in U.S. Pat. No. 5,643,575 (incorporated by reference); Morpurgo et al., *Appl. Biochem. Biotechnol.* 56:59-72, 1996; Vorobjev et al., *Nucleosides Nucleotides* 18:2745-2750, 1999; and Caliceti et al., *Bioconjug. Chem.* 10:638-646, 1999, the disclosures of each of which are incorporated by reference.

The anti-SOD1 antibodies of the invention may also be modified with a detectable label, including, but not limited to, an enzyme, prosthetic group, fluorescent material, luminescent material, bioluminescent material, radioactive material, positron emitting metal, nonradioactive paramagnetic metal ion, and affinity label for detection and isolation of SOD1. The detectable substance may be coupled or conjugated either directly to the polypeptides of the invention or indirectly, through an intermediate (such as, for example, a linker known in the art) using techniques known in the art. Non-limiting examples of suitable enzymes include horseradish peroxidase, alkaline phosphatase, (3-galactosidase, glucose oxidase, or acetylcholinesterase; non-limiting examples of suitable prosthetic group complexes include streptavidin/biotin and avidin/biotin; non-limiting examples of suitable fluorescent materials include biotin, umbelliferone, fluorescein, fluorescein isothiocyanate, rhodamine, dichlorotriazinylamine fluorescein, dansyl chloride, or phycoerythrin; an example of a luminescent material includes luminol; non-limiting examples of bioluminescent materials include luciferase, luciferin, and aequorin; and examples of suitable radioactive material include a radioactive metal ion, e.g., alpha-emitters or other radioisotopes such as, for example, iodine ($^{131}$I, $^{125}$I, $^{123}$I, $^{121}$I), carbon ($^{14}$C), sulfur ($^{35}$S), tritium ($^{3}$H), indium ($^{115}$mIn, $^{113}$mIn, $^{112}$In, $^{111}$In), and technetium ($^{99}$Tc, $^{9}$mTc), thallium ($^{201}$Ti), gallium ($^{68}$Ga, $^{67}$Ga), palladium ($^{163}$Pd), molybdenum ($^{99}$Mo), xenon ($^{133}$Xe), fluorine ($^{18}$F), $^{153}$Sm, Lu, $^{159}$Gd, $^{149}$Pm, $^{140}$La, $^{175}$Yb, $^{166}$He, $^{90}$Y, $^{47}$Sc, $^{86}$R, $^{188}$Re, $^{142}$Pr, $^{150}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, and tin ($^{113}$Sn, $^{117}$Sn). The detectable substance may be coupled or conjugated either directly to the anti-SOD1 antibodies of the invention or indirectly, through an intermediate (such as, for example, a linker known in the art) using techniques known in the art. Anti-SOD1 antibodies conjugated to a detectable substance may be used for diagnostic assays as described herein.

In another embodiment, the antibody CDR or FR sequences may be mutated to increase or improve, for example, binding affinity, binding specificity, or stability. In one embodiment, mutagenesis is used to make an antibody more similar to one or more germline sequences. This may be desirable when mutations are introduced into the framework region of an antibody through somatic mutagenesis or through error prone PCR. Germline sequences for the $V_H$ and $V_L$ domains can be identified by performing amino acid and nucleic acid sequence alignments against the VBASE database (MRC Center for Protein Engineering, UK). VBASE is a comprehensive directory of all human germline variable region sequences compiled from over a thousand published sequences, including those in the current releases of the Genbank and EMBL data libraries. In some embodiments, the FR regions of the scFvs are mutated in conformity with the closest matches in the VBASE database and the CDR portions are kept intact. Non-limiting examples of alterations to the CDR or FR sequences described herein include the antibodies labeled "M1" provided in Tables 1 and 2 and in FIGS. 3, 6, 9, 12, 15, 18, 19, 22, 25, 28, and 33.

In certain embodiments, a chimeric, humanized, or fully human antibody is optimized by the introduction of conservative substitutions, consensus sequence substitutions, germline substitutions and/or back mutations. Such altered immunoglobulin molecules can be made by any of several techniques known in the art, (e.g., Teng et al., Proc. Natl. Acad. Sci. U.S.A., 80: 7308-7312, 1983; Kozbor et al., Immunology Today, 4: 7279, 1983; Olsson et al., Meth. Enzymol., 92: 3-16, 1982), and may be made according to the teachings of PCT Publication WO92/06193 or EP 0239400).

An antibody or fragment thereof may also be modified by specific deletion of human T cell epitopes or "deimmunization" by the methods disclosed in WO 98/52976 and WO 00/34317. Briefly, the heavy and light chain variable domains of an antibody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et al. (1992) J. Mol. Biol. 227:776-798; Cook, G. P. et al. (1995) Immunol. Today Vol. 16 (5): 237-242; Chothia, D. et al. (1992) J. Mol. Biol. 227:799-817; and Tomlinson et al. (1995) EMBO J. 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

In another embodiment, the serum half-life can also be increased, for example, by attaching additional polypeptide sequences. For example, antibodies of this invention or additional polypeptides containing the amino acid sequences of this invention can be attached to serum albumin or a portion of serum albumin that binds to the FcRn receptor or a serum albumin binding peptide so that serum albumin binds to the antibody or polypeptide, e.g., such polypeptide sequences are disclosed in WO 01/45746. To increase the half-life of the antibodies or polypeptide containing the amino acid sequences of this invention, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence of this invention so that the fusion protein expressed by the engineered nucleic acid molecule comprises the salvage receptor binding epitope and a polypeptide sequence of this invention. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule (e.g., Ghetie et al., *Ann. Rev. Immunol.* 18:739-766, 2000). In one preferred embodiment, the serum albumin peptide to be attached comprises an amino acid sequence of DICLPRWGCLW (SEQ ID NO: 352).

The disclosed antibodies can be modified to alter their glycosylation; that is, at least one carbohydrate moiety can be deleted or added to the antibody. Deletion or addition of glycosylation sites can be accomplished by changing amino acid sequence to delete or create glycosylation consensus sites, which are well known in the art. Another means of adding carbohydrate moieties is the chemical or enzymatic coupling of glycosides to amino acid residues of the antibody (see WO 87/05330 and Aplin et al. (1981) CRC Crit. Rev. Biochem., 22: 259-306). Removal of carbohydrate moieties can also be accomplished chemically or enzymatically (see Hakimuddin et al. (1987) Arch. Biochem. Biophys., 259: 52; Edge et al. (1981) Anal. Biochem., 118: 131; Thotakura et al. (1987) Meth. Enzymol., 138: 350).

In certain embodiments, an anti-SOD1 antibody of the invention can contain an altered immunoglobulin constant or Fc region. For example, an antibody produced in accordance with the teachings herein may bind more strongly or with more specificity to effector molecules such as complement and/or Fc receptors, which can control several immune functions of the antibody such as effector cell activity, lysis, complement-mediated activity, antibody clearance, and antibody half-life. Typical Fc receptors that bind to an Fc region of an antibody (e.g., an IgG antibody) include, but are not limited to, receptors of the FcγRI, FcγRII, and FcγRIII and FcRn subclasses, including allelic variants and alternatively spliced forms of these receptors. Fc receptors are reviewed in Ravetch and Kinet, Annu. Rev. Immunol 9:457-92, 1991; Capel et al., Immunomethods 4:25-34, 1994; and de Haas et al., J. Lab. Clin. Med. 126:330-41, 1995).

In one example, replacing residue 297 (asparagine) with alanine in the IgG constant region significantly inhibits recruitment of effector cells, while only slightly reducing (about three fold weaker) affinity for Clq (see e.g., U.S. Pat. No. 5,624,821). The numbering of the residues in the heavy chain is that of the EU index (see Kabat et al., 1991 supra). This alteration destroys the glycosylation site and it is believed that the presence of carbohydrate is required for Fc receptor binding. Any other substitution at this site that destroys the glycosylation site is believed to cause a similar decrease in lytic activity. Other amino acid substitutions, e.g., changing any one of residues 318 (Glu), 320 (Lys) and 322 (Lys), to Ala, are also known to abolish Clq binding to the Fc region of IgG antibodies (see e.g., U.S. Pat. No. 5,624,821).

In addition, modified antibodies can be produced which have a reduced interaction with an Fc receptor. For example, it has been shown that in human $IgG_3$, which binds to the human Fcγ R1 receptor, changing Leu 235 to Glu destroys its interaction with the receptor. Mutations on adjacent or close sites in the hinge link region of an antibody (e.g., replacing residues 234, 236 or 237 with Ala) can also be used to affect antibody affinity for the Fcγ R1 receptor. The numbering of the residues in the heavy chain is based in the EU index (see Kabat et al., 1991 supra).

One of skill in the art will appreciate that the modifications described above are not all-exhaustive, and that many other modifications are obvious to a skilled artisan in light of the teachings of the present disclosure.

V. Antibody Conjugates/immunotoxins

In another aspect, the present invention features an anti-SOD1 monoclonal antibody conjugated to a therapeutic moiety, such as a cytotoxin, a drug (e.g., an immunosuppressant) or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thio guanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). An antibody of the present invention may also be conjugated to a radioisotope, e.g., radioactive iodine, to generate cytotoxic radiopharmaceuticals.

The antibody conjugates of the invention may be used to modify a given biological response. The therapeutic moiety is not to be construed as limited to compound or a nucleic acid molecule possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-I"), interleukin-2 ("IL-2"), interleukin-6 ("EL-6"), granulocyte macrophage colony stimulating factor ("GM-CSF"), granulocyte colony stimulating factor ("G-CSF"), or other cytokines or growth factors. Techniques for conjugating a therapeutic moiety to antibodies are well known, see, e.g., Arnon et al, "Monoclonal Antibodies For Immunotargeting Of Drugs In Cancer Therapy", in Monoclonal Antibodies And Cancer Therapy, Reisfeld et al (eds.), pp. 243-56 (Alan R. Liss, Inc. 1985); Hellstrom et al, "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62: 119-58 (1982). In one non-limiting example, any anti-SOD1 antibody of the invention can be conjugated to an inhibitory nucleic acid molecule (e.g., siRNA, microRNA, and the like) to downregulate or reduce expression of the disease associated SOD1 protein. In such an example, the anti-SOD1 antibody is effective in directing the inhibitory nucleic acid molecule to the target cell and/or clearing the misfolded or mutant SOD1 already present, and the inhibitory nucleic acid molecule prevents or reduces further production of the mutant or misfolded SOD1. Methods for conjugation of an anti-SOD1 antibody to an inhibitory nucleic acid molecule are known in the art. (See, for example, U.S. Pat. No. 5,276,140 and PCT publication number WO 2009/143345 for disclosures of techniques useful for conjugation of inhibitory nucleic acid molecules to a protein.)

VI. Pharmaceutical Compositions

The present invention provides a composition, e.g., a pharmaceutical composition, containing one or a combination (e.g., two or more) of monoclonal antibodies, or antigen-binding portion(s) thereof, of the present invention, formulated together with a pharmaceutically acceptable carrier. In one embodiment, the pharmaceutical composition includes two or more anti-SOD1 antibodies of the invention, wherein each of the antibodies of the composition binds to a distinct epitope of SOD1.

Pharmaceutical compositions of the invention also can be administered in combination therapy, i.e., combined with other agents. For example, the combination therapy can include a composition of the present invention with at least one or more additional therapeutic agents, such as riluzole. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intrathecal, intramuscular, subcutaneous, parenteral, spinal or epidermal administration (e.g., by injection or infusion). Depending on the route of administration, the active compound, i.e., anti-SOD antibodies of the invention or nucleic acids of the invention, may be coated in a material to protect the compound from the action of acids and other natural conditions that may inactivate the compound.

A composition of the present invention can be administered by a variety of methods known in the art. As will be appreciated by the skilled artisan, the route and/or mode of administration will vary depending upon the desired results. Administration may be parenteral, intravenous, intrathecal, subcutaneous, oral, topical, or local, for example, by direct injection into the cerebrospinal fluid. Intravenous delivery by continuous infusion is one exemplary method for administering the therapeutic antibodies of the present invention. Intrathecal delivery (e.g., using an intrathecal pump) is another exemplary method for administering the therapeutic antibodies of the invention. The therapeutic compound may be in the form of a solution, a suspension, an emulsion, an infusion device, or a delivery device for implantation, or it may be presented as a dry powder to be reconstituted with water or another suitable vehicle before use. The composition can be in the form of a pill, tablet, capsule, liquid, or sustained release tablet for oral administration; or a liquid for intravenous, intrathecal, subcutaneous or parenteral administration; or a polymer or other sustained release vehicle for local administration.

Methods well known in the art for making formulations are found, for example, in "Remington: The Science and Practice of Pharmacy" (20th ed., ed. A. R. Gennaro A R., 2000, Lippincott Williams & Wilkins, Philadelphia, Pa.). Formulations for parenteral administration may, for example, contain excipients, sterile water, saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful delivery systems include ethylene-vinyl acetate copolymer particles, osmotic pumps, intrathecal pumps, implantable infusion systems, and liposomes. The concentration of the compound in the formulation varies depending upon a number of factors, including the dosage of the drug to be administered, and the route of administration.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like. Many methods for the preparation of such formulations are generally known to those skilled in the art. See, e.g., Sustained and Controlled Release Drug Delivery Systems, J R. Robinson, ed., Marcel Dekker, Inc., New York, 1978.

To administer a compound of the invention by certain routes of administration, it may be necessary to coat the compound with, or co-administer the compound with, a material to prevent its inactivation. For example, the compound may be administered to a subject in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al. (1984) J. Neuroimmunol. 7:27). Pharmaceutically acceptable carriers include sterile aqueous solutions or dispersions and sterile powders for the extemporaneous preparation of sterile injectable solutions or dispersion. The use of such media and agents for pharmaceutically active substances is known in the art and is included in the invention except where any conventional media or agent is incompatible with the active compound. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. For example, the human antibodies of the invention may be administered once or twice weekly by subcutaneous injection or once or twice monthly by subcutaneous injection.

It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

The phrases "parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Compositions of the invention may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given alone or as a pharmaceutical composition containing, for example, 0.001 to 90% (more preferably, 0.005 to 70%, such as 0.01 to 30%) of active ingredient in combination with a pharmaceutically acceptable carrier.

For intravenous or intrathecal delivery or direct injection, the composition must be sterile and fluid to the extent that the composition is deliverable by syringe. In addition to water, the carrier can be an isotonic buffered saline solution, ethanol, polyol (for example, glycerol, propylene glycol, and liquid polyethylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian can start doses of the compounds of the invention employed in the pharmaceutical composition at levels lower than that required in order to achieve the desired therapeutic effect and gradually increase the dosage until the desired effect is achieved. In general, a suitable daily dose of a composition of the invention will be that amount of the compound which is the lowest dose effective to produce a therapeutic effect. Such an effective dose will generally depend upon the factors described above. If desired, the effective daily dose of a therapeutic composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

Therapeutic compositions can be administered with medical devices known in the art. Examples of well-known implants, delivery systems, and modules useful in the present invention are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired) they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhancing targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al); mannosides (Umezawa et al, (1988) Biochem. Biophys. Res. Commun 153:1038); antibodies (P. G. Bloeman of α/. (1995) FEBS Lett. 357:140; M. Owais et al. (1995) Antimicrob. Agents Chemother. 39:180); surfactant protein A receptor (Briscoe et al. (1995) Am. J. Physiol. 1233: 134), different species of which may comprise the formulations of the inventions, as well as components of the invented molecules; p120 (Schreier et al. (1994) J. Biol. Chem. 269:9090); see also K. Keinanen; M. L. Laukkanen (1994) FEBS Lett. 346: 123; U. Killion; U. Fidler (1994) Immunomethods 4:273. In one embodiment of the invention, the therapeutic compounds of the invention are formulated in liposomes; in a more preferred embodiment, the liposomes include a targeting moiety. The composition must be fluid to the extent that easy syringability exists. It must be stable under the conditions of manufacture and storage and must be preserved against the contaminating action of microorganisms such as bacteria and fungi.

VII. Therapeutic Applications

The anti-SOD1 antibodies of the invention, anti-SOD1 antibody nucleic acid molecules of the invention, and compositions thereof, are useful for treating, ameliorating the symptoms of, or preventing or decreasing the likelihood of developing ALS. The ability of the antibodies to treat, ameliorate one or more symptoms of, or prevent or decrease the likelihood of developing ALS can also be evaluated according to methods well known in the art.

In one example, the anti-SOD1 antibody of the invention is used to treat or ameliorate the symptoms of a subject (e.g., a human) already suffering from ALS. The therapeutic anti-SOD1 antibody may be administered until signs or symptoms of the disorder are improved or onset of the signs or symptoms is delayed. Signs or symptoms of ALS include, but are not limited to, difficulty breathing or swallowing; head drop due to weak spinal and neck muscles; muscle cramps; muscle weakness that worsens over time; muscle contractions; muscle spasms; paralysis; speech problems; voice changes; drooling; ankle, feet, and leg swelling; and weight loss. Measurement of the symptoms of ALS generally involves neurological examination, clinical testing, and patient input. The anti-SOD1 antibodies of the invention may also be used to prevent or delay onset of ALS in a subject known to be at risk for developing ALS.

The anti-SOD1 antibodies of the invention may be used alone or in combination with one or more additional therapeutic agents for the treatment or amelioration of symptoms of ALS. In one example, the additional therapeutic agent is riluzole. For combination therapies, the anti-SOD1 antibody may be administered before, simultaneously, or after the one or more additional therapeutic agent. The anti-SOD1 antibody and the additional therapeutic may optionally be in the same composition or packaged together in the same kit or package.

The invention also includes kits that include one, two, three, or more anti-SOD1 antibodies of the invention, and, optionally instructions for use. The kit can further include one or more additional agents useful for the treatment or amelioration of symptoms of ALS. In one example, the kit includes at least one anti-SOD1 antibody of the invention and riluzole and instructions for use of both.

VIII. Diagnostic Uses

The anti-SOD1 antibodies of the invention may also be used in methods and kits for the diagnosis of ALS or an increased risk of developing ALS. For the diagnostic methods and compositions, the antibody of the invention will preferably detect mutant or misfolded SOD1 and will not detect wild-type, natively folded SOD1. The anti-SOD1 antibody will bind to mutant or misfolded forms of SOD1 in a sample from a subject where a mutant or misfolded form of SOD1 is present or suspected to be present. If mutant or misfolded SOD1 is detected using an antibody of the invention, the subject may be diagnosed with ALS or an increased risk of developing ALS. The diagnostic methods and compositions can be used as an initial screen, a single test, or in conjunction with additional clinical and neurological testing used by a clinician in the diagnosis of ALS. In the diagnostic methods of the invention, the level of mutant or misfolded SOD1 protein detected in a subject sample may be compared to the level of mutant or misfolded SOD1 protein detected in a normal reference sample (e.g., a sample from a subject known not to have ALS or not be at risk for developing ALS). A positive signal in the subject sample and not in the normal reference sample is a diagnostic indicator of ALS or an increased risk of developing ALS. Diagnostic methods and compositions can include the use of diagnostic assays known in the art including, but not limited to, immunoassays and ELISAs.

IX. Examples

The following examples are intended to illustrate the invention. They are not meant to limit the invention in any way.

Materials and Methods

Throughout the examples, the following materials and methods were used unless otherwise stated.

In general, the practice of the present invention employs, unless otherwise indicated, conventional techniques of chemistry, molecular biology, recombinant DNA technology, immunology (especially, e.g., antibody technology), and standard techniques in polypeptide preparation. See, e.g., Sambrook, Fritsch and Maniatis, *Molecular Cloning: Cold Spring Harbor Laboratory Press* (1989); *Antibody Engineering Protocols* (*Methods in Molecular Biology*), 510, Paul, S., Humana Pr (1996); *Antibody Engineering: A Practical Approach* (Practical Approach Series, 169), McCafferty, Ed., Irl Pr (1996); *Antibodies: A Laboratory Manual*, Harlow et al., C.S.H.L. Press, Pub. (1999); and *Current Protocols in Molecular Biology*, eds. Ausubel et al., John Wiley & Sons (1992).

Synthesis of the Gene Encoding Human Superoxide Dismutase-1 (hSOD1)

Briefly, a nucleic acid sequence encoding hSOD1 (Genbank accession number AY450286, SEQ ID NO: 318) was obtained electronically. The nucleotide sequence was altered without changing the amino acid code to optimize expression in *Escherichia coli* (SEQ ID NO: 319). The alignment of the two versions of the hSOD1 gene is shown in FIG. 38. The sequence was purchased from Integrated DNA Technologies (IDT) and cloned into either pET32-a-myc or pGEX-4T-3 with BamHI and SalI in frame with the C-terminal myc and 6 histidine tags (for pET32-a-myc). The vectors were then sequenced to confirm the construct was correct.

Expression and Purification of Codon-optimized hSOD1

The hSOD1 expression vectors were transformed into BL21-DE3 *E. coli* bacteria (Invitrogen) and expression was induced with IPTG. Proteins expressed from pET32-a-myc contained an N-terminal thioredoxin (trx) domain and proteins expressed from pGEX-4T-3 contained an N-terminal glutathione sulfotransferase (GST) domain. Bacteria were lysed and the hSOD1 protein was purified with nickel affinity chromatography (pET32-a-myc) or glutathione affinity chromatography (pGEX-4T-3). Purified proteins were dialyzed against phosphate-buffered saline (PBS) and concentrated. Protein concentration was determined based on OD 280 nm and further evaluated by Coomassie stained SDS-PAGE and Western blot using mouse antibody specific for myc and histidine tags (pET32-a-myc) or rabbit polyclonal antibody directed against hSOD1. No exogenous copper or zinc was included in the expression or purification procedure. This would suggest that some proportion of the bacterially-expressed SOD1 is not fully metallated.

Oxidation and Reduction of hSOD1

For hSOD1 oxidation, bacterially-expressed hSOD1 (b-hSOD1) or commercially available hSOD1 purified from human erythrocytes (E-hSOD1, Sigma) were treated with 10 mM hydrogen peroxide for 24 hours at room temperature. Oxidized protein was desalted with ZEBA desalting columns and stored at −20° C. until use.

For reduction of hSOD1, b-hSOD1 or E-hSOD1 was treated with 100 mM dithiothreitol (DTT) and 2 mM ethylenediaminetetraacetic acid (EDTA) for 1 hour at room temperature. Proteins were desalted using a ZEBA column and subsequently treated with a 10-fold molar excess of N-ethylmaleimide (NEM) to cap free sulfhydryl groups created from DTT treatment. Free NEM was removed by either ZEBA column or dialysis against PBS.

Generation of b-hSOD1 Point Mutants

Site-directed mutagenesis was performed using the QuickChange II Site-Directed Mutagenesis kit (Stratagene) as described by the manufacturer. Briefly, overlapping primers containing the desired point mutations were used to amplify full-length hSOD1 genes from the codon-optimized hSOD1 gene cloned into either pET32-a-myc or pGEX-4T-3. The amplified DNA was digested with DpnI to remove the template DNA, transformed into bacteria, and screened for the intended mutation by sequencing. All constructed mutant hSOD1 sequences were sequenced by standard DNA sequencing technology to ensure the fidelity of the PCR reactions. Constructs encoding the A4V, G93A and G85R hSOD1 mutations were synthesized. All mutant proteins were expressed and purified as described above.

Generation of b-hSOD1 Truncations

Fusion proteins were engineered with N-terminal thioredoxin fusion for bacterial expression in order to allow production of small portions of b-hSOD1.

The portion of b-hSOD1 protein encoding the desired amino acids was PCR amplified using pET32-a-myc as template and cloned into a new pET32-a-myc expression vector with BamHI and SalI in frame with the C-terminal myc and 6 histidine tags and N-terminal thioredoxin domain. The vector was then sequenced to confirm that the construct was correct. All constructs are shown as a schematic in FIG. 39 and they include:

b-hSOD1-A (amino acids 1 to 38), SEQ ID NO: 320
b-hSOD1-B (amino acids 1 to 77), SEQ ID NO: 321
b-hSOD1-C (amino acids 1 to 116), SEQ ID NO: 322
b-hSOD1-D (amino acids 39 to 153), SEQ ID NO: 323
b-hSOD1-E (amino acids 78 to 153), SEQ ID NO: 324
b-hSOD1-F (amino acids 117 to 153), SEQ ID NO: 325
b-hSOD1-G (amino acids 39 to 77), SEQ ID NO: 326
b-hSOD1-H (amino acids 78 to 116), SEQ ID NO: 327
b-hSOD1-I (amino acids 39 to 116), SEQ ID NO: 328
b-hSOD1-J (amino acids 92 to 153), SEQ ID NO: 329
b-hSOD1-K (amino acids 102 to 153), SEQ ID NO: 330

The vectors were transformed into BL21-DE3 *E. coli* bacteria (Invitrogen) and expression was induced with IPTG. Bacteria were lysed and the proteins of interest were purified with nickel affinity chromatography. Protein concentration was determined based on OD 280 nm and further evaluated by Coomassie stained SDS-PAGE and Western blot using mouse antibody specific for myc and histidine tags. Bacterially-produced hSOD1 is referred to as b-hSOD1.

ELISA

ELISA was carried out with the b-hSOD1, E-hSOD1, b-hSOD1 truncations, b-hSOD1 mutants, and oxidized/reduced forms of SOD1 to determine antibody reactivity. Briefly, 96-well plates were coated with the desired protein and hybridoma supernatant or purified antibody was added to the 96 well plates to determine protein reactivity. Bound antibody was detected with anti-human alkaline phosphatase secondary antibody and PNPP substrate.

Affinity Determination

Affinity of antibodies was determined using an Octet QK (ForteBio) biomolecular interaction instrument. The Octet QK performs similarly to Biacore in the measurement of antibody affinity. The Octet QK uses biosensors to assess mass increases/decreases and determine rates of association and disassociation. A biosensor coated with amine-reactive chemistry was introduced into a solution containing E-hSOD1 or b-hSOD1 to covalently link these proteins to the surface of the biosensor. Unbound hSOD1 was washed away and the coated biosensor was introduced into a solution containing anti-SOD1 monoclonal antibodies at which time $K_{on}$ was determined. The sensor was then introduced into a buffer solution containing no antibody and the $K_{off}$ determined. Using $K_{on}$ and $K_{off}$ an affinity ($K_D$) was calculated.

Antibody Competition

Competition of human monoclonal antibodies for hSOD1 binding was assessed using the Octet QK instrument. Briefly, anti-hSOD1 human monoclonal antibody #1 was captured on anti-human IgG biosensors followed by the addition of b-hSOD1 to facilitate antigen capture. The complex was subsequently re-incubated with antibody #1 to saturate all binding sites on the dimeric hSOD1 protein. Finally, human monoclonal antibody #2 was incubated with the biosensor to determine the ability of both antibodies to interact with hSOD1 simultaneously. If the Octet QK detected a mass increase upon addition of antibody #2 the antibodies were determined to not be competitive. If no mass increase was detected on the biosensor the antibodies were considered to compete.

Immunoprecipitation

HEK-293T cells were transfected with b-hSOD1 or b-hSOD1 containing various mutations using Lipofectamine 2000 (Invitrogen). All transfected constructs encoded a C-terminal myc epitope tag for easy detection of transfected proteins. The myc tag also allowed the discrimination of transfected hSDO1 from hSOD1 expressed in HEK-293T cells. 48 hours post-transfection, cells were lysed with Triton X-100 and insoluble debris removed by centrifugation. Cleared lysate was incubated with various anti-hSOD1 monoclonal antibodies in conjunction with protein A sepharose. Precipitated proteins were resolved by SDS-PAGE, transferred to a solid support and detected using either rabbit anti-hSOD1 or mouse anti-myc tag.

Cell Staining

HEK-293T cells in chamber slides were transfected with b-hSOD1 or b-hSOD1 containing various mutations using Lipofectamine 2000 (Invitrogen). 120 hours post-transfection cells were fixed in 2% formaldehyde and incubated with human anti-hSOD1 monoclonal antibodies in the presence of Triton X-100 (permeabilization). Slides were washed and incubated with anti-human secondary antibody conjugated to Alexa-488 as well as DAPI for staining nuclei. Slides were observed with a fluorescence microscope and photographs were taken.

Mouse Immunizations

Mice transgenic for human IgG genes (HuMab mice, Medarex, Inc.) were immunized with E-hSOD1, b-hSOD1, mutant versions of b-hSOD1 or oxidized/reduced hSOD1. All mice were immunized intraperitoneally weekly with 50 µg of hSOD1 protein in the Sigma adjuvant system (Sigma) for 6-16 weeks. Mouse serum was monitored by ELISA using the immunizing protein to determine the appropriate time for splenic fusion.

Splenic Fusions and Hybridoma Selection

Mouse spleens were removed and spleen cells were isolated. Spleen cells were fused to mouse myeloma cells (P3X-AG8.653) following a standard PEG fusion protocol to generate hybridomas. Hybridoma supernatants were then screened for production of antibody reactive to hSOD1 by ELISA and positive cell cultures were expanded for further characterization.

Isolation and Sequencing of Hybridoma Antibody Genes

RNA was isolated from hybridoma cells using a Qiagen RNeasy kit as described by the manufacturer. RT-PCR was performed for the heavy chain variable region with gene-specific primers containing restrictions sites, the resulting sequence was cloned and the construct was sequenced. Rapid Amplification of mRNA Ends by PCR(RACE) was performed for the light chain variable region with gene-specific primers. The sequence was cloned into the pCR4-TOPO vector (Invitrogen) and the inserted element was sequenced. Gene specific primers were designed and used to PCR-amplify sequences from pCR4-TOPO and add restriction sites for subsequent cloning into expression vectors.

Example 1

Generation of Anti-hSOD1 Monoclonal Antibodies

Forty eight transgenic mice comprising human immunoglobulin genes generated as described above were immunized with E-hSOD1, b-hSOD1, mutant versions of b-hSOD1 or oxidized/reduced hSOD1. Various mouse strains were also used that contain different transgenes and thus may produce a wide variety of antigen responses. The antigen was administered in combination with the Sigma adjuvant system. Mouse sera responses were monitored by enzyme linked immunosorbent assay (ELISA) to b-hSOD1. Seventeen mice were determined to have strong immune responses to the relevant antigen and splenic B cells were isolated from these immunized animals and fused to mouse myeloma (P3X-AG8.653) cells using standard spleen cell fusion methods. Clonal hybridomas were generated and screened using ELISA for production of antibody reactive to b-hSOD1. This method yielded 879 b-hSOD1-reactive hybridomas that were selected for further characterization.

Example 2

Antibody Heavy Chain Sequence Determination

RNA was extracted from the 879 positive hybridomas and nucleotide sequence of the heavy chain of the reactive antibody determined. RNA was purified from all hybridomas and RT-PCR performed using a reverse oligonucleotide complimentary to the heavy chain constant region and a forward oligonucleotide cocktail designed to anneal to all human heavy chain genes expressed in the mouse. PCR products were sequenced and 60 antibodies were considered to have a unique heavy chain sequence and were further characterized.

Example 3

Antibody Epitope Mapping and Lead-Candidate Selection

To determine which region of the hSOD1 protein the 60 human antibodies recognize, carboxy- and amino-terminal truncations of b-hSOD1 were captured in ELISA and probed with the 60 lead-candidate antibodies (see FIG. 39 for map of constructs). In the ELISA, 11 antibodies were able to recognize truncated versions of the hSOD1 suggesting these antibodies recognized a linear epitope and the group was further limited to 5 antibodies based on preliminary results showing unique recognition patterns. The recognition of these five antibodies is shown in FIG. 40. Antibodies 595-16, 311-3 and 591-37 were all shown to interact with the G truncation (amino acids 38-77). Antibody 358-11 clearly bound to the H truncation (amino acids 77-116) and 591-33 bound to the K truncation (amino acids 102-153). To further define the linear epitopes elucidated in the initial experiment, a series of peptides were designed and synthesized (FIG. 41) and ELISA was performed once again. Antibodies that recognized the G truncation, 595-16, 311-3 and 591-37, clearly bound to a different group of peptides demonstrating that the epitopes were amino acids 40-47, 42-49 and 63-71, respectively (FIG. 42). The epitope for antibody 358-11 was further defined and the minimal epitope was shown to be amino acids 80-88 (FIG. 43). Finally, the epitope for 591-33 was shown to be located within amino acids 107-121 (FIG. 44). FIG. 45 represents the amino acid sequence of hSOD1 with the five unique epitopes determined by the ELISA defined by a box.

The 49 antibodies that did not recognize truncated hSOD1 proteins were suspected to be dependent on conformational determinants within hSOD1. To determine if the antibodies recognized unique conformational epitopes, 29 of the 49 antibodies were used in competition experiments to further select unique antibodies. Antibodies were tested using an Octet QK to assess the capacity of antibodies to bind to b-hSOD1 concurrently. Results of the competition analysis are represented in FIGS. 46A-46B. FIG. 46A represents antibody #1 bound first and then antibody #2 binding assessed and FIG. 46B represents the opposite order. As a result of the competition analysis, seven distinct patterns were observed (FIG. 47) and 8 lead-candidate conformation-dependant antibodies were selected for further characterization (597-120, 312-19, 114-41, 306-155, 358-22, 303-8, 312-56 and 14-173).

Example 4

Antibody Characterization

Thirteen lead-candidate antibodies were selected for characterization using multiple methods. These lead antibodies and the details regarding their isolation can be found in Table 3. Eight of the antibodies recognized determinants that were dependant on the three dimensional structure of hSOD1 whereas five interacted with a continuous linear epitope.

TABLE 3

| Antibody | Mouse number | First immunogen | # of immunizations | Second immunogen | # of immunizations |
|---|---|---|---|---|---|
| 595-16 | 181595 | GST-b-hSOD1 | 7 | — | — |
| 591-37 | 181591 | Trx-bhSOD1-A4V | 14 | — | — |
| 358-11 | 180358 | GST-b-hSOD1 | 13 | — | — |
| 358-22 | 180358 | GST-b-hSOD1 | 13 | — | — |
| 597-120 | 181597 | GST-b-hSOD1 | 7 | — | — |
| 311-3 | 176311 | E-hSOD1 red | 12 | GST-bhSOD1 | 8 |
| 312-19 | 176312 | E-hSOD1 red | 12 | GST-bhSOD1 | 8 |
| 591-33 | 181591 | Trx-b-hSOD1-A4V | 14 | — | — |
| 114-41 | 189114 | GST-b-hSOD1-A4V | 9 | — | — |
| 306-155 | 176306 | E-hSOD1 | 14 | — | — |
| 14-173 | 188014 | GST-b-hSOD1 red | 6 | — | — |
| 303-8 | 176303 | E-hSOD1 | 13 | — | — |
| 312-56 | 176312 | E-hSOD1 red | 12 | GST-bhSOD1 | 8 |

ELISA

To determine reactivity of the lead-candidate antibodies with various forms of SOD1, ELISA was employed. b-hSOD1, b-hSOD1-A4V, b-hSOD1-G85R and b-hSOD1-G93A were expressed and purified from E. coli. Also, b-hSOD1 was either reduced with DTT or oxidized with hydrogen peroxide to produce monomerized and damaged b-hSOD1 respectively. ELISA plates were coated with b-hSOD1, mutants of b-hSOD1, oxidized/reduced b-hSOD1 or E-hSOD1. Plates were washed and a series of dilutions of each of the 13 antibodies was applied to each of the various hSOD1 proteins. Antibody binding was detected with a goat anti-human alkaline phosphatase secondary antibody and the interaction developed with PNPP. Plates were read using a Molecular Devices Emax plate reader and results are shown in FIG. 48A-M. Antibodies demonstrated various patterns of recognition in ELISA on these proteins.

Immunoprecipitation

Figure 49C:
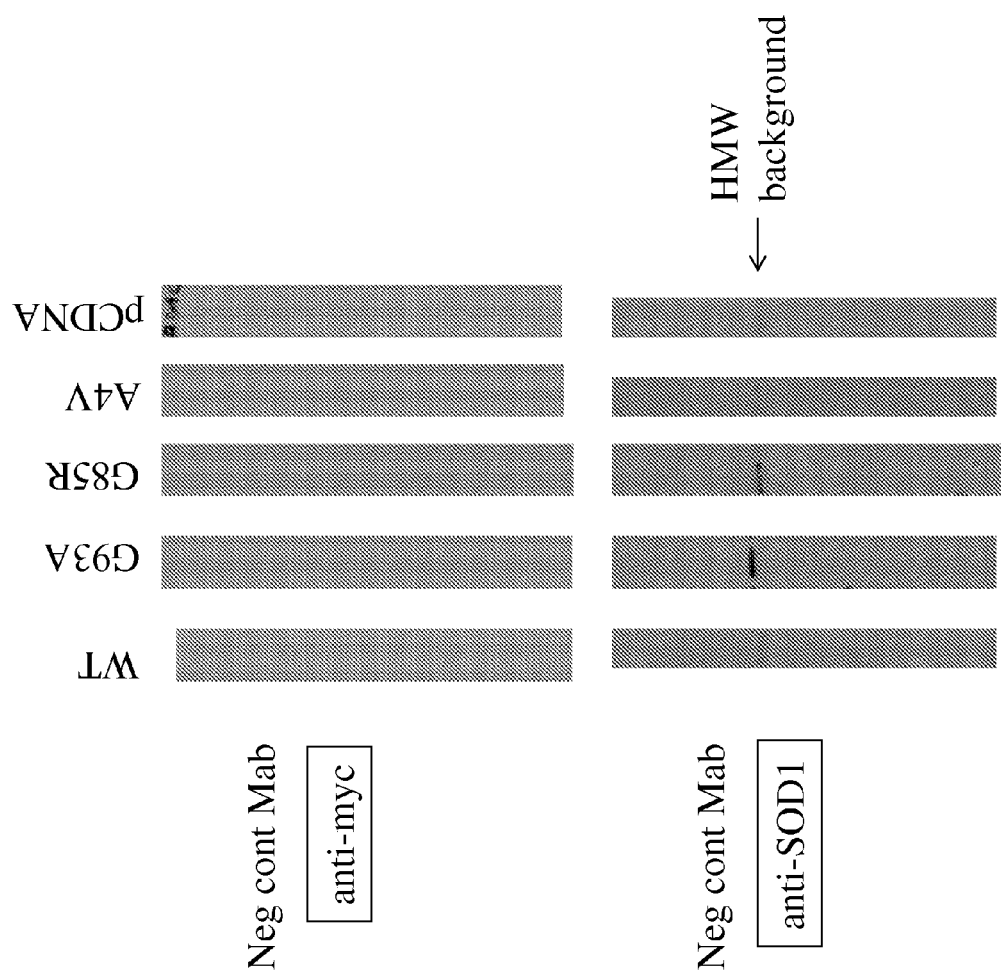

To determine if the thirteen human anti-hSOD1 antibodies could interact with mammalian-expressed hSOD1, immunoprecipitations were performed. The mammalian expression vector pCMV-myc containing the gene encoding hSOD1 (Wild type, WT), hSOD1-G93A, hSOD1-G85R, hSOD1-A4V or empty vector (pcDNA) were transfected into the human HEK-293T cells to induce protein expression. Forty-eight hours following transfection, cells were lysed and protein precipitated with the 13 antibodies for each of the five transfectants. Precipitated protein was resolved by SDS-PAGE, transferred to a solid support and proteins detected in Western blot with either mouse anti-myc tag or a rabbit polyclonal anti-hSOD1 preparation. As a control for protein expression, crude lysate was resolved and Western blot performed (FIG. 49A). In the figure, the top blots represent detection with anti-myc antibody and the bottom blot is detected with rabbit anti-hSOD1. All proteins expressed well and no transfected hSOD1 (myc-tagged) was detected in cells transfected with empty vector. Also, lysates were either mock precipitated only excluding the human antibody from the procedure or precipitated with an irrelevant human antibody and the results are shown in FIG. 49B and FIG. 49C, respectively. Endogenous and transfected, myc-tagged hSOD1 could not be seen in any samples for either of these negative controls but some high molecular weight background (HMW) was observed.

Figure 49D:
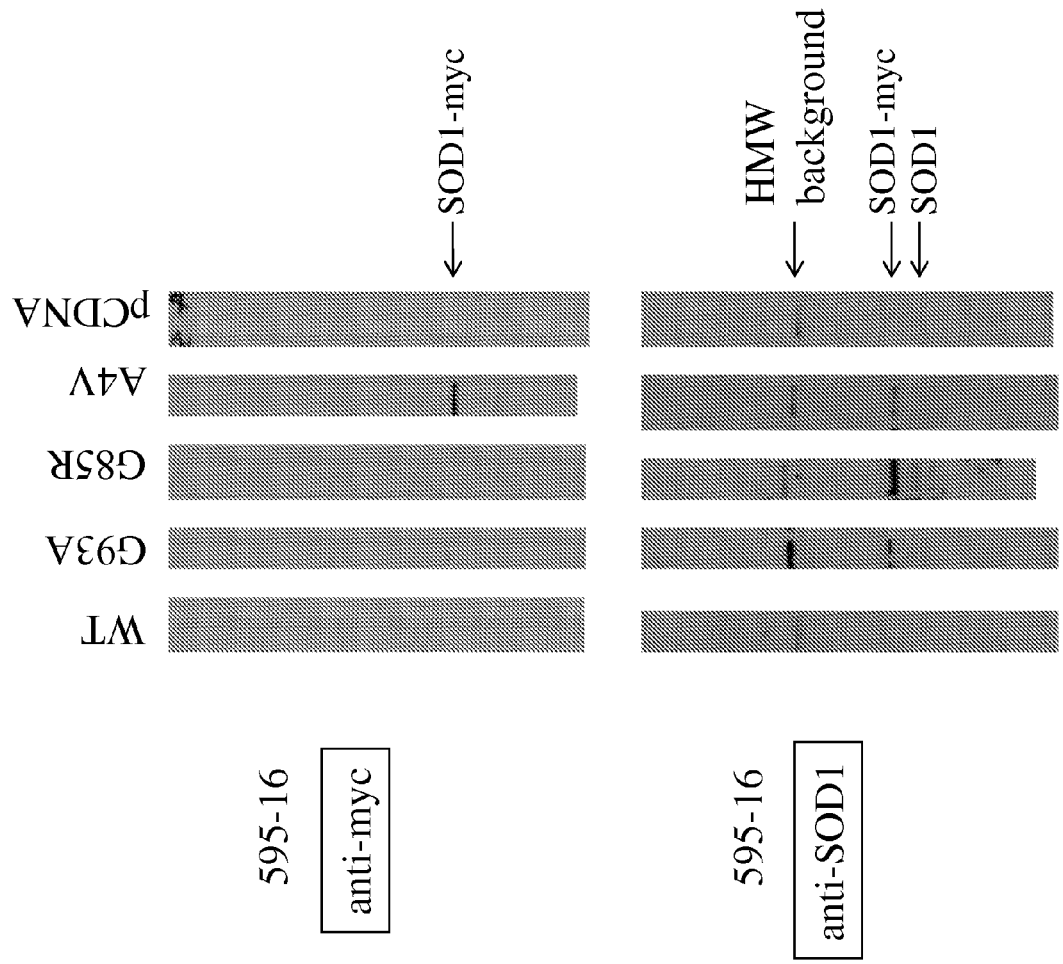
Figure 49E:
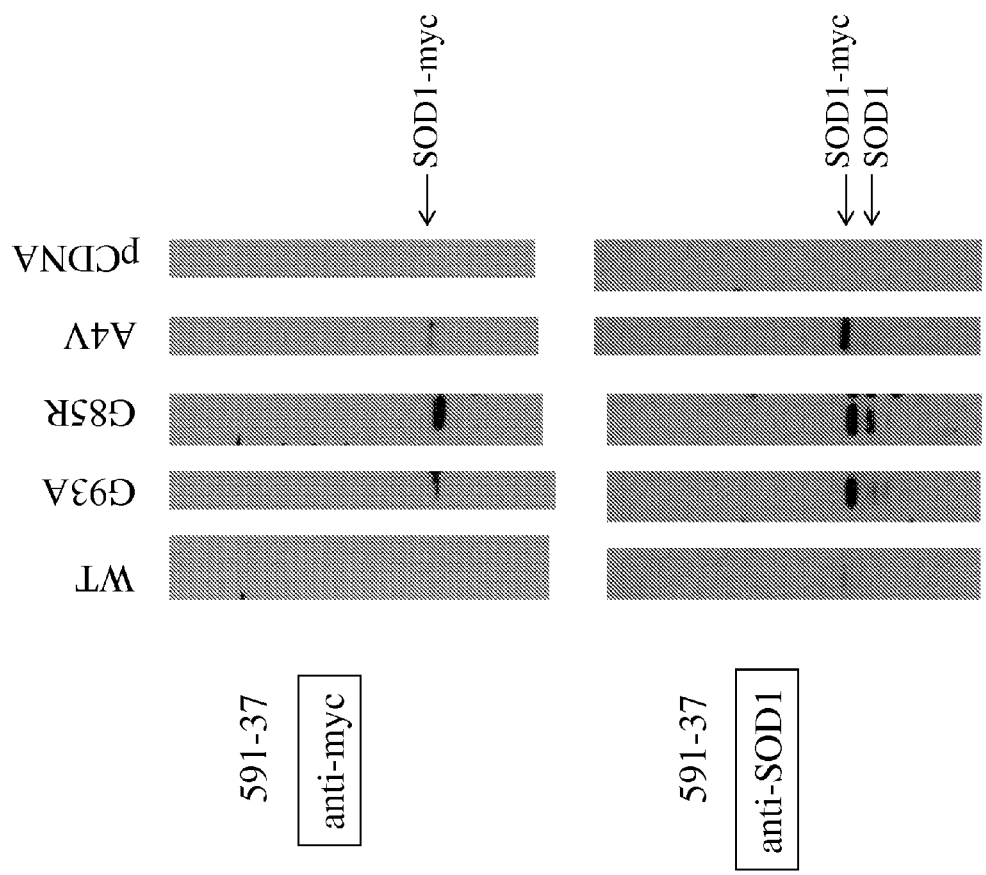
Figure 49H:
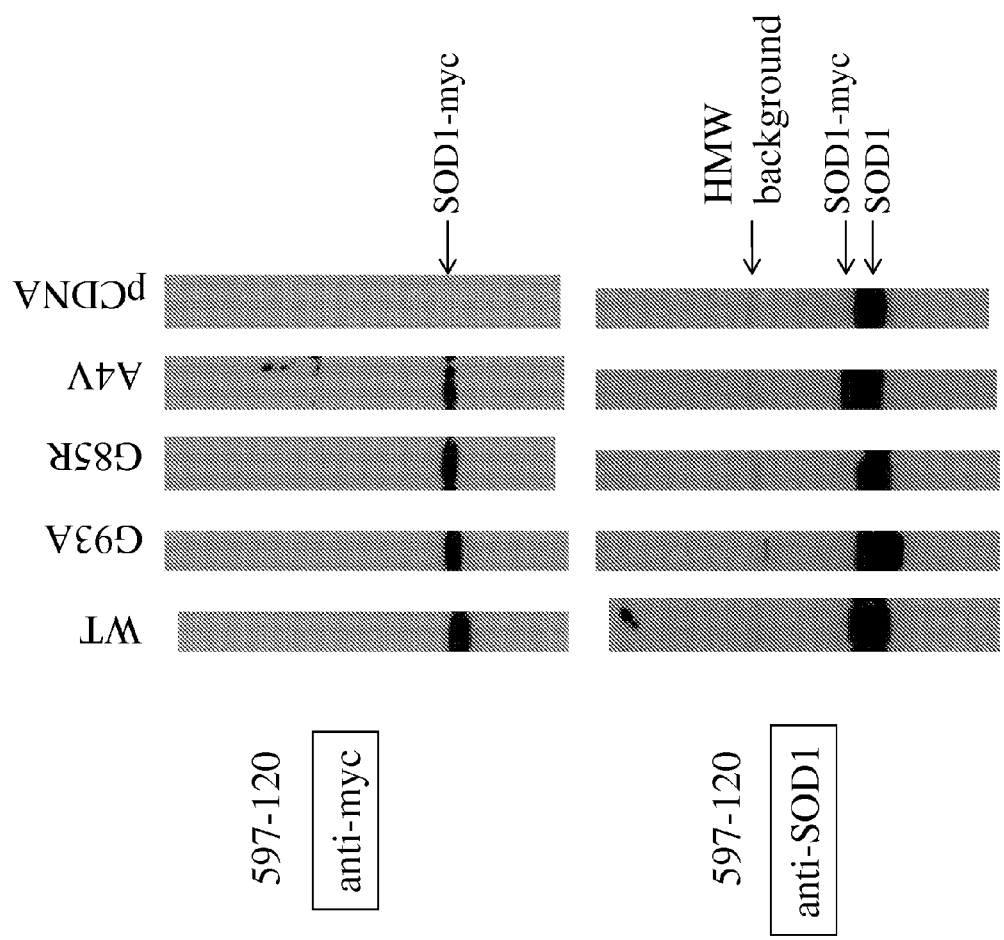
Figure 49J:
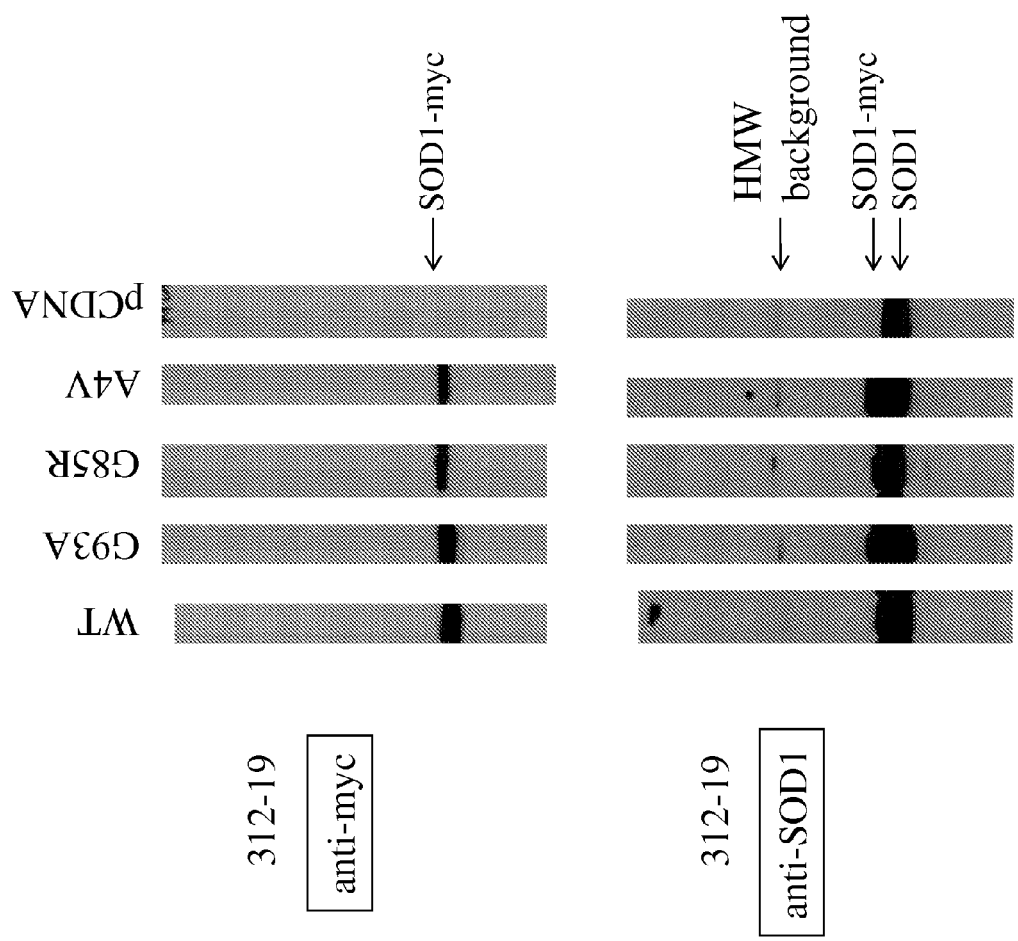
Figure 49L:
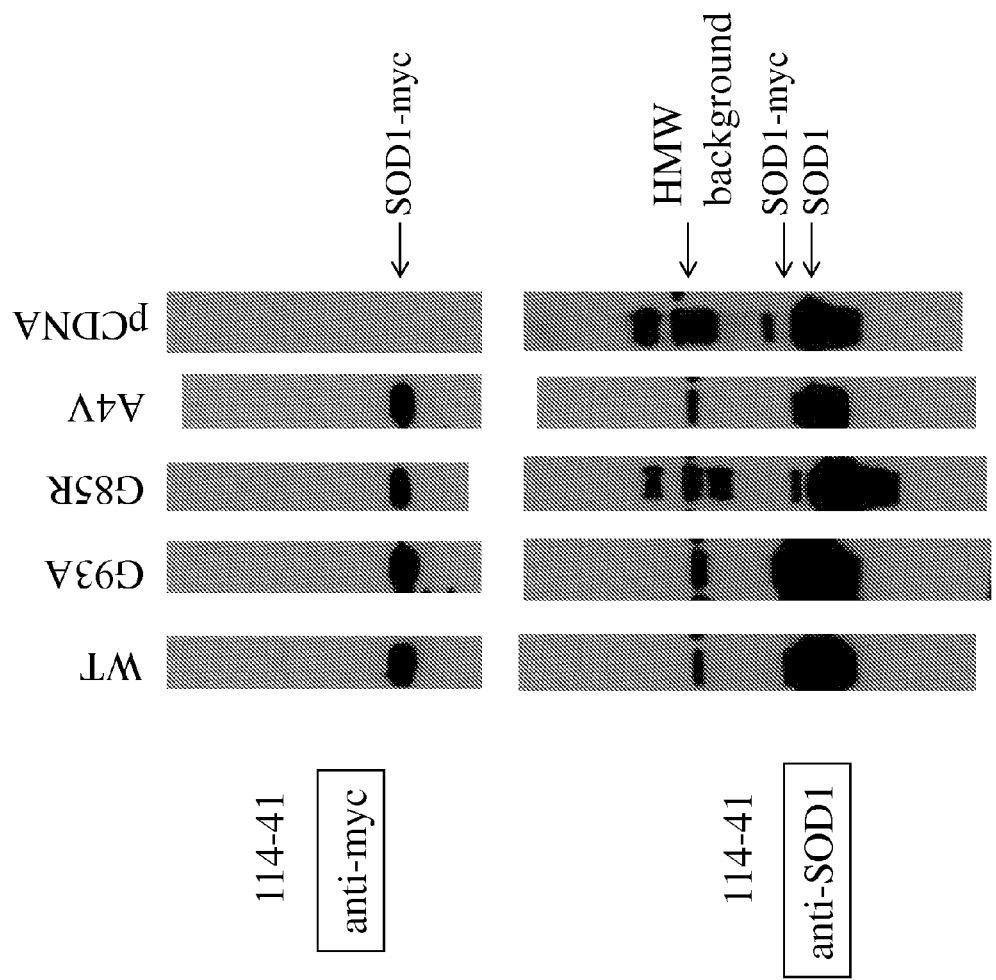
Figure 49O:
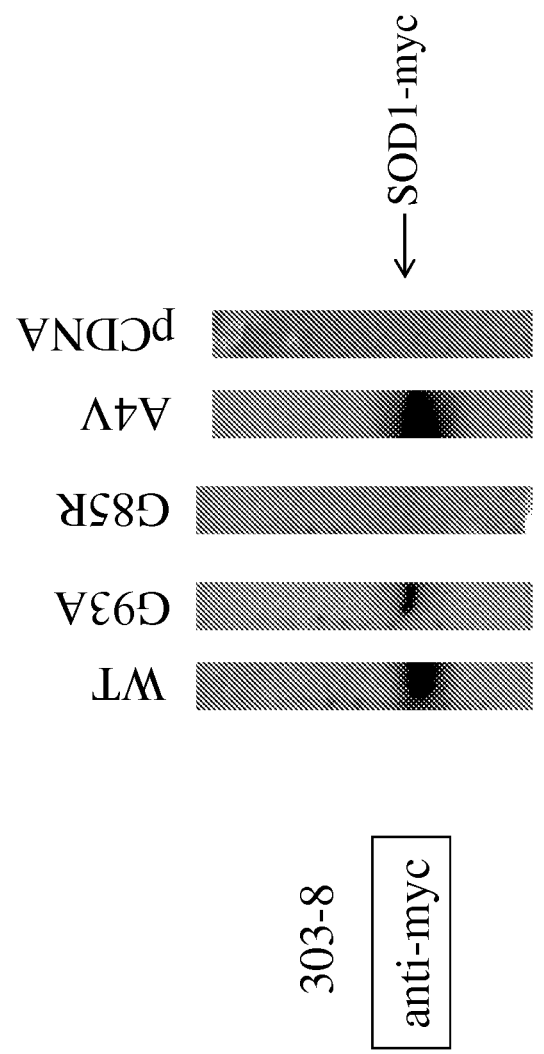

The human antibodies were used to precipitate the various hSOD1 proteins and the Western blots are shown in FIG. 49D-P. All thirteen antibodies could precipitate mutant forms of hSOD1. Detection with the anti-myc antibody consistently gave weaker results than the rabbit anti-hSOD1 but the results for each were consistent. Interestingly, the antibodies that recognize linear epitopes, 595-16 (FIG. 49D), 591-37 (FIG. 49E), 358-11 (FIG. 49F), 311-3 (FIG. 49I), and 591-33 (FIG. 49K) could only precipitate mutant forms of the protein. No detection of wild-type hSOD1 was observed in any of the blots. Also of interest, 358-11 was not able to precipitate the hSOD1-G85R mutant presumably since the mutation occurs in the epitope recognized by the antibody (amino acids 80-88). However, all conformation dependent antibodies were able to precipitate both mutant and wild-type hSOD1. It is also clear that all conformation dependent antibodies can precipitate wild-type SOD1 present in HEK-293T cells which can be distinguished from the transfected hSOD1 due to the smaller apparent molecular weight. In addition, HEK-293T hSOD1 can only be seen in the blots probed with the rabbit anti-hSOD1 since the native protein does not contain the myc epitope tag.

This experiment was repeated using mouse neuroblastoma cells (MNA) rather than the human HEK-293T cells. All precipitations and controls were as described above and the goal of this test was to determine if any of the antibodies could precipitate mouse SOD1. Interestingly, only the conformation dependant antibodies 358-22 and 14-173 were able to precipitate mouse SOD1 (FIG. 50).

Cell Staining

HEK-293T cells were transiently transfected with hSOD1-G93A. After 120 hours cells were stained with the lead-candidate human monoclonal antibodies. Cells were observed using fluorescence microscopy and photographs taken (FIG. 51). All antibodies were able to stain hSOD1 in the cells. However, it is unclear if the antibodies stain the mutant hSOD1-G93A or the native hSOD1 expressed in HEK-293T cells. Of note, only the antibodies that recognized linear epitopes, 591-33, 595-16, 311-3, 591-37, and 358-11, were able to detect granules of hSOD1 within the cell. These results suggest that the antibodies binding linear epitopes recognize aggregated forms of the hSOD1 protein. The summary of the immunoprecipitation and cell staining results are shown in Table 4. Antibodies that demonstrated aggregate staining in HEK-293T cells were also the antibodies that only recognized mutant forms of hSOD1 in the immunoprecipitation assay.

TABLE 4

| Antibody | IP from 293T cells | IF staining of aggregates in 293T cells |
|---|---|---|
| 595-16 | only mutants | + |
| 591-37 | only mutants | + |
| 358-11 | only mutants | + |
| 358-22 | all | − |
| 597-120 | all | − |
| 311-3 | only mutants | + |

TABLE 4-continued

| Antibody | IP from 293T cells | IF staining of aggregates in 293T cells |
|---|---|---|
| 312-19 | all | − |
| 591-33 | only mutants | + |
| 114-41 | all | − |
| 306-155 | all | − |
| 14-173 | all | − | hSOD1 Mouse Tissue Staining

To determine if human anti-SOD1 monoclonal antibodies could interact with hSOD1 expressed in a mouse model of ALS, animals expressing either hSOD1 or hSOD1-G93A mutant were perfused with 4% paraformaldehyde for tissue fixation. Two sections of mouse lumbar spinal cord were dissected from mice at either 90 or 139 days of age and sections were incubated with human anti-hSOD1 monoclonal antibodies. The ventral horn region of the tissue sections were observed by fluorescence microscopy and photographs were taken using either 50 or 150 millisecond exposure times (FIG. 52). A negative control mAb did not demonstrate staining of any tissues. All anti-hSOD1 human monoclonal antibodies demonstrated staining of hSOD1 (wildtype or G93A mutant) albeit with varying degrees of intensity. A proportion of the antibodies were able to interact with hSOD1 present in the central canal area of the sections presenting as a ring around the central canal. The summarized results of all staining experiments is shown in Table 5.

TABLE 5

| Antibody | hSOD1 | G93A-hSOD1 | Central canal | G93A-hSOD1 aggregate |
|---|---|---|---|---|
| 595-16 | + | ++ | + | ++ |
| 591-37 | + | + | − | +++ |
| 358-22 | + | ++ | + | + |
| 597-120 | +++ | +++ | + | + |
| 311-3 | + | + | − | ++ |
| 312-19 | + | + | + | ++ |
| 591-33 | + | ++ | − | ++ |
| 114-41 | +++ | + | ++ | +++ |
| 306-155 | ++ | ++++ | + | ++ |
| 14-173 | +++ | + | +++ | +++ |

Affinity Analysis

Affinity analysis was performed on all 13 lead-candidate anti-hSOD1 human monoclonal antibodies. Affinity was determined using an Octet QK instrument on both E-hSOD1 and b-hSOD1 (Table 6).

TABLE 6

| Antibody | $K_D$ (nM) for E-hSOD1 | $K_D$ (nM) for b-hSOD1 |
|---|---|---|
| 595-16 | None | 5.6 |
| 591-37 | None | 2.1 |
| 358-11 | None | 5.5 |
| 358-22 | 1.1 | 4.1 |
| 597-120 | 1.0 | 2.0 |
| 311-3 | None | 6.7 |
| 312-19 | 0.2 | 1.3 |
| 591-33 | None | 5.0 |
| 114-41 | 6.5 | 5.6 |
| 306-155 | 2.2 | 7.3 |
| 14-173 | 3.5 | 19.0 |
| 303-8 | 8.8 | 1.2 |
| 312-56 | 6.8 | 5.2 |

E-hSOD1 was purified from human erythrocytes and represents fully metallated, native conformation hSOD1. The b-hSOD1 was expressed and purified recombinantly from E. coli. b-hSOD1 has been shown to lack a full complement of metal and is expected to be misfolded to some extent. Affinity was measured and all antibodies demonstrated strong affinity for b-hSOD1. 358-22, 597-120, 312-19, 114-41, 306-155, 14-173, 303-8 and 312-56 all bound E-hSOD1 with high affinity. However, the antibodies that recognized a linear epitope in hSOD1 (591-33, 595-16, 311-3, 591-37 and 358-11) showed no apparent binding to E-hSOD1. These results are in full agreement with the immunoprecipitation results suggesting that the five antibodies that recognize a linear determinant in hSOD1 do not recognize properly folded, wild-type hSOD1.

Competition

To determine if the antibodies interacting with linear determinants within hSOD1 could compete with the antibodies recognizing conformation-dependant determinant, a full competition analysis for b-hSOD1 was performed using the Octet QK and the results are shown in FIG. 53. As expected, all antibodies compete with themselves for binding to b-hSOD1. All antibodies with linear epitopes were unable to compete with each other, with the exception of 311-3 and 595-16 which have overlapping linear epitopes. Interestingly, all linear antibodies competed with essentially all conformation-dependant antibodies. The one unique binding profile with regards to the linear/conformational competition was antibody 114-41. This antibody competed with all linear-reactive antibodies when it was allowed to bind to b-hSOD1 as the primary antibody. However, when 591-33 or 591-37 was bound first to b-hSOD1, 114-41 was still able to bind so the competition between this group of mAbs can be considered unidirectional. 114-41 demonstrated this same unidirectional competition when tested against the conformation-dependant antibody 14-173 (FIG. 47).

Example 5

In vivo Activity of Antibodies in the Human Mutant (G93A) SOD1 Transgenic Mice with ALS-Like Phenotype Anti-SOD1 antibodies of the present invention were dosed intrathecally into transgenic mice expressing mutant human SOD1 and having an ALS-like phenotype. Transgenic B6SJL-Tg(SOD1G93A)1Gur/J strain (expressing the G93A human SOD1 mutant) mice were obtained from Jackson Laboratories. Mice at approximately 65 days of age were surgically implanted with a lumbar intrathecal catheter into the spinal subarachnoid space. The catheter was connected to an Alzet pump channeled under the skin of the back. The Alzet pump is a miniature osmotic pump that relies on physiological tonicity to cause the inflation of an osmotic reservoir which gradually compresses an internal impermeable reservoir containing the antibody which is thus expelled through a flow regulator during the course of the experiment. Each antibody dosed in the mouse model was prepared at approximately 10 mg/mL. The Alzet model 2006 used in this study has a nominal reservoir volume of 200 μl and delivers a nominal 0.15 μl/hr over a course of approximately 6 weeks.

Pumps were implanted at around day 65 of life as this was the youngest age at which the procedure and implantation can be reasonably executed. To avoid any adverse impact on the pump system, the animals were not physically challenged in standardized tests and the primary measurement of function in the assay was weight gain and/or weight maintenance until pump removal. The pumps were removed at day 115 of life and the animals were observed for progression of the ALS phenotype. After the removal of the pumps and the termination of dosing, the primary measurement in the assay was gross motor capability/survival. Animals surviving the progression of the disease phenotype to the stage of complete bilateral hind limb paralysis were euthanized.

Control animals received dosing of an unrelated isotypic monoclonal antibody in the same formulation and, after normalizing for starting weight, manifested weight plateau at around 90 days of life, consistent with this strain. This was followed by marked weight loss with the average weight of animals falling past the starting weight at around Day 104. Animals began to reach the assay endpoint by day 118 and the average day of death was 120.5 days (n=10) (see Table 7).

In our preliminary experiments, of the six antibodies of the present invention studied in this mouse model to date, five (597-120, 591-37, 591-33, 358-22 and 358-11) showed a higher and/or later weight plateau than the control group after normalizing for starting weights (FIGS. 54A-C). Antibody 595-16 showed a plateau that was similar in terms of timing and weight gain over starting weight to that seen in the control cohort.

All six antibodies (597-120, 595-16, 591-37, 591-33, 358-22 and 358-11) studied in the preliminary studies using the mouse model maintained weight better than the control cohort as judged by the day the average weight of the cohort fell below the starting weights. This general extension of healthy function is most clearly demonstrated by the average extension in life for each cohort dosed with antibody of the present invention (n=4 for each cohort except 597-120 where n=6) over the control cohort, which ranged from a 5.8 day extension over control for antibody 358-11, 7.3 days for 358-22, 8.8 days for 591-33, 10.5 days for 595-16, 6.7 days for 597-120 and 12.8 days extension of life over the control cohort for antibody 591-37 (see Table 7).

TABLE 7

| treatment | days of survival | average | difference from control |
|---|---|---|---|
| 358-11 | 118 | 126.3 | 4.5 |
| 358-11 | 121 | | |
| 358-11 | 127 | | |
| 358-11 | 139 | | |
| 358-22 | 127 | 127.8 | 6.0 |
| 358-22 | 127 | | |
| 358-22 | 127 | | |
| 358-22 | 130 | | |
| 591-33 | 118 | 129.3 | 7.5 |
| 591-33 | 130 | | |
| 591-33 | 133 | | |
| 591-33 | 136 | | |
| 591-37 | 121 | 133.3 | 11.5 |
| 591-37 | 130 | | |
| 591-37 | 136 | | |
| 591-37 | 146 | | |
| 595-16 | 118 | 131.0 | 9.2 |
| 595-16 | 120 | | |
| 595-16 | 136 | | |
| 595-16 | 150 | | |
| 597-120 | 118 | 133.2 | 11.4 |
| 597-120 | 128 | | |
| 597-120 | 130 | | |
| 597-120 | 140 | | |
| 597-120 | 150 | | |
| 114-41 | 125 | 121.3 | −0.5 |
| 114-41 | 121 | | |
| 114-41 | 118 | | |
| 306-155 | 111 | 117.5 | −4.3 |
| 306-155 | 124 | | |
| 311-3 | 118 | 124.5 | 2.7 |
| 311-3 | 121 | | |
| 311-3 | 128 | | |
| 311-3 | 131 | | |
| 312-19 | 115 | 129.3 | 7.5 |
| 312-19 | 127 | | |
| 312-19 | 137 | | |
| 312-19 | 138 | | |
| control | 111 | 121.8 | N/A |
| control | 115 | | |
| control | 117 | | |
| control | 118 | | |
| control | 132 | | |
| control | 132 | | |
| control | 112 | | |
| control | 124 | | |
| control | 124 | | |
| control | 133 | | |

In these preliminary mouse experiments, animals receiving antibodies of the present invention showed a therapeutic benefit manifested as significant improvements in general health evidenced by gain and maintenance of body weight, and the maintenance of gross motor function, as assessed by the date of attainment of bilateral hind-limb paralysis, with respect to controls similarly dosed with an irrelevant antibody of the same isotype.

The mouse models described above are used to dose the antibodies using intraperitoneal (IP) dosing and are predicted to delay onset of symptoms and extend life compared to controls receiving an unrelated antibody. The use of IP delivery allows for dosing animals earlier in life, more frequently, and with larger doses of antibody.

Example 6

Complete Antibody Sequencing and Cloning

The heavy chain sequence for all antibodies was determined during the screening process for selection of the lead-candidate antibodies. Using PCR, a Kozak sequence (5' end) and the appropriate restriction sites (5' and 3' end) were engineered into the sequence for subsequent cloning into expression vectors. For light chain sequencing, Rapid Amplification of mRNA Ends by PCR (RACE) was performed to determine variable region sequence. The sequence was cloned into the pCR4-TOPO vector (Invitrogen) and the inserted element was sequenced. Gene specific primers were designed and used to PCR-amplify sequences from pCR4-TOPO and add restriction sites and a Kozak sequence for subsequent cloning into expression vectors. Expression vectors for the heavy and light chain genes were combined into one final expression vector construct. Also, in some instances the heavy chain and light chain leader region was replaced with an osteonectin leader (SEQ ID NO: 350) to enhance expression of the antibodies.

Example 7

Antibody Mutagenesis to Optimize Properties

Many factors are considered possibly deleterious for antibodies. Divergence of the framework region sequence from that found in the germline gene may be ultimately immunogenic in the patient. Also, certain amino acids in the antibody may be prone to modifications including but not limited to glycosylation, oxidation, deamidation, hydrolysis, isomerization or disulfide bonding. These amino acid modifications can lead to heterogeneity of an antibody product which is not desirable. In addition, the DP44 antibody gene contains two amino acids (H13 and M87) that are not found in the human repertoire and may be considered immunogenic. An analysis of the lead candidate antibodies was performed to identify amino acids that could be considered problematic in a final product. Sequences for both heavy and light chains were altered to remove these undesirable amino acids and the new sequences were named M1.

Example 8

Production of Anti-hSOD1 Antibodies for Administration in Humans

Human antibodies of the present invention can be cloned and recombinantly expressed to facilitate or increase their production using known techniques.

Nucleic acid sequences encoding the variable heavy chain and light chains of the hSOD1-reactive antibodies were cloned into a pIE-Ugamma1F vector using standard recombinant DNA methodology. The vector was amplified in $E.$ $coli$, purified, and transfected into CHO-DG44 cells. Transfected cells were plated at $4 \times 10^5$ cells per well in a 96-well dish and selected for vector transfection with G418. The expression of the antibodies was amplified by growth in the presence of increasing concentrations of methotrexate. A culture capable of growth in 175 nM methotrexate was chosen for cloning single cells for further development. Plating the culture in 96 well plates at low density allowed generation of cultures arising from a single cell or clones. The cultures were screened for production of human IgG, and the cell that produced the highest level of IgG was selected for further use. The methotrexate-amplified clone was expanded to produce a cell bank including multiple frozen vials of cells. Alternatively, glutamine synthetase (GS) vectors can be used with cell selection achieved using, e.g., methionine sulphoximine (see, e.g., U.S. Pat. Nos. 5,827,739; 5,122,464; 5,879,936; and 5,891,693).

To prepare antibodies from transfected cells, cells from a clone isolated in the previous steps are cultured and expanded as inoculum for a bioreactor. The bioreactor typically holds a 500 liter volume of culture medium. The cells are cultured in the bioreactor until cell viability drops, which indicates a maximal antibody concentration has been produced in the culture. The cells are removed by filtration. The filtrate is applied to a protein A column. Antibodies bind to the column, and are eluted with a low pH wash. Next, the antibodies are applied to a Q-sepharose column to remove residual contaminants, such as CHO cell proteins, DNA, and other contaminants (e.g., viral contaminants, if present). Antibodies are eluted from the Q-sepharose column, nano-filtered, concentrated, and washed in a buffer such as PBS. The preparation is then aseptically aliquoted into vials for administration.

Example 9

Interaction of Antibodies with SOD1 in Patients with sALS

Sporadic ALS or familial ALS not associated with SOD1 mutations may be due to misfolding of SOD1 caused by factors other than SOD1 mutations. In such cases, the antibodies of the present invention may be used to provide therapeutic benefit to patients suffering from SALS or FALS due to misfolded SOD1. To determine if antibodies directed against SOD1 differentially recognize SOD1 protein found in the CNS of SALS patients, sections of spinal cord are isolated from deceased SALS patients. Immunohistochemistry is used to determine if human anti-SOD1 monoclonal antibodies interact with SOD1 in these sections. Antibodies directed against linear epitopes of SOD1 only recognize mutant/misfolded forms of SOD1, and staining in SALS-derived spinal cord sections (excluding those cases where genotyping suggests that the SALS is associated with de novo or otherwise familiarly unknown SOD1 mutation) would suggest SOD1 was misfolded in these patients. The antibodies of the invention, or a subset thereof that binds to the misfolded SOD1 in patients may be used for therapeutic benefit in the patients suffering from SALS or FALS.

Example 10

In vitro Assays to Determine the Activity of Antibodies

One proposed mechanism is for the SOD1 effect on motor neuron loss is that SOD1 misfolds and aggregates causing direct toxicity to cells leading to motor neuron death. Antibodies inhibiting SOD1 aggregation could then provide therapeutic benefit. In vitro, aggregation can be measured by detecting exposure of hydrophobic surfaces on the SOD1 protein. Dyes such as 8-anilinonaphthalene sulfonate (ANS) bind to hydrophobic surfaces, gaining measurable alteration in fluorescence emission profiles. The ability of an antibody to block aggregation in vitro is demonstrated by reduction in ANS binding to misfolded SOD1 in the presence of an aggregation-inhibiting antibody.

SOD1 aggregation has been shown to activate immune cells such as microglia. This activation leads to microglia-induced destruction of neuronal cells in culture. When SOD1-G93A is either endogenously or exogenously applied to microglial cells cultured in the presence of motor neurons, motor neuron death is measured by apoptotic markers, as well as visible observation. In addition, microglial activation in this experiment can be measured by detection of increased levels of mRNA and/or proteins related to TNF-α, IFN-γ, and iNOS (nitric oxide synthase). Such assays may be used to further assess the antibodies of the invention for their ability to provide a therapeutic benefit and will better define the exact pathological mechanism(s) to be remediated.

It has also been shown that expression of SOD1-G93A protein in neuronal cells in culture leads to susceptibility to oxidative damage and cell death. Xanthine/xanthine oxidase is applied to SOD1-G93A expressing neuronal cells to deliver oxidative stress. The death induced by this stress is determined, for example, using a metabolic dye, such as Alamar blue. The addition of anti-SOD1 antibodies to the culture may inhibit the cell death or mitigate the cell stress associated with this oxidative insult. Such an assay may be used to assess the ability of the antibodies of the present invention to provide a therapeutic benefit, and to further define the pathological mechanism(s) underlying the ALS neurodegenerative phenotype.

Other Embodiments

The description of the specific embodiments of the invention is presented for the purposes of illustration. It is not intended to be exhaustive or to limit the scope of the invention to the specific forms described herein. Although the invention has been described with reference to several embodiments, it will be understood by one of ordinary skill in the art that various modifications can be made without departing from the spirit and the scope of the invention, as set forth in the claims. All patents, patent applications, and publications referenced herein are hereby incorporated by reference. Other embodiments are in the claims.

| Seq ID # | type | comments | FIGURES |
|---|---|---|---|
| 1 | AA | 595-16 VH | FIG. 1 |
| 2 | NT | 595-16 VH | FIG. 1 |
| 3 | AA | 595-16 VH CDR1 | FIG. 1 + 3 |
| 4 | NT | 595-16 VH CDR1 | FIG. 1 + 3 |
| 5 | AA | 595-16 VH CDR2 | FIG. 1 + 3 |
| 6 | NT | 595-16 VH CDR2 | FIG. 1 + 3 |
| 7 | AA | 595-16 VH CDR3 | FIG. 1 + 3 |
| 8 | NT | 595-16 VH CDR3 | FIG. 1 + 3 |
| 9 | AA | 595-16 VK | FIG. 2 |
| 10 | NT | 595-16 VK | FIG. 2 |
| 11 | AA | 595-16 VK CDR1 | FIG. 2 |
| 12 | NT | 595-16 VK CDR1 | FIG. 2 |
| 13 | AA | 595-16 VK CDR2 | FIG. 2 |
| 14 | NT | 595-16 VK CDR2 | FIG. 2 |
| 15 | AA | 595-16 VK CDR3 | FIG. 2 |
| 16 | NT | 595-16 VK CDR3 | FIG. 2 |
| 17 | AA | 595-16-M1 VH | FIG. 3 |
| 18 | NT | 595-16-M1 VH | FIG. 3 |
| 19 | AA | 591-37 VH | FIG. 4 |
| 20 | NT | 591-37 VH | FIG. 4 |
| 21 | AA | 591-37 VH CDR1 | FIG. 4 + 6 |
| 22 | NT | 591-37 VH CDR1 | FIG. 4 + 6 |
| 23 | AA | 591-37 VH CDR2 | FIG. 4 + 6 |
| 24 | NT | 591-37 VH CDR2 | FIG. 4 + 6 |
| 25 | AA | 591-37 VH CDR3 | FIG. 4 + 6 |
| 26 | NT | 591-37 VH CDR3 | FIG. 4 + 6 |
| 27 | AA | 591-37 VK | FIG. 5 |
| 28 | NT | 591-37 VK | FIG. 5 |
| 29 | AA | 591-37 VK CDR1 | FIG. 5 |
| 30 | NT | 591-37 VK CDR1 | FIG. 5 |
| 31 | AA | 591-37 VK CDR2 | FIG. 5 |
| 32 | NT | 591-37 VK CDR2 | FIG. 5 |
| 33 | AA | 591-37 VK CDR3 | FIG. 5 |
| 34 | NT | 591-37 VK CDR3 | FIG. 5 |
| 35 | AA | 591-37-M1 VH | FIG. 6 |
| 36 | NT | 591-37-M1 VH | FIG. 6 |
| 37 | AA | 358-11 VH | FIG. 7 |
| 38 | NT | 358-11 VH | FIG. 7 |
| 39 | AA | 358-11 VH CDR1 | FIG. 7 + 9 |
| 40 | NT | 358-11 VH CDR1 | FIG. 7 + 9 |
| 41 | AA | 358-11 VH CDR2 | FIG. 7 + 9 |
| 42 | NT | 358-11 VH CDR2 | FIG. 7 + 9 |
| 43 | AA | 358-11 VH CDR3 | FIG. 7 + 9 |
| 44 | NT | 358-11 VH CDR3 | FIG. 7 + 9 |
| 45 | AA | 358-11 VK | FIG. 8 |
| 46 | NT | 358-11 VK | FIG. 8 |
| 47 | AA | 358-11 VK CDR1 | FIG. 8 |
| 48 | NT | 358-11 VK CDR1 | FIG. 8 |
| 49 | AA | 358-11 VK CDR2 | FIG. 8 |
| 50 | NT | 358-11 VK CDR2 | FIG. 8 |
| 51 | AA | 358-11 VK CDR3 | FIG. 8 |
| 52 | NT | 358-11 VK CDR3 | FIG. 8 |
| 53 | AA | 358-11-M1 VH | FIG. 9 |
| 54 | NT | 358-11-M1 VH | FIG. 9 |
| 55 | AA | 358-22 VH | FIG. 10 |
| 56 | NT | 358-22 VH | FIG. 10 |
| 57 | AA | 358-22 VH CDR1 | FIG. 10 + 12 |
| 58 | NT | 358-22 VH CDR1 | FIG. 10 + 12 |
| 59 | AA | 358-22 VH CDR2 | FIG. 10 + 12 |
| 60 | NT | 358-22 VH CDR2 | FIG. 10 + 12 |
| 61 | AA | 358-22 VH CDR3 | FIG. 10 + 12 |
| 62 | NT | 358-22 VH CDR3 | FIG. 10 + 12 |
| 63 | AA | 358-22 VK | FIG. 11 |
| 64 | NT | 358-22 VK | FIG. 11 |
| 65 | AA | 358-22 VK CDR1 | FIG. 11 |
| 66 | NT | 358-22 VK CDR1 | FIG. 11 |
| 67 | AA | 358-22 VK CDR2 | FIG. 11 |
| 68 | NT | 358-22 VK CDR2 | FIG. 11 |
| 69 | AA | 358-22 VK CDR3 | FIG. 11 |
| 70 | NT | 358-22 VK CDR3 | FIG. 11 |
| 71 | AA | 358-22-M1 VH | FIG. 12 |
| 72 | NT | 358-22-M1 VH | FIG. 12 |
| 73 | AA | 597-120 VH | FIG. 13 |
| 74 | NT | 597-120 VH | FIG. 13 |
| 75 | AA | 597-120 VH CDR1 | FIG. 13 + 15 |
| 76 | NT | 597-120 VH CDR1 | FIG. 13 + 15 |
| 77 | AA | 597-120 VH CDR2 | FIG. 13 + 15 |
| 78 | NT | 597-120 VH CDR2 | FIG. 13 + 15 |
| 79 | AA | 597-120 VH CDR3 | FIG. 13 + 15 |
| 80 | NT | 597-120 VH CDR3 | FIG. 13 + 15 |
| 81 | AA | 597-120 VK | FIG. 14 |
| 82 | NT | 597-120 VK | FIG. 14 |
| 83 | AA | 597-120 VK CDR1 | FIG. 14 |
| 84 | NT | 597-120 VK CDR1 | FIG. 14 |
| 85 | AA | 597-120 VK CDR2 | FIG. 14 |
| 86 | NT | 597-120 VK CDR2 | FIG. 14 |
| 87 | AA | 597-120 VK CDR3 | FIG. 14 |
| 88 | NT | 597-120 VK CDR3 | FIG. 14 |
| 89 | AA | 597-120-M1 VH | FIG. 15 |
| 90 | NT | 597-120-M1 VH | FIG. 15 |
| 91 | AA | 311-3 VH | FIG. 16 |
| 92 | NT | 311-3 VH | FIG. 16 |
| 93 | AA | 311-3 VH CDR1 | FIG. 16 + 18 |
| 94 | NT | 311-3 VH CDR1 | FIG. 16 + 18 |
| 95 | AA | 311-3 VH CDR2 | FIG. 16 + 18 |
| 96 | NT | 311-3 VH CDR2 | FIG. 16 + 18 |
| 97 | AA | 311-3 VH CDR3 | FIG. 16 + 18 |
| 98 | NT | 311-3 VH CDR3 | FIG. 16 + 18 |
| 99 | AA | 311-3 VK | FIG. 17 |
| 100 | NT | 311-3 VK | FIG. 17 |
| 101 | AA | 311-3 VK CDR1 | FIG. 17 + 19 |
| 102 | NT | 311-3 VK CDR1 | FIG. 17 + 19 |
| 103 | AA | 311-3 VK CDR2 | FIG. 17 |
| 104 | NT | 311-3 VK CDR2 | FIG. 17 |
| 105 | AA | 311-3 VK CDR3 | FIG. 17 + 19 |
| 106 | NT | 311-3 VK CDR3 | FIG. 17 + 19 |
| 107 | AA | 311-3-M1 VH | FIG. 18 |
| 108 | NT | 311-3-M1 VH | FIG. 18 |
| 109 | AA | 311-3-M1 VK | FIG. 19 |
| 110 | NT | 311-3-M1 VK | FIG. 19 |
| 111 | AA | 311-3-M1 VK CDR2 | FIG. 19 |
| 112 | NT | 311-3-M1 VK CDR2 | FIG. 19 |
| 113 | AA | 312-19 VH | FIG. 20 |
| 114 | NT | 312-19 VH | FIG. 20 |
| 115 | AA | 312-19 VH CDR1 | FIG. 20 + 22 |
| 116 | NT | 312-19 VH CDR1 | FIG. 20 + 22 |
| 117 | AA | 312-19 VH CDR2 | FIG. 20 + 22 |
| 118 | NT | 312-19 VH CDR2 | FIG. 20 + 22 |
| 119 | AA | 312-19 VH CDR3 | FIG. 20 + 22 |
| 120 | NT | 312-19 VH CDR3 | FIG. 20 + 22 |
| 121 | AA | 312-19 VK | FIG. 21 |
| 122 | NT | 312-19 VK | FIG. 21 |
| 123 | AA | 312-19 VK CDR1 | FIG. 21 |
| 124 | NT | 312-19 VK CDR1 | FIG. 21 |
| 125 | AA | 312-19 VK CDR2 | FIG. 21 |
| 126 | NT | 312-19 VK CDR2 | FIG. 21 |
| 127 | AA | 312-19 VK CDR3 | FIG. 21 |
| 128 | NT | 312-19 VK CDR3 | FIG. 21 |
| 129 | AA | 312-19-M1 VH | FIG. 22 |
| 130 | NT | 312-19-M1 VH | FIG. 22 |
| 131 | AA | 591-33 VH | FIG. 23 |
| 132 | NT | 591-33 VH | FIG. 23 |
| 133 | AA | 591-33 VH CDR1 | FIG. 23 + 25 |
| 134 | NT | 591-33 VH CDR1 | FIG. 23 + 25 |
| 135 | AA | 591-33 VH CDR2 | FIG. 23 + 25 |
| 136 | NT | 591-33 VH CDR2 | FIG. 23 + 25 |
| 137 | AA | 591-33 VH CDR3 | FIG. 23 + 25 |
| 138 | NT | 591-33 VH CDR3 | FIG. 23 + 25 |
| 139 | AA | 591-33 VK | FIG. 24 |
| 140 | NT | 591-33 VK | FIG. 24 |
| 141 | AA | 591-33 VK CDR1 | FIG. 24 |
| 142 | NT | 591-33 VK CDR1 | FIG. 24 |
| 143 | AA | 591-33 VK CDR2 | FIG. 24 |
| 144 | NT | 591-33 VK CDR2 | FIG. 24 |
| 145 | AA | 591-33 VK CDR3 | FIG. 24 |
| 146 | NT | 591-33 VK CDR3 | FIG. 24 |
| 147 | AA | 591-33-M1 VH | FIG. 25 |
| 148 | NT | 591-33-M1 VH | FIG. 25 |

| Seq ID # | type | comments | FIGURES |
|---|---|---|---|
| 149 | AA | 114-41 VH | FIG. 26 |
| 150 | NT | 114-41 VH | FIG. 26 |
| 151 | AA | 114-41 VH CDR1 | FIG. 26 + 28 |
| 152 | NT | 114-41 VH CDR1 | FIG. 26 + 28 |
| 153 | AA | 114-41 VH CDR2 | FIG. 26 + 28 |
| 154 | NT | 114-41 VH CDR2 | FIG. 26 + 28 |
| 155 | AA | 114-41 VH CDR3 | FIG. 26 + 28 |
| 156 | NT | 114-41 VH CDR3 | FIG. 26 + 28 |
| 157 | AA | 114-41 VK | FIG. 27 |
| 158 | NT | 114-41 VK | FIG. 27 |
| 159 | AA | 114-41 VK CDR1 | FIG. 27 |
| 160 | NT | 114-41 VK CDR1 | FIG. 27 |
| 161 | AA | 114-41 VK CDR2 | FIG. 27 |
| 162 | NT | 114-41 VK CDR2 | FIG. 27 |
| 163 | AA | 114-41 VK CDR3 | FIG. 27 |
| 164 | NT | 114-41 VK CDR3 | FIG. 27 |
| 165 | AA | 114-41-M1 VH | FIG. 28 |
| 166 | NT | 114-41-M1 VH | FIG. 28 |
| 167 | AA | 306-155 VH | FIG. 29 |
| 168 | NT | 306-155 VH | FIG. 29 |
| 169 | AA | 306-155 VH CDR1 | FIG. 29 |
| 170 | NT | 306-155 VH CDR1 | FIG. 29 |
| 171 | AA | 306-155 VH CDR2 | FIG. 29 |
| 172 | NT | 306-155 VH CDR2 | FIG. 29 |
| 173 | AA | 306-155 VH CDR3 | FIG. 29 |
| 174 | NT | 306-155 VH CDR3 | FIG. 29 |
| 175 | AA | 306-155 VK | FIG. 30 |
| 176 | NT | 306-155 VK | FIG. 30 |
| 177 | AA | 306-155 VK CDR1 | FIG. 30 |
| 178 | NT | 306-155 VK CDR1 | FIG. 30 |
| 179 | AA | 306-155 VK CDR2 | FIG. 30 |
| 180 | NT | 306-155 VK CDR2 | FIG. 30 |
| 181 | AA | 306-155 VK CDR3 | FIG. 30 |
| 182 | NT | 306-155 VK CDR3 | FIG. 30 |
| 183 | AA | 14-173 VH | FIG. 31 |
| 184 | NT | 14-173 VH | FIG. 31 |
| 185 | AA | 14-173 VH CDR1 | FIG. 31 |
| 186 | NT | 14-173 VH CDR1 | FIG. 31 |
| 187 | AA | 14-173 VH CDR2 | FIG. 31 |
| 188 | NT | 14-173 VH CDR2 | FIG. 31 |
| 189 | AA | 14-173 VH CDR3 | FIG. 31 |
| 190 | NT | 14-173 VH CDR3 | FIG. 31 |
| 191 | AA | 14-173 VK | FIG. 32 |
| 192 | NT | 14-173 VK | FIG. 32 |
| 193 | AA | 14-173 VK CDR1 | FIG. 32 + 33 |
| 194 | NT | 14-173 VK CDR1 | FIG. 32 + 33 |
| 195 | AA | 14-173 VK CDR2 | FIG. 32 + 33 |
| 196 | NT | 14-173 VK CDR2 | FIG. 32 + 33 |
| 197 | AA | 14-173 VK CDR3 | FIG. 32 + 33 |
| 198 | NT | 14-173 VK CDR3 | FIG. 32 + 33 |
| 199 | AA | 14-173-M1 VK | FIG. 33 |
| 200 | NT | 14-173-M1 VK | FIG. 33 |
| 201 | AA | 303-8 VH | FIG. 34 |
| 202 | NT | 303-8 VH | FIG. 34 |
| 203 | AA | 303-8 VH CDR1 | FIG. 34 |
| 204 | NT | 303-8 VH CDR1 | FIG. 34 |
| 205 | AA | 303-8 VH CDR2 | FIG. 34 |
| 206 | NT | 303-8 VH CDR2 | FIG. 34 |
| 207 | AA | 303-8 VH CDR3 | FIG. 34 |
| 208 | NT | 303-8 VH CDR3 | FIG. 34 |
| 209 | AA | 303-8 VK | FIG. 35 |
| 210 | NT | 303-8 VK | FIG. 35 |
| 211 | AA | 303-8 VK CDR1 | FIG. 35 |
| 212 | NT | 303-8 VK CDR1 | FIG. 35 |
| 213 | AA | 303-8 VK CDR2 | FIG. 35 |
| 214 | NT | 303-8 VK CDR2 | FIG. 35 |
| 215 | AA | 303-8 VK CDR3 | FIG. 35 |
| 216 | NT | 303-8 VK CDR3 | FIG. 35 |
| 217 | AA | 312-56 VH | FIG. 36 |
| 218 | NT | 312-56 VH | FIG. 36 |
| 219 | AA | 312-56 VH CDR1 | FIG. 36 |
| 220 | NT | 312-56 VH CDR1 | FIG. 36 |
| 221 | AA | 312-56 VH CDR2 | FIG. 36 |
| 222 | NT | 312-56 VH CDR2 | FIG. 36 |
| 223 | AA | 312-56 VH CDR3 | FIG. 36 |
| 224 | NT | 312-56 VH CDR3 | FIG. 36 |
| 225 | AA | 312-56 VK | FIG. 37 |
| 226 | NT | 312-56 VK | FIG. 37 |
| 227 | AA | 312-56 VK CDR1 | FIG. 37 |
| 228 | NT | 312-56 VK CDR1 | FIG. 37 |
| 229 | AA | 312-56 VK CDR2 | FIG. 37 |
| 230 | NT | 312-56 VK CDR2 | FIG. 37 |
| 231 | AA | 312-56 VK CDR3 | FIG. 37 |
| 232 | NT | 312-56 VK CDR3 | FIG. 37 |
| 233 | AA | 595-16 VH with leader | none |
| 234 | NT | 595-16 VH with leader | none |
| 235 | AA | 595-16 VK with leader | none |
| 236 | NT | 595-16 VK with leader | none |
| 237 | AA | 595-16-M1 VH with leader | none |
| 238 | NT | 595-16-M1 VH with leader | none |
| 239 | AA | 591-37 VH with leader | none |
| 240 | NT | 591-37 VH with leader | none |
| 241 | AA | 591-37 VK with leader | none |
| 242 | NT | 591-37 VK with leader | none |
| 243 | AA | 591-37-M1 VH with leader | none |
| 244 | NT | 591-37-M1 VH with leader | none |
| 245 | AA | 358-11 VH with leader | none |
| 246 | NT | 358-11 VH with leader | none |
| 247 | AA | 358-11 VK with leader | none |
| 248 | NT | 358-11 VK with leader | none |
| 249 | AA | 358-11-M1 VH with leader | none |
| 250 | NT | 358-11-M1 VH with leader | none |
| 251 | AA | 358-22 VH with leader | none |
| 252 | NT | 358-22 VH with leader | none |
| 253 | AA | 358-22 VK with leader | none |
| 254 | NT | 358-22 VK with leader | none |
| 255 | AA | 358-22-M1 VH with leader | none |
| 256 | NT | 358-22-M1 VH with leader | none |
| 257 | AA | 597-120 VH with leader | none |
| 258 | NT | 597-120 VH with leader | none |
| 259 | AA | 597-120 VK with leader | none |
| 260 | NT | 597-120 VK with leader | none |
| 261 | AA | 597-120-M1 VH with leader | none |
| 262 | NT | 597-120-M1 VH with leader | none |
| 263 | AA | 311-3 VH with leader | none |
| 264 | NT | 311-3 VH with leader | none |
| 265 | AA | 311-3 VK with leader | none |
| 266 | NT | 311-3 VK with leader | none |
| 267 | AA | 311-3-M1 VH with leader | none |
| 268 | NT | 311-3-M1 VH with leader | none |
| 269 | AA | 311-3-M1 VK with leader | none |
| 270 | NT | 311-3-M1 VK with leader | none |
| 271 | AA | 312-19 VH with leader | none |
| 272 | NT | 312-19 VH with leader | none |
| 273 | AA | 312-19 VK with leader | none |
| 274 | NT | 312-19 VK with leader | none |
| 275 | AA | 312-19-M1 VH with leader | none |
| 276 | NT | 312-19-M1 VH with leader | none |
| 277 | AA | 591-33 VH with leader | none |
| 278 | NT | 591-33 VH with leader | none |
| 279 | AA | 591-33 VK with leader | none |
| 280 | NT | 591-33 VK with leader | none |
| 281 | AA | 591-33-M1 VH with leader | none |
| 282 | NT | 591-33-M1 VH with leader | none |
| 283 | AA | 114-41 VH with leader | none |
| 284 | NT | 114-41 VH with leader | none |
| 285 | AA | 114-41 VK with leader | none |
| 286 | NT | 114-41 VK with leader | none |
| 287 | AA | 114-41-M1 VH with leader | none |
| 288 | NT | 114-41-M1 VH with leader | none |
| 289 | AA | 306-155 VH with leader | none |
| 290 | NT | 306-155 VH with leader | none |
| 291 | AA | 306-155 VK with leader | none |
| 292 | NT | 306-155 VK with leader | none |
| 293 | AA | 14-173 VH with leader | none |
| 294 | NT | 14-173 VH with leader | none |
| 295 | AA | 14-173 VK with leader | none |
| 296 | NT | 14-173 VK with leader | none |
| 297 | AA | 14-173-M1 VK with leader | none |
| 298 | NT | 14-173-M1 VK with leader | none |
| 299 | AA | 303-8 VH with leader | none |
| 300 | NT | 303-8 VH with leader | none |
| 301 | AA | 303-8 VK with leader | none |
| 302 | NT | 303-8 VK with leader | none |

-continued

| Seq ID # | type | comments | FIGURES |
|---|---|---|---|
| 303 | AA | 312-56 VH with leader | none |
| 304 | NT | 312-56 VH with leader | none |
| 305 | AA | 312-56 VK with leader | none |
| 306 | NT | 312-56 VK with leader | none |
| 307 | AA | hSOD1 amino acids 40-47 | none |
| 308 | NT | hSOD1 amino acids 40-47 | none |
| 309 | AA | hSOD1 amino acids 63-71 | none |
| 310 | NT | hSOD1 amino acids 63-71 | none |
| 311 | AA | hSOD1 amino acids 80-88 | none |
| 312 | NT | hSOD1 amino acids 80-88 | none |
| 313 | AA | hSOD1 amino acids 42-49 | none |
| 314 | NT | hSOD1 amino acids 42-49 | none |
| 315 | AA | hSOD1 amino acids 107-121 | none |
| 316 | NT | hSOD1 amino acids 107-121 | none |
| 317 | AA | hSOD1 | FIG. 39 + 45 |
| 318 | NT | hSOD1 | none |
| 319 | NT | hSOD1 codon-optimized | none |
| 320 | AA | b-hSOD1-A | FIG. 39 |
| 321 | AA | b-hSOD1-B | FIG. 39 |
| 322 | AA | b-hSOD1-C | FIG. 39 |
| 323 | AA | b-hSOD1-D | FIG. 39 |
| 324 | AA | b-hSOD1-E | FIG. 39 |
| 325 | AA | b-hSOD1-F | FIG. 39 |
| 326 | AA | b-hSOD1-G | FIG. 39 |
| 327 | AA | b-hSOD1-H | FIG. 39 |
| 328 | AA | b-hSOD1-I | FIG. 39 |
| 329 | AA | b-hSOD1-J | FIG. 39 |
| 330 | AA | b-hSOD1-K | FIG. 39 |
| 331 | AA | hSOD1-G1 | FIG. 41 |
| 332 | AA | hSOD1-G1a | FIG. 41 |
| 333 | AA | hSOD1-G1b | FIG. 41 |
| 334 | AA | hSOD1-G1c | FIG. 41 |
| 335 | AA | hSOD1-G2 | FIG. 41 |
| 336 | AA | hSOD1-G3 | FIG. 41 |
| 337 | AA | hSOD1-G4 | FIG. 41 |
| 338 | AA | hSOD1-G4a | FIG. 41 |
| 339 | AA | hSOD1-G4b | FIG. 41 |
| 340 | AA | hSOD1-G4c | FIG. 41 |
| 341 | AA | hSOD1-H1 | FIG. 41 |
| 342 | AA | hSOD1-H1a | FIG. 41 |
| 343 | AA | hSOD1-H1b | FIG. 41 |
| 344 | AA | hSOD1-H1c | FIG. 41 |
| 345 | AA | hSOD1-H2 | FIG. 41 |
| 346 | AA | hSOD1-H3 | FIG. 41 |
| 347 | AA | hSOD1-H4 | FIG. 41 |
| 348 | AA | hSOD1-K1 | FIG. 41 |
| 349 | AA | hSOD1-K2 | FIG. 41 |
| 350 | AA | osteonectin leader | none |
| 351 | NT | osteonectin leader | none |
| 352 | AA | DICLPRWGCLW | none |

```
Sequence listing - hSOD1 human antibodies
                                                                    SEQ ID: 1
(595-16 VH)
EVQLVQSGGGLGHPGGSLRLSCAGSGFTFSSYSMHWLRQAPGKGLKWVSAIGTAGGTYYADSVKGRFTISRDNAKNS

FYLQMNSLRAEDMAVYYCAREYFFGSGNYGYWGQGTLVTASS

SEQ ID: 2
(595-16 VH)
GAGGTTCAGCTGGTGCAGTCTGGGGGAGGCTTGGGACATCCTGGGGGGTCCCTGAGACTCTCCTGTGCAGGCTCTGG

ATTCACTTTCAGTAGTTATTCTATGCACTGGCTTCGCCAGGCTCCAGGAAAAGGTCTGAAGTGGGTATCAGCTATTG

GTACTGCTGGTGGCACATACTATGCAGACTCCGTGAAGGGCCGATTCACCATCTCCAGAGACAATGCCAAGAACTCC

TTCTATCTTCAAATGAACAGCCTGAGAGCCGAGGACATGGCTGTGTATTACTGTGCAAGAGAGTATTTCTTTGGTTC

GGGGAATTATGGATACTGGGGCCAGGGAACCCTGGTCACCGCCTCCTCA

SEQ ID: 3
(595-16 VH CDR1)
SYSMH

SEQ ID: 4
(595-16 VH CDR1)
AGTTATTCTATGCAC

SEQ ID: 5
(595-16 VH CDR2)
AIGTAGGTYYADSVKG

SEQ ID: 6
(595-16 VH CDR2)
GCTATTGGTACTGCTGGTGGCACATACTATGCAGACTCCGTGAAGGGC

SEQ ID: 7
(595-16 VH CDR3)
EYFFGSGNYGY

SEQ ID: 8
(595-16 VH CDR3)
GAGTATTTCTTTGGTTCGGGGAATTATGGATAC

SEQ ID: 9
(595-16 VK)
EIVLTQSPATLSLSPGERATLSCRASQSVSSYLAWYQQKPGQAPRLLIYDASNRATGIPARFSGSGSGTDFTLTISS

LEPEDFAVYYCQQRSNWPPTFGQGTKVEIK
```

```
                                                                  SEQ ID: 10
(595-16 VK)
GAAATTGTGTTGACACAGTCTCCAGCCACCCTGTCTTTGTCTCCAGGGGAAAGAGCCACCCTCTCCTGCAGGGCCAG

TCAGAGTGTTAGCAGCTACTTAGCCTGGTACCAACAGAAACCTGGCCAGGCTCCCAGGCTCCTCATCTATGATGCAT

CCAACAGGGCCACTGGCATCCCAGCCAGGTTCAGTGGCAGTGGGTCTGGGACAGACTTCACTCTCACCATCAGCAGC

CTAGAGCCTGAAGATTTTGCAGTTTATTACTGTCAGCAGCGTAGCAACTGGCCTCCGACGTTCGGCCAAGGGACCAA

GGTGGAGATCAAA

SEQ ID: 11
(595-16 VK CDR1)
RASQSVSSYLA

SEQ ID: 12
(595-16 VK CDR1)
AGGGCCAGTCAGAGTGTTAGCAGCTACTTAGCC

SEQ ID: 13
(595-16 VK CDR2)
DASNRAT

SEQ ID: 14
(595-16 VK CDR2)
GATGCATCCAACAGGGCCACT

SEQ ID: 15
(595-16 VK CDR3)
QQRSNWPPT

SEQ ID: 16
(595-16 VK CDR3)
CAGCAGCGTAGCAACTGGCCTCCGACG

SEQ ID: 17
(595-16-M1 VH)
EVQLVQSGGGLVKPGGSLRLSCAGSGFTFSSYSMHWLRQAPGKGLEWVSAIGTAGGTYYADSVKGRFTISRDNAKNS

LYLQMNSLRAEDTAVYYCAREYFFGSGNYGYWGQGTLVTVSS

SEQ ID: 18
(595-16-M1 VH)
GAGGTTCAGCTGGTGCAGTCTGGGGGAGGCTTGGTAAAACCTGGGGGGTCCCTGAGACTCTCCTGTGCAGGCTCTGG

ATTCACTTTCAGTAGTTATTCTATGCACTGGCTTCGCCAGGCTCCAGGAAAAGGTCTGGAGTGGGTATCAGCTATTG

GTACTGCTGGTGGCACATACTATGCAGACTCCGTGAAGGGCCGATTCACCATCTCCAGAGACAATGCCAAGAACTCC

TTGTATCTTCAAATGAACAGCCTGAGAGCCGAGGACACGGCTGTGTATTACTGTGCAAGAGAGTATTTCTTTGGTTC

GGGGAATTATGGATACTGGGGCCAGGGAACCCTGGTCACCGTCTCCTCA

SEQ ID: 19
(591-37 VH)
EVQLVQSGGGLVHPGGSLRLSCAGSGFTFSRYALHWVRQAPGKGLEWVSAIGIGGGTFYADSVKGRFTISRDNAKNS

LYLQMNSLRAEDMAVYYCARDTYYDFFDAFDIWGQGTMVTVSS

SEQ ID: 20
(591-37 VH)
GAGGTTCAGCTGGTGCAGTCTGGGGGAGGCTTGGTACATCCTGGGGGGTCCCTGAGACTCTCCTGTGCAGGCTCTGG

ATTCACCTTCAGTCGCTATGCTTTACACTGGGTTCGCCAGGCTCCAGGAAAAGGTCTGGAGTGGGTATCAGCTATTG

GTATTGGTGGTGGCACATTCTATGCAGACTCCGTGAAGGGCCGATTCACCATCTCCAGAGACAATGCCAAGAACTCC

TTGTATCTTCAAATGAACAGCCTGAGAGCCGAGGACATGGCTGTGTATTACTGTGCAAGAGATACGTATTACGATTT

TTTTGATGCTTTTGATATCTGGGGCCAAGGGACAATGGTCACCGTCTCTTCA

SEQ ID: 21
(591-37 VH CDR1)
RYALH

SEQ ID: 22
(591-37 VH CDR1)
CGCTATGCTTTACAC
```

(591-37 VH CDR2)
AIGIGGGTFYADSVKG
SEQ ID: 23

(591-37 VH CDR2)
GCTATTGGTATTGGTGGTGGCACATTCTATGCAGACTCCGTGAAGGGC
SEQ ID: 24

(591-37 VH CDR3)
DTYYDFFDAFDI
SEQ ID: 25

(591-37 VH CDR3)
GATACGTATTACGATTTTTTTGATGCTTTTGATATC
SEQ ID: 26

(591-37 VK)
DIQMTQSPSSLSASVGDRVTITCRASQGISSWLAWYQQKPEKAPKSLIYAASSLQSGVPSRFSGSGSGTDFTLTISS

LQPEDFATYYCQQYDSYPLTFGGGTKVEIK
SEQ ID: 27

(591-37 VK)
GACATCCAGATGACCCAGTCTCCATCCTCACTGTCTGCATCTGTAGGAGACAGAGTCACCATCACTTGTCGGGCGAG

TCAGGGTATTAGCAGCTGGTTAGCCTGGTATCAGCAGAAACCAGAGAAAGCCCCTAAGTCCCTGATCTATGCTGCAT

CCAGTTTGCAAAGTGGGGTCCCATCAAGGTTCAGCGGCAGTGGATCTGGGACAGATTTCACTCTCACCATCAGCAGC

CTGCAGCCTGAAGATTTTGCAACTTATTACTGCCAACAGTATGATAGTTACCCTCTCACTTTCGGCGGAGGGACCAA

GGTGGAGATCAAA
SEQ ID: 28

(591-37 VK CDR1)
RASQGISSWLA
SEQ ID: 29

(591-37 VK CDR1)
CGGGCGAGTCAGGGTATTAGCAGCTGGTTAGCC
SEQ ID: 30

(591-37 VK CDR2)
AASSLQS
SEQ ID: 31

(591-37 VK CDR2)
GCTGCATCCAGTTTGCAAAGT
SEQ ID: 32

(591-37 VK CDR3)
QQYDSYPLT
SEQ ID: 33

(591-37 VK CDR3)
CAACAGTATGATAGTTACCCTCTCACT
SEQ ID: 34

(591-37-M1 VH)
EVQLVQSGGGLVKPGGSLRLSCAGSGFTFSRYALHWVRQAPGKGLEWVSAIGIGGGTFYADSVKGRFTISRDNAKNS

LYLQMNSLRAEDTAVYYCARDTYYDFFDAFDIWGQGTMVTVSS
SEQ ID: 35

(591-37-M1 VH)
GAGGTTCAGCTGGTGCAGTCTGGGGGAGGCTTGGTAAAACCTGGGGGGTCCCTGAGACTCTCCTGTGCAGGCTCTGG

ATTCACCTTCAGTCGCTATGCTTTACACTGGGTTCGCCAGGCTCCAGGAAAAGGTCTGGAGTGGGTATCAGCTATTG

GTATTGGTGGTGGCACATTCTATGCAGACTCCGTGAAGGGCCGATTCACCATCTCCAGAGACAATGCCAAGAACTCC

TTGTATCTTCAAATGAACAGCCTGAGAGCCGAGGACACGGCTGTGTATTACTGTGCAAGAGATACGTATTACGATTT

TTTTGATGCTTTTGATATCTGGGGCCAAGGGACAATGGTCACCGTCTCTTCA
SEQ ID: 36

(358-11 VH)
QVQLVESGGGVVQPGRSLRLSCAASGFTFSNYGIHWVRQAPGKGLEWVAIIWHDGSNSYYVDSVKGRFTMSRDNSKN

TVYLQMNSLRAEDTAVYFCARIIGGAFDIWGQGTMVTVSS
SEQ ID: 37

SEQ ID: 38
(358-11 VH)
CAGGTGCAGCTGGTGGAGTCTGGGGGAGGCGTGGTCCAGCCTGGGAGGTCCCTGAGACTCTCCTGTGCAGCGTCTGG

ATTCACCTTCAGTAACTATGGCATACACTGGGTCCGCCAGGCTCCAGGCAAGGGGCTGGAGTGGGTGGCTATTATAT

GGCATGATGGAAGTAATTCATATTATGTAGACTCCGTGAAGGGCCGATTCACCATGTCCAGAGACAATTCCAAGAAC

ACGGTGTATCTGCAAATGAACAGCCTGAGAGCCGAGGACACGGCTGTGTATTTCTGTGCGAGAATAATTGGGGCGC

TTTTGATATCTGGGGCCAAGGGACAATGGTCACCGTCTCTTCA

SEQ ID: 39
(358-11 VH CDR1)
NYGIH

SEQ ID: 40
(358-11 VH CDR1)
CACAACTATGGCATA

SEQ ID: 41
(358-11 VH CDR2)
IIWHDGSNSYYVDSVKG

SEQ ID: 42
(358-11 VH CDR2)
ATTATATGGCATGATGGAAGTAATTCATATTATGTAGACTCCGTGAAGGGC

SEQ ID: 43
(358-11 VH CDR3)
IIGGAFDI

SEQ ID: 44
(358-11 VH CDR3)
ATAATTGGGGCGCTTTTGATATC

SEQ ID: 45
(358-11 VK)
DIQMTQSPSSLSASVGDRVTITCRASQGISSWLAWYQQKPEKAPKSLIYAASSLQSGVPSRFSGSGSGTDFTLTISS

LQPEDFATYYCQQYNSYPITFGQGTRLEIK

SEQ ID: 46
(358-11 VK)
GACATCCAGATGACCCAGTCTCCATCCTCACTGTCTGCATCTGTAGGAGACAGAGTCACCATCACTTGTCGGGCGAG

TCAGGGTATTAGCAGCTGGTTAGCCTGGTATCAGCAGAAACCAGAGAAAGCCCCTAAGTCCCTGATCTATGCTGCAT

CCAGTTTGCAAAGTGGGGTCCCATCAAGGTTCAGCGGCAGTGGATCTGGGACAGATTTCACTCTCACCATCAGCAGC

CTGCAGCCTGAAGATTTTGCAACTTATTACTGCCAACAGTATAATAGTTACCCGATCACCTTCGGCCAAGGGACACG

ACTGGAGATCAAA

SEQ ID: 47
(358-11 VK CDR1)
RASQGISSWLA

SEQ ID: 48
(358-11 VK CDR1)
CGGGCGAGTCAGGGTATTAGCAGCTGGTTAGCC

SEQ ID: 49
(358-11 VK CDR2)
AASSLQS

SEQ ID: 50
(358-11 VK CDR2)
GCTGCATCCAGTTTGCAAAGT

SEQ ID: 51
(358-11 VK CDR3)
QQYNSYPIT

SEQ ID: 52
(358-11 VK CDR3)
CAACAGTATAATAGTTACCCGATCACC

-continued

SEQ ID: 53
(358-11-M1 VH)
QVQLVESGGGVVQPGRSLRLSCAASGFTFSNYGIHWVRQAPGKGLEWVAIIWHDGSNSYYVDSVKGRFTISRDNSKN
TLYLQMNSLRAEDTAVYFCARIIGGAFDIWGQGTMVTVSS

SEQ ID: 54
(358-11-M1 VH)
CAGGTGCAGCTGGTGGAGTCTGGGGGAGGCGTGGTCCAGCCTGGGAGGTCCCTGAGACTCTCCTGTGCAGCGTCTGG
ATTCACCTTCAGTAACTATGGCATACACTGGGTCCGCCAGGCTCCAGGCAAGGGGCTGGAGTGGGTGGCTATTATAT
GGCATGATGGAAGTAATTCATATTATGTAGACTCCGTGAAGGGCCGATTCACCATCTCCAGAGACAATTCCAAGAAC
ACGCTGTATCTGCAAATGAACAGCCTGAGAGCCGAGGACACGGCTGTGTATTTCTGTGCGAGAATAATTGGGGGCGC
TTTTGATATCTGGGGCCAAGGGACAATGGTCACCGTCTCTTCA

SEQ ID: 55
(358-22 VH)
QVQLVESGGGVVQPGRSLRLSCAASGFTFRSYGMHWVRQAPGKGLEWVTLIWYDGSNKYYADSVKGRFTISRDNSKN
TLYLQMNSLRVEDTAVYYCAREGFNWDAFDIWGQGTMVTVSS

SEQ ID: 56
(358-22 VH)
CAGGTGCAACTGGTGGAGTCTGGGGGAGGCGTGGTCCAGCCTGGGAGGTCCCTGAGACTCTCCTGTGCAGCGTCTGG
ATTCACCTTCAGGAGTTATGGCATGCACTGGGTCCGCCAGGCTCCAGGCAAGGGGCTGGAGTGGGTGACACTTATAT
GGTATGATGGAAGTAATAAATACTATGCAGACTCCGTGAAGGGCCGATTCACCATCTCCAGAGACAATTCCAAGAAC
ACGCTGTATCTGCAAATGAACAGCCTGAGAGTCGAGGACACGGCTGTGTATTACTGTGCGAGAGAAGGGTTTAACTG
GGATGCTTTTGATATCTGGGGCCAAGGGACAATGGTCACCGTCTCTTCA

SEQ ID: 57
(358-22 VH CDR1)
SYGMH

SEQ ID: 58
(358-22 VH CDR1)
AGTTATGGCATGCAC

SEQ ID: 59
(358-22 VH CDR2)
LIWYDGSNKYYADSVKG

SEQ ID: 60
(358-22 VH CDR2)
CTAATATGGTATGATGGAAGTAATAAATACTATGCAGACTCCGTGAAGGGC

SEQ ID: 61
(358-22 VH CDR3)
EGFNWDAFDI

SEQ ID: 62
(358-22 VH CDR3)
GAAGGGTTTAACTGGGATGCTTTTGATATC

SEQ ID: 63
(358-22 VK)
EIVLTQSPGTLSLSPGERATLSCRASQSVRISYLAWYQQKPGQAPRLLIYGTFSRATGIPDRFSGSGSGTDFTLTIS
RLEPEDFAVYYCQQYGSSMYTFGQGTKLEIK

SEQ ID: 64
(358-22 VK)
GAAATTGTGTTGACGCAGTCTCCAGGCACCCTGTCTTTGTCTCCAGGGGAAAGAGCCACCCTCTCCTGCAGGGCCAG
TCAGAGTGTTCGCATCAGCTACTTAGCCTGGTACCAGCAGAAACCTGGCCAGGCTCCCAGGCTCCTCATCTATGGTA
CATTCAGCAGGGCCACTGGCATCCCAGACAGGTTCAGTGGCAGTGGGTCTGGGACAGACTTCACTCTCACCATCAGC
AGACTGGAGCCTGAAGATTTTGCAGTGTATTACTGTCAGCAGTATGGTAGCTCAATGTACACTTTTGGCCAGGGGAC
CAAGCTGGAGATCAAA

-continued (358-22 VK CDR1)  
RASQSVRISYLA  
SEQ ID: 65

(358-22 VK CDR1)  
AGGGCCAGTCAGAGTGTTCGCATCAGCTACTTAGCC  
SEQ ID: 66

(358-22 VK CDR2)  
GTFSRAT  
SEQ ID: 67

(358-22 VK CDR2)  
GGTACATTCAGCAGGGCCACT  
SEQ ID: 68

(358-22 VK CDR3)  
QQYGSSMYT  
SEQ ID: 69

(358-22 VK CDR3)  
CAGCAGTATGGTAGCTCAATGTACACT  
SEQ ID: 70

(358-22-M1 VH)  
QVQLVESGGGVVQPGRSLRLSCAASGFTFRSYGMHWVRQAPGKGLEWVTLIWYDGSNKYYADSVKGRFTISRDNSKN

TLYLQMNSLRAEDTAVYYCAREGFNWDAFDIWGQGTMVTVSS  
SEQ ID: 71

(358-22-M1 VH)  
CAGGTGCAACTGGTGGAGTCTGGGGGAGGCGTGGTCCAGCCTGGGAGGTCCCTGAGACTCTCCTGTGCAGCGTCTGG

ATTCACCTTCAGGAGTTATGGCATGCACTGGGTCCGCCAGGCTCCAGGCAAGGGGCTGGAGTGGGTGACACTTATAT

GGTATGATGGAAGTAATAAATACTATGCAGACTCCGTGAAGGGCCGATTCACCATCTCCAGAGACAATTCCAAGAAC

ACGCTGTATCTGCAAATGAACAGCCTGAGAGCCGAGGACACGGCTGTGTATTACTGTGCGAGAGAAGGGTTTAACTG

GGATGCTTTTGATATCTGGGGCCAAGGGACAATGGTCACCGTCTCTTCA  
SEQ ID: 72

(597-120 VH)  
EVHLVESGGGLVQSGGSLRLSCAASGFSISGYWMSWVRQAPGKGLEWVANIKQDGGEKYYGDSVKGRFTISRDNAEN

SLYLQMSSLRAEDTAVYYCVMAGGLDYWGQGALVTVSS  
SEQ ID: 73

(597-120 VH)  
GAGGTGCACCTGGTGGAGTCTGGGGGAGGCTTGGTCCAGTCTGGGGGGTCCCTGAGACTCTCCTGTGCAGCCTCTGG

ATTCAGCATTAGTGGCTATTGGATGAGCTGGGTCCGCCAGGCTCCAGGGAAAGGGCTGGAGTGGGTGGCCAACATAA

AGCAAGATGGAGGTGAGAAGTACTATGGGGACTCTGTGAAGGGCCGATTCACCATCTCCAGAGACAACGCCGAAAAC

TCACTGTATCTGCAAATGAGCAGCCTGAGAGCCGAGGACACGGCTGTGTATTACTGTGTAATGGCGGGTGGCCTTGA

CTACTGGGGCCAGGGAGCCCTGGTCACCGTCTCCTCA  
SEQ ID: 74

(597-120 VH CDR1)  
GYWMS  
SEQ ID: 75

(597-120 VH CDR1)  
GGCTATTGGATGAGC  
SEQ ID: 76

(597-120 VH CDR2)  
NIKQDGGEKYYGDSVKG  
SEQ ID: 77

(597-120 VH CDR2)  
AACATAAAGCAAGATGGAGGTGAGAAGTACTATGGGGACTCTGTGAAGGGC  
SEQ ID: 78

(597-120 VH CDR3)  
AGGLDY  
SEQ ID: 79

-continued

SEQ ID: 80
(597-120 VH CDR3)
GCGGGTGGCCTTGACTAC

SEQ ID: 81
(597-120 VK)
EIVLTQSPATLSLSPGERATLSCRASQSVSSYLAWYQQKPGQAPRLLIYDASNRATGIPARFSGSGSGTDFTLTISS

LEPEDFAVYYCQQRSNWYTFGQGTKLEIK

SEQ ID: 82
(597-120 VK)
GAAATTGTGTTGACACAGTCTCCAGCCACCCTGTCTTTGTCTCCAGGGGAAAGAGCCACCCTCTCCTGCAGGGCCAG

TCAGAGTGTTAGCAGCTACTTAGCCTGGTACCAACAGAAACCTGGCCAGGCTCCCAGGCTCCTCATCTATGATGCAT

CCAACAGGGCCACTGGCATCCCAGCCAGGTTCAGTGGCAGTGGGTCTGGGACAGACTTCACTCTCACCATCAGCAGC

CTAGAGCCTGAAGATTTTGCAGTTTATTACTGTCAGCAGCGTAGCAACTGGTACACTTTTGGCCAGGGGACCAAGCT

GGAGATCAAA

SEQ ID: 83
(597-120 VK CDR1)
RASQSVSSYLA

SEQ ID: 84
(597-120 VK CDR1)
AGGGCCAGTCAGAGTGTTAGCAGCTACTTAGCC

SEQ ID: 85
(597-120 VK CDR2)
DASNRAT

SEQ ID: 86
(597-120 VK CDR2)
GATGCATCCAACAGGGCCACT

SEQ ID: 87
(597-120 VK CDR3)
QQRSNWYT

SEQ ID: 88
(597-120 VK CDR3)
CAGCAGCGTAGCAACTGGTACACT

SEQ ID: 89
(597-120-M1 VH)
EVQLVESGGGLVQPGGSLRLSCAASGFSISGYWMSWVRQAPGKGLEWVANIKQDGGEKYYGDSVKGRFTISRDNAKN

SLYLQMNSLRAEDTAVYYCVMAGGLDYWGQGTLVTVSS

SEQ ID: 90
(597-120-M1 VH)
GAGGTGCAGCTGGTGGAGTCTGGGGGAGGCTTGGTCCAGCCTGGGGGGTCCCTGAGACTCTCCTGTGCAGCCTCTGG

ATTCAGCATTAGTGGCTATTGGATGAGCTGGGTCCGCCAGGCTCCAGGGAAAGGGCTGGAGTGGGTGGCCAACATAA

AGCAAGATGGAGGTGAGAAGTACTATGGGGACTCTGTGAAGGGCCGATTCACCATCTCCAGAGACAACGCCAAGAAC

TCACTGTATCTGCAAATGAACAGCCTGAGAGCCGAGGACACGGCTGTGTATTACTGTGTAATGGCGGGTGGCCTTGA

CTACTGGGGCCAGGGAACCCTGGTCACCGTCTCCTCA

SEQ ID: 91
(311-3 VH)
QVQLQQWGAGLLKPSETLSLTCAVYGGSFSGYYWNWIRQPPGMGLEWIGEIHQSGGPHYNPSLKSRVSISVDTSKNQ

VNLKLSSVTAADTAIYYCTELDDYWGQGTLVTVSS

SEQ ID: 92
(311-3 VH)
CAGGTGCAGCTACAGCAGTGGGGCGCAGGACTGTTGAAGCCTTCGGAGACCCTGTCCCTCACCTGCGCTGTCTATGG

TGGGTCCTTCAGTGGTTACTACTGGAACTGGATCCGCCAGCCCCCAGGAATGGGGCTGGAATGGATTGGAGAAATCC

ATCAAAGTGGAGGCCCCCACTACAACCCGTCCCTCAAGAGTCGAGTCAGCATTTCAGTAGACACGTCCAAAAACCAG

GTCAACCTGAAGCTGAGCTCTGTGACCGCCGCGGATACGGCTATTTATTACTGTACGGAGTTGGATGACTATTGGGG

CCAGGGAACCCTGGTCACCGTCTCCTCA

```
                                                               SEQ ID: 93
(311-3 VH CDR1)
GYYWN

SEQ ID: 94
(311-3 VH CDR1)
GGTTACTACTGGAAC

SEQ ID: 95
(311-3 VH CDR2)
EIHQSGGPHYNPSLKS

SEQ ID: 96
(311-3 VH CDR2)
GAAATCCATCAAAGTGGAGGCCCCCACTACAACCCGTCCCTCAAGAGT

SEQ ID: 97
(311-3 VH CDR3)
LDDY

SEQ ID: 98
(311-3 VH CDR3)
TTGGATGACTAT

SEQ ID: 99
(311-3 VK)
EIVLTQSPATLSLSPGERATLSCRASQSVSSYLAWYQQKPGQAPRLLIYNASNRATGIPARFSGSGSGTDFTLTIGS

LEPEDFAVYYCQQRSNWPRTFGQGTKVEIK

SEQ ID: 100
(311-3 VK)
GAAATTGTGTTGACACAGTCTCCAGCCACCCTGTCTTTGTCTCCAGGGGAAAGAGCCACCCTCTCCTGCAGGGCCAG

TCAGAGTGTTAGCAGCTACTTAGCCTGGTACCAACAGAAACCTGGCCAGGCTCCCAGGCTCCTCATCTATAATGCAT

CCAACAGGGCCACTGGCATCCCAGCCAGGTTCAGTGGCAGTGGGTCTGGGACAGACTTCACTCTCACCATCGGCAGC

CTAGAGCCTGAAGATTTTGCAGTTTATTACTGTCAGCAGCGTAGCAACTGGCCTCGGACGTTCGGCCAAGGGACCAA

GGTGGAGATCAAA

SEQ ID: 101
(311-3 VK CDR1)
RASQSVSSYLA

SEQ ID: 102
(311-3 VK CDR1)
AGGGCCAGTCAGAGTGTTAGCAGCTACTTAGCC

SEQ ID: 103
(311-3 VK CDR2)
NASNRAT

SEQ ID: 104
(311-3 VK CDR2)
AATGCATCCAACAGGGCCACT

SEQ ID: 105
(311-3 VK CDR3)
QQRSNWPRT

SEQ ID: 106
(311-3 VK CDR3)
CAGCAGCGTAGCAACTGGCCTCGGACG

SEQ ID: 107
(311-3-M1 VH)
QVQLQQWGAGLLKPSETLSLTCAVYGGSFSGYYWNWIRQPPGKGLEWIGEIHQSGGPHYNPSLKSRVTISVDTSKNQ

FSLKLSSVTAADTAVYYCTELDDYWGQGTLVTVSS

SEQ ID: 108
(311-3-M1 VH)
CAGGTGCAGCTACAGCAGTGGGGCGCAGGACTGTTGAAGCCTTCGGAGACCCTGTCCCTCACCTGCGCTGTCTATGG

TGGGTCCTTCAGTGGTTACTACTGGAACTGGATTCGCCAGCCCCCAGGAAAGGGGCTGGAATGGATTGGAGAAATCC
```

```
ATCAAAGTGGAGGCCCCCACTACAACCCGTCCCTCAAGAGTCGAGTCACCATTTCAGTAGACACGTCCAAAAACCAG

TTCTCCCTGAAGCTGAGCTCTGTGACCGCCGCGGATACGGCTGTGTATTACTGTACGGAGTTGGATGACTATTGGGG

CCAGGGAACCCTGGTCACCGTCTCCTCA
```

```
                                                                  SEQ ID: 109
(311-3-M1 VK)
EIVLTQSPATLSLSPGERATLSCRASQSVSSYLAWYQQKPGQAPRLLIYDASNRATGIPARFSGSGSGTDFTLTISS

LEPEDFAVYYCQQRSNWPRTFGQGTKVEIK
```

```
                                                                  SEQ ID: 110
(311-3-M1 VK)
GAAATTGTGTTGACACAGTCTCCAGCCACCCTGTCTTTGTCTCCAGGGGAAAGAGCCACCCTCTCCTGCAGGGCCAG

TCAGAGTGTTAGCAGCTACTTAGCCTGGTACCAACAGAAACCTGGCCAGGCTCCCAGGCTCCTCATCTATGATGCAT

CCAACAGGGCCACTGGCATCCCAGCCAGGTTCAGTGGCAGTGGGTCTGGGACAGACTTCACTCTCACCATCAGCAGC

CTAGAGCCTGAAGATTTTGCAGTTTATTACTGTCAGCAGCGTAGCAACTGGCCTCGGACGTTCGGCCAAGGGACCAA

GGTGGAGATCAAA
```

```
                                                                  SEQ ID: 111
(311-3-M1 VK CDR2)
DASNRAT
```

```
                                                                  SEQ ID: 112
(311-3-M1 VK CDR2)
GATGCATCCAACAGGGCCACT
```

```
                                                                  SEQ ID: 113
(312-19 VH)
QVQLVQSGAEVKKPGSSVKVSCKASGGTFNNFVIGWVRQAPGQGLEWMGRIIPILDIANYAQKFQGRVTITADKSTS

TVYMELNSLRSEDTAVYYCARTGNYYKPYDYWGQGTLVTVSS
```

```
                                                                  SEQ ID: 114
(312-19 VH)
CAGGTCCAGCTGGTGCAGTCTGGGGCTGAGGTGAAGAAGCCTGGGTCCTCGGTGAAGGTCTCCTGCAAGGCTTCTGG

AGGCACCTTCAACAACTTCGTTATCGGCTGGGTGCGACAGGCCCCTGGACAAGGACTTGAGTGGATGGGAAGGATCA

TCCCTATCCTTGATATAGCAAACTACGCACAGAAGTTCCAGGGCAGAGTCACGATTACCGCGGACAAATCCACGAGC

ACAGTTTACATGGAGCTGAACAGCCTGAGATCTGAGGACACGGCCGTATACTACTGTGCGAGAACGGGGAATTATTA

TAAGCCCTATGACTACTGGGGCCAGGGAACCCTGGTCACCGTCTCCTCA
```

```
                                                                  SEQ ID: 115
(312-19 VH CDR1)
NFVIG
```

```
                                                                  SEQ ID: 116
(312-19 VH CDR1)
AACTTCGTTATCGGC
```

```
                                                                  SEQ ID: 117
(312-19 VH CDR2)
RIIPILDIANYAQKFQG
```

```
                                                                  SEQ ID: 118
(312-19 VH CDR2)
AGGATCATCCCTATCCTTGATATAGCAAACTACGCACAGAAGTTCCAGGGC
```

```
                                                                  SEQ ID: 119
(312-19 VH CDR3)
TGNYYKPYDY
```

```
                                                                  SEQ ID: 120
(312-19 VH CDR3)
ACGGGGAATTATTATAAGCCCTATGACTAC
```

```
                                                                  SEQ ID: 121
(312-19 VK)
EIVLTQSPDFQSVTPKEKVTITCRASQSIGSSLHWYQQKPDQSPKLLIKYASQSFSGVPSRFSGSGSGTDFTLTINS

LEAEDAAAYYCHQSSSLPITFGQGTRLEIK
```

-continued (312-19 VK)
GAAATTGTGCTGACTCAGTCTCCAGACTTTCAGTCTGTGACTCCAAAGGAGAAAGTCACCATCACCTGCCGGGCCAG

TCAGAGCATTGGTAGTAGCTTACACTGGTACCAGCAGAAACCAGATCAGTCTCCAAAGCTCCTCATCAAGTATGCTT

CCCAGTCCTTCTCAGGGGTCCCCTCGAGGTTCAGTGGCAGTGGATCTGGGACAGATTTCACCCTCACCATCAATAGC

CTGGAAGCTGAAGATGCTGCAGCGTATTACTGTCATCAGAGTAGTAGTTTACCGATCACCTTCGGCCAAGGGACACG

ACTGGAGATCAAA

SEQ ID: 122

SEQ ID: 123
(312-19 VK CDR1)
RASQSIGSSLH

SEQ ID: 124
(312-19 VK CDR1)
CGGGCCAGTCAGAGCATTGGTAGTAGCTTACAC

SEQ ID: 125
(312-19 VK CDR2)
YASQSFS

SEQ ID: 126
(312-19 VK CDR2)
TATGCTTCCCAGTCCTTCTCA

SEQ ID: 127
(312-19 VK CDR3)
HQSSSLPIT

SEQ ID: 128
(312-19 VK CDR3)
CATCAGAGTAGTAGTTTACCGATCACC

SEQ ID: 129
(312-19-M1 VH)
QVQLVQSGAEVKKPGSSVKVSCKASGGTFNNFVIGWVRQAPGQGLEWMGRIIPILDIANYAQKFQGRVTITADKSTS

TAYMELSSLRSEDTAVYYCARTGNYYKPYDYWGQGTLVTVSS

SEQ ID: 130
(312-19-M1 VH)
CAGGTCCAGCTGGTGCAGTCTGGGGCTGAGGTGAAGAAGCCTGGGTCCTCGGTGAAGGTCTCCTGCAAGGCTTCTGG

AGGCACCTTCAACAACTTCGTTATCGGCTGGGTGCGACAGGCCCCTGGACAAGGACTTGAGTGGATGGGAAGGATCA

TCCCTATCCTTGATATAGCAAACTACGCACAGAAGTTCCAGGGCAGAGTCACGATTACCGCGGACAAATCCACGAGC

ACAGCCTACATGGAGCTGAGCAGCCTGAGATCTGAGGACACGGCCGTATACTACTGTGCGAGAACGGGGAATTATTA

TAAGCCCTATGACTACTGGGGCCAGGGAACCCTGGTCACCGTCTCCTCA

SEQ ID: 131
(591-33 VH)
EVQLVESGGGLVQPGGSLRLSCAASGFTFSRYWMSWVRQAPGKGLEWMANIKQDGSETHYVDSVKGRFTISRDNAKN

SLYLQMNSLRAEDTAVYYCAIGDYWGQGTLVTVSS

SEQ ID: 132
(591-33 VH)
GAGGTGCAGTTGGTGGAGTCTGGGGGAGGCTTGGTCCAGCCTGGGGGGTCCCTGAGACTCTCCTGTGCAGCCTCTGG

ATTCACCTTTAGTCGCTATTGGATGAGCTGGGTCCGCCAGGCTCCAGGGAAAGGGCTGGAGTGGATGGCCAACATAA

AGCAAGATGGAAGTGAGACACACTATGTGGACTCTGTGAAGGGCCGATTCACCATCTCCAGAGACAACGCCAAGAAC

TCACTGTATCTGCAAATGAACAGCCTGAGAGCCGAGGACACGGCTGTGTATTACTGTGCGATTGGTGACTACTGGGG

CCAGGGAACCCTGGTCACCGTCTCCTCA

SEQ ID: 133
(591-33 VH CDR1)
RYWMS

SEQ ID: 134
(591-33 VH CDR1)
CGCTATTGGATGAGC

-continued (591-33 VH CDR2)
NIKQDGSETHYVDSVKG
SEQ ID: 135

(591-33 VH CDR2)
AACATAAAGCAAGATGGAAGTGAGACACACTATGTGGACTCTGTGAAGGGC
SEQ ID: 136

(591-33 VH CDR3)
GDY
SEQ ID: 137

(591-33 VH CDR3)
GGTGACTAC
SEQ ID: 138

(591-33 VK)
DIQMTQSPSSLSASVGDRVTITCRASQDISSWLAWYQQKPEKAPKSLIYAASSLQSGVPSRFSGSGSGTDFTLTISS

LQPEDFATYYCQQYKSYPLTFGGGTKVEIK
SEQ ID: 139

(591-33 VK)
GACATCCAGATGACCCAGTCTCCATCCTCACTGTCTGCATCTGTAGGAGACAGAGTCACCATCACTTGTCGGGCGAG

TCAGGATATTAGCAGCTGGTTAGCCTGGTATCAGCAGAAACCAGAGAAAGCCCCTAAGTCCCTGATCTATGCTGCAT

CCAGTTTGCAAAGTGGGGTCCCATCAAGGTTCAGCGGCAGTGGATCTGGGACAGATTTCACTCTCACCATCAGCAGC

CTGCAGCCTGAAGATTTTGCAACTTATTACTGCCAACAGTATAAAAGTTACCCGCTCACTTTCGGCGGAGGGACCAA

GGTGGAGATCAAA
SEQ ID: 140

(591-33 VK CDR1)
RASQDISSWLA
SEQ ID: 141

(591-33 VK CDR1)
CGGGCGAGTCAGGATATTAGCAGCTGGTTAGCC
SEQ ID: 142

(591-33 VK CDR2)
AASSLQS
SEQ ID: 143

(591-33 VK CDR2)
GCTGCATCCAGTTTGCAAAGT
SEQ ID: 144

(591-33 VK CDR3)
QQYKSYPLT
SEQ ID: 145

(591-33 VK CDR3)
CAACAGTATAAAAGTTACCCGCTCACT
SEQ ID: 146

(591-33-M1 VH)
EVQLVESGGGLVQPGGSLRLSCAASGFTFSRYWMSWVRQAPGKGLEWVANIKQDGSETHYVDSVKGRFTISRDNAKN

SLYLQMNSLRAEDTAVYYCAIGDYWGQGTLVTVSS
SEQ ID: 147

(591-33-M1 VH)
GAGGTGCAGTTGGTGGAGTCTGGGGGAGGCTTGGTCCAGCCTGGGGGGTCCCTGAGACTCTCCTGTGCAGCCTCTGG

ATTCACCTTTAGTCGCTATTGGATGAGCTGGGTCCGCCAGGCTCCAGGGAAAGGGCTGGAGTGGGTGGCCAACATAA

AGCAAGATGGAAGTGAGACACACTATGTGGACTCTGTGAAGGGCCGATTCACCATCTCCAGAGACAACGCCAAGAAC

TCACTGTATCTGCAAATGAACAGCCTGAGAGCCGAGGACACGGCTGTGTATTACTGTGCGATTGGTGACTACTGGGG

CCAGGGAACCCTGGTCACCGTCTCCTCA
SEQ ID: 148

(114-41 VH)
QVQLVQSGAEVKTPGASVKVSCKASGYTFTSFGISWVRQAPGQGLEWMGWISVYNDYTNYAQKFQGRVTMTTDTSTS

TAYMELRSLRSDDTAMYYCARKRGGDMDYWGQGTLVTVSS
SEQ ID: 149

```
                                                                  SEQ ID: 150
(114-41 VH)
CAGGTTCAGCTGGTGCAGTCTGGAGCTGAAGTGAAGACGCCTGGGGCCTCAGTGAAGGTCTCCTGCAAGGCTTCTGG

TTACACCTTTACCAGCTTTGGTATCAGCTGGGTGCGACAGGCCCCTGGACAAGGGCTTGAGTGGATGGGATGGATCA

GCGTTTACAATGATTACACAAACTATGCACAGAAGTTCCAGGGCAGAGTCACCATGACCACAGACACATCCACGAGC

ACAGCCTACATGGAACTGAGGAGCCTGAGATCTGACGACACGGCCATGTATTACTGTGCGAGAAAGAGGGGTGGGGA

TATGGACTATTGGGGCCAGGGAACCCTGGTCACCGTCTCCTCA

SEQ ID: 151
(114-41 VH CDR1)
SFGIS

SEQ ID: 152
(114-41 VH CDR1)
AGCTTTGGTATCAGC

SEQ ID: 153
(114-41 VH CDR2)
WISVYNDYTNYAQKFQG

SEQ ID: 154
(114-41 VH CDR2)
TGGATCAGCGTTTACAATGATTACACAAACTATGCACAGAAGTTCCAGGGC

SEQ ID: 155
(114-41 VH CDR3)
KRGGDMDY

SEQ ID: 156
(114-41 VH CDR3)
AAGAGGGGTGGGGATATGGACTAT

SEQ ID: 157
(114-41 VK)
DIQMTQSPSSVSASVGDRVTITCRASQDISSWLAWYQHKPGKAPKLLIYLASSLQSGVPSRFSGSGSGTDFTLTISS

LQPEDFATYYCQQANSFPWTFGQGTKVEIK

SEQ ID: 158
(114-41 VK)
GACATCCAGATGACCCAGTCTCCATCTTCCGTGTCTGCATCTGTAGGAGACAGAGTCACCATCACTTGTCGGGCGAG

TCAGGATATTAGCAGCTGGTTAGCCTGGTATCAGCATAAACCAGGGAAAGCCCCTAAGCTCCTGATCTATCTTGCAT

CCAGTTTGCAAAGTGGGGTCCCATCAAGGTTCAGCGGCAGTGGATCTGGGACAGATTTCACTCTCACCATCAGCAGC

CTGCAGCCTGAAGATTTTGCAACTTACTATTGTCAACAGGCTAATAGTTTTCCGTGGACGTTCGGCCAAGGGACCAA

GGTGGAGATCAAA

SEQ ID: 159
(114-41 VK CDR1)
RASQDISSWLA

SEQ ID: 160
(114-41 VK CDR1)
CGGGCGAGTCAGGATATTAGCAGCTGGTTAGCC

SEQ ID: 161
(114-41 VK CDR2)
LASSLQS

SEQ ID: 162
(114-41 VK CDR2)
CTTGCATCCAGTTTGCAAAGT

SEQ ID: 163
(114-41 VK CDR3)
QQANSFPWT

SEQ ID: 164
(114-41 VK CDR3)
CAACAGGCTAATAGTTTTCCGTGGACG
```

SEQ ID: 165

(114-41-M1 VH)
QVQLVQSGAEVKKPGASVKVSCKASGYTFTSFGISWVRQAPGQGLEWMGWISVYNDYTNYAQKFQGRVTMTTDTSTS

TAYMELRSLRSDDTAVYYCARKRGGDMDYWGQGTLVTVSS

SEQ ID: 166

(114-41-M1 VH)
CAGGTTCAGCTGGTGCAGTCTGGAGCTGAAGTGAAGAAGCCTGGGGCCTCAGTGAAGGTCTCCTGCAAGGCTTCTGG

TTACACCTTTACCAGCTTTGGTATCAGCTGGGTGCGACAGGCCCCTGGACAAGGGCTTGAGTGGATGGGATGGATCA

GCGTTTACAATGATTACACAAACTATGCACAGAAGTTCCAGGGCAGAGTCACCATGACCACAGACACATCCACGAGC

ACAGCCTACATGGAACTGAGGAGCCTGAGATCTGACGACACGGCCGTGTATTACTGTGCGAGAAAGAGGGGTGGGGA

TATGGACTATTGGGGCCAGGGAACCCTGGTCACCGTCTCCTCA

SEQ ID: 167

(306-155 VH)
EVQLVQSGAEVKKPGESLKISCKGSGYSFTSYWIGWVRQMPGKGLEWMGIIYPGDSDTRYSPSFQGQVTISADKSIS

TAYLQWSSLKASDTAMYYCARQGSGWYGNYFDYWGQGTLVTVSS

SEQ ID: 168

(306-155 VH)
GAGGTGCAGCTGGTGCAGTCTGGAGCAGAGGTGAAAAAGCCCGGGGAGTCTCTGAAGATCTCCTGTAAGGGTTCTGG

ATACAGTTTTACCAGCTACTGGATCGGCTGGGTGCGCCAGATGCCCGGGAAAGGCCTGGAGTGGATGGGGATCATCT

ATCCTGGTGACTCTGATACCAGATACAGCCCGTCCTTCCAAGGCCAGGTCACCATCTCAGCCGACAAGTCCATCAGC

ACCGCCTACCTGCAGTGGAGCAGCCTGAAGGCCTCGGACACCGCCATGTATTACTGTGCGAGACAGGGCAGCGGCTG

GTACGGGAACTACTTTGACTACTGGGGCCAGGGAACCCTGGTCACCGTCTCCTCA

SEQ ID: 169

(306-155 VH CDR1)
SYWIG

SEQ ID: 170

(306-155 VH CDR1)
AGCTACTGGATCGGC

SEQ ID: 171

(306-155 VH CDR2)
IIYPGDSDTRYSPSFQG

SEQ ID: 172

(306-155 VH CDR2)
ATCATCTATCCTGGTGACTCTGATACCAGATACAGCCCGTCCTTCCAAGGC

SEQ ID: 173

(306-155 VH CDR3)
QGSGWYGNYFDY

SEQ ID: 174

(306-155 VH CDR3)
TGGTACGGGAACTACTTTGACTACCAGGGCAGCGGC

SEQ ID: 175

(306-155 VK)
EIVLTQSPGTLSLSPGERATLSCRASQSFSRGYLAWYQQKPGQAPRLLIYGASSRVTGIPDRFSGSGSGTDFTLTIS

RLEPEDFAVYYCQQYDSSPYTFGQGTKLEIK

SEQ ID: 176

(306-155 VK)
GAAATTGTGTTGACGCAGTCTCCAGGCACCCTGTCTTTGTCTCCAGGGGAAAGAGCCACCCTCTCCTGCAGGGCCAG

TCAGAGTTTTAGCAGAGGCTACTTAGCCTGGTACCAGCAGAAACCTGGCCAGGCTCCCAGGCTCCTCATCTATGGTG

CATCCAGCAGGGTCACTGGCATCCCAGACAGGTTCAGTGGCAGTGGGTCTGGGACAGACTTCACTCTCACCATCAGC

AGACTGGAGCCTGAAGATTTTGCGGTGTATTACTGTCAGCAGTATGATAGCTCACCGTACACTTTTGGCCAGGGGAC

CAAGCTGGAGATCAAA (306-155 VK CDR1)
RASQSFSRGYLA
SEQ ID: 177

(306-155 VK CDR1)
AGGGCCAGTCAGAGTTTTAGCAGAGGCTACTTAGCC
SEQ ID: 178

(306-155 VK CDR2)
GASSRVT
SEQ ID: 179

(306-155 VK CDR2)
GGTGCATCCAGCAGGGTCACT
SEQ ID: 180

(306-155 VK CDR3)
QQYDSSPYT
SEQ ID: 181

(306-155 VK CDR3)
CAGCAGTATGATAGCTCACCGTACACT
SEQ ID: 182

(14-173 VH)
EVQLVESGGGLVQPGGSLRLSCAASGFTFSSFWMSWVRQAPGKGLEWVANIKHDGSEQDYVDSVKGRFTISRDNAKN

SLYLQMNSLRAEDTAVYYCARGGIWFGPWGQGTLVTVSS
SEQ ID: 183

(14-173 VH)
GAGGTGCAGCTGGTGGAGTCTGGGGGAGGCTTGGTCCAGCCTGGGGGGTCCCTGAGACTCTCCTGTGCAGCCTCTGG

ATTCACCTTTAGTAGCTTTTGGATGAGTTGGGTCCGCCAGGCTCCAGGGAAAGGGCTGGAGTGGGTGGCCAACATAA

AGCACGATGGAAGTGAGCAAGACTATGTGGACTCTGTGAAGGGCCGATTCACCATCTCCAGAGACAACGCCAAGAAC

TCACTGTATCTGCAAATGAACAGCCTGAGAGCCGAGGACACGGCTGTGTATTACTGTGCAAGGGGGGGTATCTGGTT

CGGCCCCTGGGGCCAGGGAACCCTGGTCACCGTCTCCTCA
SEQ ID: 184

(14-173 VH CDR1)
SFWMS
SEQ ID: 185

(14-173 VH CDR1)
AGCTTTTGGATGAGT
SEQ ID: 186

(14-173 VH CDR2)
NIKHDGSEQDYVDSVKG
SEQ ID: 187

(14-173 VH CDR2)
AACATAAAGCACGATGGAAGTGAGCAAGACTATGTGGACTCTGTGAAGGGC
SEQ ID: 188

(14-173 VH CDR3)
GGIWFGP
SEQ ID: 189

(14-173 VH CDR3)
GGGGGTATCTGGTTCGGCCCC
SEQ ID: 190

(14-173 VK)
VIWMTQSPSLLSASTGDRVTISCRMSQGISSYLAWYQQKPGKAPEVLIYAVSTLQSGVPSRFSGSGSGTDFTLTISC

LQSEDFATYYCQQYYSFPYTFGQGTKLEIK
SEQ ID: 191

(14-173 VK)
GTCATCTGGATGACCCAGTCTCCATCCTTACTCTCTGCATCTACAGGAGACAGAGTCACCATCAGTTGTCGGATGAG

TCAGGGCATTAGCAGTTATTTAGCCTGGTATCAGCAAAAACCAGGGAAAGCCCCTGAGGTCCTGATCTATGCTGTAT
SEQ ID: 192

-continued
```
CCACTTTGCAAAGTGGGGTCCCATCAAGGTTCAGTGGCAGTGGATCTGGGACAGATTTCACTCTCACCATCAGCTGC

CTGCAGTCTGAAGATTTTGCAACTTATTACTGTCAACAGTATTATAGTTTCCCGTACACTTTTGGCCAGGGGACCAA

GCTGGAGATCAAA
```

SEQ ID: 193
(14-173 VK CDR1)
RMSQGISSYLA

SEQ ID: 194
(14-173 VK CDR1)
CGGATGAGTCAGGGCATTAGCAGTTATTTAGCC

SEQ ID: 195
(14-173 VK CDR2)
AVSTLQS

SEQ ID: 196
(14-173 VK CDR2)
GCTGTATCCACTTTGCAAAGT

SEQ ID: 197
(14-173 VK CDR3)
QQYYSFPYT

SEQ ID: 198
(14-173 VK CDR3)
CAACAGTATTATAGTTTCCCGTACACT

SEQ ID: 199
(14-173-M1 VK)
VIWMTQSPSLLSASTGDRVTISCRMSQGISSYLAWYQQKPGKAPELLIYAVSTLQSGVPSRFSGSGSGTDFTLTISS

LQSEDFATYYCQQYYSFPYTFGQGTKLEIK

SEQ ID: 200
(14-173-M1 VK)
```
GTCATCTGGATGACCCAGTCTCCATCCTTACTCTCTGCATCTACAGGAGACAGAGTCACCATCAGTTGTCGGATGAG

TCAGGGCATTAGCAGTTATTTAGCCTGGTATCAGCAAAAACCAGGGAAAGCCCCTGAGCTCCTGATCTATGCTGTAT

CCACTTTGCAAAGTGGGGTCCCATCAAGGTTCAGTGGCAGTGGATCTGGGACAGATTTCACTCTCACCATCAGCTCT

CTGCAGTCTGAAGATTTTGCAACTTATTACTGTCAACAGTATTATAGTTTCCCGTACACTTTTGGCCAGGGGACCAA

GCTGGAGATCAAA
```

SEQ ID: 201
(303-8 VH)
QVQLVQSGAEVKKPGSSVKVSCKASGGSFSIYVISWVRQAPGQGLEWMGRIIPILGTTNYAQKFQGRVTITADKSTS

TAYMELSSLRSEDTAVYYCARPDSPNHSNTFDYWGQGTLVTVSS

SEQ ID: 202
(303-8 VH)
```
CAGGTCCAGCTGGTGCAGTCTGGGGCTGAGGTGAAGAAGCCTGGGTCCTCGGTGAAGGTCTCCTGCAAGGCTTCTGG

AGGCTCCTTCAGCATCTATGTTATCAGCTGGGTGCGACAGGCCCCTGGACAAGGGCTTGAGTGGATGGGAAGGATCA

TCCCTATCCTTGGTACAACAAACTACGCACAGAAGTTCCAGGGCAGAGTCACGATTACCGCGGACAAATCCACGAGC

ACAGCCTACATGGAGCTGAGCAGCCTGAGATCTGAGGACACGGCCGTGTATTACTGTGCGAGACCGGACTCCCCGAA

CCATAGTAATACATTTGACTACTGGGGCCAGGGAACCCTGGTCACCGTCTCCTCA
```

SEQ ID: 203
(303-8 VH CDR1)
IYVIS

SEQ ID: 204
(303-8 VH CDR1)
ATCTATGTTATCAGC

SEQ ID: 205
(303-8 VH CDR2)
RIIPILGTTNYAQKFQG

-continued (303-8 VH CDR2)  SEQ ID: 206
AGGATCATCCCTATCCTTGGTACAACAAACTACGCACAGAAGTTCCAGGGC (303-8 VH CDR3)  SEQ ID: 207
PDSPNHSNTFDY (303-8 VH CDR3)  SEQ ID: 208
CCGGACTCCCCGAACCATAGTAATACATTTGACTAC (303-8 VK)  SEQ ID: 209
DIQMTQSPSSLSASVGDRVTITCRASQGISSWLAWYQQKPEKAPKSLIYGASSLQSGVPSRFSGSGSGTDFTLTISS

LQPEDFATYYCQQYNSYPYTFGQGTKLEIK (303-8 VK)  SEQ ID: 210
GACATCCAGATGACCCAGTCTCCATCCTCACTGTCTGCATCTGTAGGAGACAGAGTCACCATCACTTGTCGGGCGAG

TCAGGGTATTAGCAGCTGGTTAGCCTGGTATCAGCAGAAACCAGAGAAAGCCCCTAAGTCCCTGATCTATGGTGCAT

CCAGTTTGCAAAGTGGGGTCCCATCAAGGTTCAGCGGCAGTGGATCTGGGACAGATTTCACTCTCACCATCAGCAGC

CTGCAGCCTGAAGATTTTGCAACTTATTACTGCCAACAGTATAATAGTTACCCGTACACTTTTGGCCAGGGGACCAA

GCTGGAGATCAAA (303-8 VK CDR1)  SEQ ID: 211
RASQGISSWLA (303-8 VK CDR1)  SEQ ID: 212
CGGGCGAGTCAGGGTATTAGCAGCTGGTTAGCC (303-8 VK CDR2)  SEQ ID: 213
GASSLQS (303-8 VK CDR2)  SEQ ID: 214
GGTGCATCCAGTTTGCAAAGT (303-8 VK CDR3)  SEQ ID: 215
QQYNSYPYT (303-8 VK CDR3)  SEQ ID: 216
CAACAGTATAATAGTTACCCGTACACT (312-56 VH)  SEQ ID: 217
QVQVVQSGAEVKKPGSSVKVSCKASGGTFSSYAISWVRQAPGQGLEWMGRIIPILGTAKYAQKFQGRVTIIADKSTS

TAYMELSSLRSEDTAVYYCARDQDYYGMDVWGQGTTVTVSS (312-56 VH)  SEQ ID: 218
CAGGTCCAGGTGGTGCAGTCTGGGGCTGAGGTGAAGAAGCCTGGGTCCTCGGTGAAGGTCTCCTGCAAGGCTTCTGG

AGGCACCTTCAGCAGCTATGCTATCAGCTGGGTGCGACAGGCCCCTGGACAAGGGCTTGAGTGGATGGGAAGGATCA

TCCCTATCCTTGGTACAGCAAAGTACGCACAGAAGTTCCAGGGCAGAGTCACGATTATCGCGGACAAATCCACGAGC

ACAGCCTACATGGAGCTGAGCAGCCTGAGATCTGAGGACACGGCCGTGTATTACTGTGCGAGAGATCAGGACTACTA

CGGTATGGACGTCTGGGGCCAAGGGACCACGGTCACCGTCTCCTCA (312-56 VH CDR1)  SEQ ID: 219
SYAIS

-continued (312-56 VH CDR1)  
AGCTATGCTATCAGC  
SEQ ID: 220

(312-56 VH CDR2)  
RIIPILGTAKYAQKFQG  
SEQ ID: 221

(312-56 VH CDR2)  
AGGATCATCCCTATCCTTGGTACAGCAAAGTACGCACAGAAGTTCCAGGGC  
SEQ ID: 222

(312-56 VH CDR3)  
DQDYYGMDV  
SEQ ID: 223

(312-56 VH CDR3)  
GATCAGGACTACTACGGTATGGACGTC  
SEQ ID: 224

(312-56 VK)  
DIQMTQSPSSVSASVGDRVTITCRASQGISSWLAWYQHKPGKAPKLLIYAASSLQSGVPSRFSGSGSGTDFTLTISS

LQPEDFATYYCQQTNNFPWTFGQGTKVEIK  
SEQ ID: 225

(312-56 VK)  
GACATCCAGATGACCCAGTCTCCATCTTCCGTGTCTGCATCTGTAGGAGACAGAGTCACCATCACTTGTCGGGCGAG

TCAGGGTATTAGCAGCTGGTTAGCCTGGTATCAGCATAAACCAGGGAAAGCCCCTAAGCTCCTGATCTATGCTGCAT

CCAGTTTGCAAAGTGGGGTCCCATCAAGGTTCAGCGGCAGTGGATCTGGGACAGATTTCACTCTCACCATCAGCAGC

CTGCAGCCTGAAGATTTTGCAACTTACTATTGTCAACAGACTAATAATTTCCCGTGGACGTTCGGCCAAGGGACCAA

GGTGGAGATCAAA  
SEQ ID: 226

(312-56 VK CDR1)  
RASQGISSWLA  
SEQ ID: 227

(312-56 VK CDR1)  
CGGGCGAGTCAGGGTATTAGCAGCTGGTTAGCC  
SEQ ID: 228

(312-56 VK CDR2)  
AASSLQS  
SEQ ID: 229

(312-56 VK CDR2)  
GCTGCATCCAGTTTGCAAAGT  
SEQ ID: 230

(312-56 VK CDR3)  
QQTNNFPWT  
SEQ ID: 231

(312-56 VK CDR3)  
CAACAGACTAATAATTTCCCGTGGACG  
SEQ ID: 232

(595-16 VH with leader)  
MEFVLSWVFLVAIIKGVHCEVQLVQSGGGLGHPGGSLRLSCAGSGFTFSSYSMHWLRQAPGKGLKWVSAIGTAGGTY

YADSVKGRFTISRDNAKNSFYLQMNSLRAEDMAVYYCAREYFFGSGNYGYWGQGTLVTASS  
SEQ ID: 233

(595-16 VH with leader)  
ATGGAGTTTGTGCTGAGCTGGGTTTTCCTTGTTGCTATCATAAAAGGTGTCCACTGTGAGGTTCAGCTGGTGCAGTC

TGGGGGAGGCTTGGGACATCCTGGGGGGTCCCTGAGACTCTCCTGTGCAGGCTCTGGATTCACTTTCAGTAGTTATT

CTATGCACTGGCTTCGCCAGGCTCCAGGAAAAGGTCTGAAGTGGGTATCAGCTATTGGTACTGCTGGTGGCACATAC

TATGCAGACTCCGTGAAGGGCCGATTCACCATCTCCAGAGACAATGCCAAGAACTCCTTCTATCTTCAAATGAACAG

CCTGAGAGCCGAGGACATGGCTGTGTATTACTGTGCAAGAGAGTATTTCTTTGGTTCGGGGAATTATGGATACTGGG

GCCAGGGAACCCTGGTCACCGCCTCCTCA  
SEQ ID: 234

-continued

SEQ ID: 235
(595-16 VK with leader)
MEAPAQLLFLLLLWLPDTTGEIVLTQSPATLSLSPGERATLSCRASQSVSSYLAWYQQKPGQAPRLLIYDASNRATG

IPARFSGSGSGTDFTLTISSLEPEDFAVYYCQQRSNWPPTFGQGTKVEIK

SEQ ID: 236
(595-16 VK with leader)
ATGGAAGCCCCAGCTCAGCTTCTCTTCCTCCTGCTACTCTGGCTCCCAGATACCACCGGAGAAATTGTGTTGACACA

GTCTCCAGCCACCCTGTCTTTGTCTCCAGGGGAAAGAGCCACCCTCTCCTGCAGGGCCAGTCAGAGTGTTAGCAGCT

ACTTAGCCTGGTACCAACAGAAACCTGGCCAGGCTCCCAGGCTCCTCATCTATGATGCATCCAACAGGGCCACTGGC

ATCCCAGCCAGGTTCAGTGGCAGTGGGTCTGGGACAGACTTCACTCTCACCATCAGCAGCCTAGAGCCTGAAGATTT

TGCAGTTTATTACTGTCAGCAGCGTAGCAACTGGCCTCCGACGTTCGGCCAAGGGACCAAGGTGGAGATCAAA

SEQ ID: 237
(595-16-M1 VH with leader)
MEFVLSWVFLVAILKGVQCEVQLVQSGGGLVKPGGSLRLSCAGSGFTFSSYSMHWLRQAPGKGLEWVSAIGTAGGTY

YADSVKGRFTISRDNAKNSLYLQMNSLRAEDTAVYYCAREYFFGSGNYGYWGQGTLVTVSS

SEQ ID: 238
(595-16-M1 VH with leader)
ATGGAGTTTGTGCTGAGCTGGGTTTTCCTTGTTGCTATCTTAAAAGGTGTCCAGTGTGAGGTTCAGCTGGTGCAGTC

TGGGGGAGGCTTGGTAAAACCTGGGGGGTCCCTGAGACTCTCCTGTGCAGGCTCTGGATTCACTTTCAGTAGTTATT

CTATGCACTGGCTTCGCCAGGCTCCAGGAAAAGGTCTGGAGTGGGTATCAGCTATTGGTACTGCTGGTGGCACATAC

TATGCAGACTCCGTGAAGGGCCGATTCACCATCTCCAGAGACAATGCCAAGAACTCCTTGTATCTTCAAATGAACAG

CCTGAGAGCCGAGGACACGGCTGTGTATTACTGTGCAAGAGAGTATTTCTTTGGTTCGGGGAATTATGGATACTGGG

GCCAGGGAACCCTGGTCACCGTCTCCTCA

SEQ ID: 239
(591-37 VH with leader)
MEFVLSWVFLVAILKGVQCEVQLVQSGGGLVHPGGSLRLSCAGSGFTFSRYALHWVRQAPGKGLEWVSAIGIGGGTF

YADSVKGRFTISRDNAKNSLYLQMNSLRAEDMAVYYCARDTYYDFFDAFDIWGQGTMVTVSS

SEQ ID: 240
(591-37 VH with leader)
ATGGAGTTTGTGCTGAGCTGGGTTTTCCTTGTTGCTATATTAAAAGGTGTCCAGTGTGAGGTTCAGCTGGTGCAGTC

TGGGGGAGGCTTGGTACATCCTGGGGGGTCCCTGAGACTCTCCTGTGCAGGCTCTGGATTCACCTTCAGTCGCTATG

CTTTACACTGGGTTCGCCAGGCTCCAGGAAAAGGTCTGGAGTGGGTATCAGCTATTGGTATTGGTGGTGGCACATTC

TATGCAGACTCCGTGAAGGGCCGATTCACCATCTCCAGAGACAATGCCAAGAACTCCTTGTATCTTCAAATGAACAG

CCTGAGAGCCGAGGACATGGCTGTGTATTACTGTGCAAGAGATACGTATTACGATTTTTTTGATGCTTTTGATATCT

GGGGCCAAGGGACAATGGTCACCGTCTCTTCA

SEQ ID: 241
(591-37 VK with leader)
MDMRVLAQLLGLLLLCFPGARCDIQMTQSPSSLSASVGDRVTITCRASQGISSWLAWYQQKPEKAPKSLIYAASSLQ

SGVPSRFSGSGSGTDFTLTISSLQPEDFATYYCQQYDSYPLTFGGGTKVEIK

SEQ ID: 242
(591-37 VK with leader)
ATGGACATGAGGGTCCTCGCTCAGCTCCTGGGGCTCCTGCTGCTCTGTTTCCCAGGTGCCAGATGTGACATCCAGAT

GACCCAGTCTCCATCCTCACTGTCTGCATCTGTAGGAGACAGAGTCACCATCACTTGTCGGGCGAGTCAGGGTATTA

GCAGCTGGTTAGCCTGGTATCAGCAGAAACCAGAGAAAGCCCCTAAGTCCCTGATCTATGCTGCATCCAGTTTGCAA

AGTGGGGTCCCATCAAGGTTCAGCGGCAGTGGATCTGGGACAGATTTCACTCTCACCATCAGCAGCCTGCAGCCTGA

AGATTTTGCAACTTATTACTGCCAACAGTATGATAGTTACCCTCTCACTTTCGGCGGAGGGACCAAGGTGGAGATCA

AA

SEQ ID: 243
(591-37-M1 VH with leader)
MEFVLSWVFLVAILKGVQCEVQLVQSGGGLVKPGGSLRLSCAGSGFTFSRYALHWVRQAPGKGLEWVSAIGIGGGTF

YADSVKGRFTISRDNAKNSLYLQMNSLRAEDTAVYYCARDTYYDFFDAFDIWGQGTMVTSS

SEQ ID: 244
(591-37-M1 VH with leader)
ATGGAGTTTGTGCTGAGCTGGGTTTTCCTTGTTGCTATATTAAAAGGTGTCCAGTGTGAGGTTCAGCTGGTGCAGTC

TGGGGGAGGCTTGGTAAAACCTGGGGGGTCCCTGAGACTCTCCTGTGCAGGCTCTGGATTCACCTTCAGTCGCTATG

CTTTACACTGGGTTCGCCAGGCTCCAGGAAAAGGTCTGGAGTGGGTATCAGCTATTGGTATTGGTGGTGGCACATTC

TATGCAGACTCCGTGAAGGGCCGATTCACCATCTCCAGAGACAATGCCAAGAACTCCTTGTATCTTCAAATGAACAG

CCTGAGAGCCGAGGACACGGCTGTGTATTACTGTGCAAGAGATACGTATTACGATTTTTTTGATGCTTTTGATATCT

GGGGCCAAGGGACAATGGTCACCGTCTCTTCA

SEQ ID: 245
(358-11 VH with leader)
MEFGLSWVFLVALLRGVQCQVQLVESGGGVVQPGRSLRLSCAASGFTFSNYGIHWVRQAPGKGLEWVAIIWHDGSNS

YYVDSVKGRFTMSRDNSKNTVYLQMNSLRAEDTAVYFCARIIGGAFDIWGQGTMVTVSS

SEQ ID: 246
(358-11 VH with leader)
ATGGAGTTTGGGCTGAGCTGGGTTTTCCTCGTTGCTCTTTTAAGAGGTGTCCAGTGTCAGGTGCAGCTGGTGGAGTC

TGGGGGAGGCGTGGTCCAGCCTGGGAGGTCCCTGAGACTCTCCTGTGCAGCGTCTGGATTCACCTTCAGTAACTATG

GCATACACTGGGTCCGCCAGGCTCCAGGCAAGGGGCTGGAGTGGGTGGCTATTATATGGCATGATGGAAGTAATTCA

TATTATGTAGACTCCGTGAAGGGCCGATTCACCATGTCCAGAGACAATTCCAAGAACACGGTGTATCTGCAAATGAA

CAGCCTGAGAGCCGAGGACACGGCTGTGTATTTCTGTGCGAGAATAATTGGGGGCGCTTTTGATATCTGGGGCCAAG

GGACAATGGTCACCGTCTCTTCA

SEQ ID: 247
(358-11 VK with leader)
MDMRVLAQLLGLLLLCFPGARCDIQMTQSPSSLSASVGDRVTITCRASQGISSWLAWYQQKPEKAPKSLIYAASSLQ

SGVPSRFSGSGSGTDFTLTISSLQPEDFATYYCQQYNSYPITFGQGTRLEIK

SEQ ID: 248
(358-11 VK with leader)
ATGGACATGAGGGTCCTCGCTCAGCTCCTGGGGCTCCTGCTGCTCTGTTTCCCAGGTGCCAGATGTGACATCCAGAT

GACCCAGTCTCCATCCTCACTGTCTGCATCTGTAGGAGACAGAGTCACCATCACTTGTCGGGCGAGTCAGGGTATTA

GCAGCTGGTTAGCCTGGTATCAGCAGAAACCAGAGAAAGCCCCTAAGTCCCTGATCTATGCTGCATCCAGTTTGCAA

AGTGGGGTCCCATCAAGGTTCAGCGGCAGTGGATCTGGGACAGATTTCACTCTCACCATCAGCAGCCTGCAGCCTGA

AGATTTTGCAACTTATTACTGCCAACAGTATAATAGTTACCCGATCACCTTCGGCCAAGGGACACGACTGGAGATCA

AA

SEQ ID: 249
(358-11-M1 VH with leader)
MEFGLSWVFLVALLRGVQCQVQLVESGGGVVQPGRSLRLSCAASGFTFSNYGIHWVRQAPGKGLEWVAIIWHDGSNS

YYVDSVKGRFTISRDNSKNTLYLQMNSLRAEDTAVYFCARIIGGAFDIWGQGTMVTVSS

SEQ ID: 250
(358-11-M1 VH with leader)
ATGGAGTTTGGGCTGAGCTGGGTTTTCCTCGTTGCTCTTTTAAGAGGTGTCCAGTGTCAGGTGCAGCTGGTGGAGTC

TGGGGGAGGCGTGGTCCAGCCTGGGAGGTCCCTGAGACTCTCCTGTGCAGCGTCTGGATTCACCTTCAGTAACTATG

GCATACACTGGGTCCGCCAGGCTCCAGGCAAGGGGCTGGAGTGGGTGGCTATTATATGGCATGATGGAAGTAATTCA

TATTATGTAGACTCCGTGAAGGGCCGATTCACCATCTCCAGAGACAATTCCAAGAACACGCTGTATCTGCAAATGAA

CAGCCTGAGAGCCGAGGACACGGCTGTGTATTTCTGTGCGAGAATAATTGGGGGCGCTTTTGATATCTGGGGCCAAG

GGACAATGGTCACCGTCTCTTCA

-continued

SEQ ID: 251
(358-22 VH with leader)
MEFGLSWVFLVALLRGVQCQVQLVESGGGVVQPGRSLRLSCAASGFTFRSYGMHWVRQAPGKGLEWVTLIWYDGSNK
YYADSVKGRFTISRDNSKNTLYLQMNSLRVEDTAVYYCAREGFNWDAFDIWGQGTMVTVSS SEQ ID: 252
(358-22 VH with leader)
ATGGAGTTTGGGCTGAGCTGGGTTTTCCTCGTTGCTCTTTTAAGAGGTGTCCAGTGTCAGGTGCAACTGGTGGAGTC
TGGGGGAGGCGTGGTCCAGCCTGGGAGGTCCCTGAGACTCTCCTGTGCAGCGTCTGGATTCACCTTCAGGAGTTATG
GCATGCACTGGGTCCGCCAGGCTCCAGGCAAGGGGCTGGAGTGGGTGACACTTATATGGTATGATGGAAGTAATAAA
TACTATGCAGACTCCGTGAAGGGCCGATTCACCATCTCCAGAGACAATTCCAAGAACACGCTGTATCTGCAAATGAA
CAGCCTGAGAGTCGAGGACACGGCTGTGTATTACTGTGCGAGAGAAGGGTTTAACTGGGATGCTTTTGATATCTGGG
GCCAAGGGACAATGGTCACCGTCTCTTCA SEQ ID: 253
(358-22 VK with leader)
METPAQLLFLLLLWLPDTTGEIVLTQSPGTLSLSPGERATLSCRASQSVRISYLAWYQQKPGQAPRLLIYGTFSRAT
GIPDRFSGSGSGTDFTLTISRLEPEDFAVYYCQQYGSSMYTFGQGTKLEIK SEQ ID: 254
(358-22 VK with leader)
ATGGAAACCCCAGCGCAGCTTCTCTTCCTCCTGCTACTCTGGCTCCCAGATACCACCGGAGAAATTGTGTTGACGCA
GTCTCCAGGCACCCTGTCTTTGTCTCCAGGGGAAAGAGCCACCCTCTCCTGCAGGGCCAGTCAGAGTGTTCGCATCA
GCTACTTAGCCTGGTACCAGCAGAAACCTGGCCAGGCTCCCAGGCTCCTCATCTATGGTACATTCAGCAGGGCCACT
GGCATCCCAGACAGGTTCAGTGGCAGTGGGTCTGGGACAGACTTCACTCTCACCATCAGCAGACTGGAGCCTGAAGA
TTTTGCAGTGTATTACTGTCAGCAGTATGGTAGCTCAATGTACACTTTTGGCCAGGGGACCAAGCTGGAGATCAAA SEQ ID: 255
(358-22-M1 VH with leader)
MEFGLSWVFLVALLRGVQCQVQLVESGGGVVQPGRSLRLSCAASGFTFRSYGMHWVRQAPGKGLEWVTLIWYDGSNK
YYADSVKGRFTISRDNSKNTLYLQMNSLRAEDTAVYYCAREGFNWDAFDIWGQGTMVTVSS SEQ ID: 256
(358-22-M1 VH with leader)
ATGGAGTTTGGGCTGAGCTGGGTTTTCCTCGTTGCTCTTTTAAGAGGTGTCCAGTGTCAGGTGCAACTGGTGGAGTC
TGGGGGAGGCGTGGTCCAGCCTGGGAGGTCCCTGAGACTCTCCTGTGCAGCGTCTGGATTCACCTTCAGGAGTTATG
GCATGCACTGGGTCCGCCAGGCTCCAGGCAAGGGGCTGGAGTGGGTGACACTTATATGGTATGATGGAAGTAATAAA
TACTATGCAGACTCCGTGAAGGGCCGATTCACCATCTCCAGAGACAATTCCAAGAACACGCTGTATCTGCAAATGAA
CAGCCTGAGAGCCGAGGACACGGCTGTGTATTACTGTGCGAGAGAAGGGTTTAACTGGGATGCTTTTGATATCTGGG
GCCAAGGGACAATGGTCACCGTCTCTTCA SEQ ID: 257
(597-120 VH with leader)
MELGLSWVFLVAILEGVQCEVHLVESGGGLVQSGGSLRLSCAASGFSISGYWMSWVRQAPGKGLEWVANIKQDGGEK
YYGDSVKGRFTISRDNAENSLYLQMSSLRAEDTAVYYCVMAGGLDYWGQGALVTVSS SEQ ID: 258
(597-120 VH with leader)
ATGGAATTGGGGCTGAGCTGGGTTTTCCTTGTTGCTATTTTAGAAGGTGTTCAGTGTGAGGTGCACCTGGTGGAGTC
TGGGGGAGGCTTGGTCCAGTCTGGGGGGTCCCTGAGACTCTCCTGTGCAGCCTCTGGATTCAGCATTAGTGGCTATT
GGATGAGCTGGGTCCGCCAGGCTCCAGGGAAAGGGCTGGAGTGGGTGGCAACATAAAGCAAGATGGAGGTGAGAAG
TACTATGGGGACTCTGTGAAGGGCCGATTCACCATCTCCAGAGACAACGCCGAAAACTCACTGTATCTGCAAATGAG
CAGCCTGAGAGCCGAGGACACGGCTGTGTATTACTGTGTAATGGCGGGTGGCCTTGACTACTGGGGCCAGGGAGCCC
TGGTCACCGTCTCCTCA SEQ ID: 259
(597-120 VK with leader)
MEAPAQLLFLLLLWLPDTTGEIVLTQSPATLSLSPGERATLSCRASQSVSSYLAWYQQKPGQAPRLLIYDASNRATG

IPARFSGSGSGTDFTLTISSLEPEDFAVYYCQQRSNWYTFGQGTKLEIK

SEQ ID: 260
(597-120 VK with leader)
ATGGAAGCCCCAGCTCAGCTTCTCTTCCTCCTGCTACTCTGGCTCCCAGATACCACCGGAGAAATTGTGTTGACACA

GTCTCCAGCCACCCTGTCTTTGTCTCCAGGGGAAAGAGCCACCCTCTCCTGCAGGGCCAGTCAGAGTGTTAGCAGCT

ACTTAGCCTGGTACCAACAGAAACCTGGCCAGGCTCCCAGGCTCCTCATCTATGATGCATCCAACAGGGCCACTGGC

ATCCCAGCCAGGTTCAGTGGCAGTGGGTCTGGGACAGACTTCACTCTCACCATCAGCAGCCTAGAGCCTGAAGATTT

TGCAGTTTATTACTGTCAGCAGCGTAGCAACTGGTACACTTTTGGCCAGGGGACCAAGCTGGAGATCAAA

SEQ ID: 261
(597-120-M1 VH with leader)
MELGLSWVFLVAILEGVQCEVQLVESGGGLVQPGGSLRLSCAASGFSISGYWMSWVRQAPGKGLEWVANIKQDGGEK

YYGDSVKGRFTISRDNAKNSLYLQMNSLRAEDTAVYYCVMAGGLDYWGQGTLVTVSS

SEQ ID: 262
(597-120-M1 VH with leader)
ATGGAATTGGGGCTGAGCTGGGTTTTCCTTGTTGCTATTTTAGAAGGTGTTCAGTGTGAGGTGCAGCTGGTGGAGTC

TGGGGGAGGCTTGGTCCAGCCTGGGGGGTCCCTGAGACTCTCCTGTGCAGCCTCTGGATTCAGCATTAGTGGCTATT

GGATGAGCTGGGTCCGCCAGGCTCCAGGGAAAGGGCTGGAGTGGGTGGCCAACATAAAGCAAGATGGAGGTGAGAAG

TACTATGGGGACTCTGTGAAGGGCCGATTCACCATCTCCAGAGACAACGCCAAGAACTCACTGTATCTGCAAATGAA

CAGCCTGAGAGCCGAGGACACGGCTGTGTATTACTGTGTAATGGCGGGTGGCCTTGACTACTGGGGCCAGGGAACCC

TGGTCACCGTCTCCTCA

SEQ ID: 263
(311-3 VH with leader)
MKHLWFFLLLVAAPRWVLSQVQLQQWGAGLLKPSETLSLTCAVYGGSFSGYYWNWIRQPPGMGLEWIGEIHQSGGPH

YNPSLKSRVSISVDTSKNQVNLKLSSVTAADTAIYYCTELDDYWGQGTLVTVSS

SEQ ID: 264
(311-3 VH with leader)
ATGAAACACCTGTGGTTCTTCCTCCTCCTGGTGGCAGCTCCCAGATGGGTCCTGTCCCAGGTGCAGCTACAGCAGTG

GGGCGCAGGACTGTTGAAGCCTTCGGAGACCCTGTCCCTCACCTGCGCTGTCTATGGTGGGTCCTTCAGTGGTTACT

ACTGGAACTGGATCCGCCAGCCCCCAGGAATGGGGCTGGAATGGATTGGAGAAATCCATCAAAGTGGAGGCCCCCAC

TACAACCCGTCCCTCAAGAGTCGAGTCAGCATTTCAGTAGACACGTCCAAAAACCAGGTCAACCTGAAGCTGAGCTC

TGTGACCGCCGCGGATACGGCTATTTATTACTGTACGGAGTTGGATGACTATTGGGGCCAGGGAACCCTGGTCACCG

TCTCCTCA

SEQ ID: 265
(311-3 VK with leader)
MEAPAQLLFLLLLWLPDTTGEIVLTQSPATLSLSPGERATLSCRASQSVSSYLAWYQQKPGQAPRLLIYNASNRATG

IPARFSGSGSGTDFTLTIGSLEPEDFAVYYCQQRSNWPRTFGQGTKVEIK

SEQ ID: 266
(311-3 VK with leader)
ATGGAAGCCCCAGCTCAGCTTCTCTTCCTCCTGCTACTCTGGCTCCCAGATACCACCGGAGAAATTGTGTTGACACA

GTCTCCAGCCACCCTGTCTTTGTCTCCAGGGGAAAGAGCCACCCTCTCCTGCAGGGCCAGTCAGAGTGTTAGCAGCT

ACTTAGCCTGGTACCAACAGAAACCTGGCCAGGCTCCCAGGCTCCTCATCTATAATGCATCCAACAGGGCCACTGGC

ATCCCAGCCAGGTTCAGTGGCAGTGGGTCTGGGACAGACTTCACTCTCACCATCGGCAGCCTAGAGCCTGAAGATTT

TGCAGTTTATTACTGTCAGCAGCGTAGCAACTGGCCTCGGACGTTCGGCCAAGGGACCAAGGTGGAGATCAAA

SEQ ID: 267
(311-3-M1 VH with leader)
MKHLWFFLLLVAAPRWVLSQVQLQQWGAGLLKPSETLSLTCAVYGGSFSGYYWNWIRQPPGKGLEWIGEIHQSGGPH

YNPSLKSRVTISVDTSKNQFSLKLSSVTAADTAVYYCTELDDYWGQGTLVTVSS

```
                                                                     SEQ ID: 268
(311-3-M1 VH with leader)
ATGAAACACCTGTGGTTCTTCCTCCTCCTGGTGGCAGCTCCCAGATGGGTCCTGTCCCAGGTGCAGCTACAGCAGTG

GGGCGCAGGACTGTTGAAGCCTTCGGAGACCCTGTCCCTCACCTGCGCTGTCTATGGTGGGTCCTTCAGTGGTTACT

ACTGGAACTGGATTCGCCAGCCCCCAGGAAAGGGGCTGGAATGGATTGGAGAAATCCATCAAAGTGGAGGCCCCCAC

TACAACCCGTCCCTCAAGAGTCGAGTCACCATTTCAGTAGACACGTCCAAAAACCAGTTCTCCCTGAAGCTGAGCTC

TGTGACCGCCGCGGATACGGCTGTGTATTACTGTACGGAGTTGGATGACTATTGGGGCCAGGGAACCCTGGTCACCG

TCTCCTCA

SEQ ID: 269
(311-3-M1 VK with leader)
MEAPAQLLFLLLLWLPDTTGEIVLTQSPATLSLSPGERATLSCRASQSVSSYLAWYQQKPGQAPRLLIYDASNRATG

IPARFSGSGSGTDFTLTISSLEPEDFAVYYCQQRSNWPRTFGQGTKVEIK

SEQ ID: 270
(311-3-M1 VK with leader)
ATGGAAGCCCCAGCTCAGCTTCTCTTCCTCCTGCTACTCTGGCTCCCAGATACCACCGGAGAAATTGTGTTGACACA

GTCTCCAGCCACCCTGTCTTTGTCTCCAGGGGAAAGAGCCACCCTCTCCTGCAGGGCCAGTCAGAGTGTTAGCAGCT

ACTTAGCCTGGTACCAACAGAAACCTGGCCAGGCTCCCAGGCTCCTCATCTATGATGCATCCAACAGGGCCACTGGC

ATCCCAGCCAGGTTCAGTGGCAGTGGGTCTGGGACAGACTTCACTCTCACCATCAGCAGCCTAGAGCCTGAAGATTT

TGCAGTTTATTACTGTCAGCAGCGTAGCAACTGGCCTCGGACGTTCGGCCAAGGGACCAAGGTGGAGATCAAA

SEQ ID: 271
(312-19 VH with leader)
MDWTWRFLFVVAAATGVQSQVQLVQSGAEVKKPGSSVKVSCKASGGTFNNFVIGWVRQAPGQGLEWMGRIIPILDIA

NYAQKFQGRVTITADKSTSTVYMELNSLRSEDTAVYYCARTGNYYKPYDYWGQGTLVTVSS

SEQ ID: 272
(312-19 VH with leader)
ATGGACTGGACCTGGAGGTTCCTCTTTGTGGTGGCAGCAGCTACAGGTGTCCAGTCCCAGGTCCAGCTGGTGCAGTC

TGGGGCTGAGGTGAAGAAGCCTGGGTCCTCGGTGAAGGTCTCCTGCAAGGCTTCTGGAGGCACCTTCAACAACTTCG

TTATCGGCTGGGTGCGACAGGCCCCTGGACAAGGACTTGAGTGGATGGGAAGGATCATCCCTATCCTTGATATAGCA

AACTACGCACAGAAGTTCCAGGGCAGAGTCACGATTACCGCGGACAAATCCACGAGCACAGTTTACATGGAGCTGAA

CAGCCTGAGATCTGAGGACACGGCCGTATACTACTGTGCGAGAACGGGGAATTATTATAAGCCCTATGACTACTGGG

GCCAGGGAACCCTGGTCACCGTCTCCTCA

SEQ ID: 273
(312-19 VK with leader)
MLPSQLIGFLLLWVPASRGEIVLTQSPDFQSVTPKEKVTITCRASQSIGSSLHWYQQKPDQSPKLLIKYASQSFSGV

PSRFSGSGSGTDFTLTINSLEAEDAAAYYCHQSSSLPITFGQGTRLEIK

SEQ ID: 274
(312-19 VK with leader)
ATGTTGCCATCACAACTCATTGGGTTTCTGCTGCTCTGGGTTCCAGCCTCCAGGGGTGAAATTGTGCTGACTCAGTC

TCCAGACTTTCAGTCTGTGACTCCAAAGGAGAAAGTCACCATCACCTGCCGGGCCAGTCAGAGCATTGGTAGCAGCT

TACACTGGTACCAGCAGAAACCAGATCAGTCTCCAAAGCTCCTCATCAAGTATGCTTCCCAGTCCTTCTCAGGGGTC

CCCTCGAGGTTCAGTGGCAGTGGATCTGGGACAGATTTCACCCTCACCATCAATAGCCTGGAAGCTGAAGATGCTGC

AGCGTATTACTGTCATCAGAGTAGTAGTTTACCGATCACCTTCGGCCAAGGGACACGACTGGAGATCAAA

SEQ ID: 275
(312-19-M1 VH with leader)
MDWTWRFLFVVAAATGVQSQVQLVQSGAEVKKPGSSVKVSCKASGGTFNNFVIGWVRQAPGQGLEWMGRIIPILDIA

NYAQKFQGRVTITADKSTSTAYMELSSLRSEDTAVYYCARTGNYYKPYDYWGQGTLVTVSS
```

SEQ ID: 276
(312-19-M1 VH with leader)
ATGGACTGGACCTGGAGGTTCCTCTTTGTGGTGGCAGCAGCTACAGGTGTCCAGTCCCAGGTCCAGCTGGTGCAGTC

TGGGGCTGAGGTGAAGAAGCCTGGGTCCTCGGTGAAGGTCTCCTGCAAGGCTTCTGGAGGCACCTTCAACAACTTCG

TTATCGGCTGGGTGCGACAGGCCCCTGGACAAGGACTTGAGTGGATGGGAAGGATCATCCCTATCCTTGATATAGCA

AACTACGCACAGAAGTTCCAGGGCAGAGTCACGATTACCGCGGACAAATCCACGAGCACAGCCTACATGGAGCTGAG

CAGCCTGAGATCTGAGGACACGGCCGTATACTACTGTGCGAGAACGGGGAATTATTATAAGCCCTATGACTACTGGG

GCCAGGGAACCCTGGTCACCGTCTCCTCA

SEQ ID: 277
(591-33 VH with leader)
MELGLSWVFLVAILEGVQCEVQLVESGGGLVQPGGSLRLSCAASGFTFSRYWMSWVRQAPGKGLEWMANIKQDGSET

HYVDSVKGRFTISRDNAKNSLYLQMNSLRAEDTAVYYCAIGDYWGQGTLVTVSS

SEQ ID: 278
(591-33 VH with leader)
ATGGAATTGGGGCTGAGCTGGGTTTTCCTTGTTGCTATTTTAGAAGGTGTCCAGTGTGAGGTGCAGTTGGTGGAGTC

TGGGGGAGGCTTGGTCCAGCCTGGGGGGTCCCTGAGACTCTCCTGTGCAGCCTCTGGATTCACCTTTAGTCGCTATT

GGATGAGCTGGGTCCGCCAGGCTCCAGGGAAAGGGCTGGAGTGGATGGCCAACATAAAGCAAGATGGAAGTGAGACA

CACTATGTGGACTCTGTGAAGGGCCGATTCACCATCTCCAGAGACAACGCCAAGAACTCACTGTATCTGCAAATGAA

CAGCCTGAGAGCCGAGGACACGGCTGTGTATTACTGTGCGATTGGTGACTACTGGGGCCAGGGAACCCTGGTCACCG

TCTCCTCA

SEQ ID: 279
(591-33 VK with leader)
MDMRVLAQLLGLLLLCFPGARCDIQMTQSPSSLSASVGDRVTITCRASQDISSWLAWYQQKPEKAPKSLIYAASSLQ

SGVPSRFSGSGSGTDFTLTISSLQPEDFATYYCQQYKSYPLTFGGGTKVEIK

SEQ ID: 280
(591-33 VK with leader)
ATGGACATGAGGGTCCTCGCTCAGCTCCTGGGGCTCCTGCTGCTCTGTTTCCCAGGTGCCAGATGTGACATCCAGAT

GACCCAGTCTCCATCCTCACTGTCTGCATCTGTAGGAGACAGAGTCACCATCACTTGTCGGGCGAGTCAGGATATTA

GCAGCTGGTTAGCCTGGTATCAGCAGAAACCAGAGAAAGCCCCTAAGTCCCTGATCTATGCTGCATCCAGTTTGCAA

AGTGGGGTCCCATCAAGGTTCAGCGGCAGTGGATCTGGGACAGATTTCACTCTCACCATCAGCAGCCTGCAGCCTGA

AGATTTTGCAACTTATTACTGCCAACAGTATAAAAGTTACCCGCTCACTTTCGGCGGAGGGACCAAGGTGGAGATCA

AA

SEQ ID: 281
(591-33-M1 VH with leader)
MELGLSWVFLVAILEGVQCEVQLVESGGGLVQPGGSLRLSCAASGFTFSRYWMSWVRQAPGKGLEWVANIKQDGSET

HYVDSVKGRFTISRDNAKNSLYLQMNSLRAEDTAVYYCAIGDYWGQGTLVTVSS

SEQ ID: 282
(591-33-M1 VH with leader)
ATGGAATTGGGGCTGAGCTGGGTTTTCCTTGTTGCTATTTTAGAAGGTGTCCAGTGTGAGGTGCAGTTGGTGGAGTC

TGGGGGAGGCTTGGTCCAGCCTGGGGGGTCCCTGAGACTCTCCTGTGCAGCCTCTGGATTCACCTTTAGTCGCTATT

GGATGAGCTGGGTCCGCCAGGCTCCAGGGAAAGGGCTGGAGTGGGTGGCCAACATAAAGCAAGATGGAAGTGAGACA

CACTATGTGGACTCTGTGAAGGGCCGATTCACCATCTCCAGAGACAACGCCAAGAACTCACTGTATCTGCAAATGAA

CAGCCTGAGAGCCGAGGACACGGCTGTGTATTACTGTGCGATTGGTGACTACTGGGGCCAGGGAACCCTGGTCACCG

TCTCCTCA

SEQ ID: 283
(114-41 VH with leader)
MDWTWSILFLVAAATGAHSQVQLVQSGAEVKTPGASVKVSCKASGYTFTSFGISWVRQAPGQGLEWMGWISVYNDYT

NYAQKFQGRVTMTTDTSTSTAYMELRSLRSDDTAMYYCARKRGGDMDYWGQGTLVTVSS

SEQ ID: 284
(114-41 VH with leader)
ATGGACTGGACCTGGAGCATCCTTTTCTTGGTGGCAGCAGCAACAGGTGCCCACTCCCAGGTTCAGCTGGTGCAGTC

TGGAGCTGAAGTGAAGACGCCTGGGGCCTCAGTGAAGGTCTCCTGCAAGGCTTCTGGTTACACCTTTACCAGCTTTG

GTATCAGCTGGGTGCGACAGGCCCCTGGACAAGGGCTTGAGTGGATGGGATGGATCAGCGTTTACAATGATTACACA

AACTATGCACAGAAGTTCCAGGGCAGAGTCACCATGACCACAGACACATCCACGAGCACAGCCTACATGGAACTGAG

GAGCCTGAGATCTGACGACACGGCCATGTATTACTGTGCGAGAAAGAGGGGTGGGGATATGGACTATTGGGGCCAGG

GAACCCTGGTCACCGTCTCCTCA

SEQ ID: 285
(114-41 VK with leader)
MDMMVPAQLLGLLLLWFPGSRCDIQMTQSPSSVSASVGDRVTITCRASQDISSWLAWYQHKPGKAPKLLIYLASSLQ

SGVPSRFSGSGSGTDFTLTISSLQPEDFATYYCQQANSFPWTFGQGTKVEIK

SEQ ID: 286
(114-41 VK with leader)
ATGGACATGATGGTCCCCGCTCAGCTCCTGGGGCTCCTGCTGCTCTGGTTCCCAGGTTCCAGATGCGACATCCAGAT

GACCCAGTCTCCATCTTCCGTGTCTGCATCTGTAGGAGACAGAGTCACCATCACTTGTCGGGCGAGTCAGGATATTA

GCAGCTGGTTAGCCTGGTATCAGCATAAACCAGGGAAAGCCCCTAAGCTCCTGATCTATCTTGCATCCAGTTTGCAA

AGTGGGGTCCCATCAAGGTTCAGCGGCAGTGGATCTGGGACAGATTTCACTCTCACCATCAGCAGCCTGCAGCCTGA

AGATTTTGCAACTTACTATTGTCAACAGGCTAATAGTTTTCCGTGGACGTTCGGCCAAGGGACCAAGGTGGAGATCA

AA

SEQ ID: 287
(114-41-M1 VH with leader)
MDWTWSILFLVAAPTGAHSQVQLVQSGAEVKKPGASVKVSCKASGYTFTSFGISWVRQAPGQGLEWMGWISVYNDYT

NYAQKFQGRVTMTTDTSTSTAYMELRSLRSDDTAVYYCARKRGGDMDYWGQGTLVTVSS

SEQ ID: 288
(114-41-M1 VH with leader)
ATGGACTGGACCTGGAGCATCCTTTTCTTGGTGGCAGCACCAACAGGTGCCCACTCCCAGGTTCAGCTGGTGCAGTC

TGGAGCTGAAGTGAAGAAGCCTGGGGCCTCAGTGAAGGTCTCCTGCAAGGCTTCTGGTTACACCTTTACCAGCTTTG

GTATCAGCTGGGTGCGACAGGCCCCTGGACAAGGGCTTGAGTGGATGGGATGGATCAGCGTTTACAATGATTACACA

AACTATGCACAGAAGTTCCAGGGCAGAGTCACCATGACCACAGACACATCCACGAGCACAGCCTACATGGAACTGAG

GAGCCTGAGATCTGACGACACGGCCGTGTATTACTGTGCGAGAAAGAGGGGTGGGGATATGGACTATTGGGCCAGG

GAACCCTGGTCACCGTCTCCTCA

SEQ ID: 289
(306-155 VH with leader)
MGSTAILALLLAVLQGVCAEVQLVQSGAEVKKPGESLKISCKGSGYSFTSYWIGWVRQMPGKGLEWMGIIYPGDSDT

RYSPSFQGQVTISADKSISTAYLQWSSLKASDTAMYYCARQGSGWYGNYFDYWGQGTLVTVSS

SEQ ID: 290
(306-155 VH with leader)
ATGGGGTCAACCGCCATCCTCGCCCTCCTCCTGGCTGTTCTCCAAGGAGTCTGTGCCGAGGTGCAGCTGGTGCAGTC

TGGAGCAGAGGTGAAAAAGCCCGGGGAGTCTCTGAAGATCTCCTGTAAGGGTTCTGGATACAGTTTTACCAGCTACT

GGATCGGCTGGGTGCGCCAGATGCCCGGGAAAGGCCTGGAGTGGATGGGGATCATCTATCCTGGTGACTCTGATACC

AGATACAGCCCGTCCTTCCAAGGCCAGGTCACCATCTCAGCCGACAAGTCCATCAGCACCGCCTACCTGCAGTGGAG

CAGCCTGAAGGCCTCGGACACCGCCATGTATTACTGTGCGAGACAGGGCAGCGGCTGGTACGGGAACTACTTTGACT

ACTGGGGCCAGGGAACCCTGGTCACCGTCTCCTCA

SEQ ID: 291
(306-155 VK with leader)
METPAQLLFLLLLWLPDTTGEIVLTQSPGTLSLSPGERATLSCRASQSFSRGYLAWYQQKPGQAPRLLIYGASSRVT

GIPDRFSGSGSGTDFTLTISRLEPEDFAVYYCQQYDSSPYTFGQGTKLEIK

-continued

SEQ ID: 292
(306-155 VK with leader)
ATGGAAACCCCAGCGCAGCTTCTCTTCCTCCTGCTACTCTGGCTCCCAGATACCACCGGAGAAATTGTGTTGACGCA

GTCTCCAGGCACCCTGTCTTTGTCTCCAGGGGAAAGAGCCACCCTCTCCTGCAGGGCCAGTCAGAGTTTTAGCAGAG

GCTACTTAGCCTGGTACCAGCAGAAACCTGGCCAGGCTCCCAGGCTCCTCATCTATGGTGCATCCAGCAGGGTCACT

GGCATCCCAGACAGGTTCAGTGGCAGTGGGTCTGGGACAGACTTCACTCTCACCATCAGCAGACTGGAGCCTGAAGA

TTTTGCGGTGTATTACTGTCAGCAGTATGATAGCTCACCGTACACTTTTGGCCAGGGGACCAAGCTGGAGATCAAA

SEQ ID: 293
(14-173 VH with leader)
MELGLSWVFLVAILEGVQCEVQLVESGGGLVQPGGSLRLSCAASGFTFSSFWMSWVRQAPGKGLEWVANIKHDGSEQ

DYVDSVKGRFTISRDNAKNSLYLQMNSLRAEDTAVYYCARGGIWFGPWGQGTLVTVSS

SEQ ID: 294
(14-173 VH with leader)
ATGGAATTGGGGCTGAGCTGGGTTTTCCTTGTTGCTATTTTAGAAGGTGTCCAGTGTGAGGTGCAGCTGGTGGAGTC

TGGGGGAGGCTTGGTCCAGCCTGGGGGGTCCCTGAGACTCTCCTGTGCAGCCTCTGGATTCACCTTTAGTAGCTTTT

GGATGAGTTGGGTCCGCCAGGCTCCAGGGAAAGGGCTGGAGTGGGTGGCCAACATAAAGCACGATGGAAGTGAGCAA

GACTATGTGGACTCTGTGAAGGGCCGATTCACCATCTCCAGAGACAACGCCAAGAACTCACTGTATCTGCAAATGAA

CAGCCTGAGAGCCGAGGACACGGCTGTGTATTACTGTGCAAGGGGGGGTATCTGGTTCGGCCCCTGGGGCCAGGGAA

CCCTGGTCACCGTCTCCTCA

SEQ ID: 295
(14-173 VK with leader)
MDMRVPAQLLGLLLLWLPGARCVIWMTQSPSLLSASTGDRVTISCRMSQGISSYLAWYQQKPGKAPEVLIYAVSTLQ

SGVPSRFSGSGSGTDFTLTISCLQSEDFATYYCQQYYSFPYTFGQGTKLEIK

SEQ ID: 296
(14-173 VK with leader)
ATGGACATGAGGGTGCCCGCTCAGCTCCTGGGGCTCCTGCTGCTCTGGCTCCCAGGTGCCAGATGTGTCATCTGGAT

GACCCAGTCTCCATCCTTACTCTCTGCATCTACAGGAGACAGAGTCACCATCAGTTGTCGGATGAGTCAGGGCATTA

GCAGTTATTTAGCCTGGTATCAGCAAAAACCAGGGAAAGCCCCTGAGGTCCTGATCTATGCTGTATCCACTTTGCAA

AGTGGGGTCCCATCAAGGTTCAGTGGCAGTGGATCTGGGACAGATTTCACTCTCACCATCAGCTGCCTGCAGTCTGA

AGATTTTGCAACTTATTACTGTCAACAGTATTATAGTTTCCCGTACACTTTTGGCCAGGGGACCAAGCTGGAGATCA

AA

SEQ ID: 297
(14-173-M1 VK with leader)
MDMRVPAQLLGLLLLWLPGARCVIWMTQSPSLLSASTGDRVTISCRMSQGISSYLAWYQQKPGKAPELLIYAVSTLQ

SGVPSRFSGSGSGTDFTLTISSLQSEDFATYYCQQYYSFPYTFGQGTKLEIK

SEQ ID: 298
(14-173-M1 VK with leader)
ATGGACATGAGGGTGCCCGCTCAGCTCCTGGGGCTCCTGCTGCTCTGGCTCCCAGGTGCCAGATGTGTCATCTGGAT

GACCCAGTCTCCATCCTTACTCTCTGCATCTACAGGAGACAGAGTCACCATCAGTTGTCGGATGAGTCAGGGCATTA

GCAGTTATTTAGCCTGGTATCAGCAAAAACCAGGGAAAGCCCCTGAGCTCCTGATCTATGCTGTATCCACTTTGCAA

AGTGGGGTCCCATCAAGGTTCAGTGGCAGTGGATCTGGGACAGATTTCACTCTCACCATCAGCTCTCTGCAGTCTGA

AGATTTTGCAACTTATTACTGTCAACAGTATTATAGTTTCCCGTACACTTTTGGCCAGGGGACCAAGCTGGAGATCA

AA

SEQ ID: 299
(303-8 VH with leader)
MDWTWRFLFVVAAATGVQSQVQLVQSGAEVKKPGSSVKVSCKASGGSFSIYVISWVRQAPGQGLEWMGRIIPILGTT

NYAQKFQGRVTITADKSTSTAYMELSSLRSEDTAVYYCARPDSPNHSNTFDYWGQGTLVTVSS

SEQ ID: 300
(303-8 VH with leader)
ATGGACTGGACCTGGAGGTTCCTCTTTGTGGTGGCAGCAGCTACAGGTGTCCAGTCCCAGGTCCAGCTGGTGCAGTC

TGGGGCTGAGGTGAAGAAGCCTGGGTCCTCGGTGAAGGTCTCCTGCAAGGCTTCTGGAGGCTCCTTCAGCATCTATG

TTATCAGCTGGGTGCGACAGGCCCCTGGACAAGGGCTTGAGTGGATGGGAAGGATCATCCCTATCCTTGGTACAACA

AACTACGCACAGAAGTTCCAGGGCAGAGTCACGATTACCGCGGACAAATCCACGAGCACAGCCTACATGGAGCTGAG

CAGCCTGAGATCTGAGGACACGGCCGTGTATTACTGTGCGAGACCGGACTCCCCGAACCATAGTAATACATTTGACT

ACTGGGGCCAGGGAACCCTGGTCACCGTCTCCTCA

SEQ ID: 301
(303-8 VK with leader)
MDMRVLAQLLGLLLLCFPGARCDIQMTQSPSSLSASVGDRVTITCRASQGISSWLAWYQQKPEKAPKSLIYGASSLQ

SGVPSRFSGSGSGTDFTLTISSLQPEDFATYYCQQYNSYPYTFGQGTKLEIK

SEQ ID: 302
(303-8 VK with leader)
ATGGACATGAGGGTCCTCGCTCAGCTCCTGGGGCTCCTGCTGCTCTGTTTCCCAGGTGCCAGATGTGACATCCAGAT

GACCCAGTCTCCATCCTCACTGTCTGCATCTGTAGGAGACAGAGTCACCATCACTTGTCGGGCGAGTCAGGGTATTA

GCAGCTGGTTAGCCTGGTATCAGCAGAAACCAGAGAAAGCCCCTAAGTCCCTGATCTATGGTGCATCCAGTTTGCAA

AGTGGGGTCCCATCAAGGTTCAGCGGCAGTGGATCTGGGACAGATTTCACTCTCACCATCAGCAGCCTGCAGCCTGA

AGATTTTGCAACTTATTACTGCCAACAGTATAATAGTTACCCGTACACTTTTGGCCAGGGGACCAAGCTGGAGATCA

AA

SEQ ID: 303
(312-56 VH with leader)
MDWTWRFLFVVAAATGVQSQVQVVQSGAEVKKPGSSVKVSCKASGGTFSSYAISWVRQAPGQGLEWMGRIIPILGTA

KYAQKFQGRVTIIADKSTSTAYMELSSLRSEDTAVYYCARDQDYYGMDVWGQGTTVTVSS

SEQ ID: 304
(312-56 VH with leader)
ATGGACTGGACCTGGAGGTTCCTCTTTGTGGTGGCAGCAGCTACAGGTGTCCAGTCCCAGGTCCAGGTGGTGCAGTC

TGGGGCTGAGGTGAAGAAGCCTGGGTCCTCGGTGAAGGTCTCCTGCAAGGCTTCTGGAGGCACCTTCAGCAGCTATG

CTATCAGCTGGGTGCGACAGGCCCCTGGACAAGGGCTTGAGTGGATGGGAAGGATCATCCCTATCCTTGGTACAGCA

AAGTACGCACAGAAGTTCCAGGGCAGAGTCACGATTATCGCGGACAAATCCACGAGCACAGCCTACATGGAGCTGAG

CAGCCTGAGATCTGAGGACACGGCCGTGTATTACTGTGCGAGAGATCAGGACTACTACGGTATGGACGTCTGGGGCC

AAGGGACCACGGTCACCGTCTCCTCA

SEQ ID: 305
(312-56 VK with leader)
MDMMVPAQLLGLLLLWFPGSRCDIQMTQSPSSVSASVGDRVTITCRASQGISSWLAWYQHKPGKAPKLLIYAASSLQ

SGVPSRFSGSGSGTDFTLTISSLQPEDFATYYCQQTNNFPWTFGQGTKVEIK

SEQ ID: 306
(312-56 VK with leader)
ATGGACATGATGGTCCCCGCTCAGCTCCTGGGGCTCCTGCTGCTCTGGTTCCCAGGTTCCAGATGCGACATCCAGAT

GACCCAGTCTCCATCTTCCGTGTCTGCATCTGTAGGAGACAGAGTCACCATCACTTGTCGGGCGAGTCAGGGTATTA

GCAGCTGGTTAGCCTGGTATCAGCATAAACCAGGGAAAGCCCCTAAGCTCCTGATCTATGCTGCATCCAGTTTGCAA

AGTGGGGTCCCATCAAGGTTCAGCGGCAGTGGATCTGGGACAGATTTCACTCTCACCATCAGCAGCCTGCAGCCTGA

AGATTTTGCAACTTACTATTGTCAACAGACTAATAATTTCCCGTGGACGTTCGGCCAAGGGACCAAGGTGGAGATCA

AA

SEQ ID: 307
(hSOD1 aa 40-47)
EGLHGFHV

```
                                                          SEQ ID: 308
(hSOD1 aa 40-47)
GAAGGCCTGCATGGATTCCATGTT

SEQ ID: 309
(hSOD1 aa 63-71)
HFNPLSRKH

SEQ ID: 310
(hSOD1 aa 63-71)
CACTTTAATCCTCTATCCAGAAAACAC

SEQ ID: 311
(hSOD1 aa 80-88)
HVGDLGNVT

SEQ ID: 312
(hSOD1 aa 80-88)
CATGTTGGAGACTTGGGCAATGTGACT

SEQ ID: 313
(hSOD1 aa 42-49)
LHGFHVHE

SEQ ID: 314
(hSOD1 aa 42-49)
CTGCATGGATTCCATGTTCATGAG

SEQ ID: 315
(hSOD1 aa 107-121)
SGDHCIIGRTLVVHE

SEQ ID: 316
(hSOD1 aa 107-121)
TCAGGAGACCATTGCATCATTGGCCGCACACTGGTGGTCCATGAA

SEQ ID: 317
(hSOD1)
ATKAVCVLKGDGPVQGIINFEQKESNGPVKVWGSIKGLTEGLHGFHVHEFGDNTAGCTSAGPHFNPLSRKHGGPKDE

ERHVGDLGNVTADKDGVADVSIEDSVISLSGDHCIIGRTLVVHEKADDLGKGGNEESTKTGNAGSRLACGVIGIAQ

SEQ ID: 318
(hSOD1)
GCGACGAAGGCCGTGTGCGTGCTGAAGGGCGACGGCCCAGTGCAGGGCATCATCAATTTCGAGCAGAAGGAAAGTAA

TGGACCAGTGAAGGTGTGGGGAAGCATTAAAGGACTGACTGAAGGCCTGCATGGATTCCATGTTCATGAGTTTGGAG

ATAATACAGCAGGCTGTACCAGTGCAGGTCCTCACTTTAATCCTCTATCCAGAAAACACGGTGGGCCAAAGGATGAA

GAGAGGCATGTTGGAGACTTGGGCAATGTGACTGCTGACAAAGATGGTGTGGCCGATGTGTCTATTGAAGATTCTGT

GATCTCGCTCTCAGGAGACCATTGCATCATTGGCCGCACACTGGTGGTCCATGAAAAAGCAGATGACTTGGGCAAAG

GTGGAAATGAAGAAAGTACAAAGACGGGAAACGCTGGAAGTCGTTTGGCTTGTGGTGTAATTGGGATCGCCCAA

SEQ ID: 319
(b-hSOD1)
GCGACCAAAGCAGTGTGCGTTTTGAAAGGCGATGGCCCTGTGCAAGGCATCATTAACTTCGAACAAAAAGAAAGCAA

CGGACCGGTCAAAGTGTGGGGATCAATTAAAGGTTTGACTGAGGGCCTGCATGGATTTCACGTGCATGAATTTGGTG

ACAATACCGCCGGTTGTACCTCCGCGGGTCCGCACTTTAACCCTTTGTCCCGTAAACACGGGGGCCCTAAAGACGAA

GAACGTCATGTCGGCGACTTAGGCAACGTCACTGCCGATAAAGATGGGGTCGCAGACGTCAGTATTGAGGATTCTGT

CATTTCGTTGTCTGGCGATCACTGCATCATTGGTCGCACTCTGGTCGTACACGAAAAAGCGGATGATCTGGGGAAAG

GCGGCAATGAAGAGAGCACCAAAACGGGAAATGCTGGCTCACGCCTCGCGTGTGGGGTCATTGGTATTGCCCAG

SEQ ID: 320
(b-hSOD1-A)
ATKAVCVLKGDGPVQGIINFEQKESNGPVKVWGSIKGL

SEQ ID: 321
(b-hSOD1-B)
ATKAVCVLKGDGPVQGIINFEQKESNGPVKVWGSIKGLTEGLHGFHVHEFGDNTAGCTSAGPHFNPLSRKHGGPKDE
```

-continued (b-hSOD1-C)  
ATKAVCVLKGDGPVQGIINFEQKESNGPVKVWGSIKGLTEGLHGFHVHEFGDNTAGCTSAGPHFNPLSRKHGGPKDE  
ERHVGDLGNVTADKDGVADVSIEDSVISLSGDHCIIGRT  
SEQ ID: 322

(b-hSOD1-D)  
TEGLHGFHVHEFGDNTAGCTSAGPHFNPLSRKHGGPKDEERHVGDLGNVTADKDGVADVSIEDSVISLSGDHCIIGR  
TLVVHEKADDLGKGGNEESTKTGNAGSRLACGVIGIAQ  
SEQ ID: 323

(b-hSOD1-E)  
ERHVGDLGNVTADKDGVADVSIEDSVISLSGDHCIIGRTLVVHEKADDGKGGNEESTKTGNAGSRLACGVIGIAQ  
SEQ ID: 324

(b-hSOD1-F)  
LVVHEKADDLGKGGNEESTKTGNAGSRLACGVIGIAQ  
SEQ ID: 325

(b-hSOD1-G)  
LTEGLHGFHVHEFGDNTAGCTSAGPHFNPLSRKHGGPKDE  
SEQ ID: 326

(b-hSOD1-H)  
EERHVGDLGNVTADKDGVADVSIEDSVISLSGDHCIIGRT  
SEQ ID: 327

(b-hSOD1-I)  
LTEGLHGFHVHEFGDNTAGCTSAGPHFNPLSRKHGGPKDEERHVGDLGNVTADKDGVADVSIEDSVISLSGDHCIIG  
RT  
SEQ ID: 328

(b-hSOD1-J)  
DGVADVSIEDSVISLSGDHCIIGRTLVVHEKADDLGKGGNEESTKTGNAGSRLACGVIGIAQ  
SEQ ID: 329

(b-hSOD1-K)  
SVISLSGDHCIIGRTLVVHEKADDLGKGGNEESTKTGNAGSRLACGVIGIAQ  
SEQ ID: 330

(hSOD1-G1)  
LTEGLHGFHVHEFGD  
SEQ ID: 331

(hSOD1-G1a)  
LTEGLHGFHV  
SEQ ID: 332

(hSOD1-G1b)  
EGLHGFHVHE  
SEQ ID: 333

(hSOD1-G1c)  
LHGFHVHEFG  
SEQ ID: 334

(hSOD1-G2)  
HVHEFGDNTAGCTSA  
SEQ ID: 335

(hSOD1-G3)  
TAGCTSAGPHFNPLS  
SEQ ID: 336

(hSOD1-G4)  
HFNPLSRKHGGPKDE  
SEQ ID: 337

(hSOD1-G4a)  
HFNPLSRKH  
SEQ ID: 338

(hSOD1-G4b)  
PLSRKHGGP  
SEQ ID: 339

(hSOD1-G4c)  
RKHGGPKDE  
SEQ ID: 340

-continued

```
                                                              SEQ ID: 341
(hSOD1-H1)
EERHVGDLGNVTADK

SEQ ID: 342
(hSOD1-H1a)
EERHVGDLG

SEQ ID: 343
(hSOD1-H1b)
HVGDLGNVT

SEQ ID: 344
(hSOD1-H1c)
DLGNVTADK

SEQ ID: 345
(hSOD1-H2)
GNVTADKDGVADVS

SEQ ID: 346
(hSOD1-H3)
GVADVSIEDSVISLS

SEQ ID: 347
(hSOD1-H4)
SVISLSGDHCIIGRT

SEQ ID: 348
(hSOD1-K1)
SGDHCIIGRTLVVHE

SEQ ID: 349
(hSOD1-K2)
IIGRTLVVHEKADDL

SEQ ID: 350
(osteonectin leader)
MRAWIFFLLCLAGRALA

SEQ ID: 351
(osteonectin leader)
ATGAGGGCTTGGATCTTCTTTCTGCTCTGCCTGGCCGGGCGCGCCTTGGCC SEQ ID: 352
(serum albumin peptide)
DICLPRWGCLW
```

---

What is claimed is:

1. An isolated monoclonal antibody, or antigen binding fragment thereof, wherein said monoclonal antibody, or antigen binding fragment thereof, binds to an epitope of SOD1 protein and wherein said monoclonal antibody comprises a heavy chain variable domain and a light chain variable domain, wherein the heavy chain variable domain comprises a CDRH1, CDRH2, and CDRH3, wherein:
   (a) the CDRH1 comprises an amino acid sequence of SEQ ID NO:21;
   (b) the CDRH2 comprises an amino acid sequence of SEQ ID NO:23; and
   (c) the CDRH3 comprises an amino acid sequence of SEQ ID NO:25; and wherein the light chain variable domain comprises a CDRL1, CDRL2, and CDRL3, wherein:
   (d) the CDRL1 comprises an amino acid sequence of SEQ ID NO: 29;
   (e) the CDRL2 comprises an amino acid sequence of SEQ ID NO: 31; and
   (f) the CDRL3 comprises an amino acid sequence of SEQ ID NO: 33.

2. The isolated monoclonal antibody, or antigen binding fragment thereof, of claim 1, wherein the monoclonal antibody, or antigen binding fragment thereof, comprises a heavy chain variable domain amino acid sequence of SEQ ID NO:19 and a light chain variable domain amino acid sequence of SEQ ID NO: 27.

3. The isolated monoclonal antibody, or antigen binding fragment thereof, of claim 1, wherein the antibody specifically binds to a conformational epitope of SOD1 protein.

4. The isolated monoclonal antibody, or antigen binding fragment thereof, of claim 3, wherein the conformational epitope is present in a misfolded SOD1 protein.

5. The isolated monoclonal antibody, or antigen binding fragment thereof, of claim 1, wherein the monoclonal antibody, or antigen binding fragment thereof, competes with the binding of antibody 591-37 to the SOD1 protein.

6. The isolated monoclonal antibody, or antigen binding fragment thereof, of claim 1, wherein the monoclonal antibody, or antigen binding fragment thereof, binds to SOD1 with a Kd value of 50 nM or lower.

7. The isolated monoclonal antibody, or antigen binding fragment thereof, of claim 1, wherein the monoclonal antibody, or antigen binding fragment thereof, is a chimeric, humanized, or fully human antibody, or fragment thereof.

8. The isolated monoclonal antibody, or antigen binding fragment thereof, of claim 1, wherein the monoclonal antibody, or antigen binding fragment thereof, is a single chain antibody; a diabody; an Fab, Fab', F(ab')$_2$, Fv, scFv, dsFv, or ds-scFv, fragment; an antibody dimer; a bispecific antibody; a minibody; or multimers thereof.

9. The isolated monoclonal antibody, or antigen binding fragment thereof, of claim 1, wherein the monoclonal antibody, or antigen binding fragment thereof, is conjugated to an exogenous molecule.

10. The isolated monoclonal antibody, or antigen binding fragment thereof, of claim 9, wherein the exogenous molecule is an inhibitory nucleic acid molecule.

11. A composition comprising the monoclonal antibody, or antigen binding fragment thereof, of claim 1 and a pharmaceutically acceptable carrier.

12. An isolated nucleic acid molecule encoding the isolated monoclonal antibody, or antigen binding fragment thereof, of claim 1.

13. A vector comprising the isolated nucleic acid molecule of claim 12.

14. A host cell transformed with the vector of claim 13.

15. A method of producing an antibody, said method comprising culturing the host cell of claim 14 under conditions for expression of the nucleic acid molecule and recovering the antibody from the host cell culture medium.

16. A hybridoma cell line producing the monoclonal antibody of claim 1.

17. A method of treating amyotrophic lateral sclerosis (ALS) in a subject, said method comprising administering intrathecally to the subject an isolated monoclonal antibody or antigen-binding fragment thereof, of claim 1, for a time and in an amount effective to treat said amyotrophic lateral sclerosis.

18. The method of claim 17, wherein the ALS is sporadic ALS.

19. The method of claim 17, wherein the ALS is familial ALS.

20. The method of claim 17, wherein said administering of said isolated monoclonal antibody or antigen binding fragment thereof is in an amount effective to reduce or ameliorate at least one symptom of ALS.

21. The method of claim 20, wherein said at least one symptom is selected from the group consisting of muscle weakness, muscle atrophy, difficulty swallowing, muscle cramping or stiffness, weight loss, and slurred speech.

22. The method of claim 17, wherein said subject is a human subject.

23. The method of claim 17, wherein the method further comprises administering at least one additional therapeutic agent.

24. The method of claim 23, wherein the at least one additional therapeutic agent is riluzole.

25. The method of claim 23, wherein the at least one additional therapeutic agent is a therapeutic antibody or an antibody conjugated to an exogenous molecule.

\* \* \* \* \*

SEQUENCE LISTING

<160> NUMBER OF SEQ ID NOS: 352

<210> SEQ ID NO 1
<211> LENGTH: 119
<212> TYPE: PRT
<213> ORGANISM: Homo sapiens

<400> SEQUENCE: 1

Glu Val Gln Leu Val Gln Ser Gly Gly Gly Leu Gly His Pro Gly Gly
1               5                   10                  15

Ser Leu Arg Leu Ser Cys Ala Gly Ser Gly Phe Thr Phe Ser Ser Tyr
            20                  25                  30

Ser Met His Trp Leu Arg Gln Ala Pro Gly Lys Gly Leu Lys Trp Val
        35                  40                  45

Ser Ala Ile Gly Thr Ala Gly Gly Thr Tyr Tyr Ala Asp Ser Val Lys
    50                  55                  60

Gly Arg Phe Thr Ile Ser Arg Asp Asn Ala Lys Asn Ser Phe Tyr Leu
65                  70                  75                  80

Gln Met Asn Ser Leu Arg Ala Glu Asp Met Ala Val Tyr Tyr Cys Ala
                85                  90                  95

Arg Glu Tyr Phe Phe Gly Ser Gly Asn Tyr Gly Tyr Trp Gly Gln Gly
            100                 105                 110
Thr Leu Val Thr Ala Ser Ser
        115

<210> SEQ ID NO 2
<211> LENGTH: 357
<212> TYPE: DNA
<213> ORGANISM: Homo sapiens

<400> SEQUENCE: 2
gaggttcagc tggtgcagtc tgggggaggc ttgggacatc ctgggggtc cctgagactc    60 tcctgtgcag gctctggatt cactttcagt agttattcta tgcactggct tcgccaggct   120
ccaggaaaag gtctgaagtg gtatcagct attggtactg ctggtggcac atactatgca   180
gactccgtga aggccgatt caccatctcc agagacaatg ccaagaactc cttctatctt   240
caaatgaaca gcctgagagc cgaggacatg gctgtgtatt actgtgcaag agagtatttc   300
tttggttcgg ggaattatgg atactggggc cagggaaccc tggtcaccgc ctcctca     357

<210> SEQ ID NO 3
<211> LENGTH: 5
<212> TYPE: PRT
<213> ORGANISM: Homo sapiens

<400> SEQUENCE: 3

Ser Tyr Ser Met His
1               5

<210> SEQ ID NO 4
<211> LENGTH: 15
<212> TYPE: DNA
<213> ORGANISM: Homo sapiens

<400> SEQUENCE: 4
agttattcta tgcac                                                    15

<210> SEQ ID NO 5
<211> LENGTH: 16
<212> TYPE: PRT
<213> ORGANISM: Homo sapiens

<400> SEQUENCE: 5

Ala Ile Gly Thr Ala Gly Gly Thr Tyr Tyr Ala Asp Ser Val Lys Gly
1               5                   10                  15

<210> SEQ ID NO 6
<211> LENGTH: 48
<212> TYPE: DNA
<213> ORGANISM: Homo sapiens

<400> SEQUENCE: 6
gctattggta ctgctggtgg cacatactat gcagactccg tgaagggc                48

<210> SEQ ID NO 7
<211> LENGTH: 11
<212> TYPE: PRT
<213> ORGANISM: Homo sapiens

<400> SEQUENCE: 7

Glu Tyr Phe Phe Gly Ser Gly Asn Tyr Gly Tyr
1               5                   10

```
<210> SEQ ID NO 8
<211> LENGTH: 33
<212> TYPE: DNA
<213> ORGANISM: Homo sapiens

<400> SEQUENCE: 8
gagtatttct ttggttcggg gaattatgga tac                               33

<210> SEQ ID NO 9
<211> LENGTH: 107
<212> TYPE: PRT
<213> ORGANISM: Homo sapiens

<400> SEQUENCE: 9
```

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105

```
<210> SEQ ID NO 10
<211> LENGTH: 321
<212> TYPE: DNA
<213> ORGANISM: Homo sapiens

<400> SEQUENCE: 10
gaaattgtgt tgacacagtc tccagccacc ctgtctttgt ctccagggga aagagccacc    60
ctctcctgca gggccagtca gagtgttagc agctacttag cctggtacca acagaaacct   120
ggccaggctc ccaggctcct catctatgat gcatccaaca gggccactgg catcccagcc   180
aggttcagtg gcagtgggtc tgggacagac ttcactctca ccatcagcag cctagagcct   240
gaagattttg cagtttatta ctgtcagcag cgtagcaact ggcctccgac gttcggccaa   300
gggaccaagg tggagatcaa a                                             321

<210> SEQ ID NO 11
<211> LENGTH: 11
<212> TYPE: PRT
<213> ORGANISM: Homo sapiens

<400> SEQUENCE: 11
```

Arg Ala Ser Gln Ser Val Ser Ser Tyr Leu Ala
1               5                   10

```
<210> SEQ ID NO 12
<211> LENGTH: 33
<212> TYPE: DNA
<213> ORGANISM: Homo sapiens

<400> SEQUENCE: 12
```

```
agggccagtc agagtgttag cagctactta gcc                                    33
```

<210> SEQ ID NO 13
<211> LENGTH: 7
<212> TYPE: PRT
<213> ORGANISM: Homo sapiens

<400> SEQUENCE: 13

Asp Ala Ser Asn Arg Ala Thr
1               5

<210> SEQ ID NO 14
<211> LENGTH: 21
<212> TYPE: DNA
<213> ORGANISM: Homo sapiens

<400> SEQUENCE: 14

```
gatgcatcca acagggccac t                                                 21
```

<210> SEQ ID NO 15
<211> LENGTH: 9
<212> TYPE: PRT
<213> ORGANISM: Homo sapiens

<400> SEQUENCE: 15

Gln Gln Arg Ser Asn Trp Pro Pro Thr
1               5

<210> SEQ ID NO 16
<211> LENGTH: 27
<212> TYPE: DNA
<213> ORGANISM: Homo sapiens

<400> SEQUENCE: 16

```
cagcagcgta gcaactggcc tccgacg                                           27
```

<210> SEQ ID NO 17
<211> LENGTH: 119
<212> TYPE: PRT
<213> ORGANISM: Homo sapiens

<400> SEQUENCE: 17

Glu Val Gln Leu Val Gln Ser Gly Gly Gly Leu Val Lys Pro Gly Gly
1               5                   10                  15

Ser Leu Arg Leu Ser Cys Ala Gly Ser Gly Phe Thr Phe Ser Ser Tyr
            20                  25                  30

Ser Met His Trp Leu Arg Gln Ala Pro Gly Lys Gly Leu Glu Trp Val
        35                  40                  45

Ser Ala Ile Gly Thr Ala Gly Asp Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Glu Tyr Phe Phe Gly Ser Gly Asn Tyr Gly Tyr Trp Gly Gln Gly
            100                 105                 110

Thr Leu Val Thr Val Ser Ser
        115

<210> SEQ ID NO 18
<211> LENGTH: 357

```
<212> TYPE: DNA
<213> ORGANISM: Homo sapiens

<400> SEQUENCE: 18
gaggttcagc tggtgcagtc tgggggaggc ttggtaaaac ctggggggtc cctgagactc      60
tcctgtgcag gctctggatt cactttcagt agttattcta tgcactggct tcgccaggct     120
ccaggaaaag gtctggagtg ggtatcagct attggtactg ctggtggcac atactatgca     180
gactccgtga agggccgatt caccatctcc agagacaatg ccaagaactc cttgtatctt     240
caaatgaaca gcctgagagc cgaggacacg gctgtgtatt actgtgcaag agagtatttc     300
tttggttcgg ggaattatgg atactggggc cagggaaccc tggtcaccgt ctcctca       357

<210> SEQ ID NO 19
<211> LENGTH: 120
<212> TYPE: PRT
<213> ORGANISM: Homo sapiens

<400> SEQUENCE: 19

Glu Val Gln Leu Val Gln Ser Gly Gly Gly Leu Val His Pro Gly Gly
1               5                   10                  15

Ser Leu Arg Leu Ser Cys Ala Gly Ser Gly Phe Thr Phe Ser Arg Tyr
            20                  25                  30

Ala Leu His Trp Val Arg Gln Ala Pro Gly Lys Gly Leu Glu Trp Val
        35                  40                  45

Ser Ala Ile Gly Ile Gly Gly Thr Phe Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg Asp Thr Tyr Tyr Asp Phe Phe Asp Ala Phe Asp Ile Trp Gly Gln
            100                 105                 110

Gly Thr Met Val Thr Val Ser Ser
        115                 120

<210> SEQ ID NO 20
<211> LENGTH: 357
<212> TYPE: DNA
<213> ORGANISM: Homo sapiens

<400> SEQUENCE: 20
gaggttcagc tggtgcagtc tgggggaggc ttggtaaaac ctggggggtc cctgagactc      60
tcctgtgcag gctctggatt cactttcagt agttattcta tgcactggct tcgccaggct     120
ccaggaaaag gtctggagtg ggtatcagct attggtactg ctggtggcac atactatgca     180
gactccgtga agggccgatt caccatctcc agagacaatg ccaagaactc cttgtatctt     240
caaatgaaca gcctgagagc cgaggacacg gctgtgtatt actgtgcaag agagtatttc     300
tttggttcgg ggaattatgg atactggggc cagggaaccc tggtcaccgt ctcctca       357

<210> SEQ ID NO 21
<211> LENGTH: 5
<212> TYPE: PRT
<213> ORGANISM: Homo sapiens

<400> SEQUENCE: 21

Arg Tyr Ala Leu His
1               5
```

<210> SEQ ID NO 22
<211> LENGTH: 15
<212> TYPE: DNA
<213> ORGANISM: Homo sapiens

<400> SEQUENCE: 22
cgctatgctt tacac                                                    15

<210> SEQ ID NO 23
<211> LENGTH: 16
<212> TYPE: PRT
<213> ORGANISM: Homo sapiens

<400> SEQUENCE: 23

Ala Ile Gly Ile Gly Gly Gly Thr Phe Tyr Ala Asp Ser Val Lys Gly
1               5                   10                  15

<210> SEQ ID NO 24
<211> LENGTH: 48
<212> TYPE: DNA
<213> ORGANISM: Homo sapiens

<400> SEQUENCE: 24
gctattggta ttggtggtgg cacattctat gcagactccg tgaagggc                48

<210> SEQ ID NO 25
<211> LENGTH: 12
<212> TYPE: PRT
<213> ORGANISM: Homo sapiens

<400> SEQUENCE: 25

Asp Thr Tyr Tyr Asp Phe Phe Asp Ala Phe Asp Ile
1               5                   10

<210> SEQ ID NO 26
<211> LENGTH: 36
<212> TYPE: DNA
<213> ORGANISM: Homo sapiens

<400> SEQUENCE: 26
gatacgtatt acgattttt tgatgctttt gatatc                              36

<210> SEQ ID NO 27
<211> LENGTH: 107
<212> TYPE: PRT
<213> ORGANISM: Homo sapiens

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Ser Tyr Pro Leu
                85                  90                  95

Thr Phe Gly Gly Gly Thr Lys Val Glu Ile Lys
            100                 105

<210> SEQ ID NO 28
<211> LENGTH: 321
<212> TYPE: DNA
<213> ORGANISM: Homo sapiens

<400> SEQUENCE: 28

```
gacatccaga tgacccagtc tccatcctca ctgtctgcat ctgtaggaga cagagtcacc    60
atcacttgtc gggcgagtca gggtattagc agctggttag cctggtatca gcagaaacca   120
gagaaagccc ctaagtccct gatctatgct gcatccagtt tgcaaagtgg ggtcccatca   180
aggttcagcg gcagtggatc tgggacagat ttcactctca ccatcagcag cctgcagcct   240
gaagattttg caacttatta ctgccaacag tatgatagtt accctctcac tttcggcgga   300
gggaccaagg tggagatcaa a                                             321
```

<210> SEQ ID NO 29
<211> LENGTH: 11
<212> TYPE: PRT
<213> ORGANISM: Homo sapiens

<400> SEQUENCE: 29

Arg Ala Ser Gln Gly Ile Ser Ser Trp Leu Ala
1               5                   10

<210> SEQ ID NO 30
<211> LENGTH: 33
<212> TYPE: DNA
<213> ORGANISM: Homo sapiens

<400> SEQUENCE: 30

```
cgggcgagtc agggtattag cagctggtta gcc                                 33
```

<210> SEQ ID NO 31
<211> LENGTH: 7
<212> TYPE: PRT
<213> ORGANISM: Homo sapiens

<400> SEQUENCE: 31

Ala Ala Ser Ser Leu Gln Ser
1               5

<210> SEQ ID NO 32
<211> LENGTH: 21
<212> TYPE: DNA
<213> ORGANISM: Homo sapiens

<400> SEQUENCE: 32

```
gctgcatcca gtttgcaaag t                                              21
```

<210> SEQ ID NO 33
<211> LENGTH: 9
<212> TYPE: PRT
<213> ORGANISM: Homo sapiens

<400> SEQUENCE: 33

Gln Gln Tyr Asp Ser Tyr Pro Leu Thr
1               5

<210> SEQ ID NO 34
<211> LENGTH: 27

-continued

```
<212> TYPE: DNA
<213> ORGANISM: Homo sapiens

<400> SEQUENCE: 34
caacagtatg atagttaccc tctcact                                               27

<210> SEQ ID NO 35
<211> LENGTH: 120
<212> TYPE: PRT
<213> ORGANISM: Homo sapiens

<400> SEQUENCE: 35

Glu Val Gln Leu Val Gln Ser Gly Gly Gly Leu Val Lys Pro Gly Gly
1               5                   10                  15

Ser Leu Arg Leu Ser Cys Ala Gly Ser Gly Phe Thr Phe Ser Arg Tyr
            20                  25                  30

Ala Leu His Trp Val Arg Gln Ala Pro Gly Lys Gly Leu Glu Trp Val
        35                  40                  45

Ser Ala Ile Gly Ile Gly Gly Thr Phe Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Tyr Tyr Asp Phe Phe Asp Ala Phe Asp Ile Trp Gly Gln
            100                 105                 110

Gly Thr Met Val Thr Val Ser Ser
        115                 120

<210> SEQ ID NO 36
<211> LENGTH: 360
<212> TYPE: DNA
<213> ORGANISM: Homo sapiens

<400> SEQUENCE: 36
gaggttcagc tggtgcagtc tgggggaggc ttggtaaaac ctgggggggtc cctgagactc         60 tcctgtgcag gctctggatt caccttcagt cgctatgctt tacactgggt tcgccaggct        120
ccaggaaaag gtctggagtg ggtatcagct attggtattg gtggtggcac attctatgca        180
gactccgtga agggccgatt caccatctcc agagacaatg ccaagaactc cttgtatctt        240
caaatgaaca gcctgagagc cgaggacacg gctgtgtatt actgtgcaag agatacgtat        300
tacgattttt ttgatgcttt tgatatctgg ggccaaggga caatggtcac cgtctcttca        360

<210> SEQ ID NO 37
<211> LENGTH: 117
<212> TYPE: PRT
<213> ORGANISM: Homo sapiens

<400> SEQUENCE: 37

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Ile Ile Trp His Asp Gly Ser Asn Ser Tyr Tyr Val Asp Ser Val
    50                  55                  60
```

Lys Gly Arg Phe Thr Met Ser Arg Asp Asn Ser Lys Asn Thr Val Tyr
65                  70                  75                  80

Leu Gln Met Asn Ser Leu Arg Ala Glu Asp Thr Ala Val Tyr Phe Cys
                85                  90                  95

Ala Arg Ile Ile Gly Gly Ala Phe Asp Ile Trp Gly Gln Gly Thr Met
            100                 105                 110

Val Thr Val Ser Ser
        115

<210> SEQ ID NO 38
<211> LENGTH: 351
<212> TYPE: DNA
<213> ORGANISM: Homo sapiens

<400> SEQUENCE: 38
caggtgcagc tggtggagtc tgggggaggc gtggtccagc ctgggaggtc cctgagactc      60
tcctgtgcag cgtctggatt caccttcagt aactatggca tacactgggt ccgccaggct     120
ccaggcaagg ggctggagtg ggtggctatt atatggcatg atggaagtaa ttcatattat     180
gtagactccg tgaagggccg attcaccatg tccagagaca attccaagaa cacggtgtat     240
ctgcaaatga acagcctgag agccgaggac acggctgtgt atttctgtgc gagataatt      300 gggggcgctt ttgatatctg ggccaaggg acaatggtca ccgtctcttc a              351

<210> SEQ ID NO 39
<211> LENGTH: 5
<212> TYPE: PRT
<213> ORGANISM: Homo sapiens

<400> SEQUENCE: 39

Asn Tyr Gly Ile His
1               5

<210> SEQ ID NO 40
<211> LENGTH: 15
<212> TYPE: DNA
<213> ORGANISM: Homo sapiens

<400> SEQUENCE: 40
cacaactatg gcata                                                       15

<210> SEQ ID NO 41
<211> LENGTH: 17
<212> TYPE: PRT
<213> ORGANISM: Homo sapiens

<400> SEQUENCE: 41

Ile Ile Trp His Asp Gly Ser Asn Ser Tyr Tyr Val Asp Ser Val Lys
1               5                   10                  15

Gly

<210> SEQ ID NO 42
<211> LENGTH: 51
<212> TYPE: DNA
<213> ORGANISM: Homo sapiens

<400> SEQUENCE: 42
attatatggc atgatggaag taattcatat tatgtagact ccgtgaaggg c                51

<210> SEQ ID NO 43
<211> LENGTH: 8

```
<212> TYPE: PRT
<213> ORGANISM: Homo sapiens

<400> SEQUENCE: 43

Ile Ile Gly Gly Ala Phe Asp Ile
1               5

<210> SEQ ID NO 44
<211> LENGTH: 24
<212> TYPE: DNA
<213> ORGANISM: Homo sapiens

<400> SEQUENCE: 44
ataattgggg gcgcttttga tatc                                           24

<210> SEQ ID NO 45
<211> LENGTH: 107
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Ile
                85                  90                  95

Thr Phe Gly Gln Gly Thr Arg Leu Glu Ile Lys
            100                 105

<210> SEQ ID NO 46
<211> LENGTH: 321
<212> TYPE: DNA
<213> ORGANISM: Homo sapiens

<400> SEQUENCE: 46
gacatccaga tgacccagtc tccatcctca ctgtctgcat ctgtaggaga cagagtcacc      60
atcacttgtc gggcgagtca gggtattagc agctggttag cctggtatca gcagaaacca     120
gagaaagccc ctaagtccct gatctatgct gcatccagtt tgcaaagtgg ggtcccatca     180
aggttcagcg gcagtggatc tgggacagat ttcactctca ccatcagcag cctgcagcct     240
gaagattttg caacttatta ctgccaacag tataatagtt acccgatcac cttcggccaa     300
gggacacgac tggagatcaa a                                              321

<210> SEQ ID NO 47
<211> LENGTH: 11
<212> TYPE: PRT
<213> ORGANISM: Homo sapiens

<400> SEQUENCE: 47

Arg Ala Ser Gln Gly Ile Ser Ser Trp Leu Ala
1               5                   10
```

<210> SEQ ID NO 48
<211> LENGTH: 33
<212> TYPE: DNA
<213> ORGANISM: Homo sapiens

<400> SEQUENCE: 48
cgggcgagtc agggtattag cagctggtta gcc                                    33

<210> SEQ ID NO 49
<211> LENGTH: 7
<212> TYPE: PRT
<213> ORGANISM: Homo sapiens

<400> SEQUENCE: 49

Ala Ala Ser Ser Leu Gln Ser
1               5

<210> SEQ ID NO 50
<211> LENGTH: 21
<212> TYPE: DNA
<213> ORGANISM: Homo sapiens

<400> SEQUENCE: 50
gctgcatcca gtttgcaaag t                                                 21

<210> SEQ ID NO 51
<211> LENGTH: 9
<212> TYPE: PRT
<213> ORGANISM: Homo sapiens

<400> SEQUENCE: 51

Gln Gln Tyr Asn Ser Tyr Pro Ile Thr
1               5

<210> SEQ ID NO 52
<211> LENGTH: 27
<212> TYPE: DNA
<213> ORGANISM: Homo sapiens

<400> SEQUENCE: 52
caacagtata atagttaccc gatcacc                                           27

<210> SEQ ID NO 53
<211> LENGTH: 117
<212> TYPE: PRT
<213> ORGANISM: Homo sapiens

<400> SEQUENCE: 53

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Ile Ile Trp His Asp Gly Ser Asn Ser Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Arg Ile Ile Gly Gly Ala Phe Asp Ile Trp Gly Gln Gly Thr Met
            100                 105                 110

<210> SEQ ID NO 54
<211> LENGTH: 351
<212> TYPE: DNA
<213> ORGANISM: Homo sapiens

<400> SEQUENCE: 54

```
caggtgcagc tggtggagtc tgggggaggc gtggtccagc ctggagggtc cctgagactc    60
tcctgtgcag cgtctggatt caccttcagt aactatggca tacactgggt ccgccaggct   120
ccaggcaagg ggctggagtg ggtggctatt atatggcatg atggaagtaa ttcatattat   180
gtagactccg tgaagggccg attcaccatc tccagagaca attccaagaa cacgctgtat   240
ctgcaaatga acagcctgag agccgaggac acggctgtgt atttctgtgc gagaataatt   300
gggggcgctt ttgatatctg ggccaaggg acaatggtca ccgtctcttc a             351
```

<210> SEQ ID NO 55
<211> LENGTH: 119
<212> TYPE: PRT
<213> ORGANISM: Homo sapiens

<400> SEQUENCE: 55

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Thr Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Arg Glu Gly Phe Asn Trp Asp Ala Phe Asp Ile Trp Gly Gln Gly
            100                 105                 110

Thr Met Val Thr Val Ser Ser
        115

<210> SEQ ID NO 56
<211> LENGTH: 357
<212> TYPE: DNA
<213> ORGANISM: Homo sapiens

<400> SEQUENCE: 56

```
caggtgcaac tggtggagtc tgggggaggc gtggtccagc ctggagggtc cctgagactc    60
tcctgtgcag cgtctggatt caccttcagg agttatggca tgcactgggt ccgccaggct   120
ccaggcaagg ggctggagtg ggtggacactt atatggtatg atggaagtaa taaatactat   180
gcagactccg tgaagggccg attcaccatc tccagagaca attccaagaa cacgctgtat   240
ctgcaaatga acagcctgag agtcgaggac acggctgtgt attactgtgc gagagaaggg   300
tttaactggg atgcttttga tatctggggc caagggacaa tggtcaccgt ctcttca      357
```

<210> SEQ ID NO 57
<211> LENGTH: 5

```
<212> TYPE: PRT
<213> ORGANISM: Homo sapiens

<400> SEQUENCE: 57

Ser Tyr Gly Met His
1               5

<210> SEQ ID NO 58
<211> LENGTH: 15
<212> TYPE: DNA
<213> ORGANISM: Homo sapiens

<400> SEQUENCE: 58
agttatggca tgcac                                                      15

<210> SEQ ID NO 59
<211> LENGTH: 17
<212> TYPE: PRT
<213> ORGANISM: Homo sapiens

<400> SEQUENCE: 59

Leu Ile Trp Tyr Asp Gly Ser Asn Lys Tyr Tyr Ala Asp Ser Val Lys
1               5                   10                  15

Gly

<210> SEQ ID NO 60
<211> LENGTH: 51
<212> TYPE: DNA
<213> ORGANISM: Homo sapiens

<400> SEQUENCE: 60
ctaatatggt atgatggaag taataaatac tatgcagact ccgtgaaggg c              51

<210> SEQ ID NO 61
<211> LENGTH: 10
<212> TYPE: PRT
<213> ORGANISM: Homo sapiens

<400> SEQUENCE: 61

Glu Gly Phe Asn Trp Asp Ala Phe Asp Ile
1               5                   10

<210> SEQ ID NO 62
<211> LENGTH: 30
<212> TYPE: DNA
<213> ORGANISM: Homo sapiens

<400> SEQUENCE: 62
gaagggttta actgggatgc ttttgatatc                                      30

<210> SEQ ID NO 63
<211> LENGTH: 108
<212> TYPE: PRT
<213> ORGANISM: Homo sapiens

<400> SEQUENCE: 63

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Arg Ile Ser
            20                  25                  30

Tyr Leu Ala Trp Tyr Gln Gln Lys Pro Gly Gln Ala Pro Arg Leu Leu
        35                  40                  45
```

Ile Tyr Gly Thr Phe Ser Arg Ala Thr Gly Ile Pro Asp Arg Phe Ser
            50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Met
                 85                  90                  95

Tyr Thr Phe Gly Gln Gly Thr Lys Leu Glu Ile Lys
             100                 105

<210> SEQ ID NO 64
<211> LENGTH: 324
<212> TYPE: DNA
<213> ORGANISM: Homo sapiens

<400> SEQUENCE: 64
gaaattgtgt tgacgcagtc tccaggcacc ctgtctttgt ctccagggga aagagccacc      60
ctctcctgca gggccagtca gagtgttcgc atcagctact tagcctggta ccagcagaaa     120
cctggccagg ctcccaggct cctcatctat ggtacattca gcagggccac tggcatccca     180
gacaggttca gtggcagtgg gtctgggaca gacttcactc tcaccatcag cagactggag     240
cctgaagatt ttgcagtgta ttactgtcag cagtatggta gctcaatgta cacttttggc     300
caggggacca agctggagat caaa                                            324

<210> SEQ ID NO 65
<211> LENGTH: 12
<212> TYPE: PRT
<213> ORGANISM: Homo sapiens

<400> SEQUENCE: 65

Arg Ala Ser Gln Ser Val Arg Ile Ser Tyr Leu Ala
 1               5                  10

<210> SEQ ID NO 66
<211> LENGTH: 36
<212> TYPE: DNA
<213> ORGANISM: Homo sapiens

<400> SEQUENCE: 66
agggccagtc agagtgttcg catcagctac ttagcc                                36

<210> SEQ ID NO 67
<211> LENGTH: 7
<212> TYPE: PRT
<213> ORGANISM: Homo sapiens

<400> SEQUENCE: 67

Gly Thr Phe Ser Arg Ala Thr
 1               5

<210> SEQ ID NO 68
<211> LENGTH: 21
<212> TYPE: DNA
<213> ORGANISM: Homo sapiens

<400> SEQUENCE: 68
ggtacattca gcagggccac t                                                21

<210> SEQ ID NO 69
<211> LENGTH: 9
<212> TYPE: PRT
<213> ORGANISM: Homo sapiens

<400> SEQUENCE: 69

Gln Gln Tyr Gly Ser Ser Met Tyr Thr
1               5

<210> SEQ ID NO 70
<211> LENGTH: 27
<212> TYPE: DNA
<213> ORGANISM: Homo sapiens

<400> SEQUENCE: 70
cagcagtatg gtagctcaat gtacact                                           27

<210> SEQ ID NO 71
<211> LENGTH: 119
<212> TYPE: PRT
<213> ORGANISM: Homo sapiens

<400> SEQUENCE: 71

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Lys Gly Leu Glu Trp Val
        35                  40                  45

Thr Leu Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gly Phe Asn Trp Asp Ala Phe Asp Ile Trp Gly Gln Gly
            100                 105                 110

Thr Met Val Thr Val Ser Ser
        115

<210> SEQ ID NO 72
<211> LENGTH: 357
<212> TYPE: DNA
<213> ORGANISM: Homo sapiens

<400> SEQUENCE: 72
caggtgcaac tggtggagtc tgggggaggc gtggtccagc ctgggaggtc cctgagactc       60
tcctgtgcag cgtctggatt caccttcagg agttatggca tgcactgggt ccgccaggct      120
ccaggcaagg ggctggagtg ggtgacactt atatggtatg atggaagtaa taaatactat      180
gcagactccg tgaagggccg attcaccatc tccagagaca attccaagaa cacgctgtat      240
ctgcaaatga acagcctgag agccgaggac acggctgtgt attactgtgc gagagaaggg      300
tttaactggg atgctttga tatctggggc caaggacaa tggtcaccgt ctcttca          357

<210> SEQ ID NO 73
<211> LENGTH: 115
<212> TYPE: PRT
<213> ORGANISM: Homo sapiens

<400> SEQUENCE: 73

Glu Val His Leu Val Glu Ser Gly Gly Gly Leu Val Gln Ser Gly Gly
1               5                   10                  15

```
Ser Leu Arg Leu Ser Cys Ala Ala Ser Gly Phe Ser Ile Ser Gly Tyr
         20                  25                  30

Trp Met Ser Trp Val Arg Gln Ala Pro Gly Lys Gly Leu Glu Trp Val
     35                  40                  45

Ala Asn Ile Lys Gln Asp Gly Gly Glu Lys Tyr Tyr Gly Asp Ser Val
 50                  55                  60

Lys Gly Arg Phe Thr Ile Ser Arg Asp Asn Ala Glu Asn Ser Leu Tyr
 65                  70                  75                  80

Leu Gln Met Ser Ser Leu Arg Ala Glu Asp Thr Ala Val Tyr Tyr Cys
                 85                  90                  95

Val Met Ala Gly Gly Leu Asp Tyr Trp Gly Gln Gly Ala Leu Val Thr
            100                 105                 110

Val Ser Ser
        115

<210> SEQ ID NO 74
<211> LENGTH: 345
<212> TYPE: DNA
<213> ORGANISM: Homo sapiens

<400> SEQUENCE: 74
gaggtgcacc tggtggagtc tgggggaggc ttggtccagt ctgggggtc cctgagactc      60 tcctgtgcag cctctggatt cagcattagt ggctattgga tgagctgggt ccgccaggct    120
ccagggaaag gctggagtg gtggccaac ataaagcaag atggaggtga aagtactat       180 ggggactctg tgaagggccg attcaccatc tccagagaca cgccgaaaa ctcactgtat    240 ctgcaaatga gcagcctgag agccgaggac acggctgtgt attactgtgt aatggcgggt   300
ggccttgact actggggcca gggagccctg gtcaccgtct cctca                    345

<210> SEQ ID NO 75
<211> LENGTH: 5
<212> TYPE: PRT
<213> ORGANISM: Homo sapiens

<400> SEQUENCE: 75

Gly Tyr Trp Met Ser
 1               5

<210> SEQ ID NO 76
<211> LENGTH: 15
<212> TYPE: DNA
<213> ORGANISM: Homo sapiens

<400> SEQUENCE: 76
ggctattgga tgagc                                                      15

<210> SEQ ID NO 77
<211> LENGTH: 17
<212> TYPE: PRT
<213> ORGANISM: Homo sapiens

<400> SEQUENCE: 77

Asn Ile Lys Gln Asp Gly Gly Glu Lys Tyr Tyr Gly Asp Ser Val Lys
 1               5                  10                  15

Gly

<210> SEQ ID NO 78
<211> LENGTH: 51
<212> TYPE: DNA
```

<210> SEQ ID NO 78
<211> LENGTH: 51
<212> TYPE: DNA
<213> ORGANISM: Homo sapiens

<400> SEQUENCE: 78
aacataaagc aagatggagg tgagaagtac tatggggact ctgtgaaggg c    51

<210> SEQ ID NO 79
<211> LENGTH: 6
<212> TYPE: PRT
<213> ORGANISM: Homo sapiens

<400> SEQUENCE: 79

Ala Gly Gly Leu Asp Tyr
1               5

<210> SEQ ID NO 80
<211> LENGTH: 18
<212> TYPE: DNA
<213> ORGANISM: Homo sapiens

<400> SEQUENCE: 80
gcgggtggcc ttgactac    18

<210> SEQ ID NO 81
<211> LENGTH: 106
<212> TYPE: PRT
<213> ORGANISM: Homo sapiens

<400> SEQUENCE: 81

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Tyr Thr
                85                  90                  95

Phe Gly Gln Gly Thr Lys Leu Glu Ile Lys
            100                 105

<210> SEQ ID NO 82
<211> LENGTH: 318
<212> TYPE: DNA
<213> ORGANISM: Homo sapiens

<400> SEQUENCE: 82
gaaattgtgt tgacacagtc tccagccacc ctgtctttgt ctccagggga aagagccacc    60
ctctcctgca gggccagtca gagtgttagc agctacttag cctggtacca acagaaacct    120
ggccaggctc ccaggctcct catctatgat gcatccaaca gggccactgg catcccagcc    180
aggttcagtg gcagtgggtc tgggacagac ttcactctca ccatcagcag cctagagcct    240
gaagattttg cagtttatta ctgtcagcag cgtagcaact ggtacacttt tggccagggg    300
accaagctgg agatcaaa    318

<210> SEQ ID NO 83
<211> LENGTH: 11

```
<212> TYPE: PRT
<213> ORGANISM: Homo sapiens

<400> SEQUENCE: 83

Arg Ala Ser Gln Ser Val Ser Ser Tyr Leu Ala
1               5                   10

<210> SEQ ID NO 84
<211> LENGTH: 33
<212> TYPE: DNA
<213> ORGANISM: Homo sapiens

<400> SEQUENCE: 84
agggccagtc agagtgttag cagctactta gcc                                    33

<210> SEQ ID NO 85
<211> LENGTH: 7
<212> TYPE: PRT
<213> ORGANISM: Homo sapiens

<400> SEQUENCE: 85

Asp Ala Ser Asn Arg Ala Thr
1               5

<210> SEQ ID NO 86
<211> LENGTH: 21
<212> TYPE: DNA
<213> ORGANISM: Homo sapiens

<400> SEQUENCE: 86
gatgcatcca acagggccac t                                                 21

<210> SEQ ID NO 87
<211> LENGTH: 8
<212> TYPE: PRT
<213> ORGANISM: Homo sapiens

<400> SEQUENCE: 87

Gln Gln Arg Ser Asn Trp Tyr Thr
1               5

<210> SEQ ID NO 88
<211> LENGTH: 24
<212> TYPE: DNA
<213> ORGANISM: Homo sapiens

<400> SEQUENCE: 88
cagcagcgta gcaactggta cact                                              24

<210> SEQ ID NO 89
<211> LENGTH: 115
<212> TYPE: PRT
<213> ORGANISM: Homo sapiens

<400> SEQUENCE: 89

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ile Ser Gly Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Gly Glu Lys Tyr Tyr Gly Asp Ser Val
    50                  55                  60
```

```
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Val Met Ala Gly Gly Leu Asp Tyr Trp Gly Gln Gly Thr Leu Val Thr
            100                 105                 110

Val Ser Ser
        115

<210> SEQ ID NO 90
<211> LENGTH: 345
<212> TYPE: DNA
<213> ORGANISM: Homo sapiens

<400> SEQUENCE: 90
gaggtgcagc tggtggagtc tgggggaggc ttggtccagc ctgggggtc cctgagactc      60 tcctgtgcag cctctggatt cagcattagt ggctattgga tgagctgggt ccgccaggct    120
ccagggaaag gctggagtg gtggccaac ataaagcaag atggaggtga aagtactat       180 ggggactctg tgaagggccg attcaccatc tccagagaca cgccaagaa ctcactgtat    240 ctgcaaatga acagcctgag agccgaggac acggctgtgt attactgtgt aatggcgggt   300
ggccttgact actggggcca gggaaccctg gtcaccgtct cctca                   345

<210> SEQ ID NO 91
<211> LENGTH: 112
<212> TYPE: PRT
<213> ORGANISM: Homo sapiens

<400> SEQUENCE: 91

Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
                 20                  25                  30

Tyr Trp Asn Trp Ile Arg Gln Pro Pro Gly Met Gly Leu Glu Trp Ile
             35                  40                  45

Gly Glu Ile His Gln Ser Gly Gly Pro His Tyr Asn Pro Ser Leu Lys
         50                  55                  60

Ser Arg Val Ser Ile Ser Val Asp Thr Ser Lys Asn Gln Val Asn Leu
 65                  70                  75                  80

Lys Leu Ser Ser Val Thr Ala Ala Asp Thr Ala Ile Tyr Tyr Cys Thr
                 85                  90                  95

Glu Leu Asp Asp Tyr Trp Gly Gln Gly Thr Leu Val Thr Val Ser Ser
            100                 105                 110

<210> SEQ ID NO 92
<211> LENGTH: 336
<212> TYPE: DNA
<213> ORGANISM: Homo sapiens

<400> SEQUENCE: 92
caggtgcagc tacagcagtg gggcgcagga ctgttgaagc cttcggagac cctgtccctc      60
acctgcgctg tctatggtgg gtccttcagt ggttactact ggaactggat ccgccagccc    120
ccaggaatgg ggctggaatg gattggagaa atccatcaaa gtggaggccc ccactacaac    180
ccgtccctca agagtcgagt cagcatttca gtagacacgt ccaaaaacca ggtcaacctg    240
aagctgagct ctgtgaccgc cgcggatacg gctatttatt actgtacgga gttggatgac   300
```
tattggggcc agggaaccct ggtcaccgtc tcctca 336

<210> SEQ ID NO 93
<211> LENGTH: 5
<212> TYPE: PRT
<213> ORGANISM: Homo sapiens

<400> SEQUENCE: 93

Gly Tyr Tyr Trp Asn
1               5

<210> SEQ ID NO 94
<211> LENGTH: 15
<212> TYPE: DNA
<213> ORGANISM: Homo sapiens

<400> SEQUENCE: 94
ggttactact ggaac                                                      15

<210> SEQ ID NO 95
<211> LENGTH: 16
<212> TYPE: PRT
<213> ORGANISM: Homo sapiens

<400> SEQUENCE: 95

Glu Ile His Gln Ser Gly Gly Pro His Tyr Asn Pro Ser Leu Lys Ser
1               5                   10                  15

<210> SEQ ID NO 96
<211> LENGTH: 48
<212> TYPE: DNA
<213> ORGANISM: Homo sapiens

<400> SEQUENCE: 96
gaaatccatc aaagtggagg cccccactac aacccgtccc tcaagagt                  48

<210> SEQ ID NO 97
<211> LENGTH: 4
<212> TYPE: PRT
<213> ORGANISM: Homo sapiens

<400> SEQUENCE: 97

Leu Asp Asp Tyr
1

<210> SEQ ID NO 98
<211> LENGTH: 12
<212> TYPE: DNA
<213> ORGANISM: Homo sapiens

<400> SEQUENCE: 98
ttggatgact at                                                         12

<210> SEQ ID NO 99
<211> LENGTH: 107
<212> TYPE: PRT
<213> ORGANISM: Homo sapiens

<400> SEQUENCE: 99

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asn Ala Ser Asn Arg Ala Thr Gly Ile Pro Ala Arg Phe Ser Gly
        50                  55                  60

Ser Gly Ser Gly Thr Asp Phe Thr Leu Thr Ile Gly Ser Leu Glu Pro
65                  70                  75                  80

Glu Asp Phe Ala Val Tyr Tyr Cys Gln Gln Arg Ser Asn Trp Pro Arg
                85                  90                  95

Thr Phe Gly Gln Gly Thr Lys Val Glu Ile Lys
            100                 105

<210> SEQ ID NO 100
<211> LENGTH: 321
<212> TYPE: DNA
<213> ORGANISM: Homo sapiens

<400> SEQUENCE: 100
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctataat gcatccaaca gggccactgg catcccagcc     180
aggttcagtg gcagtgggtc tgggacagac ttcactctca ccatcggcag cctagagcct     240
gaagattttg cagtttatta ctgtcagcag cgtagcaact ggcctcggac gttcggccaa     300
gggaccaagg tggagatcaa a                                               321

<210> SEQ ID NO 101
<211> LENGTH: 11
<212> TYPE: PRT
<213> ORGANISM: Homo sapiens

<400> SEQUENCE: 101

Arg Ala Ser Gln Ser Val Ser Ser Tyr Leu Ala
1               5                   10

<210> SEQ ID NO 102
<211> LENGTH: 33
<212> TYPE: DNA
<213> ORGANISM: Homo sapiens

<400> SEQUENCE: 102
agggccagtc agagtgttag cagctactta gcc                                   33

<210> SEQ ID NO 103
<211> LENGTH: 7
<212> TYPE: PRT
<213> ORGANISM: Homo sapiens

<400> SEQUENCE: 103

Asn Ala Ser Asn Arg Ala Thr
1               5

<210> SEQ ID NO 104
<211> LENGTH: 21
<212> TYPE: DNA
<213> ORGANISM: Homo sapiens

<400> SEQUENCE: 104
aatgcatcca acagggccac t                                                21

-continued

<210> SEQ ID NO 105
<211> LENGTH: 9
<212> TYPE: PRT
<213> ORGANISM: Homo sapiens

<400> SEQUENCE: 105

Gln Gln Arg Ser Asn Trp Pro Arg Thr
1               5

<210> SEQ ID NO 106
<211> LENGTH: 27
<212> TYPE: DNA
<213> ORGANISM: Homo sapiens

<400> SEQUENCE: 106
cagcagcgta gcaactggcc tcggacg                                          27

<210> SEQ ID NO 107
<211> LENGTH: 112
<212> TYPE: PRT
<213> ORGANISM: Homo sapiens

<400> SEQUENCE: 107

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Asn Trp Ile Arg Gln Pro Pro Gly Lys Gly Leu Glu Trp Ile
        35                  40                  45

Gly Glu Ile His Gln Ser Gly Gly Pro His Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Thr
                85                  90                  95

Glu Leu Asp Asp Tyr Trp Gly Gln Gly Thr Leu Val Thr Val Ser Ser
            100                 105                 110

<210> SEQ ID NO 108
<211> LENGTH: 336
<212> TYPE: DNA
<213> ORGANISM: Homo sapiens

<400> SEQUENCE: 108
caggtgcagc tacagcagtg gggcgcagga ctgttgaagc cttcggagac cctgtccctc     60
acctgcgctg tctatggtgg gtccttcagt ggttactact ggaactggat tcgccagccc    120
ccaggaaagg ggctggaatg gattggagaa atccatcaaa gtggaggccc ccactacaac    180
ccgtccctca agagtcgagt caccatttca gtagacacgt ccaaaaacca gttctccctg    240
aagctgagct ctgtgaccgc cgcggatacg gctgtgtatt actgtacgga gttggatgac    300
tattggggcc agggaaccct ggtcaccgtc tcctca                              336

<210> SEQ ID NO 109
<211> LENGTH: 107
<212> TYPE: PRT
<213> ORGANISM: Homo sapiens

<400> SEQUENCE: 109

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Arg
                 85                  90                  95

Thr Phe Gly Gln Gly Thr Lys Val Glu Ile Lys
            100                 105

<210> SEQ ID NO 110
<211> LENGTH: 321
<212> TYPE: DNA
<213> ORGANISM: Homo sapiens

<400> SEQUENCE: 110
gaaattgtgt tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctcggac gttcggccaa     300
gggaccaagg tggagatcaa a                                               321

<210> SEQ ID NO 111
<211> LENGTH: 7
<212> TYPE: PRT
<213> ORGANISM: Homo sapiens

<400> SEQUENCE: 111

Asp Ala Ser Asn Arg Ala Thr
1               5

<210> SEQ ID NO 112
<211> LENGTH: 21
<212> TYPE: DNA
<213> ORGANISM: Homo sapiens

<400> SEQUENCE: 112
gatgcatcca acagggccac t                                                21

<210> SEQ ID NO 113
<211> LENGTH: 119
<212> TYPE: PRT
<213> ORGANISM: Homo sapiens

<400> SEQUENCE: 113

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Phe
            20                  25                  30

Val Ile Gly Trp Val Arg Gln Ala Pro Gly Gln Gly Leu Glu Trp Met
        35                  40                  45

Gly Arg Ile Ile Pro Ile Leu Asp Ile Ala Asn Tyr Ala Gln Lys Phe
    50                  55                  60

-continued

Gln Gly Arg Val Thr Ile Thr Ala Asp Lys Ser Thr Ser Thr Val Tyr
65                  70                  75                  80

Met Glu Leu Asn Ser Leu Arg Ser Glu Asp Thr Ala Val Tyr Tyr Cys
            85                  90                  95

Ala Arg Thr Gly Asn Tyr Tyr Lys Pro Tyr Asp Tyr Trp Gly Gln Gly
            100                 105                 110

Thr Leu Val Thr Val Ser Ser
        115

<210> SEQ ID NO 114
<211> LENGTH: 357
<212> TYPE: DNA
<213> ORGANISM: Homo sapiens

<400> SEQUENCE: 114
caggtccagc tggtgcagtc tggggctgag gtgaagaagc ctgggtcctc ggtgaaggtc      60
tcctgcaagg cttctggagg caccttcaac aacttcgtta tcggctgggt gcgacaggcc    120
cctggacaag gacttgagtg gatgggaagg atcatcccta tccttgatat agcaaactac    180
gcacagaagt tccagggcag agtcacgatt accgcggaca atccacgag cacagtttac     240 atggagctga acagcctgag atctgaggac acggccgtat actactgtgc gagaacgggg   300
aattattata gccctatga ctactggggc cagggaaccc tggtcaccgt ctcctca       357

<210> SEQ ID NO 115
<211> LENGTH: 5
<212> TYPE: PRT
<213> ORGANISM: Homo sapiens

<400> SEQUENCE: 115

Asn Phe Val Ile Gly
1               5

<210> SEQ ID NO 116
<211> LENGTH: 15
<212> TYPE: DNA
<213> ORGANISM: Homo sapiens

<400> SEQUENCE: 116
aacttcgtta tcggc                                                      15

<210> SEQ ID NO 117
<211> LENGTH: 17
<212> TYPE: PRT
<213> ORGANISM: Homo sapiens

<400> SEQUENCE: 117

Arg Ile Ile Pro Ile Leu Asp Ile Ala Asn Tyr Ala Gln Lys Phe Gln
1               5                   10                  15

Gly

<210> SEQ ID NO 118
<211> LENGTH: 51
<212> TYPE: DNA
<213> ORGANISM: Homo sapiens

<400> SEQUENCE: 118
aggatcatcc ctatccttga tatagcaaac tacgcacaga agttccaggg c              51

<210> SEQ ID NO 119

<211> LENGTH: 10
<212> TYPE: PRT
<213> ORGANISM: Homo sapiens

<400> SEQUENCE: 119

Thr Gly Asn Tyr Tyr Lys Pro Tyr Asp Tyr
1               5                  10

<210> SEQ ID NO 120
<211> LENGTH: 30
<212> TYPE: DNA
<213> ORGANISM: Homo sapiens

<400> SEQUENCE: 120
acggggaatt attataagcc ctatgactac                                      30

<210> SEQ ID NO 121
<211> LENGTH: 107
<212> TYPE: PRT
<213> ORGANISM: Homo sapiens

<400> SEQUENCE: 121

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Ser Ser
            20                  25                  30

Leu His Trp Tyr Gln Gln Lys Pro Asp Gln Ser Pro Lys Leu Leu Ile
        35                  40                  45

Lys Tyr Ala Ser Gln Ser Phe Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Ala Tyr Tyr Cys His Gln Ser Ser Ser Leu Pro Ile
                85                  90                  95

Thr Phe Gly Gln Gly Thr Arg Leu Glu Ile Lys
            100                 105

<210> SEQ ID NO 122
<211> LENGTH: 321
<212> TYPE: DNA
<213> ORGANISM: Homo sapiens

<400> SEQUENCE: 122
gaaattgtgc tgactcagtc tccagacttt cagtctgtga ctccaaagga gaaagtcacc     60
atcacctgcc gggccagtca gagcattggt agtagcttac actggtacca gcagaaacca    120
gatcagtctc caaagctcct catcaagtat gcttcccagt ccttctcagg ggtcccctcg    180
aggttcagtg gcagtggatc tgggacagat ttcaccctca ccatcaatag cctggaagct    240
gaagatgctg cagcgtatta ctgtcatcag agtagtagtt taccgatcac cttcggccaa    300
gggacacgac tggagatcaa a                                              321

<210> SEQ ID NO 123
<211> LENGTH: 11
<212> TYPE: PRT
<213> ORGANISM: Homo sapiens

<400> SEQUENCE: 123

Arg Ala Ser Gln Ser Ile Gly Ser Ser Leu His
1               5                   10

<210> SEQ ID NO 124
<211> LENGTH: 33
<212> TYPE: DNA
<213> ORGANISM: Homo sapiens

<400> SEQUENCE: 124
cgggccagtc agagcattgg tagtagctta cac        33

<210> SEQ ID NO 125
<211> LENGTH: 7
<212> TYPE: PRT
<213> ORGANISM: Homo sapiens

<400> SEQUENCE: 125

Tyr Ala Ser Gln Ser Phe Ser
1               5

<210> SEQ ID NO 126
<211> LENGTH: 21
<212> TYPE: DNA
<213> ORGANISM: Homo sapiens

<400> SEQUENCE: 126
tatgcttccc agtccttctc a        21

<210> SEQ ID NO 127
<211> LENGTH: 9
<212> TYPE: PRT
<213> ORGANISM: Homo sapiens

<400> SEQUENCE: 127

His Gln Ser Ser Ser Leu Pro Ile Thr
1               5

<210> SEQ ID NO 128
<211> LENGTH: 27
<212> TYPE: DNA
<213> ORGANISM: Homo sapiens

<400> SEQUENCE: 128
catcagagta gtagtttacc gatcacc        27

<210> SEQ ID NO 129
<211> LENGTH: 119
<212> TYPE: PRT
<213> ORGANISM: Homo sapiens

<400> SEQUENCE: 129

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Asn Phe
            20                  25                  30

Val Ile Gly Trp Val Arg Gln Ala Pro Gly Gln Gly Leu Glu Trp Met
        35                  40                  45

Gly Arg Ile Ile Pro Ile Leu Asp Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Thr Gly Asn Tyr Tyr Lys Pro Tyr Asp Tyr Trp Gly Gln Gly

Thr Leu Val Thr Val Ser Ser
115

<210> SEQ ID NO 130
<211> LENGTH: 357
<212> TYPE: DNA
<213> ORGANISM: Homo sapiens

<400> SEQUENCE: 130

```
caggtccagc tggtgcagtc tggggctgag gtgaagaagc ctgggtcctc ggtgaaggtc      60
tcctgcaagg cttctggagg caccttcaac aacttcgtta tcggctgggt gcgacaggcc     120
cctggacaag gacttgagtg gatgggaagg atcatcccta tccttgatat agcaaactac     180
gcacagaagt tccagggcag agtcacgatt accgcggaca atccacgag cacagcctac     240
atggagctga gcagcctgag atctgaggac acggccgtat actactgtgc gagaacgggg     300
aattattata gccctatga ctactggggc cagggaaccc tggtcaccgt ctcctca        357
```

<210> SEQ ID NO 131
<211> LENGTH: 112
<212> TYPE: PRT
<213> ORGANISM: Homo sapiens

<400> SEQUENCE: 131

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Met
        35                  40                  45

Ala Asn Ile Lys Gln Asp Gly Ser Glu Thr His Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ile Gly Asp Tyr Trp Gly Gln Gly Thr Leu Val Thr Val Ser Ser
            100                 105                 110

<210> SEQ ID NO 132
<211> LENGTH: 336
<212> TYPE: DNA
<213> ORGANISM: Homo sapiens

<400> SEQUENCE: 132

```
gaggtgcagt tggtggagtc tggggaggc ttggtccagc ctggggggtc cctgagactc      60
tcctgtgcag cctctggatt cacctttagt cgctattgga tgagctgggt ccgccaggct     120
ccagggaaag gctggagtg gatggccaac ataaagcaag atggaagtga gacacactat     180
gtggactctg tgaagggccg attcaccatc tccagagaca acgccaagaa ctcactgtat     240
ctgcaaatga acagcctgag agccgaggac acggctgtgt attactgtgc gattggtgac     300
tactggggcc agggaaccct ggtcaccgtc tcctca                              336
```

<210> SEQ ID NO 133
<211> LENGTH: 5
<212> TYPE: PRT
<213> ORGANISM: Homo sapiens

```
<400> SEQUENCE: 133

Arg Tyr Trp Met Ser
1               5

<210> SEQ ID NO 134
<211> LENGTH: 15
<212> TYPE: DNA
<213> ORGANISM: Homo sapiens

<400> SEQUENCE: 134
cgctattgga tgagc                                                    15

<210> SEQ ID NO 135
<211> LENGTH: 17
<212> TYPE: PRT
<213> ORGANISM: Homo sapiens

<400> SEQUENCE: 135

Asn Ile Lys Gln Asp Gly Ser Glu Thr His Tyr Val Asp Ser Val Lys
1               5                   10                  15

Gly

<210> SEQ ID NO 136
<211> LENGTH: 51
<212> TYPE: DNA
<213> ORGANISM: Homo sapiens

<400> SEQUENCE: 136
aacataaagc aagatggaag tgagacacac tatgtggact ctgtgaaggg c            51

<210> SEQ ID NO 137
<211> LENGTH: 3
<212> TYPE: PRT
<213> ORGANISM: Homo sapiens

<400> SEQUENCE: 137

Gly Asp Tyr
1

<210> SEQ ID NO 138
<211> LENGTH: 9
<212> TYPE: DNA
<213> ORGANISM: Homo sapiens

<400> SEQUENCE: 138 ggtgactac                                                           9

<210> SEQ ID NO 139
<211> LENGTH: 107
<212> TYPE: PRT
<213> ORGANISM: Homo sapiens

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Trp
                20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
        50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Lys Ser Tyr Pro Leu
                 85                  90                  95

Thr Phe Gly Gly Gly Thr Lys Val Glu Ile Lys
            100                 105

<210> SEQ ID NO 140
<211> LENGTH: 321
<212> TYPE: DNA
<213> ORGANISM: Homo sapiens

<400> SEQUENCE: 140
gacatccaga tgacccagtc tccatcctca ctgtctgcat ctgtaggaga cagagtcacc      60
atcacttgtc gggcgagtca ggatattagc agctggttag cctggtatca gcagaaacca    120
gagaaagccc ctaagtccct gatctatgct gcatccagtt tgcaaagtgg ggtcccatca    180
aggttcagcg gcagtggatc tgggacagat ttcactctca ccatcagcag cctgcagcct    240
gaagattttg caacttatta ctgccaacag tataaaagtt acccgctcac tttcggcgga    300
gggaccaagg tggagatcaa a                                               321

<210> SEQ ID NO 141
<211> LENGTH: 11
<212> TYPE: PRT
<213> ORGANISM: Homo sapiens

<400> SEQUENCE: 141

Arg Ala Ser Gln Asp Ile Ser Ser Trp Leu Ala
 1               5                  10

<210> SEQ ID NO 142
<211> LENGTH: 33
<212> TYPE: DNA
<213> ORGANISM: Homo sapiens

<400> SEQUENCE: 142
cgggcgagtc aggatattag cagctggtta gcc                                   33

<210> SEQ ID NO 143
<211> LENGTH: 7
<212> TYPE: PRT
<213> ORGANISM: Homo sapiens

<400> SEQUENCE: 143

Ala Ala Ser Ser Leu Gln Ser
 1               5

<210> SEQ ID NO 144
<211> LENGTH: 21
<212> TYPE: DNA
<213> ORGANISM: Homo sapiens

<400> SEQUENCE: 144
gctgcatcca gtttgcaaag t                                                21

<210> SEQ ID NO 145
<211> LENGTH: 9
<212> TYPE: PRT
<213> ORGANISM: Homo sapiens

<400> SEQUENCE: 145
```

Gln Gln Tyr Lys Ser Tyr Pro Leu Thr
1               5

<210> SEQ ID NO 146
<211> LENGTH: 27
<212> TYPE: DNA
<213> ORGANISM: Homo sapiens

<400> SEQUENCE: 146
caacagtata aaagttaccc gctcact                                                27

<210> SEQ ID NO 147
<211> LENGTH: 112
<212> TYPE: PRT
<213> ORGANISM: Homo sapiens

<400> SEQUENCE: 147

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Ala Asn Ile Lys Gln Asp Gly Ser Glu Thr His Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ile Gly Asp Tyr Trp Gly Gln Gly Thr Leu Val Thr Val Ser Ser
            100                 105                 110

<210> SEQ ID NO 148
<211> LENGTH: 336
<212> TYPE: DNA
<213> ORGANISM: Homo sapiens

<400> SEQUENCE: 148
gaggtgcagt tggtggagtc tgggggaggc ttggtccagc ctgggggtc cctgagactc      60 tcctgtgcag cctctggatt cacctttagt cgctattgga tgagctgggt ccgccaggct    120
ccagggaaag gctggagtg gtggccaac ataaagcaag atggaagtga gacacactat      180
gtggactctg tgaagggccg attcaccatc tccagagaca cgccaagaa ctcactgtat     240 ctgcaaatga acagcctgag agccgaggac acggctgtgt attactgtgc gattggtgac   300
tactggggcc agggaaccct ggtcaccgtc tcctca                              336

<210> SEQ ID NO 149
<211> LENGTH: 117
<212> TYPE: PRT
<213> ORGANISM: Homo sapiens

<400> SEQUENCE: 149

Gln Val Gln Leu Val Gln Ser Gly Ala Glu Val Lys Thr Pro Gly Ala
1               5                   10                  15

Ser Val Lys Val Ser Cys Lys Ala Ser Gly Tyr Thr Phe Thr Ser Phe
            20                  25                  30

Gly Ile Ser Trp Val Arg Gln Ala Pro Gly Gln Gly Leu Glu Trp Met
        35                  40                  45

```
Gly Trp Ile Ser Val Tyr Asn Asp Tyr Thr Asn Tyr Ala Gln Lys Phe
    50                  55                  60
Gln Gly Arg Val Thr Met Thr Thr Asp Thr Ser Thr Ser Thr Ala Tyr
65                  70                  75                  80
Met Glu Leu Arg Ser Leu Arg Ser Asp Asp Thr Ala Met Tyr Tyr Cys
                85                  90                  95
Ala Arg Lys Arg Gly Gly Asp Met Asp Tyr Trp Gly Gln Gly Thr Leu
            100                 105                 110
Val Thr Val Ser Ser
        115

<210> SEQ ID NO 150
<211> LENGTH: 351
<212> TYPE: DNA
<213> ORGANISM: Homo sapiens

<400> SEQUENCE: 150
caggttcagc tggtgcagtc tggagctgaa gtgaagacgc ctggggcctc agtgaaggtc    60
tcctgcaagg cttctggtta cacctttacc agctttggta tcagctgggt gcgacaggcc   120
cctggacaag gcttgagtg gatgggatgg atcagcgttt acaatgatta cacaaactat   180
gcacagaagt tccagggcag agtcaccatg accacagaca catccacgag cacagcctac   240
atggaactga ggagcctgag atctgacgac acggccatgt attactgtgc gagaaagagg   300
ggtggggata tggactattg gggccaggga accctggtca ccgtctcctc a            351

<210> SEQ ID NO 151
<211> LENGTH: 5
<212> TYPE: PRT
<213> ORGANISM: Homo sapiens

<400> SEQUENCE: 151

Ser Phe Gly Ile Ser
1               5

<210> SEQ ID NO 152
<211> LENGTH: 15
<212> TYPE: DNA
<213> ORGANISM: Homo sapiens

<400> SEQUENCE: 152
agctttggta tcagc                                                     15

<210> SEQ ID NO 153
<211> LENGTH: 17
<212> TYPE: PRT
<213> ORGANISM: Homo sapiens

<400> SEQUENCE: 153

Trp Ile Ser Val Tyr Asn Asp Tyr Thr Asn Tyr Ala Gln Lys Phe Gln
1               5                   10                  15
Gly

<210> SEQ ID NO 154
<211> LENGTH: 51
<212> TYPE: DNA
<213> ORGANISM: Homo sapiens

<400> SEQUENCE: 154
tggatcagcg tttacaatga ttacacaaac tatgcacaga gttccaggg c              51
```

<210> SEQ ID NO 155
<211> LENGTH: 8
<212> TYPE: PRT
<213> ORGANISM: Homo sapiens

<400> SEQUENCE: 155

Lys Arg Gly Gly Asp Met Asp Tyr
1               5

<210> SEQ ID NO 156
<211> LENGTH: 24
<212> TYPE: DNA
<213> ORGANISM: Homo sapiens

<400> SEQUENCE: 156 aagagggtg gggatatgga ctat                                           24

<210> SEQ ID NO 157
<211> LENGTH: 107
<212> TYPE: PRT
<213> ORGANISM: Homo sapiens

<400> SEQUENCE: 157

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln His Lys Pro Gly Lys Ala Pro Lys Leu Leu Ile
        35                  40                  45

Tyr Leu Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
            100                 105

<210> SEQ ID NO 158
<211> LENGTH: 321
<212> TYPE: DNA
<213> ORGANISM: Homo sapiens

<400> SEQUENCE: 158
gacatccaga tgacccagtc tccatcttcc gtgtctgcat ctgtaggaga cagagtcacc    60
atcacttgtc gggcgagtca ggatattagc agctggttag cctggtatca gcataaacca   120
gggaaagccc ctaagctcct gatctatctt gcatccagtt tgcaaagtgg ggtcccatca   180
aggttcagcg gcagtggatc tgggacagat tcactctca ccatcagcag cctgcagcct    240
gaagattttg caacttacta ttgtcaacag gctaatagtt ttccgtggac gttcggccaa   300
gggaccaagg tggagatcaa a                                             321

<210> SEQ ID NO 159
<211> LENGTH: 11
<212> TYPE: PRT
<213> ORGANISM: Homo sapiens

<400> SEQUENCE: 159

```
Arg Ala Ser Gln Asp Ile Ser Ser Trp Leu Ala
1               5                   10
```

<210> SEQ ID NO 160
<211> LENGTH: 33
<212> TYPE: DNA
<213> ORGANISM: Homo sapiens

<400> SEQUENCE: 160
cgggcgagtc aggatattag cagctggtta gcc                                    33

<210> SEQ ID NO 161
<211> LENGTH: 7
<212> TYPE: PRT
<213> ORGANISM: Homo sapiens

<400> SEQUENCE: 161

```
Leu Ala Ser Ser Leu Gln Ser
1               5
```

<210> SEQ ID NO 162
<211> LENGTH: 21
<212> TYPE: DNA
<213> ORGANISM: Homo sapiens

<400> SEQUENCE: 162
cttgcatcca gtttgcaaag t                                                 21

<210> SEQ ID NO 163
<211> LENGTH: 9
<212> TYPE: PRT
<213> ORGANISM: Homo sapiens

<400> SEQUENCE: 163

```
Gln Gln Ala Asn Ser Phe Pro Trp Thr
1               5
```

<210> SEQ ID NO 164
<211> LENGTH: 27
<212> TYPE: DNA
<213> ORGANISM: Homo sapiens

<400> SEQUENCE: 164
caacaggcta atagttttcc gtggacg                                           27

<210> SEQ ID NO 165
<211> LENGTH: 117
<212> TYPE: PRT
<213> ORGANISM: Homo sapiens

<400> SEQUENCE: 165

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Phe
            20                  25                  30

Gly Ile Ser Trp Val Arg Gln Ala Pro Gly Gln Gly Leu Glu Trp Met
        35                  40                  45

Gly Trp Ile Ser Val Tyr Asn Asp Tyr Thr Asn Tyr Ala Gln Lys Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
```

```
                    85                  90                  95
Ala Arg Lys Arg Gly Gly Asp Met Asp Tyr Trp Gly Gln Gly Thr Leu
            100                 105                 110

Val Thr Val Ser Ser
        115

<210> SEQ ID NO 166
<211> LENGTH: 351
<212> TYPE: DNA
<213> ORGANISM: Homo sapiens

<400> SEQUENCE: 166
caggttcagc tggtgcagtc tggagctgaa gtgaagaagc ctggggcctc agtgaaggtc      60
tcctgcaagg cttctggtta cacctttacc agctttggta tcagctgggt gcgacaggcc    120
cctggacaag gcttgagtg gatgggatgg atcagcgttt acaatgatta cacaaactat     180
gcacagaagt tccagggcag agtcaccatg accacagaca catccacgag cacagcctac    240
atggaactga ggagcctgag atctgacgac acggccgtgt attactgtgc gagaaagagg    300
ggtggggata tggactattg gggccaggga accctggtca ccgtctcctc a             351

<210> SEQ ID NO 167
<211> LENGTH: 121
<212> TYPE: PRT
<213> ORGANISM: Homo sapiens

<400> SEQUENCE: 167

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gln Gly Ser Gly Trp Tyr Gly Asn Tyr Phe Asp Tyr Trp Gly
            100                 105                 110

Gln Gly Thr Leu Val Thr Val Ser Ser
        115                 120

<210> SEQ ID NO 168
<211> LENGTH: 363
<212> TYPE: DNA
<213> ORGANISM: Homo sapiens

<400> SEQUENCE: 168
gaggtgcagc tggtgcagtc tggagcagag gtgaaaaagc ccggggagtc tctgaagatc      60
tcctgtaagg gttctggata cagttttacc agctactgga tcggctgggt gcgccagatg    120
cccgggaaag gcctggagtg gatggggatc atctatcctg gtgactctga taccagatac    180
agcccgtcct tccaaggcca ggtcaccatc tcagccgaca agtccatcag caccgcctac    240
ctgcagtgga gcagcctgaa ggcctcggac accgccatgt attactgtgc gagacagggc    300
agcggctggt acgggaacta ctttgactac tggggccagg gaaccctggt caccgtctcc    360
```

```
<210> SEQ ID NO 169
<211> LENGTH: 5
<212> TYPE: PRT
<213> ORGANISM: Homo sapiens

<400> SEQUENCE: 169

Ser Tyr Trp Ile Gly
1               5

<210> SEQ ID NO 170
<211> LENGTH: 15
<212> TYPE: DNA
<213> ORGANISM: Homo sapiens

<400> SEQUENCE: 170
agctactgga tcggc                                                    15

<210> SEQ ID NO 171
<211> LENGTH: 17
<212> TYPE: PRT
<213> ORGANISM: Homo sapiens

<400> SEQUENCE: 171

Ile Ile Tyr Pro Gly Asp Ser Asp Thr Arg Tyr Ser Pro Ser Phe Gln
1               5                  10                  15

Gly

<210> SEQ ID NO 172
<211> LENGTH: 51
<212> TYPE: DNA
<213> ORGANISM: Homo sapiens

<400> SEQUENCE: 172
atcatctatc ctggtgactc tgataccaga tacagcccgt ccttccaagg c             51

<210> SEQ ID NO 173
<211> LENGTH: 12
<212> TYPE: PRT
<213> ORGANISM: Homo sapiens

<400> SEQUENCE: 173

Gln Gly Ser Gly Trp Tyr Gly Asn Tyr Phe Asp Tyr
1               5                  10

<210> SEQ ID NO 174
<211> LENGTH: 36
<212> TYPE: DNA
<213> ORGANISM: Homo sapiens

<400> SEQUENCE: 174
tggtacggga actactttga ctaccagggc agcggc                             36

<210> SEQ ID NO 175
<211> LENGTH: 108
<212> TYPE: PRT
<213> ORGANISM: Homo sapiens

<400> SEQUENCE: 175

Glu Ile Val Leu Thr Gln Ser Pro Gly Thr Leu Ser Leu Ser Pro Gly
1               5                  10                  15
``` tca                                                                363

```
Glu Arg Ala Thr Leu Ser Cys Arg Ala Ser Gln Ser Phe Ser Arg Gly
                20                  25                  30
Tyr Leu Ala Trp Tyr Gln Gln Lys Pro Gly Ala Pro Arg Leu Leu
            35                  40                  45
Ile Tyr Gly Ala Ser Ser Arg Val Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Asp Ser Ser Pro
                85                  90                  95
Tyr Thr Phe Gly Gln Gly Thr Lys Leu Glu Ile Lys
            100                 105
```

<210> SEQ ID NO 176
<211> LENGTH: 324
<212> TYPE: DNA
<213> ORGANISM: Homo sapiens

<400> SEQUENCE: 176

```
gaaattgtgt tgacgcagtc tccaggcacc ctgtctttgt ctccagggga aagagccacc    60
ctctcctgca gggccagtca gagttttagc agaggctact tagcctggta ccagcagaaa   120
cctggccagg ctcccaggct cctcatctat ggtgcatcca gcagggtcac tggcatccca   180
gacaggttca gtggcagtgg gtctgggaca gacttcactc tcaccatcag cagactggag   240
cctgaagatt ttgcggtgta ttactgtcag cagtatgata gctcaccgta cacttttggc   300
caggggacca agctggagat caaa                                          324
```

<210> SEQ ID NO 177
<211> LENGTH: 12
<212> TYPE: PRT
<213> ORGANISM: Homo sapiens

<400> SEQUENCE: 177

```
Arg Ala Ser Gln Ser Phe Ser Arg Gly Tyr Leu Ala
 1               5                  10
```

<210> SEQ ID NO 178
<211> LENGTH: 36
<212> TYPE: DNA
<213> ORGANISM: Homo sapiens

<400> SEQUENCE: 178

```
agggccagtc agagttttag cagaggctac ttagcc                              36
```

<210> SEQ ID NO 179
<211> LENGTH: 7
<212> TYPE: PRT
<213> ORGANISM: Homo sapiens

<400> SEQUENCE: 179

```
Gly Ala Ser Ser Arg Val Thr
 1               5
```

<210> SEQ ID NO 180
<211> LENGTH: 21
<212> TYPE: DNA
<213> ORGANISM: Homo sapiens

<400> SEQUENCE: 180

```
ggtgcatcca gcagggtcac t                                              21
```

<210> SEQ ID NO 181
<211> LENGTH: 9
<212> TYPE: PRT
<213> ORGANISM: Homo sapiens

<400> SEQUENCE: 181

Gln Gln Tyr Asp Ser Ser Pro Tyr Thr
1               5

<210> SEQ ID NO 182
<211> LENGTH: 27
<212> TYPE: DNA
<213> ORGANISM: Homo sapiens

<400> SEQUENCE: 182
cagcagtatg atagctcacc gtacact                                      27

<210> SEQ ID NO 183
<211> LENGTH: 116
<212> TYPE: PRT
<213> ORGANISM: Homo sapiens

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Trp Met Ser Trp Val Arg Gln Ala Pro Gly Lys Gly Leu Glu Trp Val
        35                  40                  45

Ala Asn Ile Lys His Asp Gly Ser Glu Gln Asp Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ile Trp Phe Gly Pro Trp Gly Gln Gly Thr Leu Val
            100                 105                 110

Thr Val Ser Ser
        115

<210> SEQ ID NO 184
<211> LENGTH: 348
<212> TYPE: DNA
<213> ORGANISM: Homo sapiens

<400> SEQUENCE: 184
gaggtgcagc tggtggagtc tgggggaggc ttggtccagc ctggggggtc cctgagactc    60
tcctgtgcag cctctggatt cacctttagt agcttttgga tgagttgggt ccgccaggct   120
ccagggaaag ggctggagtg ggtggccaac ataaagcacg atggaagtga gcaagactat   180
gtggactctg tgaagggccg attcaccatc tccagagaca acgccaagaa ctcactgtat   240
ctgcaaatga acagcctgag agccgaggac acggctgtgt attactgtgc aaggggggt    300 atctggttcg gcccctgggg ccagggaacc ctggtcaccg tctcctca              348

<210> SEQ ID NO 185
<211> LENGTH: 5
<212> TYPE: PRT
<213> ORGANISM: Homo sapiens

```
<400> SEQUENCE: 185

Ser Phe Trp Met Ser
1               5

<210> SEQ ID NO 186
<211> LENGTH: 15
<212> TYPE: DNA
<213> ORGANISM: Homo sapiens

<400> SEQUENCE: 186
agcttttgga tgagt                                                     15

<210> SEQ ID NO 187
<211> LENGTH: 17
<212> TYPE: PRT
<213> ORGANISM: Homo sapiens

<400> SEQUENCE: 187

Asn Ile Lys His Asp Gly Ser Glu Gln Asp Tyr Val Asp Ser Val Lys
1               5                   10                  15

Gly

<210> SEQ ID NO 188
<211> LENGTH: 51
<212> TYPE: DNA
<213> ORGANISM: Homo sapiens

<400> SEQUENCE: 188
aacataaagc acgatggaag tgagcaagac tatgtggact ctgtgaaggg c             51

<210> SEQ ID NO 189
<211> LENGTH: 7
<212> TYPE: PRT
<213> ORGANISM: Homo sapiens

<400> SEQUENCE: 189

Gly Gly Ile Trp Phe Gly Pro
1               5

<210> SEQ ID NO 190
<211> LENGTH: 21
<212> TYPE: DNA
<213> ORGANISM: Homo sapiens

<400> SEQUENCE: 190
gggggtatct ggttcggccc c                                              21

<210> SEQ ID NO 191
<211> LENGTH: 107
<212> TYPE: PRT
<213> ORGANISM: Homo sapiens

<400> SEQUENCE: 191

Val Ile Trp Met Thr Gln Ser Pro Ser Leu Leu Ser Ala Ser Thr Gly
1               5                   10                  15

Asp Arg Val Thr Ile Ser Cys Arg Met Ser Gln Gly Ile Ser Ser Tyr
                20                  25                  30

Leu Ala Trp Tyr Gln Gln Lys Pro Gly Lys Ala Pro Glu Val Leu Ile
            35                  40                  45

Tyr Ala Val Ser Thr Leu Gln Ser Gly Val Pro Ser Arg Phe Ser Gly
        50                  55                  60
```

Ser Gly Ser Gly Thr Asp Phe Thr Leu Thr Ile Ser Cys Leu Gln Ser
65                  70                  75                  80

Glu Asp Phe Ala Thr Tyr Tyr Cys Gln Gln Tyr Tyr Ser Phe Pro Tyr
                85                  90                  95

Thr Phe Gly Gln Gly Thr Lys Leu Glu Ile Lys
            100                 105

<210> SEQ ID NO 192
<211> LENGTH: 321
<212> TYPE: DNA
<213> ORGANISM: Homo sapiens

<400> SEQUENCE: 192
gtcatctgga tgacccagtc tccatcctta ctctctgcat ctacaggaga cagagtcacc      60
atcagttgtc ggatgagtca gggcattagc agttatttag cctggtatca gcaaaaacca    120
gggaaagccc ctgaggtcct gatctatgct gtatccactt tgcaaagtgg ggtcccatca    180
aggttcagtg gcagtggatc tgggacagat ttcactctca ccatcagctg cctgcagtct    240
gaagattttg caacttatta ctgtcaacag tattatagtt cccgtacac ttttggccag    300 gggaccaagc tggagatcaa a                                              321

<210> SEQ ID NO 193
<211> LENGTH: 11
<212> TYPE: PRT
<213> ORGANISM: Homo sapiens

<400> SEQUENCE: 193

Arg Met Ser Gln Gly Ile Ser Ser Tyr Leu Ala
1               5                   10

<210> SEQ ID NO 194
<211> LENGTH: 33
<212> TYPE: DNA
<213> ORGANISM: Homo sapiens

<400> SEQUENCE: 194
cggatgagtc agggcattag cagttattta gcc                                  33

<210> SEQ ID NO 195
<211> LENGTH: 7
<212> TYPE: PRT
<213> ORGANISM: Homo sapiens

<400> SEQUENCE: 195

Ala Val Ser Thr Leu Gln Ser
1               5

<210> SEQ ID NO 196
<211> LENGTH: 21
<212> TYPE: DNA
<213> ORGANISM: Homo sapiens

<400> SEQUENCE: 196
gctgtatcca ctttgcaaag t                                               21

<210> SEQ ID NO 197
<211> LENGTH: 9
<212> TYPE: PRT
<213> ORGANISM: Homo sapiens

<400> SEQUENCE: 197

Gln Gln Tyr Tyr Ser Phe Pro Tyr Thr
1               5

<210> SEQ ID NO 198
<211> LENGTH: 27
<212> TYPE: DNA
<213> ORGANISM: Homo sapiens

<400> SEQUENCE: 198
caacagtatt atagtttccc gtacact                                              27

<210> SEQ ID NO 199
<211> LENGTH: 107
<212> TYPE: PRT
<213> ORGANISM: Homo sapiens

<400> SEQUENCE: 199

Val Ile Trp Met Thr Gln Ser Pro Leu Leu Ser Ala Ser Thr Gly
1               5                   10                  15

Asp Arg Val Thr Ile Ser Cys Arg Met Ser Gln Gly Ile Ser Ser Tyr
                20                  25                  30

Leu Ala Trp Tyr Gln Gln Lys Pro Gly Lys Ala Pro Glu Leu Leu Ile
            35                  40                  45

Tyr Ala Val Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Thr Tyr Tyr Cys Gln Gln Tyr Tyr Ser Phe Pro Tyr
                85                  90                  95

Thr Phe Gly Gln Gly Thr Lys Leu Glu Ile Lys
            100                 105

<210> SEQ ID NO 200
<211> LENGTH: 321
<212> TYPE: DNA
<213> ORGANISM: Homo sapiens

<400> SEQUENCE: 200
gtcatctgga tgacccagtc tccatcctta ctctctgcat ctacaggaga cagagtcacc     60
atcagttgtc ggatgagtca gggcattagc agttatttag cctggtatca gcaaaaacca    120
gggaaagccc ctgagctcct gatctatgct gtatccactt tgcaaagtgg ggtcccatca    180
aggttcagtg gcagtggatc tgggacagat tcactctca ccatcagctc tctgcagtct    240
gaagattttg caacttatta ctgtcaacag tattatagtt tcccgtacac ttttggccag    300
gggaccaagc tggagatcaa a                                              321

<210> SEQ ID NO 201
<211> LENGTH: 121
<212> TYPE: PRT
<213> ORGANISM: Homo sapiens

<400> SEQUENCE: 201

Gln Val Gln Leu Val Gln Ser Gly Ala Glu Val Lys Lys Pro Gly Ser
1               5                   10                  15

Ser Val Lys Val Ser Cys Lys Ala Ser Gly Gly Ser Phe Ser Ile Tyr
                20                  25                  30

Val Ile Ser Trp Val Arg Gln Ala Pro Gly Gln Gly Leu Glu Trp Met
            35                  40                  45

Gly Arg Ile Pro Ile Leu Gly Thr Thr Asn Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Pro Asp Ser Pro Asn His Ser Asn Thr Phe Asp Tyr Trp Gly
            100                 105                 110

Gln Gly Thr Leu Val Thr Val Ser Ser
            115                 120

<210> SEQ ID NO 202
<211> LENGTH: 363
<212> TYPE: DNA
<213> ORGANISM: Homo sapiens

<400> SEQUENCE: 202
caggtccagc tggtgcagtc tggggctgag gtgaagaagc ctgggtcctc ggtgaaggtc      60
tcctgcaagg cttctggagg ctccttcagc atctatgtta tcagctgggt gcgacaggcc     120
cctggacaag gccttgagtg gatgggaagg atcatcccta tccttggtac aacaaactac     180
gcacagaagt tccagggcag agtcacgatt accgcggaca aatccacgag cacagcctac     240
atggagctga gcagcctgag atctgaggac acggccgtgt attactgtgc gagaccggac     300
tccccgaacc atagtaatac atttgactac tggggccagg gaaccctggt caccgtctcc     360
tca                                                                  363

<210> SEQ ID NO 203
<211> LENGTH: 5
<212> TYPE: PRT
<213> ORGANISM: Homo sapiens

<400> SEQUENCE: 203

Ile Tyr Val Ile Ser
1               5

<210> SEQ ID NO 204
<211> LENGTH: 15
<212> TYPE: DNA
<213> ORGANISM: Homo sapiens

<400> SEQUENCE: 204
atctatgtta tcagc                                                      15

<210> SEQ ID NO 205
<211> LENGTH: 17
<212> TYPE: PRT
<213> ORGANISM: Homo sapiens

<400> SEQUENCE: 205

Arg Ile Ile Pro Ile Leu Gly Thr Thr Asn Tyr Ala Gln Lys Phe Gln
1               5                   10                  15

Gly

<210> SEQ ID NO 206
<211> LENGTH: 36
<212> TYPE: DNA
<213> ORGANISM: Homo sapiens

<400> SEQUENCE: 206

```
ccggactccc cgaaccatag taatacattt gactac                                  36
```

<210> SEQ ID NO 207
<211> LENGTH: 12
<212> TYPE: PRT
<213> ORGANISM: Homo sapiens

<400> SEQUENCE: 207

Pro Asp Ser Pro Asn His Ser Asn Thr Phe Asp Tyr
1               5                   10

<210> SEQ ID NO 208
<211> LENGTH: 36
<212> TYPE: DNA
<213> ORGANISM: Homo sapiens

<400> SEQUENCE: 208

```
ccggactccc cgaaccatag taatacattt gactac                                  36
```

<210> SEQ ID NO 209
<211> LENGTH: 107
<212> TYPE: PRT
<213> ORGANISM: Homo sapiens

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 210
<211> LENGTH: 321
<212> TYPE: DNA
<213> ORGANISM: Homo sapiens

<400> SEQUENCE: 210

```
gacatccaga tgacccagtc tccatcctca ctgtctgcat ctgtaggaga cagagtcacc        60
atcacttgtc gggcgagtca gggtattagc agctggttag cctggtatca gcagaaacca      120
gagaaagccc ctaagtccct gatctatggt gcatccagtt tgcaaagtgg ggtcccatca      180
aggttcagcg gcagtggatc tgggacagat ttcactctca ccatcagcag cctgcagcct      240
gaagattttg caacttatta ctgccaacag tataatagtt acccgtacac ttttggccag      300
gggaccaagc tggagatcaa a                                                321
```

<210> SEQ ID NO 211
<211> LENGTH: 11
<212> TYPE: PRT
<213> ORGANISM: Homo sapiens

<400> SEQUENCE: 211

Arg Ala Ser Gln Gly Ile Ser Ser Trp Leu Ala
1               5                   10

<210> SEQ ID NO 212
<211> LENGTH: 33
<212> TYPE: DNA
<213> ORGANISM: Homo sapiens

<400> SEQUENCE: 212
cgggcgagtc agggtattag cagctggtta gcc         33

<210> SEQ ID NO 213
<211> LENGTH: 7
<212> TYPE: PRT
<213> ORGANISM: Homo sapiens

<400> SEQUENCE: 213

Gly Ala Ser Ser Leu Gln Ser
1               5

<210> SEQ ID NO 214
<211> LENGTH: 21
<212> TYPE: DNA
<213> ORGANISM: Homo sapiens

<400> SEQUENCE: 214
ggtgcatcca gtttgcaaag t         21

<210> SEQ ID NO 215
<211> LENGTH: 9
<212> TYPE: PRT
<213> ORGANISM: Homo sapiens

<400> SEQUENCE: 215

Gln Gln Tyr Asn Ser Tyr Pro Tyr Thr
1               5

<210> SEQ ID NO 216
<211> LENGTH: 27
<212> TYPE: DNA
<213> ORGANISM: Homo sapiens

<400> SEQUENCE: 216
caacagtata atagttaccc gtacact         27

<210> SEQ ID NO 217
<211> LENGTH: 118
<212> TYPE: PRT
<213> ORGANISM: Homo sapiens

<400> SEQUENCE: 217

Gln Val Gln Val Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Thr Ala Lys Tyr Ala Gln Lys Phe
        50                  55                  60

Gln Gly Arg Val Thr Ile Ile Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Asp Gln Asp Tyr Tyr Gly Met Asp Val Trp Gly Gln Gly Thr
            100                 105                 110

Thr Val Thr Val Ser Ser
        115

<210> SEQ ID NO 218
<211> LENGTH: 354
<212> TYPE: DNA
<213> ORGANISM: Homo sapiens

<400> SEQUENCE: 218
caggtccagg tggtgcagtc tggggctgag gtgaagaagc ctgggtcctc ggtgaaggtc    60
tcctgcaagg cttctggagg caccttcagc agctatgcta tcagctgggt gcgacaggcc   120
cctggacaag gcttgagtg gatgggaagg atcatcccta tccttggtac agcaaagtac    180
gcacagaagt tccagggcag agtcacgatt atcgcggaca atccacgag cacagcctac    240 atggagctga gcagcctgag atctgaggac acggccgtgt attactgtgc gagagatcag   300
gactactacg gtatggacgt ctggggccaa gggaccacgg tcaccgtctc ctca         354

<210> SEQ ID NO 219
<211> LENGTH: 5
<212> TYPE: PRT
<213> ORGANISM: Homo sapiens

<400> SEQUENCE: 219

Ser Tyr Ala Ile Ser
1               5

<210> SEQ ID NO 220
<211> LENGTH: 15
<212> TYPE: DNA
<213> ORGANISM: Homo sapiens

<400> SEQUENCE: 220
agctatgcta tcagc                                                     15

<210> SEQ ID NO 221
<211> LENGTH: 17
<212> TYPE: PRT
<213> ORGANISM: Homo sapiens

<400> SEQUENCE: 221

Arg Ile Ile Pro Ile Leu Gly Thr Ala Lys Tyr Ala Gln Lys Phe Gln
1               5                   10                  15

Gly

<210> SEQ ID NO 222
<211> LENGTH: 51
<212> TYPE: DNA
<213> ORGANISM: Homo sapiens

<400> SEQUENCE: 222
aggatcatcc ctatccttgg tacagcaaag tacgcacaga gttccaggg c              51

<210> SEQ ID NO 223
<211> LENGTH: 9
<212> TYPE: PRT
<213> ORGANISM: Homo sapiens
```

<400> SEQUENCE: 223

Asp Gln Asp Tyr Tyr Gly Met Asp Val
1               5

<210> SEQ ID NO 224
<211> LENGTH: 27
<212> TYPE: DNA
<213> ORGANISM: Homo sapiens

<400> SEQUENCE: 224
gatcaggact actacggtat ggacgtc                                       27

<210> SEQ ID NO 225
<211> LENGTH: 107
<212> TYPE: PRT
<213> ORGANISM: Homo sapiens

<400> SEQUENCE: 225

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln His Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Asn Phe Pro Trp
                85                  90                  95

Thr Phe Gly Gln Gly Thr Lys Val Glu Ile Lys
            100                 105

<210> SEQ ID NO 226
<211> LENGTH: 321
<212> TYPE: DNA
<213> ORGANISM: Homo sapiens

<400> SEQUENCE: 226
gacatccaga tgacccagtc tccatcttcc gtgtctgcat ctgtaggaga cagagtcacc      60
atcacttgtc gggcgagtca gggtattagc agctggttag cctggtatca gcataaacca     120
gggaaagccc ctaagctcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag actaataatt tcccgtggac gttcggccaa     300
gggaccaagg tggagatcaa a                                              321

<210> SEQ ID NO 227
<211> LENGTH: 11
<212> TYPE: PRT
<213> ORGANISM: Homo sapiens

<400> SEQUENCE: 227

Arg Ala Ser Gln Gly Ile Ser Ser Trp Leu Ala
1               5                   10

<210> SEQ ID NO 228
<211> LENGTH: 33

```
<212> TYPE: DNA
<213> ORGANISM: Homo sapiens

<400> SEQUENCE: 228
cgggcgagtc agggtattag cagctggtta gcc                                    33

<210> SEQ ID NO 229
<211> LENGTH: 7
<212> TYPE: PRT
<213> ORGANISM: Homo sapiens

<400> SEQUENCE: 229

Ala Ala Ser Ser Leu Gln Ser
1               5

<210> SEQ ID NO 230
<211> LENGTH: 21
<212> TYPE: DNA
<213> ORGANISM: Homo sapiens

<400> SEQUENCE: 230
gctgcatcca gtttgcaaag t                                                 21

<210> SEQ ID NO 231
<211> LENGTH: 9
<212> TYPE: PRT
<213> ORGANISM: Homo sapiens

<400> SEQUENCE: 231

Gln Gln Thr Asn Asn Phe Pro Trp Thr
1               5

<210> SEQ ID NO 232
<211> LENGTH: 27
<212> TYPE: DNA
<213> ORGANISM: Homo sapiens

<400> SEQUENCE: 232
caacagacta ataatttccc gtggacg                                           27

<210> SEQ ID NO 233
<211> LENGTH: 138
<212> TYPE: PRT
<213> ORGANISM: Homo sapiens

<400> SEQUENCE: 233

Met Glu Phe Val Leu Ser Trp Val Phe Leu Val Ala Ile Ile Lys Gly
1               5                   10                  15

Val His Cys Glu Val Gln Leu Val Gln Ser Gly Gly Gly Leu Gly His
                20                  25                  30

Pro Gly Gly Ser Leu Arg Leu Ser Cys Ala Gly Ser Gly Phe Thr Phe
            35                  40                  45

Ser Ser Tyr Ser Met His Trp Leu Arg Gln Ala Pro Gly Lys Gly Leu
        50                  55                  60

Lys Trp Val Ser Ala Ile Gly Thr Ala Gly Gly Thr Tyr Tyr Ala Asp
65                  70                  75                  80

Ser Val Lys Gly Arg Phe Thr Ile Ser Arg Asp Asn Ala Lys Asn Ser
                85                  90                  95

Phe Tyr Leu Gln Met Asn Ser Leu Arg Ala Glu Asp Met Ala Val Tyr
            100                 105                 110

Tyr Cys Ala Arg Glu Tyr Phe Phe Gly Ser Gly Asn Tyr Gly Tyr Trp
```

Gly Gln Gly Thr Leu Val Thr Ala Ser Ser
            130                 135

<210> SEQ ID NO 234
<211> LENGTH: 414
<212> TYPE: DNA
<213> ORGANISM: Homo sapiens

<400> SEQUENCE: 234
atggagtttg tgctgagctg ggttttcctt gttgctatca taaaaggtgt ccactgtgag    60
gttcagctgg tgcagtctgg gggaggcttg ggacatcctg gggggtccct gagactctcc   120
tgtgcaggct ctggattcac tttcagtagt tattctatgc actggcttcg ccaggctcca   180
ggaaaaggtc tgaagtgggt atcagctatt ggtactgctg gtggcacata ctatgcagac   240
tccgtgaagg gccgattcac catctccaga gacaatgcca agaactcctt ctatcttcaa   300
atgaacagcc tgagagccga ggacatggct gtgtattact gtgcaagaga gtatttcttt   360
ggttcgggga attatggata ctggggccag ggaaccctgg tcaccgcctc ctca          414

<210> SEQ ID NO 235
<211> LENGTH: 127
<212> TYPE: PRT
<213> ORGANISM: Homo sapiens

<400> SEQUENCE: 235

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Thr Phe Gly Gln Gly Thr Lys Val Glu Ile Lys
        115                 120                 125

<210> SEQ ID NO 236
<211> LENGTH: 381
<212> TYPE: DNA
<213> ORGANISM: Homo sapiens

<400> SEQUENCE: 236
atggaagccc cagctcagct tctcttcctc ctgctactct ggctcccaga taccaccgga    60
gaaattgtgt tgacacagtc tccagccacc ctgtctttgt ctccagggga aagagccacc   120
ctctcctgca gggccagtca gagtgttagc agctacttag cctggtacca acagaaacct   180
ggccaggctc ccaggctcct catctatgat gcatccaaca gggccactgg catcccagcc   240
aggttcagtg gcagtgggtc tgggacagac ttcactctca ccatcagcag cctagagcct   300
gaagattttg cagtttatta ctgtcagcag cgtagcaact ggcctccgac gttcggccaa   360
gggaccaagg tggagatcaa a                                              381

<210> SEQ ID NO 237
<211> LENGTH: 138
<212> TYPE: PRT
<213> ORGANISM: Homo sapiens

<400> SEQUENCE: 237

Met Glu Phe Val Leu Ser Trp Val Phe Leu Val Ala Ile Leu Lys Gly
1               5                   10                  15

Val Gln Cys Glu Val Gln Leu Val Gln Ser Gly Gly Gly Leu Val Lys
                20                  25                  30

Pro Gly Gly Ser Leu Arg Leu Ser Cys Ala Gly Ser Gly Phe Thr Phe
            35                  40                  45

Ser Ser Tyr Ser Met His Trp Leu Arg Gln Ala Pro Gly Lys Gly Leu
        50                  55                  60

Glu Trp Val Ser Ala Ile Gly Thr Ala Gly Gly Thr Tyr Tyr Ala Asp
65                  70                  75                  80

Ser Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Glu Tyr Phe Phe Gly Ser Gly Asn Tyr Gly Tyr Trp
        115                 120                 125

Gly Gln Gly Thr Leu Val Thr Val Ser Ser
    130                 135

<210> SEQ ID NO 238
<211> LENGTH: 414
<212> TYPE: DNA
<213> ORGANISM: Homo sapiens

<400> SEQUENCE: 238
atggagtttg tgctgagctg ggttttcctt gttgctatct taaaaggtgt ccagtgtgag     60
gttcagctgg tgcagtctgg gggaggcttg gtaaaacctg gggggtccct gagactctcc    120
tgtgcaggct ctggattcac tttcagtagt tattctatgc actggcttcg ccaggctcca    180
ggaaaaggtc tggagtgggt atcagctatt ggtactgctg gtggcacata ctatgcagac    240
tccgtgaagg gccgattcac catctccaga gacaatgcca agaactcctt gtatcttcaa    300
atgaacagcc tgagagccga ggacacggct gtgtattact gtgcaagaga gtatttcttt    360
ggttcgggga attatggata ctggggccag ggaaccctgg tcaccgtctc ctca           414

<210> SEQ ID NO 239
<211> LENGTH: 139
<212> TYPE: PRT
<213> ORGANISM: Homo sapiens

<400> SEQUENCE: 239

Met Glu Phe Val Leu Ser Trp Val Phe Leu Val Ala Ile Leu Lys Gly
1               5                   10                  15

Val Gln Cys Glu Val Gln Leu Val Gln Ser Gly Gly Gly Leu Val His
                20                  25                  30

Pro Gly Gly Ser Leu Arg Leu Ser Cys Ala Gly Ser Gly Phe Thr Phe
            35                  40                  45

Ser Arg Tyr Ala Leu His Trp Val Arg Gln Ala Pro Gly Lys Gly Leu
        50                  55                  60

Glu Trp Val Ser Ala Ile Gly Ile Gly Gly Thr Phe Tyr Ala Asp
65                  70                  75                  80

Ser Val Lys Gly Arg Phe Thr Ile Ser Arg Asp Asn Ala Lys Asn Ser
            85                  90                  95

Leu Tyr Leu Gln Met Asn Ser Leu Arg Ala Glu Asp Met Ala Val Tyr
            100                 105                 110

Tyr Cys Ala Arg Asp Thr Tyr Tyr Asp Phe Phe Asp Ala Phe Asp Ile
        115                 120                 125

Trp Gly Gln Gly Thr Met Val Thr Val Ser Ser
    130                 135

<210> SEQ ID NO 240
<211> LENGTH: 417
<212> TYPE: DNA
<213> ORGANISM: Homo sapiens

<400> SEQUENCE: 240
atggagtttg tgctgagctg ggttttcctt gttgctatat taaaaggtgt ccagtgtgag      60
gttcagctgg tgcagtctgg gggaggcttg gtacatcctg gggggtccct gagactctcc    120
tgtgcaggct ctggattcac cttcagtcgc tatgctttac actgggttcg ccaggctcca    180
ggaaaaggtc tggagtgggt atcagctatt ggtattggtg gtggcacatt ctatgcagac    240
tccgtgaagg gccgattcac catctccaga gacaatgcca agaactccct gtatcttcaa    300
atgaacagcc tgagagccga ggacatggct gtgtattact gtgcaagaga tacgtattac    360 gattttttg atgcttttga tatctggggc caagggacaa tggtcaccgt ctcttca        417

<210> SEQ ID NO 241
<211> LENGTH: 129
<212> TYPE: PRT
<213> ORGANISM: Homo sapiens

<400> SEQUENCE: 241

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
            85                  90                  95

Ile Ser Ser Leu Gln Pro Glu Asp Phe Ala Thr Tyr Tyr Cys Gln Gln
            100                 105                 110

Tyr Asp Ser Tyr Pro Leu Thr Phe Gly Gly Gly Thr Lys Val Glu Ile
        115                 120                 125

Lys

<210> SEQ ID NO 242
<211> LENGTH: 387
<212> TYPE: DNA
<213> ORGANISM: Homo sapiens

<400> SEQUENCE: 242

```
atggacatga gggtcctcgc tcagctcctg gggctcctgc tgctctgttt cccaggtgcc      60
agatgtgaca tccagatgac ccagtctcca tcctcactgt ctgcatctgt aggagacaga     120
gtcaccatca cttgtcgggc gagtcagggt attagcagct ggttagcctg gtatcagcag     180
aaaccagaga aagcccctaa gtccctgatc tatgctgcat ccagtttgca aagtggggtc     240
ccatcaaggt tcagcggcag tggatctggg acagatttca ctctcaccat cagcagcctg     300
cagcctgaag attttgcaac ttattactgc aacagtatg atagttaccc tctcactttc     360
ggcggaggga ccaaggtgga gatcaaa                                         387
```

<210> SEQ ID NO 243
<211> LENGTH: 139
<212> TYPE: PRT
<213> ORGANISM: Homo sapiens

<400> SEQUENCE: 243

```
Met Glu Phe Val Leu Ser Trp Val Phe Leu Val Ala Ile Leu Lys Gly
1               5                   10                  15
Val Gln Cys Glu Val Gln Leu Val Gln Ser Gly Gly Gly Leu Val Lys
                20                  25                  30
Pro Gly Gly Ser Leu Arg Leu Ser Cys Ala Gly Ser Gly Phe Thr Phe
            35                  40                  45
Ser Arg Tyr Ala Leu His Trp Val Arg Gln Ala Pro Gly Lys Gly Leu
        50                  55                  60
Glu Trp Val Ser Ala Ile Gly Ile Gly Gly Thr Phe Tyr Ala Asp
65                  70                  75                  80
Ser Val Lys Gly Arg Phe Thr Ile Ser Arg Asp Asn Ala Lys Asn Ser
                85                  90                  95
Leu Tyr Leu Gln Met Asn Ser Leu Arg Ala Glu Asp Thr Ala Val Tyr
            100                 105                 110
Tyr Cys Ala Arg Asp Thr Tyr Tyr Asp Phe Phe Asp Ala Phe Asp Ile
        115                 120                 125
Trp Gly Gln Gly Thr Met Val Thr Val Ser Ser
    130                 135
```

<210> SEQ ID NO 244
<211> LENGTH: 417
<212> TYPE: DNA
<213> ORGANISM: Homo sapiens

<400> SEQUENCE: 244

```
atggagtttg tgctgagctg ggttttcctt gttgctatat taaaaggtgt ccagtgtgag      60
gttcagctgg tgcagtctgg gggaggcttg gtaaaacctg gggggtccct gagactctcc     120
tgtgcaggct ctggattcac cttcagtcgc tatgctttac actgggttcg ccaggctcca     180
ggaaaaggtc tggagtgggt atcagctatt ggtattggtg gtggcacatt ctatgcagac     240
tccgtgaagg gccgattcac catctcccga gacaatgcca gaactccttt gtatcttcaa     300
atgaacagcc tgagagccga ggacacggct gtgtattact gtgcaagaga tacgtattac     360
gatttttttg atgcttttga tatctggggc caagggacaa tggtcaccgt ctcttca       417
```

<210> SEQ ID NO 245
<211> LENGTH: 136
<212> TYPE: PRT
<213> ORGANISM: Homo sapiens

<400> SEQUENCE: 245

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Asn Tyr Gly Ile His Trp Val Arg Gln Ala Pro Gly Lys Gly Leu
    50                  55                  60

Glu Trp Val Ala Ile Ile Trp His Asp Gly Ser Asn Ser Tyr Tyr Val
65                  70                  75                  80

Asp Ser Val Lys Gly Arg Phe Thr Met Ser Arg Asp Asn Ser Lys Asn
                85                  90                  95

Thr Val Tyr Leu Gln Met Asn Ser Leu Arg Ala Glu Asp Thr Ala Val
            100                 105                 110

Tyr Phe Cys Ala Arg Ile Ile Gly Gly Ala Phe Asp Ile Trp Gly Gln
        115                 120                 125

Gly Thr Met Val Thr Val Ser Ser
    130                 135

<210> SEQ ID NO 246
<211> LENGTH: 408
<212> TYPE: DNA
<213> ORGANISM: Homo sapiens

<400> SEQUENCE: 246
atggagtttg ggctgagctg ggttttcctc gttgctcttt taagaggtgt ccagtgtcag      60
gtgcagctgg tggagtctgg gggaggcgtg gtccagcctg ggaggtccct gagactctcc     120
tgtgcagcgt ctggattcac cttcagtaac tatggcatac actgggtccg ccaggctcca     180
ggcaaggggc tggagtgggt ggctattata tggcatgatg aagtaattc atattatgta      240
gactccgtga aggccgatt caccatgtcc agagacaatt ccaagaacac ggtgtatctg      300
caaatgaaca gcctgagagc cgaggacacg gctgtgtatt tctgtgcgag ataattggg      360
ggcgcttttg atatctgggg ccaagggaca atggtcaccg tctcttca                  408

<210> SEQ ID NO 247
<211> LENGTH: 129
<212> TYPE: PRT
<213> ORGANISM: Homo sapiens

<400> SEQUENCE: 247

Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Ser Ser Trp Leu Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Asn Ser Tyr Pro Ile Thr Phe Gly Gln Gly Thr Arg Leu Glu Ile

Lys

<210> SEQ ID NO 248
<211> LENGTH: 387
<212> TYPE: DNA
<213> ORGANISM: Homo sapiens

<400> SEQUENCE: 248

```
atggacatga gggtcctcgc tcagctcctg gggctcctgc tgctctgttt cccaggtgcc      60
agatgtgaca tccagatgac ccagtctcca tcctcactgt ctgcatctgt aggagacaga     120
gtcaccatca cttgtcgggc gagtcagggt attagcagct ggttagcctg gtatcagcag     180
aaaccagaga aagcccctaa gtccctgatc tatgctgcat ccagtttgca aagtggggtc     240
ccatcaaggt tcagcggcag tggatctggg acagatttca ctctcaccat cagcagcctg     300
cagcctgaag attttgcaac ttattactgc caacagtata atagttaccc gatcaccttc     360
ggccaaggga cacgactgga gatcaaa                                         387
```

<210> SEQ ID NO 249
<211> LENGTH: 136
<212> TYPE: PRT
<213> ORGANISM: Homo sapiens

<400> SEQUENCE: 249

```
Met Glu Phe Gly Leu Ser Trp Val Phe Leu Val Ala Leu Leu Arg Gly
1               5                   10                  15
Val Gln Cys Gln Val Gln Leu Val Glu Ser Gly Gly Gly Val Val Gln
            20                  25                  30
Pro Gly Arg Ser Leu Arg Leu Ser Cys Ala Ala Ser Gly Phe Thr Phe
        35                  40                  45
Ser Asn Tyr Gly Ile His Trp Val Arg Gln Ala Pro Gly Lys Gly Leu
    50                  55                  60
Glu Trp Val Ala Ile Ile Trp His Asp Gly Ser Asn Ser Tyr Tyr Val
65                  70                  75                  80
Asp Ser Val Lys Gly Arg Phe Thr Ile Ser Arg Asp Asn Ser Lys Asn
                85                  90                  95
Thr Leu Tyr Leu Gln Met Asn Ser Leu Arg Ala Glu Asp Thr Ala Val
            100                 105                 110
Tyr Phe Cys Ala Arg Ile Ile Gly Gly Ala Phe Asp Ile Trp Gly Gln
        115                 120                 125
Gly Thr Met Val Thr Val Ser Ser
    130                 135
```

<210> SEQ ID NO 250
<211> LENGTH: 408
<212> TYPE: DNA
<213> ORGANISM: Homo sapiens

<400> SEQUENCE: 250

```
atggagtttg gctgagctg gttttcctc gttgctcttt taagaggtgt ccagtgtcag       60
gtgcagctgg tggagtctgg gggaggcgtg gtccagcctg gaggtccct gagactctcc     120
tgtgcagcgt ctggattcac cttcagtaac tatggcatac actgggtccg ccaggctcca   180
ggcaaggggc tggagtgggt ggctattata tggcatgatg gaagtaattc atattatgta   240
gactccgtga agggccgatt caccatctcc agagacaatt ccaagaacac gctgtatctg   300
```

```
caaatgaaca gcctgagagc cgaggacacg gctgtgtatt tctgtgcgag aataattggg      360
ggcgcttttg atatctgggg ccaagggaca atggtcaccg tctcttca                  408
```

<210> SEQ ID NO 251
<211> LENGTH: 138
<212> TYPE: PRT
<213> ORGANISM: Homo sapiens

<400> SEQUENCE: 251

```
Met Glu Phe Gly Leu Ser Trp Val Phe Leu Val Ala Leu Leu Arg Gly
  1               5                  10                  15

Val Gln Cys Gln Val Gln Leu Val Glu Ser Gly Gly Gly Val Val Gln
             20                  25                  30

Pro Gly Arg Ser Leu Arg Leu Ser Cys Ala Ala Ser Gly Phe Thr Phe
         35                  40                  45

Arg Ser Tyr Gly Met His Trp Val Arg Gln Ala Pro Gly Lys Gly Leu
     50                  55                  60

Glu Trp Val Thr Leu Ile Trp Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                 85                  90                  95

Thr Leu Tyr Leu Gln Met Asn Ser Leu Arg Val Glu Asp Thr Ala Val
            100                 105                 110

Tyr Tyr Cys Ala Arg Glu Gly Phe Asn Trp Asp Ala Phe Asp Ile Trp
        115                 120                 125

Gly Gln Gly Thr Met Val Thr Val Ser Ser
    130                 135
```

<210> SEQ ID NO 252
<211> LENGTH: 414
<212> TYPE: DNA
<213> ORGANISM: Homo sapiens

<400> SEQUENCE: 252

```
atggagtttg gctgagctg ggttttcctc gttgctcttt taagaggtgt ccagtgtcag      60
gtgcaactgg tggagtctgg gggaggcgtg gtccagcctg gaaggtccct gagactctcc    120
tgtgcagcgt ctggattcac cttcaggagt tatggcatgc actgggtccg ccaggctcca    180 ggcaagggc tggagtgggt gacacttata tggtatgatg gaagtaataa atactatgca    240
gactccgtga agggccgatt caccatctcc agagacaatt ccaagaacac gctgtatctg    300
caaatgaaca gcctgagagt cgaggacacg gctgtgtatt actgtgcgag agaagggttt    360 aactggatg cttttgatat ctggggccaa gggacaatgg tcaccgtctc ttca           414
```

<210> SEQ ID NO 253
<211> LENGTH: 128
<212> TYPE: PRT
<213> ORGANISM: Homo sapiens

<400> SEQUENCE: 253

```
Met Glu Thr Pro Ala Gln Leu Leu Phe Leu Leu Leu Leu Trp Leu Pro
  1               5                  10                  15

Asp Thr Thr Gly Glu Ile Val Leu Thr Gln Ser Pro Gly Thr Leu Ser
             20                  25                  30

Leu Ser Pro Gly Glu Arg Ala Thr Leu Ser Cys Arg Ala Ser Gln Ser
         35                  40                  45

Val Arg Ile Ser Tyr Leu Ala Trp Tyr Gln Gln Lys Pro Gly Gln Ala
```

```
            50                  55                  60
Pro Arg Leu Leu Ile Tyr Gly Thr Phe Ser Arg Ala Thr Gly Ile Pro
 65                  70                  75                  80

Asp Arg Phe Ser Gly Ser Gly Ser Gly Thr Asp Phe Thr Leu Thr Ile
                     85                  90                  95

Ser Arg Leu Glu Pro Glu Asp Phe Ala Val Tyr Tyr Cys Gln Gln Tyr
                100                 105                 110

Gly Ser Ser Met Tyr Thr Phe Gly Gln Gly Thr Lys Leu Glu Ile Lys
            115                 120                 125
```

<210> SEQ ID NO 254
<211> LENGTH: 384
<212> TYPE: DNA
<213> ORGANISM: Homo sapiens

<400> SEQUENCE: 254

```
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagtgttcgc atcagctact tagcctggta ccagcagaaa     180
cctggccagg ctcccaggct cctcatctat ggtacattca gcagggccac tggcatccca     240
gacaggttca gtggcagtgg gtctgggaca gacttcactc tcaccatcag cagactggag     300
cctgaagatt ttgcagtgta ttactgtcag cagtatggta gctcaatgta cacttttggc     360
caggggacca agctggagat caaa                                            384
```

<210> SEQ ID NO 255
<211> LENGTH: 138
<212> TYPE: PRT
<213> ORGANISM: Homo sapiens

<400> SEQUENCE: 255

```
Met Glu Phe Gly Leu Ser Trp Val Phe Leu Val Ala Leu Leu Arg Gly
 1               5                  10                  15

Val Gln Cys Gln Val Gln Leu Val Glu Ser Gly Gly Gly Val Val Gln
                20                  25                  30

Pro Gly Arg Ser Leu Arg Leu Ser Cys Ala Ala Ser Gly Phe Thr Phe
            35                  40                  45

Arg Ser Tyr Gly Met His Trp Val Arg Gln Ala Pro Gly Lys Gly Leu
 50                  55                  60

Glu Trp Val Thr Leu Ile Trp Tyr Asp Gly Ser Asn Lys Tyr Tyr Ala
 65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Ser Leu Arg Ala Glu Asp Thr Ala Val
            100                 105                 110

Tyr Tyr Cys Ala Arg Glu Gly Phe Asn Trp Asp Ala Phe Asp Ile Trp
            115                 120                 125

Gly Gln Gly Thr Met Val Thr Val Ser Ser
            130                 135
```

<210> SEQ ID NO 256
<211> LENGTH: 414
<212> TYPE: DNA
<213> ORGANISM: Homo sapiens

<400> SEQUENCE: 256

```
atggagtttg ggctgagctg ggttttcctc gttgctcttt taagaggtgt ccagtgtcag      60
gtgcaactgg tggagtctgg gggaggcgtg gtccagcctg gaggtccct gagactctcc      120 tgtgcagcgt ctggattcac cttcaggagt tatggcatgc actgggtccg ccaggctcca     180
ggcaaggggc tggagtgggt gacacttata tggtatgatg aagtaataa atactatgca      240 gactccgtga agggccgatt caccatctcc agagacaatt ccaagaacac gctgtatctg     300
caaatgaaca gcctgagagc cgaggacacg gctgtgtatt actgtgcgag agaagggttt     360
aactgggatg cttttgatat ctggggccaa gggacaatgg tcaccgtctc ttca           414
```

<210> SEQ ID NO 257
<211> LENGTH: 134
<212> TYPE: PRT
<213> ORGANISM: Homo sapiens

<400> SEQUENCE: 257

```
Met Glu Leu Gly Leu Ser Trp Val Phe Leu Val Ala Ile Leu Glu Gly
 1               5                  10                  15

Val Gln Cys Glu Val His Leu Val Glu Ser Gly Gly Gly Leu Val Gln
            20                  25                  30

Ser Gly Gly Ser Leu Arg Leu Ser Cys Ala Ala Ser Gly Phe Ser Ile
        35                  40                  45

Ser Gly Tyr Trp Met Ser Trp Val Arg Gln Ala Pro Gly Lys Gly Leu
    50                  55                  60

Glu Trp Val Ala Asn Ile Lys Gln Asp Gly Gly Glu Lys Tyr Tyr Gly
65                  70                  75                  80

Asp Ser Val Lys Gly Arg Phe Thr Ile Ser Arg Asp Asn Ala Glu Asn
                85                  90                  95

Ser Leu Tyr Leu Gln Met Ser Ser Leu Arg Ala Glu Asp Thr Ala Val
            100                 105                 110

Tyr Tyr Cys Val Met Ala Gly Gly Leu Asp Tyr Trp Gly Gln Gly Ala
        115                 120                 125

Leu Val Thr Val Ser Ser
    130
```

<210> SEQ ID NO 258
<211> LENGTH: 402
<212> TYPE: DNA
<213> ORGANISM: Homo sapiens

<400> SEQUENCE: 258

```
atggaattgg ggctgagctg ggttttcctt gttgctattt tagaaggtgt tcagtgtgag      60
gtgcacctgg tggagtctgg gggaggcttg gtccagtctg gggggtccct gagactctcc     120
tgtgcagcct ctggattcag cattagtggc tattggatga gctgggtccg ccaggctcca     180
gggaaagggc tggagtgggt ggccaacata aagcaagatg gaggtgagaa gtactatggg     240
gactctgtga agggccgatt caccatctcc agagacaacg ccgaaaactc actgtatctg     300
caaatgagca gcctgagagc cgaggacacg gctgtgtatt actgtgtaat ggcgggtggc     360
cttgactact ggggccaggg agccctggtc accgtctcct ca                        402
```

<210> SEQ ID NO 259
<211> LENGTH: 126
<212> TYPE: PRT
<213> ORGANISM: Homo sapiens

<400> SEQUENCE: 259

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
            85                  90                  95

Ser Leu Glu Pro Glu Asp Phe Ala Val Tyr Tyr Cys Gln Gln Arg Ser
            100                 105                 110

Asn Trp Tyr Thr Phe Gly Gln Gly Thr Lys Leu Glu Ile Lys
            115                 120                 125

<210> SEQ ID NO 260
<211> LENGTH: 378
<212> TYPE: DNA
<213> ORGANISM: Homo sapiens

<400> SEQUENCE: 260
atggaagccc cagctcagct tctcttcctc ctgctactct ggctcccaga taccaccgga      60
gaaattgtgt tgacacagtc tccagccacc ctgtctttgt ctccagggga agagccacc     120 ctctcctgca gggccagtca gagtgttagc agctacttag cctggtacca acagaaacct    180
ggccaggctc ccaggctcct catctatgat gcatccaaca gggccactgg catcccagcc    240
aggttcagtg gcagtgggtc tgggacagac ttcactctca ccatcagcag cctagagcct    300
gaagattttg cagtttatta ctgtcagcag cgtagcaact ggtacacttt tggccagggg    360
accaagctgg agatcaaa                                                   378

<210> SEQ ID NO 261
<211> LENGTH: 134
<212> TYPE: PRT
<213> ORGANISM: Homo sapiens

<400> SEQUENCE: 261

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Ile
        35                  40                  45

Ser Gly Tyr Trp Met Ser Trp Val Arg Gln Ala Pro Gly Lys Gly Leu
    50                  55                  60

Glu Trp Val Ala Asn Ile Lys Gln Asp Gly Gly Glu Lys Tyr Tyr Gly
65                  70                  75                  80

Asp Ser Val Lys Gly Arg Phe Thr Ile Ser Arg Asp Asn Ala Lys Asn
            85                  90                  95

Ser Leu Tyr Leu Gln Met Asn Ser Leu Arg Ala Glu Asp Thr Ala Val
            100                 105                 110

Tyr Tyr Cys Val Met Ala Gly Gly Leu Asp Tyr Trp Gly Gln Gly Thr
            115                 120                 125

Leu Val Thr Val Ser Ser

<210> SEQ ID NO 262
<211> LENGTH: 402
<212> TYPE: DNA
<213> ORGANISM: Homo sapiens

<400> SEQUENCE: 262

```
atggaattgg ggctgagctg ggttttcctt gttgctattt tagaaggtgt tcagtgtgag     60
gtgcagctgg tggagtctgg gggaggcttg gtccagcctg ggggtccct gagactctcc    120
tgtgcagcct ctggattcag cattagtggc tattggatga gctgggtccg ccaggctcca   180
gggaaagggc tggagtgggt ggccaacata aagcaagatg gaggtgagaa gtactatggg   240
gactctgtga aggccgatt caccatctcc agagacaacg ccaagaactc actgtatctg    300
caaatgaaca gcctgagagc cgaggacacg gctgtgtatt actgtgtaat ggcgggtggc   360
cttgactact ggggccaggg aaccctggtc accgtctcct ca                     402
```

<210> SEQ ID NO 263
<211> LENGTH: 131
<212> TYPE: PRT
<213> ORGANISM: Homo sapiens

<400> SEQUENCE: 263

Met Lys His Leu Trp Phe Phe Leu Leu Leu Val Ala Ala Pro Arg Trp
1               5                   10                  15
Val Leu Ser Gln Val Gln Leu Gln Gln Trp Gly Ala Gly Leu Leu Lys
            20                  25                  30
Pro Ser Glu Thr Leu Ser Leu Thr Cys Ala Val Tyr Gly Gly Ser Phe
        35                  40                  45
Ser Gly Tyr Tyr Trp Asn Trp Ile Arg Gln Pro Pro Gly Met Gly Leu
    50                  55                  60
Glu Trp Ile Gly Glu Ile His Gln Ser Gly Gly Pro His Tyr Asn Pro
65                  70                  75                  80
Ser Leu Lys Ser Arg Val Ser Ile Ser Val Asp Thr Ser Lys Asn Gln
                85                  90                  95
Val Asn Leu Lys Leu Ser Ser Val Thr Ala Ala Asp Thr Ala Ile Tyr
            100                 105                 110
Tyr Cys Thr Glu Leu Asp Asp Tyr Trp Gly Gln Gly Thr Leu Val Thr
        115                 120                 125
Val Ser Ser
    130

<210> SEQ ID NO 264
<211> LENGTH: 393
<212> TYPE: DNA
<213> ORGANISM: Homo sapiens

<400> SEQUENCE: 264

```
atgaaacacc tgtggttctt cctcctcctg gtggcagctc ccagatgggt cctgtcccag     60
gtgcagctac agcagtgggg cgcaggactg ttgaagcctt cggagaccct gtccctcacc   120
tgcgctgtct atggtgggtc cttcagtggt tactactgga actggatccg ccagcccca   180
ggaatgggc tggaatggat tggagaaatc catcaaagtg gaggccccca ctacaacccg   240
tccctcaaga gtcgagtcag catttcagta gacacgtcca aaaccaggt caacctgaag   300
ctgagctctg tgaccgccgc ggatacggct atttattact gtacggagtt ggatgactat   360
```
tggggccagg gaaccctggt caccgtctcc tca    393

<210> SEQ ID NO 265
<211> LENGTH: 127
<212> TYPE: PRT
<213> ORGANISM: Homo sapiens

<400> SEQUENCE: 265

Met Glu Ala Pro Ala Gln Leu Leu Phe Leu Leu Leu Trp Leu Pro
1               5                   10                  15

Asp Thr Thr Gly Glu Ile Val Leu Thr Gln Ser Pro Ala Thr Leu Ser
                20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
        50                  55                  60

Arg Leu Leu Ile Tyr Asn Ala Ser Asn Arg Ala Thr Gly Ile Pro Ala
65                  70                  75                  80

Arg Phe Ser Gly Ser Gly Ser Gly Thr Asp Phe Thr Leu Thr Ile Gly
                85                  90                  95

Ser Leu Glu Pro Glu Asp Phe Ala Val Tyr Tyr Cys Gln Gln Arg Ser
            100                 105                 110

Asn Trp Pro Arg Thr Phe Gly Gln Gly Thr Lys Val Glu Ile Lys
        115                 120                 125

<210> SEQ ID NO 266
<211> LENGTH: 381
<212> TYPE: DNA
<213> ORGANISM: Homo sapiens

<400> SEQUENCE: 266
atggaagccc cagctcagct tctcttcctc ctgctactct ggctcccaga taccaccgga    60
gaaattgtgt tgacacagtc tccagccacc ctgtctttgt ctccagggga aagagccacc   120
ctctcctgca gggccagtca gagtgttagc agctacttag cctggtacca acagaaacct   180
ggccaggctc ccaggctcct catctataat gcatccaaca gggccactgg catcccagcc   240
aggttcagtg gcagtgggtc tgggacagac ttcactctca ccatcggcag cctagagcct   300
gaagattttg cagtttatta ctgtcagcag cgtagcaact ggcctcggac gttcggccaa   360
gggaccaagg tggagatcaa a   381

<210> SEQ ID NO 267
<211> LENGTH: 131
<212> TYPE: PRT
<213> ORGANISM: Homo sapiens

<400> SEQUENCE: 267

Met Lys His Leu Trp Phe Phe Leu Leu Leu Val Ala Ala Pro Arg Trp
1               5                   10                  15

Val Leu Ser Gln Val Gln Leu Gln Gln Trp Gly Ala Gly Leu Leu Lys
                20                  25                  30

Pro Ser Glu Thr Leu Ser Leu Thr Cys Ala Val Tyr Gly Gly Ser Phe
            35                  40                  45

Ser Gly Tyr Tyr Trp Asn Trp Ile Arg Gln Pro Pro Gly Lys Gly Leu
        50                  55                  60

Glu Trp Ile Gly Glu Ile His Gln Ser Gly Gly Pro Tyr Asn Pro
65                  70                  75                  80

Ser Leu Lys Ser Arg Val Thr Ile Ser Val Asp Thr Ser Lys Asn Gln
            85                  90                  95

Phe Ser Leu Lys Leu Ser Ser Val Thr Ala Ala Asp Thr Ala Val Tyr
            100                 105                 110

Tyr Cys Thr Glu Leu Asp Asp Tyr Trp Gly Gln Gly Thr Leu Val Thr
            115                 120                 125

Val Ser Ser
    130

<210> SEQ ID NO 268
<211> LENGTH: 393
<212> TYPE: DNA
<213> ORGANISM: Homo sapiens

<400> SEQUENCE: 268
atgaaacacc tgtggttctt cctcctcctg gtggcagctc ccagatgggt cctgtcccag    60
gtgcagctac agcagtgggg cgcaggactg ttgaagcctt cggagaccct gtccctcacc   120
tgcgctgtct atggtgggtc cttcagtggt tactactgga actggattcg ccagccccca   180
ggaaaggggc tggaatggat tggagaaatc atcaaagtg gaggccccca ctacaacccg    240
tccctcaaga gtcgagtcac catttcagta gacacgtcca aaaaccagtt ctccctgaag   300
ctgagctctg tgaccgccgc ggatacggct gtgtattact gtacggagtt ggatgactat   360
tggggccagg gaaccctggt caccgtctcc tca                                393

<210> SEQ ID NO 269
<211> LENGTH: 127
<212> TYPE: PRT
<213> ORGANISM: Homo sapiens

<400> SEQUENCE: 269

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
            85                  90                  95

Ser Leu Glu Pro Glu Asp Phe Ala Val Tyr Tyr Cys Gln Gln Arg Ser
            100                 105                 110

Asn Trp Pro Arg Thr Phe Gly Gln Gly Thr Lys Val Glu Ile Lys
        115                 120                 125

<210> SEQ ID NO 270
<211> LENGTH: 381
<212> TYPE: DNA
<213> ORGANISM: Homo sapiens

<400> SEQUENCE: 270
atggaagccc cagctcagct tctcttcctc ctgctactct ggctcccaga taccaccgga    60
gaaattgtgt tgacacagtc tccagccacc ctgtctttgt ctccagggga aagagccacc   120
ctctcctgca gggccagtca gagtgttagc agctacttag cctggtacca acagaaacct   180

```
ggccaggctc ccaggctcct catctatgat gcatccaaca gggccactgg catcccagcc    240
aggttcagtg gcagtgggtc tgggacagac ttcactctca ccatcagcag cctagagcct    300
gaagattttg cagttttatta ctgtcagcag cgtagcaact ggcctcggac gttcggccaa    360
gggaccaagg tggagatcaa a                                                381

<210> SEQ ID NO 271
<211> LENGTH: 138
<212> TYPE: PRT
<213> ORGANISM: Homo sapiens

<400> SEQUENCE: 271

Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Thr Phe
        35                  40                  45

Asn Asn Phe Val Ile Gly Trp Val Arg Gln Ala Pro Gly Gln Gly Leu
    50                  55                  60

Glu Trp Met Gly Arg Ile Ile Pro Ile Leu Asp Ile Ala Asn Tyr Ala
65                  70                  75                  80

Gln Lys Phe Gln Gly Arg Val Thr Ile Thr Ala Asp Lys Ser Thr Ser
                85                  90                  95

Thr Val Tyr Met Glu Leu Asn Ser Leu Arg Ser Glu Asp Thr Ala Val
            100                 105                 110

Tyr Tyr Cys Ala Arg Thr Gly Asn Tyr Tyr Lys Pro Tyr Asp Tyr Trp
        115                 120                 125

Gly Gln Gly Thr Leu Val Thr Val Ser Ser
    130                 135

<210> SEQ ID NO 272
<211> LENGTH: 414
<212> TYPE: DNA
<213> ORGANISM: Homo sapiens

<400> SEQUENCE: 272
atggactgga cctggaggtt cctctttgtg gtggcagcag ctacaggtgt ccagtcccag    60
gtccagctgg tgcagtctgg ggctgaggtg aagaagcctg gtcctcggt gaaggtctcc    120 tgcaaggctt ctggaggcac cttcaacaac ttcgttatcg gctgggtgcg acaggcccct    180
ggacaaggac ttgagtggat gggaaggatc atccctatcc ttgatatagc aaactacgca    240
cagaagttcc agggcagagt cacgattacc gcggacaaat ccacgagcac agtttacatg    300
gagctgaaca gcctgagatc tgaggacacg gccgtatact actgtgcgag aacggggaat    360
tattataagc cctatgacta ctggggccag ggaaccctgg tcaccgtctc ctca          414

<210> SEQ ID NO 273
<211> LENGTH: 126
<212> TYPE: PRT
<213> ORGANISM: Homo sapiens

<400> SEQUENCE: 273

Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30
```

```
Thr Pro Lys Glu Lys Val Thr Ile Thr Cys Arg Ala Ser Gln Ser Ile
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
 65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Ile Thr Phe Gly Gln Gly Thr Arg Leu Glu Ile Lys
            115                 120                 125

<210> SEQ ID NO 274
<211> LENGTH: 378
<212> TYPE: DNA
<213> ORGANISM: Homo sapiens

<400> SEQUENCE: 274
atgttgccat cacaactcat tgggtttctg ctgctctggg ttccagcctc caggggtgaa      60
attgtgctga ctcagtctcc agactttcag tctgtgactc caaaggagaa agtcaccatc     120
acctgccggg ccagtcagag cattggtagt agcttacact ggtaccagca gaaaccagat     180
cagtctccaa agctcctcat caagtatgct tcccagtcct tctcaggggt cccctcgagg     240
ttcagtggca gtggatctgg gacagatttc accctcacca tcaatagcct ggaagctgaa     300
gatgctgcag cgtattactg tcatcagagt agtagtttac cgatcacctt cggccaaggg     360
acacgactgg agatcaaa                                                   378

<210> SEQ ID NO 275
<211> LENGTH: 138
<212> TYPE: PRT
<213> ORGANISM: Homo sapiens

<400> SEQUENCE: 275

Met Asp Trp Thr Trp Arg Phe Leu Phe Val Val Ala Ala Ala Thr Gly
  1               5                  10                  15

Val Gln Ser Gln Val Gln Leu Val Gln Ser Gly Ala Glu Val Lys Lys
             20                  25                  30

Pro Gly Ser Ser Val Lys Val Ser Cys Lys Ala Ser Gly Gly Thr Phe
         35                  40                  45

Asn Asn Phe Val Ile Gly Trp Val Arg Gln Ala Pro Gly Gln Gly Leu
 50                  55                  60

Glu Trp Met Gly Arg Ile Ile Pro Ile Leu Asp Ile Ala Asn Tyr Ala
 65                  70                  75                  80

Gln Lys Phe Gln Gly Arg Val Thr Ile Thr Ala Asp Lys Ser Thr Ser
             85                  90                  95

Thr Ala Tyr Met Glu Leu Ser Ser Leu Arg Ser Glu Asp Thr Ala Val
            100                 105                 110

Tyr Tyr Cys Ala Arg Thr Gly Asn Tyr Tyr Lys Pro Tyr Asp Tyr Trp
        115                 120                 125

Gly Gln Gly Thr Leu Val Thr Val Ser Ser
        130                 135

<210> SEQ ID NO 276
<211> LENGTH: 414
```

<212> TYPE: DNA
<213> ORGANISM: Homo sapiens

<400> SEQUENCE: 276

```
atggactgga cctggaggtt cctctttgtg gtggcagcag ctacaggtgt ccagtcccag    60
gtccagctgg tgcagtctgg ggctgaggtg aagaagcctg gtcctcggt  gaaggtctcc   120
tgcaaggctt ctggaggcac cttcaacaac ttcgttatcg gctgggtgcg acaggcccct   180
ggacaaggac ttgagtggat gggaaggatc atccctatcc ttgatatagc aaactacgca   240
cagaagttcc agggcagagt cacgattacc gcggacaaat ccacgagcac agcctacatg   300
gagctgagca gcctgagatc tgaggacacg gccgtatact actgtgcgag aacgggaat   360
tattataagc cctatgacta ctggggccag ggaaccctgg tcaccgtctc ctca         414
```

<210> SEQ ID NO 277
<211> LENGTH: 131
<212> TYPE: PRT
<213> ORGANISM: Homo sapiens

<400> SEQUENCE: 277

```
Met Glu Leu Gly Leu Ser Trp Val Phe Leu Val Ala Ile Leu Glu Gly
1               5                   10                  15
Val Gln Cys Glu Val Gln Leu Val Glu Ser Gly Gly Gly Leu Val Gln
                20                  25                  30
Pro Gly Gly Ser Leu Arg Leu Ser Cys Ala Ala Ser Gly Phe Thr Phe
            35                  40                  45
Ser Arg Tyr Trp Met Ser Trp Val Arg Gln Ala Pro Gly Lys Gly Leu
        50                  55                  60
Glu Trp Met Ala Asn Ile Lys Gln Asp Gly Ser Glu Thr His Tyr Val
65                  70                  75                  80
Asp Ser Val Lys Gly Arg Phe Thr Ile Ser Arg Asp Asn Ala Lys Asn
                85                  90                  95
Ser Leu Tyr Leu Gln Met Asn Ser Leu Arg Ala Glu Asp Thr Ala Val
            100                 105                 110
Tyr Tyr Cys Ala Ile Gly Asp Tyr Trp Gly Gln Gly Thr Leu Val Thr
        115                 120                 125
Val Ser Ser
    130
```

<210> SEQ ID NO 278
<211> LENGTH: 393
<212> TYPE: DNA
<213> ORGANISM: Homo sapiens

<400> SEQUENCE: 278

```
atggaattgg ggctgagctg gttttccctt gttgctattt tagaaggtgt ccagtgtgag    60
gtgcagttgg tggagtctgg gggaggcttg gtccagcctg ggggtccct gagactctcc   120
tgtgcagcct ctggattcac ctttagtcgc tattggatga gctgggtccg ccaggctcca   180
gggaagggc tggagtggat ggccaacata aagcaagatg gaagtgagac acactatgtg   240
gactctgtga aggccgatt caccatctcc agagacaacg ccaagaactc actgtatctg   300
caaatgaaca gcctgagagc cgaggacacg gctgtgtatt actgtgcgat tggtgactac   360
tggggccagg gaaccctggt caccgtctcc tca                                393
```

<210> SEQ ID NO 279
<211> LENGTH: 129

<212> TYPE: PRT
<213> ORGANISM: Homo sapiens

<400> SEQUENCE: 279

```
Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Asp Ile Ser Ser Trp Leu Ala Trp Tyr Gln Gln Lys Pro Glu Lys
    50                  55                  60

Ala Pro Lys Ser Leu Ile Tyr Ala Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Tyr Lys Ser Tyr Pro Leu Thr Phe Gly Gly Gly Thr Lys Val Glu Ile
        115                 120                 125

Lys
```

<210> SEQ ID NO 280
<211> LENGTH: 387
<212> TYPE: DNA
<213> ORGANISM: Homo sapiens

<400> SEQUENCE: 280

```
atggacatga gggtcctcgc tcagctcctg gggctcctgc tgctctgttt cccaggtgcc      60
agatgtgaca tccagatgac ccagtctcca tcctcactgt ctgcatctgt aggagacaga     120
gtcaccatca cttgtcgggc gagtcaggat attagcagct ggttagcctg gtatcagcag     180
aaaccagaga agccccctaa gtccctgatc tatgctgcat ccagtttgca aagtggggtc     240
ccatcaaggt tcagcggcag tggatctggg acagatttca ctctcaccat cagcagcctg     300
cagcctgaag attttgcaac ttattactgc caacagtata aaagttaccc gctcactttc     360
ggcggaggga ccaaggtgga gatcaaa                                         387
```

<210> SEQ ID NO 281
<211> LENGTH: 131
<212> TYPE: PRT
<213> ORGANISM: Homo sapiens

<400> SEQUENCE: 281

```
Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg Tyr Trp Met Ser Trp Val Arg Gln Ala Pro Gly Lys Gly Leu
    50                  55                  60

Glu Trp Val Ala Asn Ile Lys Gln Asp Gly Ser Glu Thr His Tyr Val
65                  70                  75                  80

Asp Ser Val Lys Gly Arg Phe Thr Ile Ser Arg Asp Asn Ala Lys Asn
                85                  90                  95
```

Ser Leu Tyr Leu Gln Met Asn Ser Leu Arg Ala Glu Asp Thr Ala Val
            100                 105                 110

Tyr Tyr Cys Ala Ile Gly Asp Tyr Trp Gly Gln Gly Thr Leu Val Thr
        115                 120                 125

Val Ser Ser
    130

<210> SEQ ID NO 282
<211> LENGTH: 393
<212> TYPE: DNA
<213> ORGANISM: Homo sapiens

<400> SEQUENCE: 282
atggaattgg ggctgagctg ggttttcctt gttgctattt tagaaggtgt ccagtgtgag    60
gtgcagttgg tggagtctgg gggaggcttg gtccagcctg gggggtccct gagactctcc   120
tgtgcagcct ctggattcac ctttagtcgc tattggatga gctgggtccg ccaggctcca   180
gggaaagggc tggagtgggt ggccaacata aagcaagatg gaagtgagac acactatgtg   240
gactctgtga agggccgatt caccatctcc agagacaacg ccaagaactc actgtatctg   300
caaatgaaca gcctgagagc cgaggacacg gctgtgtatt actgtgcgat tggtgactac   360
tggggccagg gaaccctggt caccgtctcc tca                                393

<210> SEQ ID NO 283
<211> LENGTH: 136
<212> TYPE: PRT
<213> ORGANISM: Homo sapiens

<400> SEQUENCE: 283

Met Asp Trp Thr Trp Ser Ile Leu Phe Leu Val Ala Ala Ala Thr Gly
1               5                   10                  15

Ala His Ser Gln Val Gln Leu Val Gln Ser Gly Ala Glu Val Lys Thr
            20                  25                  30

Pro Gly Ala Ser Val Lys Val Ser Cys Lys Ala Ser Gly Tyr Thr Phe
        35                  40                  45

Thr Ser Phe Gly Ile Ser Trp Val Arg Gln Ala Pro Gly Gln Gly Leu
    50                  55                  60

Glu Trp Met Gly Trp Ile Ser Val Tyr Asn Asp Tyr Thr Asn Tyr Ala
65                  70                  75                  80

Gln Lys Phe Gln Gly Arg Val Thr Met Thr Thr Asp Thr Ser Thr Ser
                85                  90                  95

Thr Ala Tyr Met Glu Leu Arg Ser Leu Arg Ser Asp Asp Thr Ala Met
            100                 105                 110

Tyr Tyr Cys Ala Arg Lys Arg Gly Gly Asp Met Asp Tyr Trp Gly Gln
        115                 120                 125

Gly Thr Leu Val Thr Val Ser Ser
    130                 135

<210> SEQ ID NO 284
<211> LENGTH: 408
<212> TYPE: DNA
<213> ORGANISM: Homo sapiens

<400> SEQUENCE: 284
atggactgga cctggagcat ccttttcttg gtggcagcag caacaggtgc ccactcccag    60
gttcagctgg tgcagtctgg agctgaagtg aagacgcctg ggcctcagt gaaggtctcc   120 tgcaaggctt ctggttacac ctttaccagc tttggtatca gctgggtgcg acaggcccct   180

```
ggacaagggc ttgagtggat gggatggatc agcgtttaca atgattacac aaactatgca      240
cagaagttcc agggcagagt caccatgacc acagacacat ccacgagcac agcctacatg      300
gaactgagga gcctgagatc tgacgacacg gccatgtatt actgtgcgag aaagaggggt      360
ggggatatgg actattgggg ccagggaacc ctggtcaccg tctcctca                   408
```

<210> SEQ ID NO 285
<211> LENGTH: 129
<212> TYPE: PRT
<213> ORGANISM: Homo sapiens

<400> SEQUENCE: 285

```
Met Asp Met Met Val Pro Ala Gln Leu Leu Gly Leu Leu Leu Leu Trp
1               5                   10                  15

Phe Pro Gly Ser Arg Cys Asp Ile Gln Met Thr Gln Ser Pro Ser Ser
                20                  25                  30

Val Ser Ala Ser Val Gly Asp Arg Val Thr Ile Thr Cys Arg Ala Ser
            35                  40                  45

Gln Asp Ile Ser Ser Trp Leu Ala Trp Tyr Gln His Lys Pro Gly Lys
        50                  55                  60

Ala Pro Lys Leu Leu Ile Tyr Leu Ala Ser Ser Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
                100                 105                 110

Ala Asn Ser Phe Pro Trp Thr Phe Gly Gln Gly Thr Lys Val Glu Ile
            115                 120                 125

Lys
```

<210> SEQ ID NO 286
<211> LENGTH: 387
<212> TYPE: DNA
<213> ORGANISM: Homo sapiens

<400> SEQUENCE: 286

```
atggacatga tggtccccgc tcagctcctg gggctcctgc tgctctggtt cccaggttcc       60
agatgcgaca tccagatgac ccagtctcca tcttccgtgt ctgcatctgt aggagacaga      120
gtcaccatca cttgtcgggc gagtcaggat attagcagct ggttagcctg gtatcagcat      180
aaaccaggga aagcccctaa gctcctgatc tatcttgcat ccagtttgca aagtggggtc      240
ccatcaaggt tcagcggcag tggatctggg acagatttca ctctcaccat cagcagcctg      300
cagcctgaag attttgcaac ttactattgt caacaggcta atagttttcc gtggacgttc      360
ggccaaggga ccaaggtgga gatcaaa                                          387
```

<210> SEQ ID NO 287
<211> LENGTH: 136
<212> TYPE: PRT
<213> ORGANISM: Homo sapiens

<400> SEQUENCE: 287

```
Met Asp Trp Thr Trp Ser Ile Leu Phe Leu Val Ala Ala Pro Thr Gly
1               5                   10                  15

Ala His Ser Gln Val Gln Leu Val Gln Ser Gly Ala Glu Val Lys Lys
                20                  25                  30
```

Pro Gly Ala Ser Val Lys Val Ser Cys Lys Ala Ser Gly Tyr Thr Phe
                35                  40                  45

Thr Ser Phe Gly Ile Ser Trp Val Arg Gln Ala Pro Gly Gln Gly Leu
     50                  55                  60

Glu Trp Met Gly Trp Ile Ser Val Tyr Asn Asp Tyr Thr Asn Tyr Ala
 65                  70                  75                  80

Gln Lys Phe Gln Gly Arg Val Thr Met Thr Asp Thr Ser Thr Ser Thr
                 85                  90                  95

Thr Ala Tyr Met Glu Leu Arg Ser Leu Arg Ser Asp Asp Thr Ala Val
             100                 105                 110

Tyr Tyr Cys Ala Arg Lys Arg Gly Gly Asp Met Asp Tyr Trp Gly Gln
         115                 120                 125

Gly Thr Leu Val Thr Val Ser Ser
     130                 135

<210> SEQ ID NO 288
<211> LENGTH: 408
<212> TYPE: DNA
<213> ORGANISM: Homo sapiens

<400> SEQUENCE: 288
atggactgga cctggagcat cctttcttg gtggcagcac caacaggtgc ccactcccag      60
gttcagctgg tgcagtctgg agctgaagtg aagaagcctg gggcctcagt gaaggtctcc     120
tgcaaggctt ctggttacac ctttaccagc tttggtatca gctgggtgcg acaggcccct    180
ggacaagggc ttgagtggat gggatggatc agcgtttaca atgattacac aaactatgca    240
cagaagttcc agggcagagt caccatgacc acagacacat ccacgagcac agcctacatg    300
gaactgagga gcctgagatc tgacgacacg gccgtgtatt actgtgcgag aaagaggggt    360
ggggatatgg actattgggg ccagggaacc ctggtcaccg tctcctca                 408

<210> SEQ ID NO 289
<211> LENGTH: 140
<212> TYPE: PRT
<213> ORGANISM: Homo sapiens

<400> SEQUENCE: 289

Met Gly Ser Thr Ala Ile Leu Ala Leu Leu Leu Ala Val Leu Gln Gly
 1               5                  10                  15

Val Cys Ala Glu Val Gln Leu Val Gln Ser Gly Ala Glu Val Lys Lys
                 20                  25                  30

Pro Gly Glu Ser Leu Lys Ile Ser Cys Lys Gly Ser Gly Tyr Ser Phe
             35                  40                  45

Thr Ser Tyr Trp Ile Gly Trp Val Arg Gln Met Pro Gly Lys Gly Leu
     50                  55                  60

Glu Trp Met Gly Ile Ile Tyr Pro Gly Asp Ser Asp Thr Arg Tyr Ser
 65                  70                  75                  80

Pro Ser Phe Gln Gly Gln Val Thr Ile Ser Ala Asp Lys Ser Ile Ser
                 85                  90                  95

Thr Ala Tyr Leu Gln Trp Ser Ser Leu Lys Ala Ser Asp Thr Ala Met
             100                 105                 110

Tyr Tyr Cys Ala Arg Gln Gly Ser Gly Trp Tyr Gly Asn Tyr Phe Asp
         115                 120                 125

Tyr Trp Gly Gln Gly Thr Leu Val Thr Val Ser Ser
     130                 135                 140

-continued

<210> SEQ ID NO 290
<211> LENGTH: 420
<212> TYPE: DNA
<213> ORGANISM: Homo sapiens

<400> SEQUENCE: 290

```
atggggtcaa ccgccatcct cgccctcctc ctggctgttc tccaaggagt ctgtgccgag      60
gtgcagctgg tgcagtctgg agcagaggtg aaaaagcccg gggagtctct gaagatctcc     120
tgtaagggtt ctggatacag ttttaccagc tactggatcg gctgggtgcg ccagatgccc     180
gggaaaggcc tggagtggat ggggatcatc tatcctggtg actctgatac cagatacagc     240
ccgtccttcc aaggccaggt caccatctca gccgacaagt ccatcagcac cgcctacctg     300
cagtggagca gcctgaaggc ctcggacacc gccatgtatt actgtgcgag acagggcagc     360
ggctggtacg ggaactactt tgactactgg ggccagggaa ccctggtcac cgtctcctca     420
```

<210> SEQ ID NO 291
<211> LENGTH: 128
<212> TYPE: PRT
<213> ORGANISM: Homo sapiens

<400> SEQUENCE: 291

```
Met Glu Thr Pro Ala Gln Leu Leu Phe Leu Leu Leu Trp Leu Pro
1               5                   10                  15

Asp Thr Thr Gly Glu Ile Val Leu Thr Gln Ser Pro Gly Thr Leu Ser
                20                  25                  30

Leu Ser Pro Gly Glu Arg Ala Thr Leu Ser Cys Arg Ala Ser Gln Ser
            35                  40                  45

Phe Ser Arg Gly Tyr Leu Ala Trp Tyr Gln Gln Lys Pro Gly Gln Ala
        50                  55                  60

Pro Arg Leu Leu Ile Tyr Gly Ala Ser Ser Arg Val Thr Gly Ile Pro
65                  70                  75                  80

Asp Arg Phe Ser Gly Ser Gly Ser Gly Thr Asp Phe Thr Leu Thr Ile
                85                  90                  95

Ser Arg Leu Glu Pro Glu Asp Phe Ala Val Tyr Tyr Cys Gln Gln Tyr
            100                 105                 110

Asp Ser Ser Pro Tyr Thr Phe Gly Gln Gly Thr Lys Leu Glu Ile Lys
        115                 120                 125
```

<210> SEQ ID NO 292
<211> LENGTH: 384
<212> TYPE: DNA
<213> ORGANISM: Homo sapiens

<400> SEQUENCE: 292

```
atggaaaccc cagcgcagct tctcttcctc ctgctactct ggctcccaga taccaccgga      60
gaaattgtgt tgacgcagtc tccaggcacc ctgtctttgt ctccagggga aagagccacc     120
ctctcctgca gggccagtca gagttttagc agaggctact tagcctggta ccagcagaaa     180
cctggccagg ctcccaggct cctcatctat ggtgcatcca gcagggtcac tggcatccca     240
gacaggttca gtggcagtgg gtctgggaca gacttcactc tcaccatcag cagactggag     300
cctgaagatt ttgcggtgta ttactgtcag cagtatgata gctcaccgta cacttttggc     360
caggggacca agctggagat caaa                                             384
```

<210> SEQ ID NO 293
<211> LENGTH: 135
<212> TYPE: PRT

<213> ORGANISM: Homo sapiens

<400> SEQUENCE: 293

Met Glu Leu Gly Leu Ser Trp Val Phe Leu Val Ala Ile Leu Glu Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Ser Phe Trp Met Ser Trp Val Arg Gln Ala Pro Gly Lys Gly Leu
    50                  55                  60

Glu Trp Val Ala Asn Ile Lys His Asp Gly Ser Glu Gln Asp Tyr Val
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Gly Gly Ile Trp Phe Gly Pro Trp Gly Gln Gly
        115                 120                 125

Thr Leu Val Thr Val Ser Ser
    130                 135

<210> SEQ ID NO 294
<211> LENGTH: 405
<212> TYPE: DNA
<213> ORGANISM: Homo sapiens

<400> SEQUENCE: 294
atggaattgg ggctgagctg ggttttcctt gttgctattt tagaaggtgt ccagtgtgag    60
gtgcagctgg tggagtctgg gggaggcttg gtccagcctg ggggtccct gagactctcc   120
tgtgcagcct ctggattcac ctttagtagc ttttggatga gttgggtccg ccaggctcca   180
gggaaagggc tggagtgggt ggccaacata aagcacgatg gaagtgagca agactatgtg   240
gactctgtga aggccgatt caccatctcc agagacaacg ccaagaactc actgtatctg   300
caaatgaaca gcctgagagc cgaggacacg gctgtgtatt actgtgcaag ggggggtatc   360
tggttcggcc cctggggcca gggaaccctg gtcaccgtct cctca                   405

<210> SEQ ID NO 295
<211> LENGTH: 129
<212> TYPE: PRT
<213> ORGANISM: Homo sapiens

<400> SEQUENCE: 295

Met Asp Met Arg Val Pro Ala Gln Leu Leu Gly Leu Leu Leu Leu Trp
1               5                   10                  15

Leu Pro Gly Ala Arg Cys Val Ile Trp Met Thr Gln Ser Pro Ser Leu
            20                  25                  30

Leu Ser Ala Ser Thr Gly Asp Arg Val Thr Ile Ser Cys Arg Met Ser
        35                  40                  45

Gln Gly Ile Ser Ser Tyr Leu Ala Trp Tyr Gln Gln Lys Pro Gly Lys
    50                  55                  60

Ala Pro Glu Val Leu Ile Tyr Ala Val Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

```
Ile Ser Cys Leu Gln Ser Glu Asp Phe Ala Thr Tyr Tyr Cys Gln Gln
            100                 105                 110

Tyr Tyr Ser Phe Pro Tyr Thr Phe Gly Gln Gly Thr Lys Leu Glu Ile
        115                 120                 125

Lys

<210> SEQ ID NO 296
<211> LENGTH: 387
<212> TYPE: DNA
<213> ORGANISM: Homo sapiens

<400> SEQUENCE: 296
atggacatga gggtgcccgc tcagctcctg gggctcctgc tgctctggct cccaggtgcc      60
agatgtgtca tctggatgac ccagtctcca tccttactct ctgcatctac aggagacaga    120
gtcaccatca gttgtcggat gagtcagggc attagcagtt atttagcctg gtatcagcaa    180
aaaccaggga agcccctga ggtcctgatc tatgctgtat ccactttgca aagtggggtc     240
ccatcaaggt tcagtggcag tggatctggg acagatttca ctctcaccat cagctgcctg    300
cagtctgaag attttgcaac ttattactgt caacagtatt atagtttccc gtacactttt    360
ggccagggga ccaagctgga gatcaaa                                         387

<210> SEQ ID NO 297
<211> LENGTH: 129
<212> TYPE: PRT
<213> ORGANISM: Homo sapiens

<400> SEQUENCE: 297

Met Asp Met Arg Val Pro Ala Gln Leu Leu Gly Leu Leu Leu Leu Trp
1               5                   10                  15

Leu Pro Gly Ala Arg Cys Val Ile Trp Met Thr Gln Ser Pro Ser Leu
            20                  25                  30

Leu Ser Ala Ser Thr Gly Asp Arg Val Thr Ile Ser Cys Arg Met Ser
        35                  40                  45

Gln Gly Ile Ser Ser Tyr Leu Ala Trp Tyr Gln Gln Lys Pro Gly Lys
    50                  55                  60

Ala Pro Glu Leu Leu Ile Tyr Ala Val Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Cys Leu Gln Ser Glu Asp Phe Ala Thr Tyr Tyr Cys Gln Gln
            100                 105                 110

Tyr Tyr Ser Phe Pro Tyr Thr Phe Gly Gln Gly Thr Lys Leu Glu Ile
        115                 120                 125

Lys

<210> SEQ ID NO 298
<211> LENGTH: 387
<212> TYPE: DNA
<213> ORGANISM: Homo sapiens

<400> SEQUENCE: 298
atggacatga gggtgcccgc tcagctcctg gggctcctgc tgctctggct cccaggtgcc      60
agatgtgtca tctggatgac ccagtctcca tccttactct ctgcatctac aggagacaga    120
gtcaccatca gttgtcggat gagtcagggc attagcagtt atttagcctg gtatcagcaa    180
aaaccaggga agcccctga gctcctgatc tatgctgtat ccactttgca aagtggggtc     240
```

```
ccatcaaggt tcagtggcag tggatctggg acagatttca ctctcaccat cagctctctg      300
cagtctgaag attttgcaac ttattactgt caacagtatt atagtttccc gtacactttt      360
ggccagggga ccaagctgga gatcaaa                                          387
```

<210> SEQ ID NO 299
<211> LENGTH: 140
<212> TYPE: PRT
<213> ORGANISM: Homo sapiens
<400> SEQUENCE: 299

```
Met Asp Trp Thr Trp Arg Phe Leu Phe Val Val Ala Ala Ala Thr Gly
1               5                   10                  15

Val Gln Ser Gln Val Gln Leu Val Gln Ser Gly Ala Glu Val Lys Lys
            20                  25                  30

Pro Gly Ser Ser Val Lys Val Ser Cys Lys Ala Ser Gly Gly Ser Phe
        35                  40                  45

Ser Ile Tyr Val Ile Ser Trp Val Arg Gln Ala Pro Gly Gln Gly Leu
    50                  55                  60

Glu Trp Met Gly Arg Ile Ile Pro Ile Leu Gly Thr Thr Asn Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Pro Asp Ser Pro Asn His Ser Asn Thr Phe Asp
        115                 120                 125

Tyr Trp Gly Gln Gly Thr Leu Val Thr Val Ser Ser
    130                 135                 140
```

<210> SEQ ID NO 300
<211> LENGTH: 420
<212> TYPE: DNA
<213> ORGANISM: Homo sapiens
<400> SEQUENCE: 300

```
atggactgga cctggaggtt cctctttgtg gtggcagcag ctacaggtgt ccagtcccag      60
gtccagctgg tgcagtctgg ggctgaggtg aagaagcctg gtcctcggt gaaggtctcc       120 tgcaaggctt ctggaggctc cttcagcatc tatgttatca gctgggtgcg acaggcccct     180
ggacaagggc ttgagtggat gggaaggatc atccctatcc ttggtacaac aaactacgca     240
cagaagttcc agggcagagt cacgattacc gcggacaaat ccacgagcac agcctacatg     300
gagctgagca gcctgagatc tgaggacacg gccgtgtatt actgtgcgag accggactcc     360
ccgaaccata gtaatacatt tgactactgg ggccaggaa ccctggtcac cgtctcctca      420
```

<210> SEQ ID NO 301
<211> LENGTH: 129
<212> TYPE: PRT
<213> ORGANISM: Homo sapiens
<400> SEQUENCE: 301

```
Met Asp Met Arg Val Leu Ala Gln Leu Leu Gly Leu Leu Leu Leu Cys
1               5                   10                  15

Phe Pro Gly Ala Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
```

```
                35                  40                  45
Gln Gly Ile Ser Ser Trp Leu Ala Trp Tyr Gln Gln Lys Pro Glu Lys
         50                  55                  60
Ala Pro Lys Ser Leu Ile Tyr Gly Ala Ser Ser Leu Gln Ser Gly Val
 65                  70                  75                  80
Pro Ser Arg Phe Ser Gly Ser Gly Ser Gly Thr Asp Phe Thr Leu Thr
                 85                  90                  95
Ile Ser Ser Leu Gln Pro Glu Asp Phe Ala Thr Tyr Tyr Cys Gln Gln
            100                 105                 110
Tyr Asn Ser Tyr Pro Tyr Thr Phe Gly Gln Gly Thr Lys Leu Glu Ile
        115                 120                 125
Lys

<210> SEQ ID NO 302
<211> LENGTH: 387
<212> TYPE: DNA
<213> ORGANISM: Homo sapiens

<400> SEQUENCE: 302
atggacatga gggtcctcgc tcagctcctg gggctcctgc tgctctgttt cccaggtgcc      60
agatgtgaca tccagatgac ccagtctcca tcctcactgt ctgcatctgt aggagacaga     120
gtcaccatca cttgtcgggc gagtcagggt attagcagct ggttagcctg gtatcagcag     180
aaaccagaga agcccctaa gtccctgatc tatggtgcat ccagtttgca aagtggggtc      240
ccatcaaggt tcagcggcag tggatctggg acagatttca ctctcaccat cagcagcctg     300
cagcctgaag attttgcaac ttattactgc aacagtata atagttaccc gtacactttt      360
ggccagggga ccaagctgga gatcaaa                                         387

<210> SEQ ID NO 303
<211> LENGTH: 137
<212> TYPE: PRT
<213> ORGANISM: Homo sapiens

<400> SEQUENCE: 303

Met Asp Trp Thr Trp Arg Phe Leu Phe Val Val Ala Ala Ala Thr Gly
  1               5                  10                  15
Val Gln Ser Gln Val Gln Val Val Gln Ser Gly Ala Glu Val Lys Lys
             20                  25                  30
Pro Gly Ser Ser Val Lys Val Ser Cys Lys Ala Ser Gly Gly Thr Phe
         35                  40                  45
Ser Ser Tyr Ala Ile Ser Trp Val Arg Gln Ala Pro Gly Gln Gly Leu
     50                  55                  60
Glu Trp Met Gly Arg Ile Ile Pro Ile Leu Gly Thr Ala Lys Tyr Ala
 65                  70                  75                  80
Gln Lys Phe Gln Gly Arg Val Thr Ile Ile Ala Asp Lys Ser Thr Ser
                 85                  90                  95
Thr Ala Tyr Met Glu Leu Ser Ser Leu Arg Ser Glu Asp Thr Ala Val
            100                 105                 110
Tyr Tyr Cys Ala Arg Asp Gln Asp Tyr Tyr Gly Met Asp Val Trp Gly
        115                 120                 125
Gln Gly Thr Thr Val Thr Val Ser Ser
    130                 135

<210> SEQ ID NO 304
<211> LENGTH: 411
```

<212> TYPE: DNA
<213> ORGANISM: Homo sapiens

<400> SEQUENCE: 304

```
atggactgga cctggaggtt cctctttgtg gtggcagcag ctacaggtgt ccagtcccag      60
gtccaggtgg tgcagtctgg ggctgaggtg aagaagcctg gtcctcggt gaaggtctcc     120
tgcaaggctt ctggaggcac cttcagcagc tatgctatca gctgggtgcg acaggcccct    180
ggacaagggc ttgagtggat gggaaggatc atccctatcc ttggtacagc aaagtacgca    240
cagaagttcc agggcagagt cacgattatc gcggacaaat ccacgagcac agcctacatg    300
gagctgagca gcctgagatc tgaggacacg gccgtgtatt actgtgcgag agatcaggac    360
tactacggta tggacgtctg gggccaaggg accacggtca ccgtctcctc a             411
```

<210> SEQ ID NO 305
<211> LENGTH: 129
<212> TYPE: PRT
<213> ORGANISM: Homo sapiens

<400> SEQUENCE: 305

```
Met Asp Met Met Val Pro Ala Gln Leu Leu Gly Leu Leu Leu Leu Trp
1               5                   10                  15
Phe Pro Gly Ser Arg Cys Asp Ile Gln Met Thr Gln Ser Pro Ser Ser
                20                  25                  30
Val Ser Ala Ser Val Gly Asp Arg Val Thr Ile Thr Cys Arg Ala Ser
            35                  40                  45
Gln Gly Ile Ser Ser Trp Leu Ala Trp Tyr Gln His Lys Pro Gly Lys
        50                  55                  60
Ala Pro Lys Leu Leu Ile Tyr Ala Ala Ser Ser Leu Gln Ser Gly Val
65                  70                  75                  80
Pro Ser Arg Phe Ser Gly Ser Gly Ser Gly Thr Asp Phe Thr Leu Thr
                85                  90                  95
Ile Ser Ser Leu Gln Pro Glu Asp Phe Ala Thr Tyr Tyr Cys Gln Gln
            100                 105                 110
Thr Asn Asn Phe Pro Trp Thr Phe Gly Gln Gly Thr Lys Val Glu Ile
        115                 120                 125
Lys
```

<210> SEQ ID NO 306
<211> LENGTH: 387
<212> TYPE: DNA
<213> ORGANISM: Homo sapiens

<400> SEQUENCE: 306

```
atggacatga tggtccccgc tcagctcctg gggctcctgc tgctctggtt cccaggttcc      60
agatgcgaca tccagatgac ccagtctcca tcttccgtgt ctgcatctgt aggagacaga    120
gtcaccatca cttgtcgggc gagtcagggt attagcagct ggttagcctg gtatcagcat    180
aaaccaggga aagcccctaa gctcctgatc tatgctgcat ccagtttgca aagtggggtc    240
ccatcaaggt tcagcggcag tggatctggg acagatttca ctctcaccat cagcagcctg    300
cagcctgaag attttgcaac ttactattgt caacagacta taatttcccc gtggacgttc    360
ggccaaggga ccaaggtgga gatcaaa                                        387
```

<210> SEQ ID NO 307
<211> LENGTH: 8
<212> TYPE: PRT

<213> ORGANISM: Homo sapiens

<400> SEQUENCE: 307

Glu Gly Leu His Gly Phe His Val
1               5

<210> SEQ ID NO 308
<211> LENGTH: 24
<212> TYPE: DNA
<213> ORGANISM: Homo sapiens

<400> SEQUENCE: 308
gaaggcctgc atggattcca tgtt    24

<210> SEQ ID NO 309
<211> LENGTH: 9
<212> TYPE: PRT
<213> ORGANISM: Homo sapiens

<400> SEQUENCE: 309

His Phe Asn Pro Leu Ser Arg Lys His
1               5

<210> SEQ ID NO 310
<211> LENGTH: 27
<212> TYPE: DNA
<213> ORGANISM: Homo sapiens

<400> SEQUENCE: 310
cactttaatc ctctatccag aaaacac    27

<210> SEQ ID NO 311
<211> LENGTH: 9
<212> TYPE: PRT
<213> ORGANISM: Homo sapiens

<400> SEQUENCE: 311

His Val Gly Asp Leu Gly Asn Val Thr
1               5

<210> SEQ ID NO 312
<211> LENGTH: 27
<212> TYPE: DNA
<213> ORGANISM: Homo sapiens

<400> SEQUENCE: 312
catgttggag acttgggcaa tgtgact    27

<210> SEQ ID NO 313
<211> LENGTH: 8
<212> TYPE: PRT
<213> ORGANISM: Homo sapiens

<400> SEQUENCE: 313

Leu His Gly Phe His Val His Glu
1               5

<210> SEQ ID NO 314
<211> LENGTH: 24
<212> TYPE: DNA
<213> ORGANISM: Homo sapiens

<400> SEQUENCE: 314
ctgcatggat tccatgttca tgag    24

<210> SEQ ID NO 315
<211> LENGTH: 15
<212> TYPE: PRT
<213> ORGANISM: Homo sapiens

<400> SEQUENCE: 315

Ser Gly Asp His Cys Ile Ile Gly Arg Thr Leu Val Val His Glu
1               5                   10                  15

<210> SEQ ID NO 316
<211> LENGTH: 45
<212> TYPE: DNA
<213> ORGANISM: Homo sapiens

<400> SEQUENCE: 316
tcaggagacc attgcatcat tggccgcaca ctggtggtcc atgaa            45

<210> SEQ ID NO 317
<211> LENGTH: 153
<212> TYPE: PRT
<213> ORGANISM: Homo sapiens

<400> SEQUENCE: 317

Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr Leu Val Val His Glu Lys Ala Asp Asp Leu Gly Lys
        115                 120                 125

Gly Gly Asn Glu Glu Ser Thr Lys Thr Gly Asn Ala Gly Ser Arg Leu
    130                 135                 140

Ala Cys Gly Val Ile Gly Ile Ala Gln
145                 150

<210> SEQ ID NO 318
<211> LENGTH: 459
<212> TYPE: DNA
<213> ORGANISM: Homo sapiens

<400> SEQUENCE: 318
gcgacgaagg ccgtgtgcgt gctgaagggc gacggcccag tgcagggcat catcaatttc      60
gagcagaagg aaagtaatgg accagtgaag gtgtggggaa gcattaaagg actgactgaa     120
ggcctgcatg gattccatgt tcatgagttt ggagataata cagcaggctg taccagtgca     180
ggtcctcact ttaatcctct atccagaaaa cacggtgggc caaaggatga agagaggcat     240
gttggagact gggcaatgt gactgctgac aaagatggtg tggccgatgt gtctattgaa     300
gattctgtga tctcgctctc aggagaccat tgcatcattg ccgcacact ggtggtccat     360

```
gaaaaagcag atgacttggg caaaggtgga aatgaagaaa gtacaaagac gggaaacgct    420
ggaagtcgtt tggcttgtgg tgtaattggg atcgcccaa                          459
```

<210> SEQ ID NO 319
<211> LENGTH: 459
<212> TYPE: DNA
<213> ORGANISM: Homo sapiens

<400> SEQUENCE: 319

```
gcgaccaaag cagtgtgcgt tttgaaaggc gatggccctg tgcaaggcat cattaacttc     60
gaacaaaaag aaagcaacgg accggtcaaa gtgtggggat caattaaagg tttgactgag   120
ggcctgcatg gatttcacgt gcatgaattt ggtgacaata ccgccggttg tacctccgcg   180
ggtccgcact ttaacccttt gtcccgtaaa cacgggggcc ctaaagacga agaacgtcat   240
gtcggcgact taggcaacgt cactgccgat aaagatgggg tcgcagacgt cagtattgag   300
gattctgtca tttcgttgtc tggcgatcac tgcatcattg gtcgcactct ggtcgtacac   360
gaaaaagcgg atgatctggg gaaaggcggc aatgaagaga gcaccaaaac gggaaatgct   420
ggctcacgcc tcgcgtgtgg ggtcattggt attgcccag                          459
```

<210> SEQ ID NO 320
<211> LENGTH: 38
<212> TYPE: PRT
<213> ORGANISM: Homo sapiens

<400> SEQUENCE: 320

```
Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu
        35
```

<210> SEQ ID NO 321
<211> LENGTH: 77
<212> TYPE: PRT
<213> ORGANISM: Homo sapiens

<400> SEQUENCE: 321

```
Ala Thr Lys Ala Val Cys Val Leu Lys Gly Asp Gly Pro Val Gln Gly
1               5                   10                  15

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
    50                  55                  60

Asn Pro Leu Ser Arg Lys His Gly Gly Pro Lys Asp Glu
65                  70                  75
```

<210> SEQ ID NO 322
<211> LENGTH: 116
<212> TYPE: PRT
<213> ORGANISM: Homo sapiens

<400> SEQUENCE: 322

```
Ala Thr Lys Ala Val Cys Val Leu Lys Gly Asp Gly Pro Val Gln Gly
1               5                   10                  15
```

-continued

Ile Ile Asn Phe Glu Gln Lys Glu Ser Asn Gly Pro Val Lys Val Trp
            20                  25                  30

Gly Ser Ile Lys Gly Leu Thr Glu Gly Leu His Gly Phe His Val His
        35                  40                  45

Glu Phe Gly Asp Asn Thr Ala Gly Cys Thr Ser Ala Gly Pro His Phe
50                  55                  60

Asn Pro Leu Ser Arg Lys His Gly Gly Pro Lys Asp Glu Glu Arg His
65                  70                  75                  80

Val Gly Asp Leu Gly Asn Val Thr Ala Asp Lys Asp Gly Val Ala Asp
                85                  90                  95

Val Ser Ile Glu Asp Ser Val Ile Ser Leu Ser Gly Asp His Cys Ile
            100                 105                 110

Ile Gly Arg Thr
        115

<210> SEQ ID NO 323
<211> LENGTH: 115
<212> TYPE: PRT
<213> ORGANISM: Homo sapiens

<400> SEQUENCE: 323

Thr Glu Gly Leu His Gly Phe His Val His Glu Phe Gly Asp Asn Thr
1               5                   10                  15

Ala Gly Cys Thr Ser Ala Gly Pro His Phe Asn Pro Leu Ser Arg Lys
            20                  25                  30

His Gly Gly Pro Lys Asp Glu Glu Arg His Val Gly Asp Leu Gly Asn
        35                  40                  45

Val Thr Ala Asp Lys Asp Gly Val Ala Asp Val Ser Ile Glu Asp Ser
    50                  55                  60

Val Ile Ser Leu Ser Gly Asp His Cys Ile Ile Gly Arg Thr Leu Val
65                  70                  75                  80

Val His Glu Lys Ala Asp Asp Leu Gly Lys Gly Gly Asn Glu Glu Ser
                85                  90                  95

Thr Lys Thr Gly Asn Ala Gly Ser Arg Leu Ala Cys Gly Val Ile Gly
            100                 105                 110

Ile Ala Gln
        115

<210> SEQ ID NO 324
<211> LENGTH: 75
<212> TYPE: PRT
<213> ORGANISM: Homo sapiens

<400> SEQUENCE: 324

Glu Arg His Val Gly Asp Leu Gly Asn Val Thr Ala Asp Lys Asp Gly
1               5                   10                  15

Val Ala Asp Val Ser Ile Glu Asp Ser Val Ile Ser Leu Ser Gly Asp
            20                  25                  30

His Cys Ile Ile Gly Arg Thr Leu Val Val His Glu Lys Ala Asp Asp
        35                  40                  45

Gly Lys Gly Gly Asn Glu Glu Ser Thr Lys Thr Gly Asn Ala Gly Ser
    50                  55                  60

Arg Leu Ala Cys Gly Val Ile Gly Ile Ala Gln
65                  70                  75

<210> SEQ ID NO 325

```
<211> LENGTH: 37
<212> TYPE: PRT
<213> ORGANISM: Homo sapiens

<400> SEQUENCE: 325

Leu Val Val His Glu Lys Ala Asp Asp Leu Gly Lys Gly Gly Asn Glu
1               5                   10                  15

Glu Ser Thr Lys Thr Gly Asn Ala Gly Ser Arg Leu Ala Cys Gly Val
            20                  25                  30

Ile Gly Ile Ala Gln
        35

<210> SEQ ID NO 326
<211> LENGTH: 40
<212> TYPE: PRT
<213> ORGANISM: Homo sapiens

<400> SEQUENCE: 326

Leu Thr Glu Gly Leu His Gly Phe His Val His Glu Phe Gly Asp Asn
1               5                   10                  15

Thr Ala Gly Cys Thr Ser Ala Gly Pro His Phe Asn Pro Leu Ser Arg
            20                  25                  30

Lys His Gly Gly Pro Lys Asp Glu
        35                  40

<210> SEQ ID NO 327
<211> LENGTH: 40
<212> TYPE: PRT
<213> ORGANISM: Homo sapiens

<400> SEQUENCE: 327

Glu Glu Arg His Val Gly Asp Leu Gly Asn Val Thr Ala Asp Lys Asp
1               5                   10                  15

Gly Val Ala Asp Val Ser Ile Glu Asp Ser Val Ile Ser Leu Ser Gly
            20                  25                  30

Asp His Cys Ile Ile Gly Arg Thr
        35                  40

<210> SEQ ID NO 328
<211> LENGTH: 79
<212> TYPE: PRT
<213> ORGANISM: Homo sapiens

<400> SEQUENCE: 328

Leu Thr Glu Gly Leu His Gly Phe His Val His Glu Phe Gly Asp Asn
1               5                   10                  15

Thr Ala Gly Cys Thr Ser Ala Gly Pro His Phe Asn Pro Leu Ser Arg
            20                  25                  30

Lys His Gly Gly Pro Lys Asp Glu Glu Arg His Val Gly Asp Leu Gly
        35                  40                  45

Asn Val Thr Ala Asp Lys Asp Gly Val Ala Asp Val Ser Ile Glu Asp
    50                  55                  60

Ser Val Ile Ser Leu Ser Gly Asp His Cys Ile Ile Gly Arg Thr
65                  70                  75

<210> SEQ ID NO 329
<211> LENGTH: 62
<212> TYPE: PRT
<213> ORGANISM: Homo sapiens

<400> SEQUENCE: 329
```

Asp Gly Val Ala Asp Val Ser Ile Glu Asp Ser Val Ile Ser Leu Ser
1               5                   10                  15

Gly Asp His Cys Ile Ile Gly Arg Thr Leu Val Val His Glu Lys Ala
            20                  25                  30

Asp Asp Leu Gly Lys Gly Gly Asn Glu Glu Ser Thr Lys Thr Gly Asn
        35                  40                  45

Ala Gly Ser Arg Leu Ala Cys Gly Val Ile Gly Ile Ala Gln
    50                  55                  60

<210> SEQ ID NO 330
<211> LENGTH: 52
<212> TYPE: PRT
<213> ORGANISM: Homo sapiens

<400> SEQUENCE: 330

Ser Val Ile Ser Leu Ser Gly Asp His Cys Ile Ile Gly Arg Thr Leu
1               5                   10                  15

Val Val His Glu Lys Ala Asp Asp Leu Gly Lys Gly Gly Asn Glu Glu
            20                  25                  30

Ser Thr Lys Thr Gly Asn Ala Gly Ser Arg Leu Ala Cys Gly Val Ile
        35                  40                  45

Gly Ile Ala Gln
    50

<210> SEQ ID NO 331
<211> LENGTH: 15
<212> TYPE: PRT
<213> ORGANISM: Homo sapiens

<400> SEQUENCE: 331

Leu Thr Glu Gly Leu His Gly Phe His Val His Glu Phe Gly Asp
1               5                   10                  15

<210> SEQ ID NO 332
<211> LENGTH: 10
<212> TYPE: PRT
<213> ORGANISM: Homo sapiens

<400> SEQUENCE: 332

Leu Thr Glu Gly Leu His Gly Phe His Val
1               5                   10

<210> SEQ ID NO 333
<211> LENGTH: 10
<212> TYPE: PRT
<213> ORGANISM: Homo sapiens

<400> SEQUENCE: 333

Glu Gly Leu His Gly Phe His Val His Glu
1               5                   10

<210> SEQ ID NO 334
<211> LENGTH: 10
<212> TYPE: PRT
<213> ORGANISM: Homo sapiens

<400> SEQUENCE: 334

Leu His Gly Phe His Val His Glu Phe Gly
1               5                   10

<210> SEQ ID NO 335

```
<211> LENGTH: 15
<212> TYPE: PRT
<213> ORGANISM: Homo sapiens

<400> SEQUENCE: 335

His Val His Glu Phe Gly Asp Asn Thr Ala Gly Cys Thr Ser Ala
1               5                   10                  15

<210> SEQ ID NO 336
<211> LENGTH: 15
<212> TYPE: PRT
<213> ORGANISM: Homo sapiens

<400> SEQUENCE: 336

Thr Ala Gly Cys Thr Ser Ala Gly Pro His Phe Asn Pro Leu Ser
1               5                   10                  15

<210> SEQ ID NO 337
<211> LENGTH: 15
<212> TYPE: PRT
<213> ORGANISM: Homo sapiens

<400> SEQUENCE: 337

His Phe Asn Pro Leu Ser Arg Lys His Gly Gly Pro Lys Asp Glu
1               5                   10                  15

<210> SEQ ID NO 338
<211> LENGTH: 9
<212> TYPE: PRT
<213> ORGANISM: Homo sapiens

<400> SEQUENCE: 338

His Phe Asn Pro Leu Ser Arg Lys His
1               5

<210> SEQ ID NO 339
<211> LENGTH: 9
<212> TYPE: PRT
<213> ORGANISM: Homo sapiens

<400> SEQUENCE: 339

Pro Leu Ser Arg Lys His Gly Gly Pro
1               5

<210> SEQ ID NO 340
<211> LENGTH: 9
<212> TYPE: PRT
<213> ORGANISM: Homo sapiens

<400> SEQUENCE: 340

Arg Lys His Gly Gly Pro Lys Asp Glu
1               5

<210> SEQ ID NO 341
<211> LENGTH: 15
<212> TYPE: PRT
<213> ORGANISM: Homo sapiens

<400> SEQUENCE: 341

Glu Glu Arg His Val Gly Asp Leu Gly Asn Val Thr Ala Asp Lys
1               5                   10                  15

<210> SEQ ID NO 342
<211> LENGTH: 9
<212> TYPE: PRT
```

```
<213> ORGANISM: Homo sapiens

<400> SEQUENCE: 342

Glu Glu Arg His Val Gly Asp Leu Gly
1               5

<210> SEQ ID NO 343
<211> LENGTH: 9
<212> TYPE: PRT
<213> ORGANISM: Homo sapiens

<400> SEQUENCE: 343

His Val Gly Asp Leu Gly Asn Val Thr
1               5

<210> SEQ ID NO 344
<211> LENGTH: 9
<212> TYPE: PRT
<213> ORGANISM: Homo sapiens

<400> SEQUENCE: 344

Asp Leu Gly Asn Val Thr Ala Asp Lys
1               5

<210> SEQ ID NO 345
<211> LENGTH: 14
<212> TYPE: PRT
<213> ORGANISM: Homo sapiens

<400> SEQUENCE: 345

Gly Asn Val Thr Ala Asp Lys Asp Gly Val Ala Asp Val Ser
1               5                   10

<210> SEQ ID NO 346
<211> LENGTH: 15
<212> TYPE: PRT
<213> ORGANISM: Homo sapiens

<400> SEQUENCE: 346

Gly Val Ala Asp Val Ser Ile Glu Asp Ser Val Ile Ser Leu Ser
1               5                   10                  15

<210> SEQ ID NO 347
<211> LENGTH: 15
<212> TYPE: PRT
<213> ORGANISM: Homo sapiens

<400> SEQUENCE: 347

Ser Val Ile Ser Leu Ser Gly Asp His Cys Ile Ile Gly Arg Thr
1               5                   10                  15

<210> SEQ ID NO 348
<211> LENGTH: 15
<212> TYPE: PRT
<213> ORGANISM: Homo sapiens

<400> SEQUENCE: 348

Ser Gly Asp His Cys Ile Ile Gly Arg Thr Leu Val Val His Glu
1               5                   10                  15

<210> SEQ ID NO 349
<211> LENGTH: 15
<212> TYPE: PRT
<213> ORGANISM: Homo sapiens
```

-continued

```
<400> SEQUENCE: 349

Ile Ile Gly Arg Thr Leu Val Val His Glu Lys Ala Asp Asp Leu
1               5                   10                  15

<210> SEQ ID NO 350
<211> LENGTH: 17
<212> TYPE: PRT
<213> ORGANISM: Homo sapiens

<400> SEQUENCE: 350

Met Arg Ala Trp Ile Phe Phe Leu Leu Cys Leu Ala Gly Arg Ala Leu
1               5                   10                  15

Ala

<210> SEQ ID NO 351
<211> LENGTH: 51
<212> TYPE: DNA
<213> ORGANISM: Homo sapiens

<400> SEQUENCE: 351
atgagggctt ggatcttctt tctgctctgc ctggccgggc gcgccttggc c          51

<210> SEQ ID NO 352
<211> LENGTH: 11
<212> TYPE: PRT
<213> ORGANISM: Homo sapiens

<400> SEQUENCE: 352

Asp Ile Cys Leu Pro Arg Trp Gly Cys Leu Trp
1               5                   10
```